(12) United States Patent
Lesser et al.

(10) Patent No.: US 10,702,559 B2
(45) Date of Patent: Jul. 7, 2020

(54) METHODS AND COMPOSITIONS RELATING TO ENGINEERED MICROBIAL CELLS

(71) Applicant: THE GENERAL HOSPITAL CORPORATION, Boston, MA (US)

(72) Inventors: Cammie Lesser, Cambridge, MA (US); Analise Reeves, Cambridge, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 152 days.

(21) Appl. No.: 16/075,410

(22) PCT Filed: Feb. 8, 2017

(86) PCT No.: PCT/US2017/016997
§ 371 (c)(1),
(2) Date: Aug. 3, 2018

(87) PCT Pub. No.: WO2017/139366
PCT Pub. Date: Aug. 17, 2017

(65) Prior Publication Data
US 2019/0038679 A1 Feb. 7, 2019

Related U.S. Application Data

(60) Provisional application No. 62/292,961, filed on Feb. 9, 2016.

(51) Int. Cl.
| | | |
|---|---|---|
| *C12N 1/20* | (2006.01) | |
| *A61K 35/74* | (2015.01) | |
| *C07K 14/25* | (2006.01) | |
| *C12N 15/70* | (2006.01) | |
| *C12N 15/74* | (2006.01) | |
| *C07K 14/195* | (2006.01) | |
| *A61P 1/00* | (2006.01) | |
| *A61P 35/00* | (2006.01) | |
| *A61K 9/00* | (2006.01) | |
| *C07K 14/245* | (2006.01) | |
| *C07K 14/255* | (2006.01) | |
| *C07K 14/33* | (2006.01) | |
| *A61K 31/70* | (2006.01) | |

(52) U.S. Cl.
CPC ............ *A61K 35/74* (2013.01); *A61K 9/0019* (2013.01); *A61K 9/0053* (2013.01); *A61P 1/00* (2018.01); *A61P 35/00* (2018.01); *C07K 14/195* (2013.01); *C07K 14/245* (2013.01); *C07K 14/25* (2013.01); *C07K 14/255* (2013.01); *C07K 14/33* (2013.01); *C12N 15/70* (2013.01); *C12N 15/74* (2013.01); *A61K 31/70* (2013.01); *Y02A 50/469* (2018.01)

(58) Field of Classification Search
CPC ................................ C07K 14/33; C12N 15/74
USPC ..................................................... 435/252.3
See application file for complete search history.

(56) References Cited

U.S. PATENT DOCUMENTS

| | | |
|---|---|---|
| 6,306,387 B1 | 10/2001 | Galan |
| 9,951,340 B2 * | 4/2018 | Lesser .................... C12N 15/70 |
| 2010/0120124 A1 | 5/2010 | Herrero et al. |
| 2012/0021517 A1 | 1/2012 | Jin et al. |
| 2015/0359909 A1 | 12/2015 | O'Sullivan et al. |

FOREIGN PATENT DOCUMENTS

| | | | |
|---|---|---|---|
| WO | 1998053854 A1 | 12/1998 | |
| WO | 1999024576 A1 | 5/1999 | |
| WO | 2012012605 A2 | 1/2012 | |
| WO | 2014138324 A1 | 9/2014 | |
| WO | WO-2014138324 A1 * | 9/2014 | ............. A61K 35/74 |

OTHER PUBLICATIONS

Botteaux et al., "MxiC is secreted by and controls the substrate specificity of the Shigella flexneri type III secretion apparatus." Molecular Microbiology 71(2):449-460 (2009).
Buchrieser et al., "The virulence plasmid pWR100 and the repertoire of proteins secreted by the type III secretion apparatus of Shigella flexneri." Molecular Microbiology 38(4):760-771 (2000).
Carayol et al., "Tips and tricks about Shigella invasion of epithelial cells", Curr Opin Microbiol, 16(1):32-7 (2013).
Chamekh et al., "Delivery of biologically active anti-inflammatory cytokines IL-10 and IL-1ra in vivo by the Shigella type III secretion apparatus", J Immunol, 180(6):4292-8 (2008).
Costa et al., "A new means to identify type 3 secreted effectors: functionally interchangeable class IB chaperones recognize a conserved sequence", Mbio, 3(1):e00243-11 (2012).
Deane et al., "Molecular model of a type III secretion system needle: Implications for host-cell sensing," PNAS 103 (33):12529-12533 (2006).
Eichelberg et al., "Differential regulation of *Salmonella typhimurium* type III secreted proteins by pathogenicity island 1 (SPI-1)-encoded transcriptional activators InvF and HilA", Infection and immunity, 67(8):4099-105 (1999).
Galan et al., "Molecular and functional characterization of the *Salmonella* invasion gene invA: homology of InvA to members of a new protein family", J Bacteriol, 174(13):4338-49 (1992).
Hegazy et al., "Evaluations of *Salmonella enterica* Type III Secretion System Effector Proteins as Carriers for Heterologous Vaccine Antigens", Infection and Immunity, 1193-1202 (2012).

(Continued)

*Primary Examiner* — Tekchand Saidha
(74) *Attorney, Agent, or Firm* — Nixon Peabody LLP; David S. Resnick; Nicole D. Kling

(57) ABSTRACT

Described herein are compositions and methods relating to engineered bacteria which have a modified Type 3 Secretion System (T3SS) which permits them to deliver proteins to the extracellular space (e.g., as opposed to the intracellular space of a target cell as done with a wild-type T3SS). In some embodiments, the engineered bacteria comprise a transgenic T3SS. In some embodiments, the delivered protein is non-native or transgenic with respect to the engineered bacteria.

18 Claims, 6 Drawing Sheets

Specification includes a Sequence Listing.

(56) References Cited

OTHER PUBLICATIONS

Hensel et al., "Genes encoding putative effector proteins of the type III secretion system of *Salmonella* pathogenicity island 2 are required for bacterial virulence and proliferation in macrophages." Molecular Microbiology 30(1):163-174 (1998).
Juarez-Rodriguez et al., "Live Attenuated *Salmonella* Vaccines against *Mycobactyerium tuberculosis* with Antigen Delivery via the Type III Secretion System", Infection and Immunity, 798-814 (2012).
Kenjale et al., "The needle component of the type III secretory of Shigella regulates the activity of the secretion apparatus." Journal of Biological Chemistry 280(52):42929-42937 (2005).
Kuhlman et al., "Site-specific chromosomal integration of large synthetic constructs", Nucleic Acids Res, 38(6):e92 (2010).
Lee et al., "Molecular mechanisms of host cytoskeletal rearrangements by Shigella invasins", Int J Mol Sci, 15(10):18253-66 (2014).
Martinez-Argudo et al., "The Shigella T3SS needle transmits a signal for MxiC release, which controls secretion of effectors." Molecular Microbiology 78(6):1365-1378 (2010).
Maurelli et al., "Cloning of plasmid DNA Sequences Involved in Invasion of HeLa Cells by Shigella flexneri." Infection and Immunity 49(1):164-171 (1985).
Mirsky, Ethan, "Refactoring the *Salmonella* type III secretion system" Dissertation. University of California, San Francisco 2012 (60 pages).
Moest et al, "*Salmonella* T3SSs: successful mission of the secret (ion) agents." Current Opinion in Microbiology 16(1):38-44 (2013).
Nguyen et al., "Phylogenetic analyses of the constituents of Type III protein secretion systems", J Mol Microbiol Biotechnol, 2(2):125-44 (2000).
O'Callaghan et al., "A novel host-responsive sensor mediates virulence and type III secretion during Pseudomonas aeruginosa—host cell interactions," Microbiology 158(4):1057-1070 (2012).
Paetzold et al., "Shigella flexneri phagosomal escape is independent of invasion." Infection and immunity 75(10):4826-4830 (2007).
Parsot, "*Shigella* spp. and enteroinvasive *Escherichia coli* pathogenicity factors." FEMS microbiology letters 252(1):11-18 (2005).
Reeves et al., "Engineering *Escherichia coli* into a Protein Delivery System for Mammalian Cells." ACS Synthetic Biology 4(5):644-654 (2015).
Sansonetti et al., "Alterations in the pathogenicity of *Escherichia coli* K-12 after transfer of plasmid and chromosomal genes from Shigella flexneri." Infection and Immunity 39(3):1392-1402 (1983).
Schroeder et al., "Molecular pathogenesis of *Shigella* spp.: controlling host cell signaling, invasion, and death by type III secretion." Clinical microbiology reviews 21(1):134-156 (2008).
Sha et al., "Further characterization of a type III secretion system (T3SS) and of a new effector protein from a clinical isolate of Aeromonas hydrophila—part I", Microb Pathog, 43(4):127-46 (2007).
Singh et al., "LcrH, a class II chaperone from the type three secretion system, has a highly flexible native structure", J Biol Chem, 288(6):4048-55 (2013).
Veenendaal et al., , Andreas KJ, et al. "The type III secretion system needle tip complex mediates host cell sensing and translocon insertion." Molecular Microbiology 63(6):1719-1730 (2007).
Widmaier et al., "Engineering the *Salmonella* type III secretion system to export spider silk monomers", Mol Syst Biol, 5:309 (2009).
Wieser et al., "First multi-epitope subunit vaccine against extraintestinal pathogenic *Escherichia coli* delivered by a bacterial type-3 secretaion system (T3SS)", International Journal of Medical Microbiology, 302:10-18 (2012).
Wilson et al., "Cloning and transfer of the *Salmonella* pathogenicity island 2 type III secretion system for studies of a range of gram-negative genera", Appl Environ Microbiol, 73(18):5911-5918 (2007).
Wilson et al., "Cloning of a functional *Salmonella* SPI-1 type III secretion system and development of a method to create mutations and epitope fusions in the cloned genes." Journal of Biotechnology 122(2):147-160 (2006).

* cited by examiner

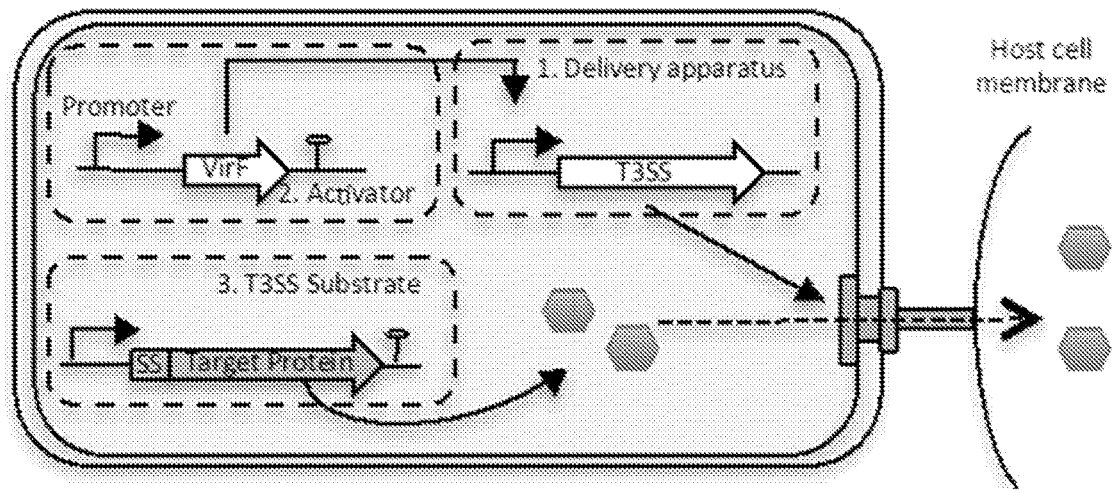
Fig. 8
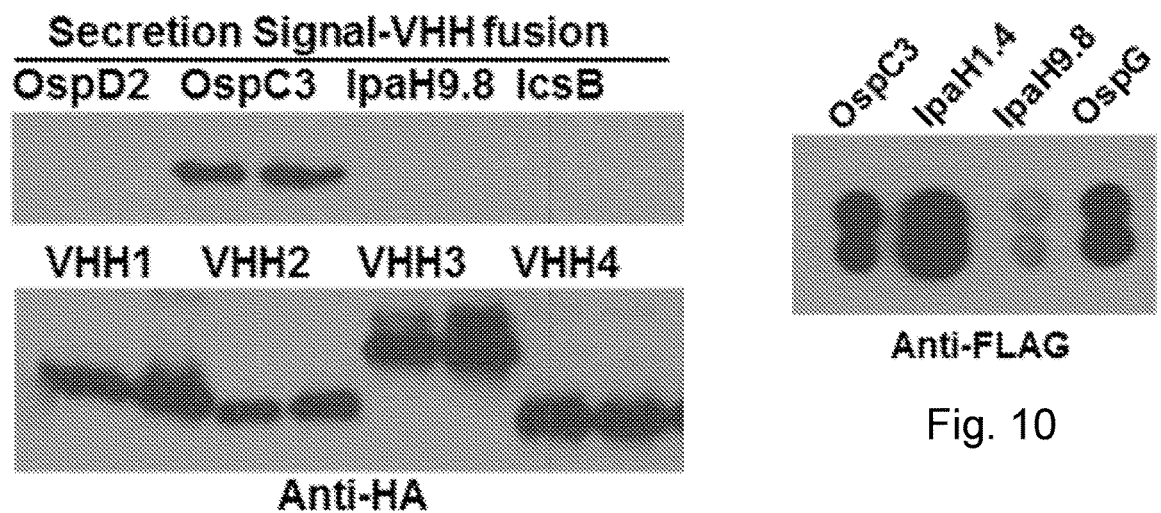
Fig. 9
Fig. 10

SEQUENCE LISTING

<160> NUMBER OF SEQ ID NOS: 102

<210> SEQ ID NO 1
<211> LENGTH: 222
<212> TYPE: DNA
<213> ORGANISM: Escherichia coli

<400> SEQUENCE: 1

```
ttaaaaacta cggttagaaa tggttgagac cagatctttt atcgttttca acattccact    60
ttctacgtta acataagcag aatattgctg aaccgcaaac tgcaactcta acatttttc    120
agggtcatta accaaatcgg tgctattaag taactctggc acagaatcgc tcagcgtttt   180
acctacttca cccatttgtt gagtaatttc agataaattc at                       222
```

<210> SEQ ID NO 2
<211> LENGTH: 73
<212> TYPE: PRT
<213> ORGANISM: Unknown
<220> FEATURE:
<223> OTHER INFORMATION: Description of Unknown:
    Enterobacteriaceae sequence

<400> SEQUENCE: 2

```
Met Asn Leu Ser Glu Ile Thr Gln Gln Met Gly Glu Val Gly Lys Thr
1               5                   10                  15

Leu Ser Asp Ser Val Pro Glu Leu Leu Asn Ser Thr Asp Leu Val Asn
            20                  25                  30

Asp Pro Glu Lys Met Leu Glu Leu Gln Phe Ala Val Gln Gln Tyr Ser
        35                  40                  45

Ala Tyr Val Asn Val Glu Ser Gly Met Leu Lys Thr Ile Lys Asp Leu
    50                  55                  60

Val Ser Thr Ile Ser Asn Arg Ser Phe
65                  70
```

<210> SEQ ID NO 3
<211> LENGTH: 339
<212> TYPE: DNA
<213> ORGANISM: Yersinia pestis

<400> SEQUENCE: 3

```
tcaccccccc ttcgacaagg tttcaacatt ttggctcatt cgcccggcag tcttggcgat     60
aagttcttct tggattgtta tacggataag tgaccattgc attagcatca ggtcgttggg    120
attatcaact gaaacagcca gcttagtgtg taagtcactt ttaaccgtct taaaagactt    180
ctgaatatca ctaacctcct tgaggagtga atggcccagt ccctgcgtat cttctgacat    240
tgccgcatca aagcgcatta tttggtcagt tgttggctct gccggcccta attcctccag    300
cgtggttatg atcacctcat cggcctgagc tatttctat                           339
```

<210> SEQ ID NO 4
<211> LENGTH: 112
<212> TYPE: PRT
<213> ORGANISM: Yersinia pseudotuberculosis

<400> SEQUENCE: 4

```
Met Glu Ile Ala Gln Ala Asp Glu Val Ile Ile Thr Thr Leu Glu Glu
1               5                   10                  15

Leu Gly Pro Ala Glu Pro Thr Thr Asp Gln Ile Met Arg Phe Asp Ala
            20                  25                  30

Ala Met Ser Glu Asp Thr Gln Gly Leu Gly His Ser Leu Leu Lys Glu
        35                  40                  45

Val Ser Asp Ile Gln Lys Ser Phe Lys Thr Val Lys Ser Asp Leu His
    50                  55                  60

Thr Lys Leu Ala Val Ser Val Asp Asn Pro Asn Asp Leu Met Leu Met
65                  70                  75                  80
```

-continued

```
Gln Trp Ser Leu Ile Arg Ile Thr Ile Gln Glu Glu Leu Ile Ala Lys
                85                  90                  95

Thr Ala Gly Arg Met Ser Gln Asn Val Glu Thr Leu Ser Lys Gly Gly
            100                 105                 110

<210> SEQ ID NO 5
<211> LENGTH: 378
<212> TYPE: DNA
<213> ORGANISM: Escherichia coli

<400> SEQUENCE: 5
atgaacaaca ttaatcaatc ggaaaacatt aatattcaat taaataaagc gccccaaaca      60
aatttcgttg atgagcatac ctcgttagcc tcagcccccct ctgcggcagg tgcggctcag     120
tttcttgatc aattactccc taaaacagcg ggagtgtctt ctccagaaca agtgttgatt     180
gaagaaatta aaaagagaca tcttgcaaca atgaacagcg atctcagttt cgatgctcta     240
tctgcaggtg ggctctcgcc agaagacgtg ctcaccttac aaaagaatgt gctcaacgca     300
aacgtcaacg ttgatgtcgt atctaagtta gcaagcctcc tttcaacatc ggttacaaaa     360
ttagtttcga tgcaataa                                                    378

<210> SEQ ID NO 6
<211> LENGTH: 125
<212> TYPE: PRT
<213> ORGANISM: Escherichia coli

<400> SEQUENCE: 6

Met Asn Asn Ile Asn Gln Ser Glu Asn Ile Asn Ile Gln Leu Asn Lys
1               5                   10                  15

Ala Pro Gln Thr Asn Phe Val Asp Glu His Thr Ser Leu Ala Ser Ala
            20                  25                  30

Pro Ser Ala Ala Gly Ala Ala Gln Phe Leu Asp Gln Leu Leu Pro Lys
        35                  40                  45

Thr Ala Gly Val Ser Ser Pro Glu Gln Val Leu Ile Glu Glu Ile Lys
    50                  55                  60

Lys Arg His Leu Ala Thr Met Asn Ser Asp Leu Ser Phe Asp Ala Leu
65                  70                  75                  80

Ser Ala Gly Gly Leu Ser Pro Glu Asp Val Leu Thr Leu Gln Lys Asn
                85                  90                  95

Val Leu Asn Ala Asn Val Asn Val Asp Val Val Ser Lys Leu Ala Ser
            100                 105                 110

Leu Leu Ser Thr Ser Val Thr Lys Leu Val Ser Met Gln
        115                 120                 125

<210> SEQ ID NO 7
<211> LENGTH: 1368
<212> TYPE: DNA
<213> ORGANISM: Yersinia pestis

<400> SEQUENCE: 7
atgaataaaa tcaccactcg ttccccatta gaacctgagt atcaacctct ggggaagccg      60
catcatgctt tgcaagcatg tgtcgatttt gagcaagcgc tgttgcataa taataagggg     120
aattgtcatc ccaaagaaga gtcgcttaaa cctgtacgtc cgcatgacct tggcaaaaaa     180
gaaggtcaga aaggagatgg cttgcgtgcg catgcgccat tagcggcgac gtctcaaccc     240
ggaaggaaag aggtaggatt aaaacctcaa cacaaccatc agaataatca tgatttcaac     300
ttatctccgc ttgccgaagg tgctaccaat agagcgcact tataccagca ggatagccgt     360
```

```
tttgatgacc gcgtagagag tattattaat gctctcatgc cattggcgcc cttttagag      420 ggggtgactt gtgaaacggg gacatcaagt gaatccccct gcgagccgtc tggacatgat      480
gagttatttg ttcagcaatc gcctatcgat tccgctcaac cagttcaatt gaatagcaag      540
ccgactgttc agccattgaa tccggctgct gacggcgcag aggttattgt atggtctgtc      600
ggtagggaaa ctccggccag tatagcaaaa aaccagcgcg atagcaggca aaaacgcctt      660
gcagaagaac cgttagctct tcatcaaaaa gcattgccag agatatgtcc cccggcagtt      720
agtgccacac cggatgatca tttggtagca agatggtgtg ctactcctgt gactgaggta      780
gcagaaaaat ctgctcgttt tccgtacaaa gcgacagtgc agtcagagca actggacatg      840
accgagctgg cggatcggtc ccaacatctt actgatggcg ttgatagcag caaagatacc      900
atcgaaccac cgcgaccaga aaaactgtta cttccgcgcg aagaaacctt gccggagatg      960
tattccttgt cttttacagc accggttgtc acgccgggtg atcacctatt agcaacaatg     1020
cgcgcgacca ggctggcatc agtctcagag caacttatac agttagcaca gcgactagcg     1080
gtagaactag aactgcgcgg cggctcatcc caagtaaccc aattacacct taacttacct     1140
gaattggggg ctattatggt tcgtattgct gagattccgg gaaaactgca tgtagaactg     1200
atcgccagtc gggaagcttt aagaatttta gcgcagggaa gttatgatct tcttgagcga     1260
ttacaacgca ttgagccaac acaacttgat tttcaagcta gcgatgacag tgaacaggag     1320
tcacgtcaga aacgccacgt ctatgaggag tgggaggctg aagaatga                  1368
```

<210> SEQ ID NO 8
<211> LENGTH: 455
<212> TYPE: PRT
<213> ORGANISM: Yersinia pseudotuberculosis

<400> SEQUENCE: 8

```
Met Asn Lys Ile Thr Thr Arg Ser Pro Leu Glu Pro Glu Tyr Gln Pro
1               5                   10                  15

Leu Gly Lys Pro His His Ala Leu Gln Ala Cys Val Asp Phe Glu Gln
            20                  25                  30

Ala Leu Leu His Asn Asn Lys Gly Asn Cys His Pro Lys Glu Glu Ser
        35                  40                  45

Leu Lys Pro Val Arg Pro His Asp Leu Gly Lys Lys Glu Gly Gln Lys
    50                  55                  60

Gly Asp Gly Leu Arg Ala His Ala Pro Leu Ala Ala Thr Ser Gln Pro
65                  70                  75                  80

Gly Arg Lys Glu Val Gly Leu Lys Pro Gln His Asn His Gln Asn Asn
                85                  90                  95

His Asp Phe Asn Leu Ser Pro Leu Ala Glu Gly Ala Thr Asn Arg Ala
            100                 105                 110

His Leu Tyr Gln Gln Asp Ser Arg Phe Asp Asp Arg Val Glu Ser Ile
        115                 120                 125

Ile Asn Ala Leu Met Pro Leu Ala Pro Phe Leu Glu Gly Val Thr Cys
    130                 135                 140

Glu Thr Gly Thr Ser Ser Glu Ser Pro Cys Glu Pro Ser Gly His Asp
145                 150                 155                 160

Glu Leu Phe Val Gln Gln Ser Pro Ile Asp Ser Ala Gln Pro Val Gln
                165                 170                 175

Leu Asn Ser Lys Pro Thr Val Gln Pro Leu Asn Pro Ala Ala Asp Gly
            180                 185                 190
```

Ala Glu Val Ile Val Trp Ser Val Gly Arg Glu Thr Pro Ala Ser Ile
            195                 200                 205

Ala Lys Asn Gln Arg Asp Ser Arg Gln Lys Arg Leu Ala Glu Glu Pro
    210                 215                 220

Leu Ala Leu His Gln Lys Ala Leu Pro Glu Ile Cys Pro Pro Ala Val
225                 230                 235                 240

Ser Ala Thr Pro Asp Asp His Leu Val Ala Arg Trp Cys Ala Thr Pro
                245                 250                 255

Val Thr Glu Val Ala Glu Lys Ser Ala Arg Phe Pro Tyr Lys Ala Thr
            260                 265                 270

Val Gln Ser Glu Gln Leu Asp Met Thr Glu Leu Ala Asp Arg Ser Gln
    275                 280                 285

His Leu Thr Asp Gly Val Asp Ser Ser Lys Asp Thr Ile Glu Pro Pro
290                 295                 300

Arg Pro Glu Lys Leu Leu Leu Pro Arg Glu Glu Thr Leu Pro Glu Met
305                 310                 315                 320

Tyr Ser Leu Ser Phe Thr Ala Pro Val Val Thr Pro Gly Asp His Leu
                325                 330                 335

Leu Ala Thr Met Arg Ala Thr Arg Leu Ala Ser Val Ser Glu Gln Leu
            340                 345                 350

Ile Gln Leu Ala Gln Arg Leu Ala Val Glu Leu Glu Leu Arg Gly Gly
    355                 360                 365

Ser Ser Gln Val Thr Gln Leu His Leu Asn Leu Pro Glu Leu Gly Ala
370                 375                 380

Ile Met Val Arg Ile Ala Glu Ile Pro Gly Lys Leu His Val Glu Leu
385                 390                 395                 400

Ile Ala Ser Arg Glu Ala Leu Arg Ile Leu Ala Gln Gly Ser Tyr Asp
                405                 410                 415

Leu Leu Glu Arg Leu Gln Arg Ile Glu Pro Thr Gln Leu Asp Phe Gln
            420                 425                 430

Ala Ser Asp Asp Ser Glu Gln Glu Ser Arg Gln Lys Arg His Val Tyr
    435                 440                 445

Glu Glu Trp Glu Ala Glu Glu
    450                 455

<210> SEQ ID NO 9
<211> LENGTH: 417
<212> TYPE: DNA
<213> ORGANISM: Escherichia coli

<400> SEQUENCE: 9
ttaattttca tattcaattg tgaactcaat ggcttcatca ggaaagattt cttttaactt     60
atcgaaaaca tagtcttttt tatgatataa aaaaacatga tttctattat ttgggcttac    120
tttaatagac agataaatga ttccgttact acatttaatt gttaaaacaa ttcctcgtaa    180
tcttccacaa agaatactaa acgagtgctc cccttcttca agtagcgtcg tcttcggcc     240 cgaggagtaa aacaatctct tccataaaga agccattcgt atgaacaacg tatcaggcga    300
tctttttttt atatgataaa aaatatcatt aaaactttct tctccttgcg gccaatcatc    360
tgatggccga aaagaaacag gctctatcaa atttcttttt agagaaactc tagtcaa       417

<210> SEQ ID NO 10
<211> LENGTH: 138
<212> TYPE: PRT
<213> ORGANISM: Unknown
<220> FEATURE:

<223> OTHER INFORMATION: Description of Unknown:
    Enterobacteriaceae sequence

<400> SEQUENCE: 10

Met Thr Arg Val Ser Leu Lys Arg Asn Leu Ile Glu Pro Val Ser Phe
1               5                   10                  15

Arg Pro Ser Asp Asp Trp Pro Gln Gly Glu Ser Phe Asn Asp Ile
            20                  25                  30

Phe Tyr His Ile Lys Lys Arg Ser Pro Asp Thr Leu Phe Ile Arg Met
        35                  40                  45

Ala Ser Leu Trp Lys Arg Leu Phe Tyr Ser Ser Gly Arg Arg Arg
    50                  55                  60

Tyr Phe Glu Glu Gly Glu His Ser Phe Ser Ile Leu Cys Gly Arg Leu
65                  70                  75                  80

Arg Gly Ile Val Leu Thr Ile Lys Cys Ser Asn Gly Ile Ile Tyr Leu
                85                  90                  95

Ser Ile Lys Val Ser Pro Asn Asn Arg Asn His Val Phe Leu Tyr His
                100                 105                 110

Lys Lys Asp Tyr Val Phe Asp Lys Leu Lys Glu Ile Phe Pro Asp Glu
            115                 120                 125

Ala Ile Glu Phe Thr Ile Glu Tyr Glu Asn
        130                 135

<210> SEQ ID NO 11
<211> LENGTH: 1341
<212> TYPE: DNA
<213> ORGANISM: Escherichia coli

<400> SEQUENCE: 11
tcaggcaacc actttgaata ggctttcaat cgttttttcg taactactga tatctttggt       60
gctttgttgt ataaagttct gaattaattt cctatttttt attgccttat ctgcttcagg      120
atcttgcccc atcgtgtact caccaatacg aataagcagc tcaacatttt tataagttgc      180
aataagcttt ttgcattctg ccgccgcacg caaatgctcc gatgtaacaa cgttatgcat      240
aacacgactg gcacttaaac caatatcaat tgcagggaaa tggttttcct ctgcaagttc      300
tcgggtaagt acgatgtgcc catcaagaat agagcggact tcatcgccaa taggatcatt      360
aacattatcg ctttctaaca acaccgtata aatcgcggtt attgaacctt ttggcgcagg      420
ccccgctcgc tctaataatt tgggtaacga agaaaaaaca ctcggaggga atccccccct      480
tacatcaggt tctcccgatg caagcccaac atcacgtgcg gctcgggcat aacgagttac      540
agaatccatc attaataata cattttttacc ttgatcgcgg aagtactctg caatagtcgt      600
cgccgtaaat gcggctttca tccttttccag cgcggggcgg tctgacgttg tgacgaccag      660
tacacattta gaaagcgtgg attgaggtaa gagcgcgagg aattcattta cttcgcgacc      720
acgttcgccg ataagagcaa ggacaataat atctgcggat gcgccattac aaatcatccc      780
caaaagcgta ctttaccaa cgcctgaacc agcaaaaata ccgatacgct gcccaatacc      840
gcaagttagt agcccatcaa ttgccctgac gccaagtata aatggctgat caataacctg      900
ccttaataaa ggatctggtg gttcagcata caagctgcgt tcaaacggaa gataggggc      960
agcaatatta ctctccattg gtctgcctat gccatcaaca agccgcccaa gtagtgcgtc     1020
tccaacacga atcttgaact catctccctg ataacttaac cactgaccac agtcacatgcc     1080
ggaaacatgc tcaaaaggca acaagaaaac ctcatcttca tcaatagcga tcacctcggc     1140
taaacgttga ctgggttcta tcttataaaa ggcgccaata cgcgcttttg gtaaacgcgc     1200

```
cttaataatc gtcccgccga tattgataat cttgccttca tatctggtag acgaatttaa   1260
tgataatgcc ggcacagtgc tattgagcac tttctgaata cgtgggtatt tttccaatac   1320
agaatcatgc tctgaaatca t                                             1341
```

<210> SEQ ID NO 12
<211> LENGTH: 446
<212> TYPE: PRT
<213> ORGANISM: Unknown
<220> FEATURE:
<223> OTHER INFORMATION: Description of Unknown:
      Enterobacteriaceae sequence

<400> SEQUENCE: 12

```
Met Ile Ser Glu His Asp Ser Val Leu Glu Lys Tyr Pro Arg Ile Gln
1               5                   10                  15

Lys Val Leu Asn Ser Thr Val Pro Ala Leu Ser Leu Asn Ser Ser Thr
            20                  25                  30

Arg Tyr Glu Gly Lys Ile Ile Asn Ile Gly Gly Thr Ile Ile Lys Ala
        35                  40                  45

Arg Leu Pro Lys Ala Arg Ile Gly Ala Phe Tyr Lys Ile Glu Pro Ser
    50                  55                  60

Gln Arg Leu Ala Glu Val Ile Ala Ile Asp Glu Asp Glu Val Phe Leu
65                  70                  75                  80

Leu Pro Phe Glu His Val Ser Gly Met Tyr Cys Gly Gln Trp Leu Ser
                85                  90                  95

Tyr Gln Gly Asp Glu Phe Lys Ile Arg Val Gly Asp Ala Leu Leu Gly
            100                 105                 110

Arg Leu Val Asp Gly Ile Gly Arg Pro Met Glu Ser Asn Ile Ala Ala
        115                 120                 125

Pro Tyr Leu Pro Phe Glu Arg Ser Leu Tyr Ala Glu Pro Pro Asp Pro
    130                 135                 140

Leu Leu Arg Gln Val Ile Asp Gln Pro Phe Ile Leu Gly Val Arg Ala
145                 150                 155                 160

Ile Asp Gly Leu Leu Thr Cys Gly Ile Gly Gln Arg Ile Gly Ile Phe
                165                 170                 175

Ala Gly Ser Gly Val Gly Lys Ser Thr Leu Leu Gly Met Ile Cys Asn
            180                 185                 190

Gly Ala Ser Ala Asp Ile Ile Val Leu Ala Leu Ile Gly Glu Arg Gly
        195                 200                 205

Arg Glu Val Asn Glu Phe Leu Ala Leu Leu Pro Gln Ser Thr Leu Ser
    210                 215                 220

Lys Cys Val Leu Val Val Thr Thr Ser Asp Arg Pro Ala Leu Glu Arg
225                 230                 235                 240

Met Lys Ala Ala Phe Thr Ala Thr Thr Ile Ala Glu Tyr Phe Arg Asp
                245                 250                 255

Gln Gly Lys Asn Val Leu Leu Met Met Asp Ser Val Thr Arg Tyr Ala
            260                 265                 270

Arg Ala Ala Arg Asp Val Gly Leu Ala Ser Gly Glu Pro Asp Val Arg
        275                 280                 285

Gly Gly Phe Pro Pro Ser Val Phe Ser Ser Leu Pro Lys Leu Leu Glu
    290                 295                 300

Arg Ala Gly Pro Ala Pro Lys Gly Ser Ile Thr Ala Ile Tyr Thr Val
305                 310                 315                 320

Leu Leu Glu Ser Asp Asn Val Asn Asp Pro Ile Gly Asp Glu Val Arg
```

```
                325                 330                 335
Ser Ile Leu Asp Gly His Ile Val Leu Thr Arg Glu Leu Ala Glu Glu
            340                 345                 350

Asn His Phe Pro Ala Ile Asp Ile Gly Leu Ser Ala Ser Arg Val Met
            355                 360                 365

His Asn Val Val Thr Ser Glu His Leu Arg Ala Ala Ala Glu Cys Lys
        370                 375                 380

Lys Leu Ile Ala Thr Tyr Lys Asn Val Glu Leu Leu Ile Arg Ile Gly
385                 390                 395                 400

Glu Tyr Thr Met Gly Gln Asp Pro Glu Ala Asp Lys Ala Ile Lys Asn
                405                 410                 415

Arg Lys Leu Ile Gln Asn Phe Ile Gln Gln Ser Thr Lys Asp Ile Ser
            420                 425                 430

Ser Tyr Glu Lys Thr Ile Glu Ser Leu Phe Lys Val Val Ala
            435                 440                 445

<210> SEQ ID NO 13
<211> LENGTH: 507
<212> TYPE: DNA
<213> ORGANISM: Yersinia pestis

<400> SEQUENCE: 13
atgcaacaag agacgacaga cactcaagaa taccagctgg caatggaatc cttcctaaaa      60
ggagggggaa ctatcgccat gctcaacgaa atttcaagtg cactttaga gcaactctac     120 tctcttgcat ttaaccaata ccagtcagga aaatacgagg atgctcacaa ggtctttcaa     180
gctctctgtg tgctagacca ctatgattca cgtttctttt tagggctagg cgcttgtcgt     240
caagccatgg gcaatacga cttagcgatt catagctaca gctatggcgc cataatggat     300
ataaaagaac ctcgttttcc gtttcatgcg ccgaatgtt tactgcaaaa gggagagctt     360
gctgaagcag aaagtggctt gttcttggct caagagctta tcgcagacaa aactgagttt     420
aaggagcttt ccacccgagt tagctcaatg ttagaagcaa ttaaattgaa aaaggagatg     480
gaacatgagt gcgttgataa cccatga                                         507

<210> SEQ ID NO 14
<211> LENGTH: 168
<212> TYPE: PRT
<213> ORGANISM: Yersinia pseudotuberculosis

<400> SEQUENCE: 14

Met Gln Gln Glu Thr Thr Asp Thr Gln Glu Tyr Gln Leu Ala Met Glu
1               5                   10                  15

Ser Phe Leu Lys Gly Gly Gly Thr Ile Ala Met Leu Asn Glu Ile Ser
            20                  25                  30

Ser Asp Thr Leu Glu Gln Leu Tyr Ser Leu Ala Phe Asn Gln Tyr Gln
        35                  40                  45

Ser Gly Lys Tyr Glu Asp Ala His Lys Val Phe Gln Ala Leu Cys Val
    50                  55                  60

Leu Asp His Tyr Asp Ser Arg Phe Phe Leu Gly Leu Gly Ala Cys Arg
65                  70                  75                  80

Gln Ala Met Gly Gln Tyr Asp Leu Ala Ile His Ser Tyr Ser Tyr Gly
                85                  90                  95

Ala Ile Met Asp Ile Lys Glu Pro Arg Phe Pro Phe His Ala Ala Glu
            100                 105                 110

Cys Leu Leu Gln Lys Gly Glu Leu Ala Glu Ala Glu Ser Gly Leu Phe
```

```
            115                 120                 125
Leu Ala Gln Glu Leu Ile Ala Asp Lys Thr Glu Phe Lys Glu Leu Ser
        130                 135                 140

Thr Arg Val Ser Ser Met Leu Glu Ala Ile Lys Leu Lys Lys Glu Met
145                 150                 155                 160

Glu His Glu Cys Val Asp Asn Pro
                165
```

<210> SEQ ID NO 15
<211> LENGTH: 882
<212> TYPE: DNA
<213> ORGANISM: Yersinia pestis

<400> SEQUENCE: 15

```
atgacgacgc ttcataacct atcttatggc aatacccgc tgcataatga gcgtccagag      60
attgccagta gtcagatcgt aaatcagact ctgggtcaat ttcggggaga atctgtgcag    120
atagtcagcg gcactctgca gtctatagct gatatggcag aagaggtaac atttgtcttc    180
tccgagcgta aggagttctc cctcgacaaa cgcaaattaa gtgacagcca ggctcgagtt    240
agcgacgttg aggagcaggt taatcaatac cttagcaaag ttccagagtt ggaacaaaaa    300
cagaatgtga gtgagctgct cagtctgttg agtaacagcc ccaatataag cttgtcccag    360
ttaaaggctt atctggaggg gaaatcagaa gaaccgagtg agcaattcaa atgctctgc     420
ggcttgcgtg atgccctgaa agggcgccct gaattagcac atctttcgca tttggttgaa    480
caagctctgg tcagcatggc tgaagagcaa ggagaaacca ttgtattggg tgccaggata    540
accccggaag cgtacagaga atcccagtcg ggtgttaatc cactgcagcc gctccgtgat    600
acctaccgcg atgcagtgat gggttatcaa ggaatttatg cgatctggag tgatttacaa    660
aaacgttttc ctaatgggga tatagactcg gtgatattat tcctgcaaaa ggcgcttagt    720
gcagatctac aaagtcaaca aagcgggtct ggacgggaaa aattaggaat agttattagt    780
gacttacaga agctaaagga gtttggtagc gtgagtgacc aagttaaagg attttggcaa    840
ttttttttcag agggtaaaac taatggcgta cgacctttct ga                      882
```

<210> SEQ ID NO 16
<211> LENGTH: 293
<212> TYPE: PRT
<213> ORGANISM: Yersinia pestis

<400> SEQUENCE: 16

```
Met Thr Thr Leu His Asn Leu Ser Tyr Gly Asn Thr Pro Leu His Asn
1               5                   10                  15

Glu Arg Pro Glu Ile Ala Ser Ser Gln Ile Val Asn Gln Thr Leu Gly
            20                  25                  30

Gln Phe Arg Gly Glu Ser Val Gln Ile Val Ser Gly Thr Leu Gln Ser
        35                  40                  45

Ile Ala Asp Met Ala Glu Glu Val Thr Phe Val Phe Ser Glu Arg Lys
    50                  55                  60

Glu Phe Ser Leu Asp Lys Arg Lys Leu Ser Asp Ser Gln Ala Arg Val
65                  70                  75                  80

Ser Asp Val Glu Glu Gln Val Asn Gln Tyr Leu Ser Lys Val Pro Glu
                85                  90                  95

Leu Glu Gln Lys Gln Asn Val Ser Glu Leu Leu Ser Leu Leu Ser Asn
            100                 105                 110

Ser Pro Asn Ile Ser Leu Ser Gln Leu Lys Ala Tyr Leu Glu Gly Lys
```

```
            115                 120                 125
Ser Glu Glu Pro Ser Glu Gln Phe Lys Met Leu Cys Gly Leu Arg Asp
    130                 135                 140

Ala Leu Lys Gly Arg Pro Glu Leu Ala His Leu Ser His Leu Val Glu
145                 150                 155                 160

Gln Ala Leu Val Ser Met Ala Glu Glu Gln Gly Glu Thr Ile Val Leu
                165                 170                 175

Gly Ala Arg Ile Thr Pro Glu Ala Tyr Arg Glu Ser Gln Ser Gly Val
            180                 185                 190

Asn Pro Leu Gln Pro Leu Arg Asp Thr Tyr Arg Asp Ala Val Met Gly
        195                 200                 205

Tyr Gln Gly Ile Tyr Ala Ile Trp Ser Asp Leu Gln Lys Arg Phe Pro
    210                 215                 220

Asn Gly Asp Ile Asp Ser Val Ile Leu Phe Leu Gln Lys Ala Leu Ser
225                 230                 235                 240

Ala Asp Leu Gln Ser Gln Gln Ser Gly Ser Gly Arg Glu Lys Leu Gly
                245                 250                 255

Ile Val Ile Ser Asp Leu Gln Lys Leu Lys Glu Phe Gly Ser Val Ser
            260                 265                 270

Asp Gln Val Lys Gly Phe Trp Gln Phe Phe Ser Glu Gly Lys Thr Asn
        275                 280                 285

Gly Val Arg Pro Phe
    290
```

<210> SEQ ID NO 17
<211> LENGTH: 1056
<212> TYPE: DNA
<213> ORGANISM: Escherichia coli

<400> SEQUENCE: 17

```
tcaaataatt tcctccttat agtcgataac tttaccaatc attaataatg cattctctct    60
ctgctcacta tcaataaagc aagcatctgg taatgatgta aaaagtctt tcaataaatg    120
aaaataataa atatgtttat cttcgacaat cgatacccga aaggactct ccagcaacca    180
gtcttctgtt agccagacat gttcaataat cgataacact tcatttaaaa tgatatcttt    240
atctttctta atagagatcg aaataatatc tgcatagtta tcaagtgata aaaaaatgat    300
taccctgcat aaatcactaa taattgaaga tgtctttact ttgtcttcaa agaagacat    360
ataagagaga tcgaacgaca gcgccctaat aatgactttt aagtgcttct cacgctcggg    420
aagatcctta atctccataa accagtcaag taaagaggcg ccattttcag aatcctcatc    480
cttagccttt tcataaagct tcttgatctt ctggatacct tcctgattta actcacccac    540
ccctaaccag gaaagcagag ccagctccca atcatcttcg cctaataaat ctaataataa    600
cctggcatat ttcttttta attcaatctt aacaaactta gattgcaata agaagatat    660
tagcgcaaca atttccccct ttggcatgtt gccaaacatc gccaaagtag gatcgtgttg    720
ttccagcagc ccgctgtttt taatgatag ttctttatt ttatcactat cggtaagagt    780
aagcagctct tgcatatcat tgagcagctt ctcgattgtc gagccttcct cttctttcct    840
tgcgctacct ttgcgatatc ccaggcttag cccttcaatc gtttcagaaa gcatgaact    900
agtaatcatt gctaattcat tttgcaaatt tattaatggc gaagaaatat agaagaatt    960
tttttgcgtt aattgctgag attctaattc aaaatctaat gaattagaat taaaaacaga    1020
tgcggggttt tgattaaatt caataccatt agccat                             1056
```

<210> SEQ ID NO 18
<211> LENGTH: 351
<212> TYPE: PRT
<213> ORGANISM: Escherichia coli

<400> SEQUENCE: 18

Met Ala Asn Gly Ile Glu Phe Asn Gln Asn Pro Ala Ser Val Phe Asn
1               5                   10                  15

Ser Asn Ser Leu Asp Phe Glu Leu Glu Ser Gln Gln Leu Thr Gln Lys
            20                  25                  30

Asn Ser Ser Asn Ile Ser Ser Pro Leu Ile Asn Leu Gln Asn Glu Leu
        35                  40                  45

Ala Met Ile Thr Ser Ser Leu Ser Glu Thr Ile Glu Gly Leu Ser
50                  55                  60

Leu Gly Tyr Arg Lys Gly Ser Ala Arg Lys Glu Glu Gly Ser Thr
65                  70                  75                  80

Ile Glu Lys Leu Leu Asn Asp Met Gln Glu Leu Leu Thr Leu Thr Asp
            85                  90                  95

Ser Asp Lys Ile Lys Glu Leu Ser Leu Lys Asn Ser Gly Leu Leu Glu
            100                 105                 110

Gln His Asp Pro Thr Leu Ala Met Phe Gly Asn Met Pro Lys Gly Glu
        115                 120                 125

Ile Val Ala Leu Ile Ser Ser Leu Leu Gln Ser Lys Phe Val Lys Ile
130                 135                 140

Glu Leu Lys Lys Lys Tyr Ala Arg Leu Leu Asp Leu Leu Gly Glu
145                 150                 155                 160

Asp Asp Trp Glu Leu Ala Leu Leu Ser Trp Leu Gly Val Gly Glu Leu
            165                 170                 175

Asn Gln Glu Gly Ile Gln Lys Ile Lys Lys Leu Tyr Glu Lys Ala Lys
        180                 185                 190

Asp Glu Asp Ser Glu Asn Gly Ala Ser Leu Leu Asp Trp Phe Met Glu
        195                 200                 205

Ile Lys Asp Leu Pro Glu Arg Glu Lys His Leu Lys Val Ile Ile Arg
210                 215                 220

Ala Leu Ser Phe Asp Leu Ser Tyr Met Ser Ser Phe Glu Asp Lys Val
225                 230                 235                 240

Lys Thr Ser Ser Ile Ile Ser Asp Leu Cys Arg Val Ile Ile Phe Leu
            245                 250                 255

Ser Leu Asp Asn Tyr Ala Asp Ile Ile Ser Ile Ser Ile Lys Lys Asp
        260                 265                 270

Lys Asp Ile Ile Leu Asn Glu Val Leu Ser Ile Glu His Val Trp
        275                 280                 285

Leu Thr Glu Asp Trp Leu Leu Glu Ser Pro Ser Arg Val Ser Ile Val
290                 295                 300

Glu Asp Lys His Ile Tyr Tyr Phe His Leu Leu Lys Asp Phe Phe Thr
305                 310                 315                 320

Ser Leu Pro Asp Ala Cys Phe Ile Asp Ser Glu Gln Arg Glu Asn Ala
            325                 330                 335

Leu Leu Met Ile Gly Lys Val Ile Asp Tyr Lys Glu Glu Ile Ile
            340                 345                 350

<210> SEQ ID NO 19
<211> LENGTH: 252
<212> TYPE: DNA
<213> ORGANISM: Shigella flexneri

<400> SEQUENCE: 19

```
atgagtgtta cagtaccgaa tgatgattgg acattgagtt cattatctga aactttttgat    60
gatggaactc aaacattaca aggtgaacta acattggcac tagataaatt agctaaaaat   120
ccttcgaatc cacagttgct ggctgaatac caaagtaaat tatctgaata tacattatat   180
aggaacgcgc aatccaatac agtgaaagtg attaaggatg ttgatgctgc aattattcaa   240
aacttcagat aa                                                       252
```

<210> SEQ ID NO 20
<211> LENGTH: 83
<212> TYPE: PRT
<213> ORGANISM: Shigella flexneri

<400> SEQUENCE: 20

```
Met Ser Val Thr Val Pro Asn Asp Asp Trp Thr Leu Ser Ser Leu Ser
1               5                   10                  15

Glu Thr Phe Asp Asp Gly Thr Gln Thr Leu Gln Gly Glu Leu Thr Leu
            20                  25                  30

Ala Leu Asp Lys Leu Ala Lys Asn Pro Ser Asn Pro Gln Leu Leu Ala
        35                  40                  45

Glu Tyr Gln Ser Lys Leu Ser Glu Tyr Thr Leu Tyr Arg Asn Ala Gln
    50                  55                  60

Ser Asn Thr Val Lys Val Ile Lys Asp Val Asp Ala Ala Ile Ile Gln
65                  70                  75                  80

Asn Phe Arg
```

<210> SEQ ID NO 21
<211> LENGTH: 250
<212> TYPE: DNA
<213> ORGANISM: Salmonella enterica

<400> SEQUENCE: 21

```
agtcattatg caacaccctt ggtcaggcta tctggatgac gtctcagcaa aatttgatac    60
gggcgttgat aatctacaaa cgcaggtaac agaggcgctg ataaattag cagcaaaacc   120
ctccgatccg gcgctactgg cggcgtatca gagtaagctc tcggaatata acttgtaccg   180
taacgcgcaa tcgaacacgg taaaagtctt taaggatatt gatgctgcca ttattcagaa   240
cttccgttaa                                                         250
```

<210> SEQ ID NO 22
<211> LENGTH: 80
<212> TYPE: PRT
<213> ORGANISM: Salmonella enterica

<400> SEQUENCE: 22

```
Met Ala Thr Pro Trp Ser Gly Tyr Leu Asp Asp Val Ser Ala Lys Phe
1               5                   10                  15

Asp Thr Gly Val Asp Asn Leu Gln Thr Gln Val Thr Glu Ala Leu Asp
            20                  25                  30

Lys Leu Ala Ala Lys Pro Ser Asp Pro Ala Leu Leu Ala Ala Tyr Gln
        35                  40                  45

Ser Lys Leu Ser Glu Tyr Asn Leu Tyr Arg Asn Ala Gln Ser Asn Thr
    50                  55                  60

Val Lys Val Phe Lys Asp Ile Asp Ala Ala Ile Ile Gln Asn Phe Arg
65                  70                  75                  80
```

```
<210> SEQ ID NO 23
<211> LENGTH: 264
<212> TYPE: DNA
<213> ORGANISM: Yersinia pestis

<400> SEQUENCE: 23
atgagtaact tctctggatt tacgaaagga accgatatcg cagacttaga tgcggtggct     60
caaacgctca agaagccagc agacgatgca aacaaagcgg ttaatgactc gatagcagca    120
ttgaaagata agcctgacaa cccggcgcta cttgctgact tacaacattc aattaataaa    180
tggtcggtaa tttacaatat aaactcaacc atagttcgta gcatgaaaga cttaatgcaa    240
ggcatcctac agaagttccc ataa                                           264

<210> SEQ ID NO 24
<211> LENGTH: 87
<212> TYPE: PRT
<213> ORGANISM: Yersinia pestis

<400> SEQUENCE: 24

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85

<210> SEQ ID NO 25
<211> LENGTH: 222
<212> TYPE: DNA
<213> ORGANISM: Escherichia coli

<400> SEQUENCE: 25
atgaatttat ctgaaattac tcaacaaatg ggtgaagtag gtaaaacgct gagcgattct     60
gtgccagagt tacttaatag caccgatttg gttaatgacc ctgaaaaaat gttagagttg    120
cagtttgcgg ttcagcaata ttctgcttat gttaacgtag aaagtggaat gttgaaaacg    180
ataaaagatc tggtctcaac catttctaac cgtagttttt aa                       222

<210> SEQ ID NO 26
<211> LENGTH: 73
<212> TYPE: PRT
<213> ORGANISM: Escherichia coli

<400> SEQUENCE: 26

Met Asn Leu Ser Glu Ile Thr Gln Gln Met Gly Glu Val Gly Lys Thr
1               5                   10                  15

Leu Ser Asp Ser Val Pro Glu Leu Leu Asn Ser Thr Asp Leu Val Asn
            20                  25                  30

Asp Pro Glu Lys Met Leu Glu Leu Gln Phe Ala Val Gln Gln Tyr Ser
        35                  40                  45

Ala Tyr Val Asn Val Glu Ser Gly Met Leu Lys Thr Ile Lys Asp Leu
    50                  55                  60
```

Val Ser Thr Ile Ser Asn Arg Ser Phe
65                  70

<210> SEQ ID NO 27
<211> LENGTH: 294
<212> TYPE: DNA
<213> ORGANISM: Shigella flexneri

<400> SEQUENCE: 27
atgaattaca tttatccagt caatcaggtt gatattatca aagccagtga ttttcaatct     60
caagagatat caagtctgga agacgtcgtg tcggctaaat atagtgatat taagatggat    120
acagatattc aagtatcaca ataatggag atggtaagca atccagaatc attaaaccca    180
gaatctttgg ccaagttaca gacgacgctc tcaaattatt caataggagt atcattagct    240
ggcacgttag caagaaaaac agtttcggct gttgaaactt tattaaagtc ttaa          294

<210> SEQ ID NO 28
<211> LENGTH: 97
<212> TYPE: PRT
<213> ORGANISM: Shigella flexneri

<400> SEQUENCE: 28

Met Asn Tyr Ile Tyr Pro Val Asn Gln Val Asp Ile Ile Lys Ala Ser
1               5                   10                  15

Asp Phe Gln Ser Gln Glu Ile Ser Ser Leu Glu Asp Val Val Ser Ala
            20                  25                  30

Lys Tyr Ser Asp Ile Lys Met Asp Thr Asp Ile Gln Val Ser Gln Ile
        35                  40                  45

Met Glu Met Val Ser Asn Pro Glu Ser Leu Asn Pro Glu Ser Leu Ala
    50                  55                  60

Lys Leu Gln Thr Thr Leu Ser Asn Tyr Ser Ile Gly Val Ser Leu Ala
65                  70                  75                  80

Gly Thr Leu Ala Arg Lys Thr Val Ser Ala Val Glu Thr Leu Leu Lys
                85                  90                  95

Ser

<210> SEQ ID NO 29
<211> LENGTH: 312
<212> TYPE: DNA
<213> ORGANISM: Salmonella enterica

<400> SEQUENCE: 29
tggattatgt cgattgcaac tattgtccct gagaatgccg ttatagggca ggcggtcaat     60
atcaggtcta tggaaacgga cattgtctcg ctggatgacc ggctactcca ggcttttct    120 ggttcggcga ttgccacggc tgtggataaa cagacgatta ccaacaggat tgaggaccct    180
aatctggtga cggatcctaa agagctggct atttcgcaag atgatttca agattataac    240 ctgtatgttt ctatggtcag tacccttact cgtaaaggag tcggggctgt tgaaacgcta    300
ttacgctcat ga                                                        312

<210> SEQ ID NO 30
<211> LENGTH: 101
<212> TYPE: PRT
<213> ORGANISM: Salmonella enterica

<400> SEQUENCE: 30

Met Ser Ile Ala Thr Ile Val Pro Glu Asn Ala Val Ile Gly Gln Ala

-continued

```
1               5                   10                  15

Val Asn Ile Arg Ser Met Glu Thr Asp Ile Val Ser Leu Asp Asp Arg
            20                  25                  30

Leu Leu Gln Ala Phe Ser Gly Ser Ala Ile Ala Thr Ala Val Asp Lys
        35                  40                  45

Gln Thr Ile Thr Asn Arg Ile Glu Asp Pro Asn Leu Val Thr Asp Pro
    50                  55                  60

Lys Glu Leu Ala Ile Ser Gln Glu Met Ile Ser Asp Tyr Asn Leu Tyr
65                  70                  75                  80

Val Ser Met Val Ser Thr Leu Thr Arg Lys Gly Val Gly Ala Val Glu
                85                  90                  95

Thr Leu Leu Arg Ser
            100

<210> SEQ ID NO 31
<211> LENGTH: 348
<212> TYPE: DNA
<213> ORGANISM: Yersinia pestis

<400> SEQUENCE: 31
atgccgaaca tagaaatagc tcaggccgat gaggtgatca taaccacgct ggaggaatta     60
gggccggcag agccaacaac tgaccaaata atgcgctttg atgcggcaat gtcagaagat    120
acgcagggac tgggccattc actcctcaag gaggttagtg atattcagaa gtcttttaag    180
acggttaaaa gtgacttaca cactaagctg gctgtttcag ttgataatcc caacgacctg    240
atgctaatgc aatggtcact tatccgtata acaatccaag aagaacttat cgccaagact    300
gccgggcgaa tgagccaaaa tgttgaaacc ttgtcgaagg gggggtga                 348

<210> SEQ ID NO 32
<211> LENGTH: 115
<212> TYPE: PRT
<213> ORGANISM: Yersinia pestis

<400> SEQUENCE: 32

Met Pro Asn Ile Glu Ile Ala Gln Ala Asp Glu Val Ile Ile Thr Thr
1               5                   10                  15

Leu Glu Glu Leu Gly Pro Ala Glu Pro Thr Thr Asp Gln Ile Met Arg
            20                  25                  30

Phe Asp Ala Ala Met Ser Glu Asp Thr Gln Gly Leu Gly His Ser Leu
        35                  40                  45

Leu Lys Glu Val Ser Asp Ile Gln Lys Ser Phe Lys Thr Val Lys Ser
    50                  55                  60

Asp Leu His Thr Lys Leu Ala Val Ser Val Asp Asn Pro Asn Asp Leu
65                  70                  75                  80

Met Leu Met Gln Trp Ser Leu Ile Arg Ile Thr Ile Gln Glu Glu Leu
                85                  90                  95

Ile Ala Lys Thr Ala Gly Arg Met Ser Gln Asn Val Glu Thr Leu Ser
            100                 105                 110

Lys Gly Gly
        115

<210> SEQ ID NO 33
<211> LENGTH: 429
<212> TYPE: DNA
<213> ORGANISM: Escherichia coli

<400> SEQUENCE: 33
```

```
atggatgtat tatgcccttg cctctttcat aaaaagaggc taacagtaaa tatgaacaac      60
attaatcaat cggaaaacat taatattcaa ttaaataaag cgccccaaac aaatttcgtt     120
gatgagcata cctcgttagc ctcagccccc tctgcggcag gtgcggctca gtttcttgat     180
caattactcc ctaaaacagc gggagtgtct tctccagaac aagtgttgat tgaagaaatt     240
aaaaagagac atcttgcaac aatgaacagc gatctcagtt tcgatgctct atctgcaggt     300
gggctctcgc cagaagacgt gctcaccttg caaaagaatg tgctcaacgc aaacgtcaac     360
gttgatgtcg tatctaagtt agcaagcctc ctttcaacat cggttacaaa attagtttcg     420
atgcaataa                                                             429
```

<210> SEQ ID NO 34
<211> LENGTH: 142
<212> TYPE: PRT
<213> ORGANISM: Escherichia coli

<400> SEQUENCE: 34

```
Met Asp Val Leu Cys Pro Cys Leu Phe His Lys Lys Arg Leu Thr Val
1               5                   10                  15

Asn Met Asn Asn Ile Asn Gln Ser Glu Asn Ile Asn Ile Gln Leu Asn
            20                  25                  30

Lys Ala Pro Gln Thr Asn Phe Val Asp Glu His Thr Ser Leu Ala Ser
        35                  40                  45

Ala Pro Ser Ala Ala Gly Ala Ala Gln Phe Leu Asp Gln Leu Leu Pro
    50                  55                  60

Lys Thr Ala Gly Val Ser Ser Pro Glu Gln Val Leu Ile Glu Glu Ile
65                  70                  75                  80

Lys Lys Arg His Leu Ala Thr Met Asn Ser Asp Leu Ser Phe Asp Ala
                85                  90                  95

Leu Ser Ala Gly Gly Leu Ser Pro Glu Asp Val Leu Thr Leu Gln Lys
            100                 105                 110

Asn Val Leu Asn Ala Asn Val Asn Val Asp Val Val Ser Lys Leu Ala
        115                 120                 125

Ser Leu Leu Ser Thr Ser Val Thr Lys Leu Val Ser Met Gln
    130                 135                 140
```

<210> SEQ ID NO 35
<211> LENGTH: 1149
<212> TYPE: DNA
<213> ORGANISM: Shigella flexneri

<400> SEQUENCE: 35

```
atgttgcaaa agcaattttg caacaaacta ctgcttgata caaataagga gaatgttatg      60
gaaattcaaa acacaaaacc aacccagact ttatatacag atatatccac aaaacaaact     120
caaagttctt ccgaaacaca aaaatcacaa aattatcagc agattgcagc gcatattcca     180
cttaatgtcg gtaaaaatcc cgtattaaca accacattaa atgatgatca acttttaaag     240
ttatcagagc aggttcagca tgattcagaa atcattgctc gccttactga caaaaagatg     300
aaagatcttt cagagatgag tcacacccct actccagaga acactctgga tatttccagt     360
ctttcttcta atgctgtttc tttaattatt agtgtagccg ttctactttc tgctctccgc     420
actgcagaaa ctaaattggg ctctcaattg tcattgattg cgttcgatgc tacaaaatca     480
gctgcagaga acattgttcg gcaaggcctg cagccctat catcaagcat tactggagca     540
gtcacacaag taggtataac gggtatcggt gccaaaaaaa cgcattcagg gattagcgac     600
```

-continued

```
caaaaaggag ccttaagaaa gaaccttgcc actgctcaat ctcttgaaaa agagcttgca    660
ggttctaaat tagggttaaa taaacaaata gatacaaata tcacctcacc acaaactaac    720
tctagcacaa aatttttagg taaaaataaa ctggcgccag ataatatatc cctgtcaact    780
gaacataaaa cttctcttag ttctcccgat atttctttgc aggataaaat tgacacccag    840
agaagaactt acgagctcaa taccctttct gcgcagcaaa aacaaaacat tggccgtgca    900
acaatggaaa catcagccgt tgctggtaat atatccacat caggagggcg ttatgcatct    960
gctcttgaag aagaagaaca actaatcagt caggccagca gtaaacaagc agaggaagca   1020
tcccaagtat ctaaagaagc atcccaagcg acaaatcaat taatacaaaa attattgaat   1080
ataattgaca gcatcaacca atcaaagaat tcggcagcca gtcagattgc tggtaacatt   1140
cgagcttaa                                                           1149
```

<210> SEQ ID NO 36
<211> LENGTH: 382
<212> TYPE: PRT
<213> ORGANISM: Shigella flexneri

<400> SEQUENCE: 36

```
Met Leu Gln Lys Gln Phe Cys Asn Lys Leu Leu Asp Thr Asn Lys
1               5                   10                  15

Glu Asn Val Met Glu Ile Gln Asn Thr Lys Pro Thr Gln Thr Leu Tyr
            20                  25                  30

Thr Asp Ile Ser Thr Lys Gln Thr Gln Ser Ser Glu Thr Gln Lys
        35                  40                  45

Ser Gln Asn Tyr Gln Gln Ile Ala Ala His Ile Pro Leu Asn Val Gly
    50                  55                  60

Lys Asn Pro Val Leu Thr Thr Thr Leu Asn Asp Asp Gln Leu Leu Lys
65                  70                  75                  80

Leu Ser Glu Gln Val Gln His Asp Ser Glu Ile Ile Ala Arg Leu Thr
                85                  90                  95

Asp Lys Lys Met Lys Asp Leu Ser Glu Met Ser His Thr Leu Thr Pro
            100                 105                 110

Glu Asn Thr Leu Asp Ile Ser Ser Leu Ser Ser Asn Ala Val Ser Leu
        115                 120                 125

Ile Ile Ser Val Ala Val Leu Leu Ser Ala Leu Arg Thr Ala Glu Thr
    130                 135                 140

Lys Leu Gly Ser Gln Leu Ser Leu Ile Ala Phe Asp Ala Thr Lys Ser
145                 150                 155                 160

Ala Ala Glu Asn Ile Val Arg Gln Gly Leu Ala Ala Leu Ser Ser Ser
                165                 170                 175

Ile Thr Gly Ala Val Thr Gln Val Gly Ile Thr Gly Ile Gly Ala Lys
            180                 185                 190

Lys Thr His Ser Gly Ile Ser Asp Gln Lys Gly Ala Leu Arg Lys Asn
        195                 200                 205

Leu Ala Thr Ala Gln Ser Leu Glu Lys Glu Leu Ala Gly Ser Lys Leu
    210                 215                 220

Gly Leu Asn Lys Gln Ile Asp Thr Asn Ile Thr Ser Pro Gln Thr Asn
225                 230                 235                 240

Ser Ser Thr Lys Phe Leu Gly Lys Asn Lys Leu Ala Pro Asp Asn Ile
                245                 250                 255

Ser Leu Ser Thr Glu His Lys Thr Ser Leu Ser Ser Pro Asp Ile Ser
            260                 265                 270
```

Leu Gln Asp Lys Ile Asp Thr Gln Arg Arg Thr Tyr Glu Leu Asn Thr
        275                 280                 285

Leu Ser Ala Gln Gln Lys Gln Asn Ile Gly Arg Ala Thr Met Glu Thr
    290                 295                 300

Ser Ala Val Ala Gly Asn Ile Ser Thr Ser Gly Gly Arg Tyr Ala Ser
305                 310                 315                 320

Ala Leu Glu Glu Glu Gln Leu Ile Ser Gln Ala Ser Ser Lys Gln
            325                 330                 335

Ala Glu Glu Ala Ser Gln Val Ser Lys Glu Ala Ser Gln Ala Thr Asn
            340                 345                 350

Gln Leu Ile Gln Lys Leu Leu Asn Ile Ile Asp Ser Ile Asn Gln Ser
        355                 360                 365

Lys Asn Ser Ala Ala Ser Gln Ile Ala Gly Asn Ile Arg Ala
        370                 375                 380

<210> SEQ ID NO 37
<211> LENGTH: 1789
<212> TYPE: DNA
<213> ORGANISM: Salmonella enterica

<400> SEQUENCE: 37

| | | | | | |
|---|---|---|---|---|---|
| aataattatg | gtaaatgacg | caagtagcat | tagccgtagc | ggatataccc | aaaatccgcg | 60 |
| cctcgctgag | gcggcttttg | aaggcgttcg | taagaacacg | gacttttttaa | aagcggcgga | 120 |
| taaagctttt | aaagatgtgg | tggcaacgaa | agcgggcgac | cttaaagccg | gaacaaagtc | 180 |
| cggcgagagc | gctattaata | cggtgggtct | aaagccgcct | acggacgccg | cccgggaaaa | 240 |
| actctccagc | gaagggcaat | tgacattact | gcttggcaag | ttaatgaccc | tactgggcga | 300 |
| tgtttcgctg | tctcaactgg | agtctcgtct | ggcggtatgg | caggcgatga | ttgagtcaca | 360 |
| aaaagagatg | gggattcagg | tatcgaaaga | attccagacg | gctctgggag | aggctcagga | 420 |
| ggcgacggat | ctctatgaag | ccagtatcaa | aaagacggat | accgccaaga | gtgtttatga | 480 |
| cgctgcgacc | aaaaaactga | cgcaggcgca | aaataaattg | caatcgctgg | acccggctga | 540 |
| cccggctat | gcacaagctg | aagccgcggt | agaacaggcc | ggaaaagaag | cgacagaggc | 600 |
| gaaagaggcc | ttagataagg | ccacggatgc | gacggttaaa | gcaggcacag | acgccaaagc | 660 |
| gaaagccgag | aaagcggata | acattctgac | caaattccag | gaacggcta | atgccgcctc | 720 |
| tcagaatcag | gtttcccagg | gtgagcagga | taatctgtca | aatgtcgccc | gcctcactat | 780 |
| gctcatggcc | atgtttattg | agattgtggg | caaaaatacg | gaagaaagcc | tgcaaaacga | 840 |
| tcttgcgctt | ttcaacgcct | tgcaggaagg | gcgtcaggcg | gagatggaaa | agaaatcggc | 900 |
| tgaattccag | gaagagacgc | gcaaagccga | ggaaacgaac | cgcattatgg | gatgtatcgg | 960 |
| gaaagtcctc | ggcgcgctgc | taaccattgt | cagcgttgtg | gccgctgttt | ttaccggtgg | 1020 |
| ggcgagtctg | gcgctggctg | cggtgggact | tgcggtaatg | gtggccgatg | aaattgtgaa | 1080 |
| ggcggcgacg | ggagtgtcgt | ttattcagca | ggcgctaaac | ccgattatgg | agcatgtgct | 1140 |
| gaagccgtta | atggagctga | ttggcaaggc | gattaccaaa | gcgctggaag | gattaggcgt | 1200 |
| cgataagaaa | acggcagaga | tggccggcag | cattgttggt | gcgattgtcg | ccgctattgc | 1260 |
| catggtggcg | gtcattgtgg | tggtcgcagt | tgtcgggaaa | ggcgcggcgg | cgaaactggg | 1320 |
| taacgcgctg | agcaaaatga | tgggcgaaac | gattaagaag | ttggtgccta | acgtgctgaa | 1380 |
| acagttggcg | caaaacggca | gcaaactctt | tacccagggg | atgcaacgta | ttactagcgg | 1440 |
| tctgggtaat | gtgggtagca | agatgggcct | gcaaacgaat | gccttaagta | aagagctggt | 1500 |

```
aggtaatacc ctaaataaag tggcgttggg catggaagtc acgaataccg cagcccagtc   1560
agccggtggt gttgccgagg gcgtatttat taaaaatgcc agcgaggcgc ttgctgattt   1620
tatgctcgcc cgttttgcca tggatcagat tcagcagtgg cttaaacaat ccgtagaaat   1680
atttggtgaa aaccagaagg taacggcgga actgcaaaaa gccatgtctt ctgcggtaca   1740
gcaaaatgcg gatgcttcgc gttttattct gcgccagagt cgcgcataa               1789
```

<210> SEQ ID NO 38
<211> LENGTH: 593
<212> TYPE: PRT
<213> ORGANISM: Salmonella enterica

<400> SEQUENCE: 38

```
Met Val Asn Asp Ala Ser Ser Ile Ser Arg Ser Gly Tyr Thr Gln Asn
1               5                   10                  15

Pro Arg Leu Ala Glu Ala Ala Phe Glu Gly Val Arg Lys Asn Thr Asp
            20                  25                  30

Phe Leu Lys Ala Ala Asp Lys Ala Phe Lys Asp Val Ala Thr Lys
        35                  40                  45

Ala Gly Asp Leu Lys Ala Gly Thr Lys Ser Gly Glu Ser Ala Ile Asn
    50                  55                  60

Thr Val Gly Leu Lys Pro Pro Thr Asp Ala Ala Arg Glu Lys Leu Ser
65                  70                  75                  80

Ser Glu Gly Gln Leu Thr Leu Leu Gly Lys Leu Met Thr Leu Leu
                85                  90                  95

Gly Asp Val Ser Leu Ser Gln Leu Glu Ser Arg Leu Ala Val Trp Gln
            100                 105                 110

Ala Met Ile Glu Ser Gln Lys Glu Met Gly Ile Gln Val Ser Lys Glu
        115                 120                 125

Phe Gln Thr Ala Leu Gly Glu Ala Gln Glu Ala Thr Asp Leu Tyr Glu
    130                 135                 140

Ala Ser Ile Lys Lys Thr Asp Thr Ala Lys Ser Val Tyr Asp Ala Ala
145                 150                 155                 160

Thr Lys Lys Leu Thr Gln Ala Gln Asn Lys Leu Gln Ser Leu Asp Pro
                165                 170                 175

Ala Asp Pro Gly Tyr Ala Gln Ala Glu Ala Val Glu Gln Ala Gly
            180                 185                 190

Lys Glu Ala Thr Glu Ala Lys Glu Ala Leu Asp Lys Ala Thr Asp Ala
        195                 200                 205

Thr Val Lys Ala Gly Thr Asp Ala Lys Ala Lys Ala Glu Lys Ala Asp
    210                 215                 220

Asn Ile Leu Thr Lys Phe Gln Gly Thr Ala Asn Ala Ala Ser Gln Asn
225                 230                 235                 240

Gln Val Ser Gln Gly Glu Gln Asp Asn Leu Ser Asn Val Ala Arg Leu
                245                 250                 255

Thr Met Leu Met Ala Met Phe Ile Glu Ile Val Gly Lys Asn Thr Glu
            260                 265                 270

Glu Ser Leu Gln Asn Asp Leu Ala Leu Phe Asn Ala Leu Gln Glu Gly
        275                 280                 285

Arg Gln Ala Glu Met Glu Lys Lys Ser Ala Glu Phe Gln Glu Glu Thr
    290                 295                 300

Arg Lys Ala Glu Glu Thr Asn Arg Ile Met Gly Cys Ile Gly Lys Val
305                 310                 315                 320
```

```
Leu Gly Ala Leu Leu Thr Ile Val Ser Val Val Ala Ala Val Phe Thr
                325                 330                 335

Gly Gly Ala Ser Leu Ala Leu Ala Ala Val Gly Leu Ala Val Met Val
            340                 345                 350

Ala Asp Glu Ile Val Lys Ala Ala Thr Gly Val Ser Phe Ile Gln Gln
        355                 360                 365

Ala Leu Asn Pro Ile Met Glu His Val Leu Lys Pro Leu Met Glu Leu
    370                 375                 380

Ile Gly Lys Ala Ile Thr Lys Ala Leu Glu Gly Leu Gly Val Asp Lys
385                 390                 395                 400

Lys Thr Ala Glu Met Ala Gly Ser Ile Val Gly Ala Ile Val Ala Ala
                405                 410                 415

Ile Ala Met Val Ala Val Ile Val Val Ala Val Val Gly Lys Gly
            420                 425                 430

Ala Ala Ala Lys Leu Gly Asn Ala Leu Ser Lys Met Met Gly Glu Thr
        435                 440                 445

Ile Lys Lys Leu Val Pro Asn Val Leu Lys Gln Leu Ala Gln Asn Gly
    450                 455                 460

Ser Lys Leu Phe Thr Gln Gly Met Gln Arg Ile Thr Ser Gly Leu Gly
465                 470                 475                 480

Asn Val Gly Ser Lys Met Gly Leu Gln Thr Asn Ala Leu Ser Lys Glu
                485                 490                 495

Leu Val Gly Asn Thr Leu Asn Lys Val Ala Leu Gly Met Glu Val Thr
            500                 505                 510

Asn Thr Ala Ala Gln Ser Ala Gly Gly Val Ala Glu Gly Val Phe Ile
        515                 520                 525

Lys Asn Ala Ser Glu Ala Leu Ala Asp Phe Met Leu Ala Arg Phe Ala
    530                 535                 540

Met Asp Gln Ile Gln Gln Trp Leu Lys Gln Ser Val Glu Ile Phe Gly
545                 550                 555                 560

Glu Asn Gln Lys Val Thr Ala Glu Leu Gln Lys Ala Met Ser Ser Ala
                565                 570                 575

Val Gln Gln Asn Ala Asp Ala Ser Arg Phe Ile Leu Arg Gln Ser Arg
            580                 585                 590

Ala

<210> SEQ ID NO 39
<211> LENGTH: 1235
<212> TYPE: DNA
<213> ORGANISM: Salmonella enterica

<400> SEQUENCE: 39
aaaatatgtt aattagtaat gtgggaataa atcccgccgc ttatttaaat aatcattctg      60
ttgagaatag ttcacagaca gcttcgcaat ccgttagcgc taaagatatt ctgaatagta     120
ttggtattag cagcagtaaa gtcagtgacc tggggttgag tcctacactg agcgcgcctg     180 cgccagggt attaacgcaa accccggaa cgatcacgtc ctttttaaaa gccagtattc      240
aaaataccga catgaatcag gatttgaatg ctctggcaaa taatgtcacg actaaagcga     300
atgaggttgt gcaaacccag ttacgcgagc agcaggcaga agtcggaaag ttttttgata     360
ttagcggaat gtcttccagt gccgttgcgc tgttggctgc cgcgaatacg ttaatgctga     420
cgttgaacca ggctgatagc aaactgtctg gtaagttgtc attagtcagt tttgatgcag     480
ctaaaacgac ggcaagctcc atgatgcgcg aagggatgaa tgcgttgtcc ggtagtattt     540
```

-continued

```
cccagagcgc gcttcagttg gggatcactg gcgtgggcgc caaactggaa tataaggggc    600
tgcagaatga agaggcgcg cttaaacata atgccgcgaa gatcgataaa ctgaccactg    660
aaagccacag tattaaaaac gtgctgaacg ggcagaatag cgtcaaactc ggtgctgaag    720
gcgtcgattc tctgaaatcg ttaaatatga agaaaaccgg taccgatgcg acgaaaaatc    780
ttaatgatgc gacgcttaaa tctaatgccg gaaccagcgc cacggaaagt ctgggtatta    840
aagacagtaa taaacaaatc tcccctgaac atcaggctat tctgtcgaaa cgtcttgagt    900
ctgtcgaatc cgatattcgt cttgagcaga ataccatgga tatgacccga atcgatgcgc    960
gcaagatgca gatgacgggc gatctgatta tgaagaactc ggtcacggtc ggtggtattg    1020
caggggcgtc cgggcagtac gccgctactc aggaacgttc cgagcagcaa attagccagg    1080
tgaataaccg ggttgccagc accgcatcgg acgaagcccg tgaaagttca cgtaaatcga    1140
ccagcctgat tcaggaaatg ctgaaaacaa tggagagcat taaccagtcg aaagcatccg    1200
cactcgctgc tatcgcaggc aatattcgcg cttaa    1235
```

<210> SEQ ID NO 40
<211> LENGTH: 409
<212> TYPE: PRT
<213> ORGANISM: Salmonella enterica

<400> SEQUENCE: 40

```
Met Leu Ile Ser Asn Val Gly Ile Asn Pro Ala Ala Tyr Leu Asn Asn
1               5                   10                  15

His Ser Val Glu Asn Ser Ser Gln Thr Ala Ser Gln Ser Val Ser Ala
            20                  25                  30

Lys Asp Ile Leu Asn Ser Ile Gly Ile Ser Ser Ser Lys Val Ser Asp
        35                  40                  45

Leu Gly Leu Ser Pro Thr Leu Ser Ala Pro Ala Pro Gly Val Leu Thr
    50                  55                  60

Gln Thr Pro Gly Thr Ile Thr Ser Phe Leu Lys Ala Ser Ile Gln Asn
65                  70                  75                  80

Thr Asp Met Asn Gln Asp Leu Asn Ala Leu Ala Asn Asn Val Thr Thr
                85                  90                  95

Lys Ala Asn Glu Val Val Gln Thr Gln Leu Arg Glu Gln Gln Ala Glu
            100                 105                 110

Val Gly Lys Phe Phe Asp Ile Ser Gly Met Ser Ser Ala Val Ala
        115                 120                 125

Leu Leu Ala Ala Ala Asn Thr Leu Met Leu Thr Leu Asn Gln Ala Asp
    130                 135                 140

Ser Lys Leu Ser Gly Lys Leu Ser Leu Val Ser Phe Asp Ala Ala Lys
145                 150                 155                 160

Thr Thr Ala Ser Ser Met Met Arg Glu Gly Met Asn Ala Leu Ser Gly
                165                 170                 175

Ser Ile Ser Gln Ser Ala Leu Gln Leu Gly Ile Thr Gly Val Gly Ala
            180                 185                 190

Lys Leu Glu Tyr Lys Gly Leu Gln Asn Glu Arg Gly Ala Leu Lys His
        195                 200                 205

Asn Ala Ala Lys Ile Asp Lys Leu Thr Thr Glu Ser His Ser Ile Lys
    210                 215                 220

Asn Val Leu Asn Gly Gln Asn Ser Val Lys Leu Gly Ala Glu Gly Val
225                 230                 235                 240

Asp Ser Leu Lys Ser Leu Asn Met Lys Lys Thr Gly Thr Asp Ala Thr
                245                 250                 255
```

-continued

```
Lys Asn Leu Asn Asp Ala Thr Leu Lys Ser Asn Ala Gly Thr Ser Ala
            260                 265                 270

Thr Glu Ser Leu Gly Ile Lys Asp Ser Asn Lys Gln Ile Ser Pro Glu
        275                 280                 285

His Gln Ala Ile Leu Ser Lys Arg Leu Glu Ser Val Glu Ser Asp Ile
    290                 295                 300

Arg Leu Glu Gln Asn Thr Met Asp Met Thr Arg Ile Asp Ala Arg Lys
305                 310                 315                 320

Met Gln Met Thr Gly Asp Leu Ile Met Lys Asn Ser Val Thr Val Gly
                325                 330                 335

Gly Ile Ala Gly Ala Ser Gly Gln Tyr Ala Ala Thr Gln Glu Arg Ser
            340                 345                 350

Glu Gln Gln Ile Ser Gln Val Asn Asn Arg Val Ala Ser Thr Ala Ser
        355                 360                 365

Asp Glu Ala Arg Glu Ser Ser Arg Lys Ser Thr Ser Leu Ile Gln Glu
    370                 375                 380

Met Leu Lys Thr Met Glu Ser Ile Asn Gln Ser Lys Ala Ser Ala Leu
385                 390                 395                 400

Ala Ala Ile Ala Gly Asn Ile Arg Ala
                405

<210> SEQ ID NO 41
<211> LENGTH: 1206
<212> TYPE: DNA
<213> ORGANISM: Yersinia enterocolitica

<400> SEQUENCE: 41
atgagtgcgt tgataaccca tgatcgctca acgccagtaa ctggaagtct acttccctac     60
gtcgagacac cagcgcccgc cccccttcag actcaacaag tcgcgggaga actgaaggat    120
aaaaatggtg gggtgagttc tcagggcgta cagctccctg caccactagc agtggttgcc    180
agccaagtca ctgaaggaca acagcaagaa atcactaaat tattggagtc ggtcacccgc    240
ggcacggcag gatctcaact gatatcaaat tatgtttcag tgctaacgaa ttttacgctc    300
gcttcacctg atacatttga gattgagtta ggtaagctag tttctaattt agaagaagta    360
cgcaaagaca taaaaatcgc tgatattcag cgtcttcatg aacaaaacat gaagaaaatt    420
gaagagaatc aagagaaaat caaagaaaca gaagagaatg ccaagcaagt caagaaatcc    480
ggcatggcat caaagatttt tggctggctc agcgccatag cctcagtggt tatcggtgcc    540
atcatggtgg cctcaggggt aggagccgtt gccggtgcaa tgatgattgc ctcaggcgta    600
attgggatgg cgaatatggc tgtgaaacaa gcggcggaag atggcctgat atcccaagag    660
gcaatgcaag tattagggcc gatactcact gcgattgaag tcgcattgac tgtagtttca    720
accgtaatga cctttggcgg ttcggcacta aaatgcctgg ctgatattgg cgcaaaactc    780
ggtgctaaca ccgcaagtct tgctgctaaa ggagccgagt tttcggccaa agttgcccaa    840
atttcgacag gcatatcaaa cactgtcggg aatgcagtga ctaaattagg gggcagtttt    900
ggtagtttaa caatgagcca tgtaatccgt acaggatcac aggcaacaca agtcgccgtt    960
ggtgtgggca gcggaataac tcagaccatc aataataaaa aacaagctga tttacaacat   1020
aataacgctg atttggcctt gaacaaggca gacatggcag cgttacaaag tattattgac   1080
cgactcaaag aagagttatc ccatttgtca gagtcacatc aacaagtgat ggaactgatt   1140
ttccagatga ttaatgcaaa aggtgacatg ctgcataatt tggccggcag accccatact   1200
``` gtttaa                                                             1206

<210> SEQ ID NO 42
<211> LENGTH: 401
<212> TYPE: PRT
<213> ORGANISM: Yersinia enterocolitica

<400> SEQUENCE: 42

Met Ser Ala Leu Ile Thr His Asp Arg Ser Thr Pro Val Thr Gly Ser
1               5                   10                  15

Leu Leu Pro Tyr Val Glu Thr Pro Ala Pro Ala Pro Leu Gln Thr Gln
            20                  25                  30

Gln Val Ala Gly Glu Leu Lys Asp Lys Asn Gly Gly Val Ser Ser Gln
        35                  40                  45

Gly Val Gln Leu Pro Ala Pro Leu Ala Val Val Ala Ser Gln Val Thr
50                  55                  60

Glu Gly Gln Gln Gln Glu Ile Thr Lys Leu Leu Glu Ser Val Thr Arg
65                  70                  75                  80

Gly Thr Ala Gly Ser Gln Leu Ile Ser Asn Tyr Val Ser Val Leu Thr
                85                  90                  95

Asn Phe Thr Leu Ala Ser Pro Asp Thr Phe Glu Ile Glu Leu Gly Lys
            100                 105                 110

Leu Val Ser Asn Leu Glu Glu Val Arg Lys Asp Ile Lys Ile Ala Asp
        115                 120                 125

Ile Gln Arg Leu His Glu Gln Asn Met Lys Lys Ile Glu Glu Asn Gln
130                 135                 140

Glu Lys Ile Lys Glu Thr Glu Glu Asn Ala Lys Gln Val Lys Lys Ser
145                 150                 155                 160

Gly Met Ala Ser Lys Ile Phe Gly Trp Leu Ser Ala Ile Ala Ser Val
                165                 170                 175

Val Ile Gly Ala Ile Met Val Ala Ser Gly Val Gly Ala Val Ala Gly
            180                 185                 190

Ala Met Met Ile Ala Ser Gly Val Ile Gly Met Ala Asn Met Ala Val
        195                 200                 205

Lys Gln Ala Ala Glu Asp Gly Leu Ile Ser Gln Glu Ala Met Gln Val
210                 215                 220

Leu Gly Pro Ile Leu Thr Ala Ile Glu Val Ala Leu Thr Val Val Ser
225                 230                 235                 240

Thr Val Met Thr Phe Gly Gly Ser Ala Leu Lys Cys Leu Ala Asp Ile
                245                 250                 255

Gly Ala Lys Leu Gly Ala Asn Thr Ala Ser Leu Ala Ala Lys Gly Ala
            260                 265                 270

Glu Phe Ser Ala Lys Val Ala Gln Ile Ser Thr Gly Ile Ser Asn Thr
        275                 280                 285

Val Gly Asn Ala Val Thr Lys Leu Gly Gly Ser Phe Gly Ser Leu Thr
290                 295                 300

Met Ser His Val Ile Arg Thr Gly Ser Gln Ala Thr Gln Val Ala Val
305                 310                 315                 320

Gly Val Gly Ser Gly Ile Thr Gln Thr Ile Asn Asn Lys Lys Gln Ala
                325                 330                 335

Asp Leu Gln His Asn Asn Ala Asp Leu Ala Leu Asn Lys Ala Asp Met
            340                 345                 350

Ala Ala Leu Gln Ser Ile Ile Asp Arg Leu Lys Glu Glu Leu Ser His
        355                 360                 365

```
Leu Ser Glu Ser His Gln Gln Val Met Glu Leu Ile Phe Gln Met Ile
    370                 375                 380

Asn Ala Lys Gly Asp Met Leu His Asn Leu Ala Gly Arg Pro His Thr
385                 390                 395                 400

Val

<210> SEQ ID NO 43
<211> LENGTH: 921
<212> TYPE: DNA
<213> ORGANISM: Yersinia enterocolitica

<400> SEQUENCE: 43
atgacaataa atatcaagac agacagccca attatcacga ccggttcaca gattgatgcc      60
atcactacag agacagtcgg gcaaagcggt gaggttaaaa aaacagaaga cacccgtcat     120
gaagcacaag caataaagag tagcgaggca agcttatctc ggtcacaagt gcctgaattg     180
atcaaaccga gtcagggaat caatgttgca ttactgagta aaagccaggg agatcttaat     240
ggtactttaa gtatcttgtt gttgctgttg gaactggcac gtaaagcgcg agaaatgggt     300
ttgcaacaaa gggatataga aaataaagct gctattactg cccaaaagga gcaggtagcg     360
gagatggtca gcggtgcaaa actgatgatc gccatggcgg tggtgtctgg catcatggct     420
gctacttcta cggttgctag tgctttttct atagcgaaag aggtgaaaat agttaaacag     480
gaacaaattc taaacagtaa tattgctggc cgcgatcaac ttattgatac aaaaatgcaa     540
caaatgagta acaccagtga taaagcggta agcagagagg atatcgggag aatatggaaa     600
ccagagcagg tagcggatca aaataagctg gcattattgg ataaagaatt cagaatgacc     660
gactcaaaag ccaatgcgtt taatgccgca acgcagccgt taggacaaat ggcaaacagt     720
gcgattcaag ttcatcaagg gtattctcaa gccgaggtca aagagaaaga agtcaatgca     780
agtattgctg ccaacgagaa gcaaaaagcc gaagaggcga tgaactataa tgataacttt     840
atgaaagatg tcctgcgctt gattgaacaa tatgttagca gtcatactca cgccatgaaa     900
gccgcttttg gtgttgtctg a                                               921

<210> SEQ ID NO 44
<211> LENGTH: 306
<212> TYPE: PRT
<213> ORGANISM: Yersinia enterocolitica

<400> SEQUENCE: 44

Met Thr Ile Asn Ile Lys Thr Asp Ser Pro Ile Ile Thr Thr Gly Ser
1               5                   10                  15

Gln Ile Asp Ala Ile Thr Thr Glu Thr Val Gly Gln Ser Gly Glu Val
            20                  25                  30

Lys Lys Thr Glu Asp Thr Arg His Glu Ala Gln Ala Ile Lys Ser Ser
        35                  40                  45

Glu Ala Ser Leu Ser Arg Ser Gln Val Pro Glu Leu Ile Lys Pro Ser
    50                  55                  60

Gln Gly Ile Asn Val Ala Leu Leu Ser Lys Ser Gln Gly Asp Leu Asn
65                  70                  75                  80

Gly Thr Leu Ser Ile Leu Leu Leu Leu Leu Glu Leu Ala Arg Lys Ala
                85                  90                  95

Arg Glu Met Gly Leu Gln Gln Arg Asp Ile Glu Asn Lys Ala Ala Ile
            100                 105                 110

Thr Ala Gln Lys Glu Gln Val Ala Glu Met Val Ser Gly Ala Lys Leu
        115                 120                 125
```

Met Ile Ala Met Ala Val Val Ser Gly Ile Met Ala Ala Thr Ser Thr
            130                 135                 140

Val Ala Ser Ala Phe Ser Ile Ala Lys Glu Val Lys Ile Val Lys Gln
145                 150                 155                 160

Glu Gln Ile Leu Asn Ser Asn Ile Ala Gly Arg Asp Gln Leu Ile Asp
                165                 170                 175

Thr Lys Met Gln Gln Met Ser Asn Thr Ser Asp Lys Ala Val Ser Arg
            180                 185                 190

Glu Asp Ile Gly Arg Ile Trp Lys Pro Glu Gln Val Ala Asp Gln Asn
        195                 200                 205

Lys Leu Ala Leu Leu Asp Lys Glu Phe Arg Met Thr Asp Ser Lys Ala
    210                 215                 220

Asn Ala Phe Asn Ala Ala Thr Gln Pro Leu Gly Gln Met Ala Asn Ser
225                 230                 235                 240

Ala Ile Gln Val His Gln Gly Tyr Ser Gln Ala Glu Val Lys Glu Lys
                245                 250                 255

Glu Val Asn Ala Ser Ile Ala Ala Asn Glu Lys Gln Lys Ala Glu Glu
            260                 265                 270

Ala Met Asn Tyr Asn Asp Asn Phe Met Lys Asp Val Leu Arg Leu Ile
        275                 280                 285

Glu Gln Tyr Val Ser Ser His Thr His Ala Met Lys Ala Ala Phe Gly
    290                 295                 300

Val Val
305

<210> SEQ ID NO 45
<211> LENGTH: 555
<212> TYPE: DNA
<213> ORGANISM: Mycobacterium tuberculosis

<400> SEQUENCE: 45
gtggacttgc ccggaaatga ctttgacagc aacgatttcg acgccgtgga tctctggggt      60
gccgacggcg cggagggctg gactgcggat ccgattattg cgtcgggtc ggcggcgacc      120 ccggacaccg gacccgacct ggacaatgcc acggtcagg cggagacgga caccgaacaa      180
gagatcgcgc tttttaccgt gacgaatccc ccacgcacgg tgtcggtatc gacgctgatg      240
gacggccgga ttgaccatgt cgagctgtcg gccagggtgg cctggatgag tgagtcgcag      300
ctcgcttctg agatcctggt gattgccgac ctggcgcggc agaaggcgca gtcggcccag      360
tacgccttca tccttgacag gatgagtcaa caggtcgatg cagatgaaca ccgcgtcgca      420
ctgctacgta agaccgtggg cgaaacctgg gggttaccat cgccggaaga agccgcggca      480
gcagaagctg aggtgttcgc gacgcgctac agcgacgatt gtccagcacc agacgacgag      540
agcgatccat ggtga                                                      555

<210> SEQ ID NO 46
<211> LENGTH: 184
<212> TYPE: PRT
<213> ORGANISM: Mycobacterium tuberculosis

<400> SEQUENCE: 46

Met Asp Leu Pro Gly Asn Asp Phe Asp Ser Asn Asp Phe Asp Ala Val
1               5                   10                  15

Asp Leu Trp Gly Ala Asp Gly Ala Glu Gly Trp Thr Ala Asp Pro Ile
            20                  25                  30

Ile Gly Val Gly Ser Ala Ala Thr Pro Asp Thr Gly Pro Asp Leu Asp
                35                  40                  45

Asn Ala His Gly Gln Ala Glu Thr Asp Thr Glu Gln Glu Ile Ala Leu
 50                  55                  60

Phe Thr Val Thr Asn Pro Pro Arg Thr Val Ser Val Ser Thr Leu Met
 65                  70                  75                  80

Asp Gly Arg Ile Asp His Val Glu Leu Ser Ala Arg Val Ala Trp Met
                 85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
        115                 120                 125

Ser Gln Gln Val Asp Ala Asp Glu His Arg Val Ala Leu Leu Arg Lys
130                 135                 140

Thr Val Gly Glu Thr Trp Gly Leu Pro Ser Pro Glu Glu Ala Ala Ala
145                 150                 155                 160

Ala Glu Ala Glu Val Phe Ala Thr Arg Tyr Ser Asp Asp Cys Pro Ala
                165                 170                 175

Pro Asp Asp Glu Ser Asp Pro Trp
            180

<210> SEQ ID NO 47
<211> LENGTH: 945
<212> TYPE: DNA
<213> ORGANISM: Escherichia coli

<400> SEQUENCE: 47
atgaatacta ttgattatac taatcaagta atgacggtta attctgtttc ggagaatact      60
accggctcta tgcaattac cgcatctgct attaattcat ctttgcttac cgatggtaag     120
gtcgatgttt ctaaactgat gctggaaatt caaaaactcc tgggcaagat ggtgcgtata     180
ttgcaggatt accaacagca acagttgtcg cagagctatc agatccaact ggccgttttt     240
gagagccaga ataaagccat tgatgaaaaa aaggccgctg caacagccgc tctggttggt     300
ggggctattt catcagtatt ggggatctta ggctcttttg cagcaattaa cagtgctacg     360
aaaggcgcga gtgatattgc tcaacaaacc gcctctacat cttctaaggc tattgatgcg     420
gcttctgata ctgcgactaa acgttgact aaggcaacgg aaagcgttgc tgatgctgtt     480
gaagatgcat ccagcgtgat gcagcaagcg atgactacag caacgagagc ggccagccgt     540
acatctgacg ttgcagatga cattgccgat tctgctcaga gagcttctca gctggctgaa     600
aacgctgcag atgccgctca gaaggcaagt cgggcaagcc gctttatggc tgcagtagat     660
aagattactg ctctctacac atttattgcc gttaccagtc ttgccgaagg cacgaagaca     720
ttgccaacaa cggtatctga atcagtcaaa tctaaccatg agattagcga acagcgttat     780
aagtctgtgg agaacttcca gcagggtaat ttggatctgt ataagcaaga agttcgcaga     840
gcgcaggatg atatcgctag ccgtctgcgt gatatgacaa cagccgctcg cgatctcact     900
gatcttcaga atcgtatggg tcaatcggtt cgcttagctg ggtaa                    945

<210> SEQ ID NO 48
<211> LENGTH: 314
<212> TYPE: PRT
<213> ORGANISM: Escherichia coli

<400> SEQUENCE: 48

Met Asn Thr Ile Asp Tyr Thr Asn Gln Val Met Thr Val Asn Ser Val

```
  1               5                   10                  15
Ser Glu Asn Thr Thr Gly Ser Asn Ala Ile Thr Ala Ser Ala Ile Asn
                 20                  25                  30
Ser Ser Leu Leu Thr Asp Gly Lys Val Asp Val Ser Lys Leu Met Leu
                 35                  40                  45
Glu Ile Gln Lys Leu Leu Gly Lys Met Val Arg Ile Leu Gln Asp Tyr
 50                  55                  60
Gln Gln Gln Gln Leu Ser Gln Ser Tyr Gln Ile Gln Leu Ala Val Phe
 65                  70                  75                  80
Glu Ser Gln Asn Lys Ala Ile Asp Glu Lys Lys Ala Ala Thr Ala
                 85                  90                  95
Ala Leu Val Gly Gly Ala Ile Ser Ser Val Leu Gly Ile Leu Gly Ser
                 100                 105                 110
Phe Ala Ala Ile Asn Ser Ala Thr Lys Gly Ala Ser Asp Ile Ala Gln
                 115                 120                 125
Gln Thr Ala Ser Thr Ser Lys Ala Ile Asp Ala Ala Ser Asp Thr
                 130                 135                 140
Ala Thr Lys Thr Leu Thr Lys Ala Thr Glu Ser Val Ala Asp Ala Val
145                 150                 155                 160
Glu Asp Ala Ser Ser Val Met Gln Gln Ala Met Thr Thr Ala Thr Arg
                 165                 170                 175
Ala Ala Ser Arg Thr Ser Asp Val Ala Asp Ile Ala Asp Ser Ala
                 180                 185                 190
Gln Arg Ala Ser Gln Leu Ala Glu Asn Ala Ala Asp Ala Ala Gln Lys
                 195                 200                 205
Ala Ser Arg Ala Ser Arg Phe Met Ala Ala Val Asp Lys Ile Thr Gly
                 210                 215                 220
Ser Thr Pro Phe Ile Ala Val Thr Ser Leu Ala Glu Gly Thr Lys Thr
225                 230                 235                 240
Leu Pro Thr Thr Val Ser Glu Ser Val Lys Ser Asn His Glu Ile Ser
                 245                 250                 255
Glu Gln Arg Tyr Lys Ser Val Glu Asn Phe Gln Gln Gly Asn Leu Asp
                 260                 265                 270
Leu Tyr Lys Gln Glu Val Arg Arg Ala Gln Asp Asp Ile Ala Ser Arg
                 275                 280                 285
Leu Arg Asp Met Thr Thr Ala Ala Arg Asp Leu Thr Asp Leu Gln Asn
                 290                 295                 300
Arg Met Gly Gln Ser Val Arg Leu Ala Gly
305                 310
```

<210> SEQ ID NO 49
<211> LENGTH: 999
<212> TYPE: DNA
<213> ORGANISM: Shigella flexneri

<400> SEQUENCE: 49

```
atgaatataa caactctgac taatagtatt tccacctcat cattcagtcc aaacaatacc      60
aacggttcat caaccgaaac agttaattct gatataaaaa caacgaccag ttctcatcct     120
gtaagttccc ttactatgct caacgacacc cttcataata tcagaacaac aaatcaggca     180
ttaaagaaag agctttcaca aaaaacgttg actaaaacat cgctagaaga aatagcatta     240
cattcatctc agattagcat ggatgtaaat aaatccgctc aactattgga tattcttttcc    300 aggaacgaat atccaattaa taagacgca agagaattat tacattcagc cccgaaagaa      360
```

```
gccgagcttg atggagatca aatgatatct catagagaac tgtgggctaa aattgcaaac    420
tccatcaatg atattaatga acagtatctg aaagtatatg aacatgccgt tagttcatat    480
actcaaatgt atcaagattt tagcgctgtt ctttccagtc ttgccggctg gatctctccc    540
ggaggtaacg acggaaactc cgtgaaatta caagtcaact cgcttaaaaa ggcattggaa    600
gaactcaagg aaaatataa agataaaccg ctatatccag caaataatac tgttagtcag    660
gaacaagcaa ataatggct tacagaatta ggtggaacaa tcggcaaggt atctcaaaaa    720
aacgggggat atgttgtcag tataaacatg accccaatag acaatatgtt aaaaagctta    780
gataatctag gtgaaatgg cgaggttgtg ctagataatg caaatatca ggcatggaat    840 gccggattct ctgccgaaga tgaaacaatg aaaaataatc ttcaaacttt agttcaaaaa    900
tacagtaatg ccaatagtat ttttgataat ttagtaaagg ttttgagtag tacaataagc    960
tcatgtacag atacagataa actttttctc catttctga                          999
```

```
<210> SEQ ID NO 50
<211> LENGTH: 332
<212> TYPE: PRT
<213> ORGANISM: Shigella flexneri

<400> SEQUENCE: 50

Met Asn Ile Thr Thr Leu Thr Asn Ser Ile Ser Thr Ser Ser Phe Ser
1               5                   10                  15

Pro Asn Asn Thr Asn Gly Ser Ser Glu Thr Val Asn Ser Asp Ile
            20                  25                  30

Lys Thr Thr Thr Ser Ser His Pro Val Ser Ser Leu Thr Met Leu Asn
        35                  40                  45

Asp Thr Leu His Asn Ile Arg Thr Thr Asn Gln Ala Leu Lys Lys Glu
    50                  55                  60

Leu Ser Gln Lys Thr Leu Thr Lys Thr Ser Leu Glu Glu Ile Ala Leu
65                  70                  75                  80

His Ser Ser Gln Ile Ser Met Asp Val Asn Lys Ser Ala Gln Leu Leu
                85                  90                  95

Asp Ile Leu Ser Arg Asn Glu Tyr Pro Ile Asn Lys Asp Ala Arg Glu
            100                 105                 110

Leu Leu His Ser Ala Pro Lys Glu Ala Glu Leu Asp Gly Asp Gln Met
        115                 120                 125

Ile Ser His Arg Glu Leu Trp Ala Lys Ile Ala Asn Ser Ile Asn Asp
    130                 135                 140

Ile Asn Glu Gln Tyr Leu Lys Val Tyr Glu His Ala Val Ser Ser Tyr
145                 150                 155                 160

Thr Gln Met Tyr Gln Asp Phe Ser Ala Val Leu Ser Ser Leu Ala Gly
                165                 170                 175

Trp Ile Ser Pro Gly Gly Asn Asp Gly Asn Ser Val Lys Leu Gln Val
            180                 185                 190

Asn Ser Leu Lys Lys Ala Leu Glu Glu Leu Lys Glu Lys Tyr Lys Asp
        195                 200                 205

Lys Pro Leu Tyr Pro Ala Asn Asn Thr Val Ser Gln Glu Gln Ala Asn
    210                 215                 220

Lys Trp Leu Thr Glu Leu Gly Gly Thr Ile Gly Lys Val Ser Gln Lys
225                 230                 235                 240

Asn Gly Gly Tyr Val Val Ser Ile Asn Met Thr Pro Ile Asp Asn Met
                245                 250                 255

Leu Lys Ser Leu Asp Asn Leu Gly Gly Asn Gly Glu Val Val Leu Asp
```

```
                   260             265             270
Asn Ala Lys Tyr Gln Ala Trp Asn Ala Gly Phe Ser Ala Glu Asp Glu
            275                 280                 285

Thr Met Lys Asn Asn Leu Gln Thr Leu Val Gln Lys Tyr Ser Asn Ala
        290                 295                 300

Asn Ser Ile Phe Asp Asn Leu Val Lys Val Leu Ser Ser Thr Ile Ser
305                 310                 315                 320

Ser Cys Thr Asp Thr Asp Lys Leu Phe Leu His Phe
                325                 330
```

<210> SEQ ID NO 51
<211> LENGTH: 1038
<212> TYPE: DNA
<213> ORGANISM: Salmonella enterica

<400> SEQUENCE: 51

```
gatattatgc ttaatattca aaattattcc gcttctcctc atccggggat cgttgccgaa    60
cggccgcaga ctccctcggc gagcgagcac gtcgagactg ccgtggtacc gtctaccaca   120
gaacatcgcg gtacagatat catttcatta tcgcaggcgg ctactaaaat ccaccaggca   180
cagcagacgc tgcagtcaac gccaccgatc tctgaagaga taatgacga gcgcacgctg    240
gcgcgccagc agttgaccag cagcctgaat gcgctggcga agtccggcgt gtcattatcc   300
gcagaacaaa atgagaacct gcggagcgcg ttttctgcgc cgacgtcggc cttatttagc   360
gcttcgccta tggcgcagcc gagaacaacc atttctgatg ctgagatttg ggatatggtt   420
tcccaaaata tatcggcgat aggtgacagc tatctgggcg tttatgaaaa cgttgtcgca   480
gtctataccg atttttatca ggccttcagt gatattcttt ccaaaatggg aggctggtta   540
ttaccaggta aggacggtaa taccgttaag ctagatgtta cctcactcaa aaatgattta   600
aacagtttag tcaataaata taatcaaata aacagtaata ccgtttttatt tccagcgcag   660
tcaggcagcg gcgttaaagt agccactgaa gcggaagcga cagtggct cagtgaattg     720
aatttaccga atagctgcct gaaatcttat ggatccggtt atgtcgtcac cgttgatctg    780
acgccattac aaaaaatggt tcaggatatt gatggtttag gcgcgccggg aaaagactca    840
aaactcgaaa tggataacgc caaatatcaa gcctggcagt cgggttttaa agcgcaggaa    900
gaaaatatga aaaccacatt acagacgctg acgcaaaaat atagcaatgc caattcattg    960
tacgacaacc tggtaaaagt gctgagcagt acgataagta gcagcctgga aaccgccaaa   1020
agcttcctgc aaggataa                                                  1038
```

<210> SEQ ID NO 52
<211> LENGTH: 343
<212> TYPE: PRT
<213> ORGANISM: Salmonella enterica

<400> SEQUENCE: 52

```
Met Leu Asn Ile Gln Asn Tyr Ser Ala Ser Pro His Pro Gly Ile Val
1               5                   10                  15

Ala Glu Arg Pro Gln Thr Pro Ser Ala Ser Glu His Val Glu Thr Ala
            20                  25                  30

Val Val Pro Ser Thr Thr Glu His Arg Gly Thr Asp Ile Ile Ser Leu
        35                  40                  45

Ser Gln Ala Ala Thr Lys Ile His Gln Ala Gln Gln Thr Leu Gln Ser
    50                  55                  60

Thr Pro Pro Ile Ser Glu Glu Asn Asn Asp Glu Arg Thr Leu Ala Arg
```

```
                65                  70                  75                  80
        Gln Gln Leu Thr Ser Ser Leu Asn Ala Leu Ala Lys Ser Gly Val Ser
                        85                  90                  95

Leu Ser Ala Glu Gln Asn Glu Asn Leu Arg Ser Ala Phe Ser Ala Pro
                    100                 105                 110

Thr Ser Ala Leu Phe Ser Ala Ser Pro Met Ala Gln Pro Arg Thr Thr
                    115                 120                 125

Ile Ser Asp Ala Glu Ile Trp Asp Met Val Ser Gln Asn Ile Ser Ala
                    130                 135                 140

Ile Gly Asp Ser Tyr Leu Gly Val Tyr Glu Asn Val Ala Val Tyr
        145                 150                 155                 160

Thr Asp Phe Tyr Gln Ala Phe Ser Asp Ile Leu Ser Lys Met Gly Gly
                        165                 170                 175

Trp Leu Leu Pro Gly Lys Asp Gly Asn Thr Val Lys Leu Asp Val Thr
                    180                 185                 190

Ser Leu Lys Asn Asp Leu Asn Ser Leu Val Asn Lys Tyr Asn Gln Ile
                    195                 200                 205

Asn Ser Asn Thr Val Leu Phe Pro Ala Gln Ser Gly Ser Gly Val Lys
        210                 215                 220

Val Ala Thr Glu Ala Glu Ala Arg Gln Trp Leu Ser Glu Leu Asn Leu
        225                 230                 235                 240

Pro Asn Ser Cys Leu Lys Ser Tyr Gly Ser Gly Tyr Val Val Thr Val
                        245                 250                 255

Asp Leu Thr Pro Leu Gln Lys Met Val Gln Asp Ile Asp Gly Leu Gly
                    260                 265                 270

Ala Pro Gly Lys Asp Ser Lys Leu Glu Met Asp Asn Ala Lys Tyr Gln
                    275                 280                 285

Ala Trp Gln Ser Gly Phe Lys Ala Gln Glu Glu Asn Met Lys Thr Thr
                    290                 295                 300

Leu Gln Thr Leu Thr Gln Lys Tyr Ser Asn Ala Asn Ser Leu Tyr Asp
        305                 310                 315                 320

Asn Leu Val Lys Val Leu Ser Ser Thr Ile Ser Ser Ser Leu Glu Thr
                        325                 330                 335

Ala Lys Ser Phe Leu Gln Gly
                    340

<210> SEQ ID NO 53
<211> LENGTH: 981
<212> TYPE: DNA
<213> ORGANISM: Yersinia pestis

<400> SEQUENCE: 53
atgattagag cctacgaaca aaacccacaa cattttattg aggatctaga aaaagttagg      60
gtggaacaac ttactggtca tggttcttca gttttagaag aattggttca gttagtcaaa     120
gataaaaata tagatatttc cattaaatat gatcccagaa aagattcgga ggttttgcc      180 aatagagtaa ttactgatga tatcgaattg ctcaagaaaa tcctagctta ttttctaccc     240
gaggatgcca ttcttaaagg cggtcattat gacaaccaac tgcaaaatgg catcaagcga     300
gtaaaagagt tccttgaatc atcgccgaat acacaatggg aattgcgggc gttcatggca     360
gtaatgcatt tctctttaac cgccgatcgt atcgatgatg atattttgaa agtgattgtt     420
gattcaatga atcatcatgg tgatgcccgt agcaagttgc gtgaagaatt agctgagctt     480
accgccgaat taaagattta ttcagttatt caagccgaaa ttaataagca tctgtctagt     540
```

```
agtggcacca taaatatcca tgataaatcc attaatctca tggataaaaa tttatatggt    600
tatacagatg aagagatttt taaagccagc gcagagtaca aaattctcga gaaaatgcct    660
caaaccacca ttcaggtgga tgggagcgag aaaaaaatag tctcgataaa ggactttctt    720
ggaagtgaga ataaaagaac cggggcgttg ggtaatctga aaaactcata ctcttataat    780
aaagataata atgaattatc tcactttgcc accacctgct cggataagtc caggccgctc    840
aacgacttgg ttagccaaaa aacaactcag ctgtctgata ttacatcacg ttttaattca    900
gctattgaag cactgaaccg tttcattcag aaatatgatt cagtgatgca acgtctgcta    960
gatgacacgt ctggtaaatg a                                              981
```

```
<210> SEQ ID NO 54
<211> LENGTH: 326
<212> TYPE: PRT
<213> ORGANISM: Yersinia pestis

<400> SEQUENCE: 54
```

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala

```
                290                 295                 300
Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 55
<211> LENGTH: 579
<212> TYPE: DNA
<213> ORGANISM: Escherichia coli

<400> SEQUENCE: 55
atggatacat caaatgcaac atccgttgtt aatgtgagtg cgagttcttc gacatcgacg      60
atctatgact taggtaatat gtcgaaggat gaggtggtta agctatttga ggaactcggt     120
gtttttcagg ctgcgattct catgtttctc tatatgtatc aggcacaaag taatctgtcg     180
attgcaaagt ttgctgatat gaatgaggca tctaaagcgt caaccacggc acaaaagatg     240
gctaatcttg tggatgccaa aattgctgat gttcagagta gcactgataa gaatgcgaaa     300
gccaaacttc ctcaagacgt gattgactat ataaacgatc cacgtaatga cataagtgta     360
actggtattc gtgatcttag tggtgattta agcgctggtg atctgcaaac agtgaaggcg     420
gctatttcag ctaaagcgaa taacctgaca acggtagtga ataatagcca gctcgaaatt     480
cagcaaatgt cgaatacatt aaatctctta acgagtgcac gttctgatgt gcaatctcta     540
caatatagaa ctatttcagc aatatcccct ggtaaataa                            579

<210> SEQ ID NO 56
<211> LENGTH: 192
<212> TYPE: PRT
<213> ORGANISM: Escherichia coli

<400> SEQUENCE: 56

Met Asp Thr Ser Asn Ala Thr Ser Val Val Asn Val Ser Ala Ser Ser
1               5                   10                  15

Ser Thr Ser Thr Ile Tyr Asp Leu Gly Asn Met Ser Lys Asp Glu Val
            20                  25                  30

Val Lys Leu Phe Glu Glu Leu Gly Val Phe Gln Ala Ala Ile Leu Met
        35                  40                  45

Phe Ser Tyr Met Tyr Gln Ala Gln Ser Asn Leu Ser Ile Ala Lys Phe
    50                  55                  60

Ala Asp Met Asn Glu Ala Ser Lys Ala Ser Thr Thr Ala Gln Lys Met
65                  70                  75                  80

Ala Asn Leu Val Asp Ala Lys Ile Ala Asp Val Gln Ser Ser Thr Asp
                85                  90                  95

Lys Asn Ala Lys Ala Lys Leu Pro Gln Asp Val Ile Asp Tyr Ile Asn
            100                 105                 110

Asp Pro Arg Asn Asp Ile Ser Val Thr Gly Ile Arg Asp Leu Ser Gly
        115                 120                 125

Asp Leu Ser Ala Gly Asp Leu Gln Thr Val Lys Ala Ala Ile Ser Ala
    130                 135                 140

Lys Ala Asn Asn Leu Thr Thr Val Val Asn Asn Ser Gln Leu Glu Ile
145                 150                 155                 160

Gln Gln Met Ser Asn Thr Leu Asn Leu Leu Thr Ser Ala Arg Ser Asp
                165                 170                 175

Val Gln Ser Leu Gln Tyr Arg Thr Ile Ser Ala Ile Ser Leu Gly Lys
            180                 185                 190
```

<210> SEQ ID NO 57
<211> LENGTH: 879
<212> TYPE: DNA
<213> ORGANISM: Shigella flexneri

<400> SEQUENCE: 57

```
atggcattag ataatataaa cctaaatttt agtagtgaca acagataga aaaatgtgag      60
aaactatctt caatagataa tattgatagt ctcgttttga agaagaagag gaaggttgaa     120
attcctgagt actctttaat tgcatctaac tattttacta ttgataagca ctttgaacat     180
aagcatgata aaggagaaat ttatagtggc attaaaaatg cgttcgaact tagaaacgaa     240
cgagcgacat attctgatat tccagaatca atggccatta agaaaatat tttgatacca      300
gatcaagata tcaaagcaag ggaaaaaata aatatcggcg atatgagggg gatcttttca     360
tataataaga gtggaaatgc agacaagaac ttcgaaagaa gtcatacttc ttctgtaaac     420
cctgataatc tgctagaatc tgataataga atggtcaaa ttggtttaaa aaatcatagc      480
ttgtctattg ataagaatat tgctgacatc atttctttac taaatggaag tgttgctaaa     540
tcatttgagc tgcctgtaat gaataaaaat actgcagaca taaccccatc catgtcattg     600
caagaaaaat caatagttga aaatgataaa aatgttttc aaaaaaatag tgaaatgact      660
taccacttta acagtggggg ggctggacat tctgttagta tttcagtgga gtctggttct     720
tttgttctaa aaccgtcaga tcaatttgta ggaaataaac ttgacttaat tttgaaacaa     780
gatgctgagg gtaattacag atttgatagc agtcaacata taaggggaa taaaaataat    840
agtacaggat ataatgaaca gagtgaagaa gaatgctaa                            879
```

<210> SEQ ID NO 58
<211> LENGTH: 292
<212> TYPE: PRT
<213> ORGANISM: Shigella flexneri

<400> SEQUENCE: 58

```
Met Ala Leu Asp Asn Ile Asn Leu Asn Phe Ser Ser Asp Lys Gln Ile
1               5                   10                  15

Glu Lys Cys Glu Lys Leu Ser Ser Ile Asp Asn Ile Asp Ser Leu Val
            20                  25                  30

Leu Lys Lys Lys Arg Lys Val Glu Ile Pro Glu Tyr Ser Leu Ile Ala
        35                  40                  45

Ser Asn Tyr Phe Thr Ile Asp Lys His Phe Glu His Lys His Asp Lys
    50                  55                  60

Gly Glu Ile Tyr Ser Gly Ile Lys Asn Ala Phe Glu Leu Arg Asn Glu
65                  70                  75                  80

Arg Ala Thr Tyr Ser Asp Ile Pro Glu Ser Met Ala Ile Lys Glu Asn
                85                  90                  95

Ile Leu Ile Pro Asp Gln Asp Ile Lys Ala Arg Glu Lys Ile Asn Ile
            100                 105                 110

Gly Asp Met Arg Gly Ile Phe Ser Tyr Asn Lys Ser Gly Asn Ala Asp
        115                 120                 125

Lys Asn Phe Glu Arg Ser His Thr Ser Ser Val Asn Pro Asp Asn Leu
    130                 135                 140

Leu Glu Ser Asp Asn Arg Asn Gly Gln Ile Gly Leu Lys Asn His Ser
145                 150                 155                 160

Leu Ser Ile Asp Lys Asn Ile Ala Asp Ile Ile Ser Leu Leu Asn Gly
                165                 170                 175
```

Ser Val Ala Lys Ser Phe Glu Leu Pro Val Met Asn Lys Asn Thr Ala
            180                 185                 190

Asp Ile Thr Pro Ser Met Ser Leu Gln Glu Lys Ser Ile Val Glu Asn
        195                 200                 205

Asp Lys Asn Val Phe Gln Lys Asn Ser Glu Met Thr Tyr His Phe Lys
    210                 215                 220

Gln Trp Gly Ala Gly His Ser Val Ser Ile Ser Val Glu Ser Gly Ser
225                 230                 235                 240

Phe Val Leu Lys Pro Ser Asp Gln Phe Val Gly Asn Lys Leu Asp Leu
                245                 250                 255

Ile Leu Lys Gln Asp Ala Glu Gly Asn Tyr Arg Phe Asp Ser Ser Gln
            260                 265                 270

His Asn Lys Gly Asn Lys Asn Asn Ser Thr Gly Tyr Asn Glu Gln Ser
        275                 280                 285

Glu Glu Glu Cys
    290

<210> SEQ ID NO 59
<211> LENGTH: 1019
<212> TYPE: DNA
<213> ORGANISM: Salmonella enterica

<400> SEQUENCE: 59
ataatttaat gggcgatgtg tcagctgtca gttcatccgg gaacatttta ctgccgcagc      60
aggatgaggt tggcggttta tcagaagcat taaaaaaagc ggtggaaaaa cataagacag     120
aatattccgg tgataaaaaa gatcgcgact atggcgatgc tttcgtaatg cataaagaaa     180
cggctttacc gttattactg gcggcatggc gacatggcgc gccagcgaaa tcagaacatc     240
acaatggcaa cgtttctggt ctgcatcata cggaaaaag cgaactcagg attgctgaaa      300
aactgttgaa agtcactgct gaaaaatctg tcggtttgat ctctgcggag gccaaagtag     360
ataaatccgc agcgttgcta tcgtctaaaa ataggccgtt agaaagcgta agcggtaaaa     420
aattatctgc tgatttaaaa gctgtggaat ccgttagtga agtaaccgat aacgccacgg     480
gaatctctga cgataatatc aaggcattgc ctggggataa taaagccatc gcgggcgaag     540
gcgttcgtaa agagggcgcg ccgctggcg gggatgtcgc acctgcccga atggccgcag      600
ccaataccgg taagcctgaa gataaagatc ataaaaaggt taaagatgtt tctcagcttc     660
cgctgcaacc aaccactatc gccgatctta gccaattaac cggcggcgat gaaaaaatgc     720
ctttagcggc gcaatcaaag ccgatgatga ctattttttcc cactgccgat ggcgtgaaag     780
gagaggatag ctcgctgact taccgttttc agcgctgggg aaatgactat ccgtcaata      840 ttcaggcgcg gcaagcaggg gagttttcgt taataccgtc aaatacgcag gttgaacatc     900
gtttgcatga tcaatggcaa aacggtaatc cccagcgctg gcacctgacg cgagacgatc     960
aacaaaatcc gcagcagcaa cagcacagac agcaatctgg cgaggaggat gacgcctga    1019

<210> SEQ ID NO 60
<211> LENGTH: 336
<212> TYPE: PRT
<213> ORGANISM: Salmonella enterica

<400> SEQUENCE: 60

Met Gly Asp Val Ser Ala Val Ser Ser Ser Gly Asn Ile Leu Leu Pro
1               5                   10                  15

Gln Gln Asp Glu Val Gly Gly Leu Ser Glu Ala Leu Lys Lys Ala Val

```
            20                  25                  30

Glu Lys His Lys Thr Glu Tyr Ser Gly Asp Lys Lys Asp Arg Asp Tyr
        35                  40                  45

Gly Asp Ala Phe Val Met His Lys Glu Thr Ala Leu Pro Leu Leu Leu
    50                  55                  60

Ala Ala Trp Arg His Gly Ala Pro Ala Lys Ser Glu His His Asn Gly
65                  70                  75                  80
Asn Val Ser Gly Leu His His Asn Gly Lys Ser Glu Leu Arg Ile Ala
                85                  90                  95
Glu Lys Leu Leu Lys Val Thr Ala Glu Lys Ser Val Gly Leu Ile Ser
            100                 105                 110
Ala Glu Ala Lys Val Asp Lys Ser Ala Ala Leu Leu Ser Ser Lys Asn
        115                 120                 125

Arg Pro Leu Glu Ser Val Ser Gly Lys Lys Leu Ser Ala Asp Leu Lys
    130                 135                 140

Ala Val Glu Ser Val Ser Glu Val Thr Asp Asn Ala Thr Gly Ile Ser
145                 150                 155                 160
Asp Asp Asn Ile Lys Ala Leu Pro Gly Asp Asn Lys Ala Ile Ala Gly
                165                 170                 175
Glu Gly Val Arg Lys Glu Gly Ala Pro Leu Ala Arg Asp Val Ala Pro
            180                 185                 190
Ala Arg Met Ala Ala Ala Asn Thr Gly Lys Pro Glu Asp Lys Asp His
        195                 200                 205

Lys Lys Val Lys Asp Val Ser Gln Leu Pro Leu Gln Pro Thr Thr Ile
    210                 215                 220

Ala Asp Leu Ser Gln Leu Thr Gly Gly Asp Glu Lys Met Pro Leu Ala
225                 230                 235                 240
Ala Gln Ser Lys Pro Met Met Thr Ile Phe Pro Thr Ala Asp Gly Val
                245                 250                 255
Lys Gly Glu Asp Ser Ser Leu Thr Tyr Arg Phe Gln Arg Trp Gly Asn
            260                 265                 270
Asp Tyr Ser Val Asn Ile Gln Ala Arg Gln Ala Gly Glu Phe Ser Leu
        275                 280                 285

Ile Pro Ser Asn Thr Gln Val Glu His Arg Leu His Asp Gln Trp Gln
    290                 295                 300

Asn Gly Asn Pro Gln Arg Trp His Leu Thr Arg Asp Asp Gln Gln Asn
305                 310                 315                 320
Pro Gln Gln Gln Gln His Arg Gln Gln Ser Gly Glu Glu Asp Asp Ala
                325                 330                 335
```

<210> SEQ ID NO 61
<211> LENGTH: 1368
<212> TYPE: DNA
<213> ORGANISM: Yersinia pestis

<400> SEQUENCE: 61

```
atgaataaaa tcaccactcg ttccccatta gaacctgagt atcaacctct ggggaagccg      60
catcatgctt tgcaagcatg tgtcgatttt gagcaagcgc tgttgcataa taataagggg     120
aattgtcatc ccaaagaaga gtcgcttaaa cctgtacgtc cgcatgacct tggcaaaaaa     180
gaaggtcaga aaggagatgg cttgcgtgcg catgcgccat tagcggcgac gtctcaaccc     240
ggaaggaaag aggtaggatt aaaacctcaa cacaaccatc agaataatca tgatttcaac     300
ttatctccgc ttgccgaagg tgctaccaat agagcgcact tataccagca ggatagccgt     360
```

-continued

```
tttgatgacc gcgtagagag tattattaat gctctcatgc cattggcgcc cttttagag      420
ggggtgactt gtgaaacggg gacatcaagt gaatccccct gcgagccgtc tggacatgat     480
gagttatttg ttcagcaatc gcctatcgat tccgctcaac cagttcaatt gaatagcaag     540
ccgactgttc agccattgaa tccggctgct gacggcgcag aggttattgt atggtctgtc     600
ggtagggaaa ctccggccag tatagcaaaa aaccagcgcg atagcaggca aaaacgcctt     660
gcagaagaac cgttagctct tcatcaaaaa gcattgccag agatatgtcc cccggcagtt     720
agtgccacac cggatgatca tttggtagca agatggtgtg ctactcctgt gactgaggta     780
gcagaaaaat ctgctcgttt tccgtacaaa gcgacagtgc agtcagagca actggacatg     840
accgagctgg cggatcggtc ccaacatctt actgatggcg ttgatagcag caaagatacc     900
atcgaaccac cgcgaccaga aaactgttac cttccgcgcg aagaaacctt gccggagatg     960
tattccttgt cttttacagc accggttgtc acgccgggtg atcacctatt agcaacaatg    1020
cgcgcgacca ggctggcatc agtctcagag caacttatac agttagcaca gcgactagcg    1080
gtagaactag aactgcgcgg cggctcatcc caagtaaccc aattacacct taacttacct    1140
gaattggggg ctattatggt tcgtattgct gagattccgg gaaaactgca tgtagaactg    1200
atcgccagtc gggaagcttt aagaatttta gcgcagggaa gttatgatct tcttgagcga    1260
ttacaacgca ttgagccaac acaacttgat tttcaagcta gcgatgacag tgaacaggag    1320
tcacgtcaga aacgccacgt ctatgaggag tgggaggctg aagaatga                 1368
```

<210> SEQ ID NO 62
<211> LENGTH: 455
<212> TYPE: PRT
<213> ORGANISM: Yersinia pestis

<400> SEQUENCE: 62

```
Met Asn Lys Ile Thr Thr Arg Ser Pro Leu Glu Pro Glu Tyr Gln Pro
 1               5                  10                  15

Leu Gly Lys Pro His His Ala Leu Gln Ala Cys Val Asp Phe Glu Gln
            20                  25                  30

Ala Leu Leu His Asn Asn Lys Gly Asn Cys His Pro Lys Glu Glu Ser
        35                  40                  45

Leu Lys Pro Val Arg Pro His Asp Leu Gly Lys Lys Glu Gly Gln Lys
    50                  55                  60

Gly Asp Gly Leu Arg Ala His Ala Pro Leu Ala Ala Thr Ser Gln Pro
65                  70                  75                  80

Gly Arg Lys Glu Val Gly Leu Lys Pro Gln His Asn His Gln Asn Asn
                85                  90                  95

His Asp Phe Asn Leu Ser Pro Leu Ala Glu Gly Ala Thr Asn Arg Ala
            100                 105                 110

His Leu Tyr Gln Gln Asp Ser Arg Phe Asp Asp Arg Val Glu Ser Ile
        115                 120                 125

Ile Asn Ala Leu Met Pro Leu Ala Pro Phe Leu Glu Gly Val Thr Cys
    130                 135                 140

Glu Thr Gly Thr Ser Ser Glu Ser Pro Cys Glu Pro Ser Gly His Asp
145                 150                 155                 160

Glu Leu Phe Val Gln Gln Ser Pro Ile Asp Ser Ala Gln Pro Val Gln
                165                 170                 175

Leu Asn Ser Lys Pro Thr Val Gln Pro Leu Asn Pro Ala Ala Asp Gly
            180                 185                 190

Ala Glu Val Ile Val Trp Ser Val Gly Arg Glu Thr Pro Ala Ser Ile
```

```
    195                 200                 205
Ala Lys Asn Gln Arg Asp Ser Arg Gln Lys Arg Leu Ala Glu Glu Pro
    210                 215                 220

Leu Ala Leu His Gln Lys Ala Leu Pro Glu Ile Cys Pro Pro Ala Val
225                 230                 235                 240

Ser Ala Thr Pro Asp Asp His Leu Val Ala Arg Trp Cys Ala Thr Pro
                245                 250                 255

Val Thr Glu Val Ala Glu Lys Ser Ala Arg Phe Pro Tyr Lys Ala Thr
            260                 265                 270

Val Gln Ser Glu Gln Leu Asp Met Thr Glu Leu Ala Asp Arg Ser Gln
        275                 280                 285

His Leu Thr Asp Gly Val Asp Ser Ser Lys Asp Thr Ile Glu Pro Pro
    290                 295                 300

Arg Pro Glu Lys Leu Leu Leu Pro Arg Glu Glu Thr Leu Pro Glu Met
305                 310                 315                 320

Tyr Ser Leu Ser Phe Thr Ala Pro Val Val Thr Pro Gly Asp His Leu
                325                 330                 335

Leu Ala Thr Met Arg Ala Thr Arg Leu Ala Ser Val Ser Glu Gln Leu
            340                 345                 350

Ile Gln Leu Ala Gln Arg Leu Ala Val Glu Leu Glu Leu Arg Gly Gly
        355                 360                 365

Ser Ser Gln Val Thr Gln Leu His Leu Asn Leu Pro Glu Leu Gly Ala
    370                 375                 380

Ile Met Val Arg Ile Ala Glu Ile Pro Gly Lys Leu His Val Glu Leu
385                 390                 395                 400

Ile Ala Ser Arg Glu Ala Leu Arg Ile Leu Ala Gln Gly Ser Tyr Asp
                405                 410                 415

Leu Leu Glu Arg Leu Gln Arg Ile Glu Pro Thr Gln Leu Asp Phe Gln
            420                 425                 430

Ala Ser Asp Asp Ser Gln Glu Ser Arg Gln Lys Arg His Val Tyr
        435                 440                 445

Glu Glu Trp Glu Ala Glu Glu
    450                 455
```

<210> SEQ ID NO 63
<211> LENGTH: 417
<212> TYPE: DNA
<213> ORGANISM: Escherichia coli

<400> SEQUENCE: 63

```
ttgactagag tttctctaaa aagaaatttg atagagcctg tttcttttcg gccatcagat      60
gattggccgc aaggagaaga agttttaat gatattttt atcatataaa aaaaagatcg      120
cctgatacgt tgttcatacg aatggcttct ttatggaaga gattgtttta ctcctcgggc     180
cgaagacgac gctactttga agaaggggag cactcgttta gtattctttg tggaagatta    240
cgaggaattg ttttaacaat taatgtagt aacggaatca tttatctgtc tattaaagta     300
agcccaaata atagaaatca tgtttttta tcatcataaaa aagactatgt tttcgataag   360
ttaaaagaaa tctttcctga tgaagccatt gagttcacaa ttgaatatga aaattaa      417
```

<210> SEQ ID NO 64
<211> LENGTH: 138
<212> TYPE: PRT
<213> ORGANISM: Escherichia coli

<400> SEQUENCE: 64

```
Met Thr Arg Val Ser Leu Lys Arg Asn Leu Ile Glu Pro Val Ser Phe
1               5                   10                  15

Arg Pro Ser Asp Asp Trp Pro Gln Gly Glu Ser Phe Asn Asp Ile
            20                  25                  30

Phe Tyr His Ile Lys Lys Arg Ser Pro Asp Thr Leu Phe Ile Arg Met
        35                  40                  45

Ala Ser Leu Trp Lys Arg Leu Phe Tyr Ser Ser Gly Arg Arg Arg Arg
    50                  55                  60

Tyr Phe Glu Glu Gly Glu His Ser Phe Ser Ile Leu Cys Gly Arg Leu
65                  70                  75                  80

Arg Gly Ile Val Leu Thr Ile Lys Cys Ser Asn Gly Ile Ile Tyr Leu
                85                  90                  95

Ser Ile Lys Val Ser Pro Asn Asn Arg Asn His Val Phe Leu Tyr His
                100                 105                 110

Lys Lys Asp Tyr Val Phe Asp Lys Leu Lys Glu Ile Phe Pro Asp Glu
            115                 120                 125

Ala Ile Glu Phe Thr Ile Glu Tyr Glu Asn
    130                 135

<210> SEQ ID NO 65
<211> LENGTH: 1293
<212> TYPE: DNA
<213> ORGANISM: Shigella flexneri

<400> SEQUENCE: 65
atgagctata caaaattgct cactcaatta tcttttccta atagaatctc ggggccaatc      60
ttggaaacaa gtcttagcga tgtttcgatt ggtgagattt gtaacattca ggctggaatt     120
gaaagtaatg aaattgttgc aagagctcag gttgtaggat tcatgatga aaaaacaata     180 ttaagcttga ttggaaattc tcgtggactt tcacggcaaa cattgattaa gcccactgcc     240
cagtttcttc atacgcaagt cggccgtgga ttattgggag cagtagtcaa tcctttaggg     300
gaggttactg ataagtttgc tgttacggat aacagtgaaa ttctttatcg acctgtagat     360
aatgctcctc cgctatatag tgaaagggct gcaattgaga agccttttt aacaggtatt     420 aaggttattg attctttact cacgtgtggt gaaggacagc gaatggggat ttttgcgtca     480
gctggttgtg gcaaaacttt tctcatgaat atgctcattg aacatagtgg tgctgatata     540
tatgttattg ggttaattgg tgagcgaggt cgagaggtta ctgaaacggt tgattatttg     600
aaaaactctg agaaaaaaag caggtgtgtt ttagtatatg caacttcgga ttactcttcg     660
gttgatcgtt gtaatgctgc atatatagcc actgctatag ccgaattttt taggactgaa     720
ggacataaag tagcgctttt tattgattca ttaacaaggt atgccagagc attacgtgat     780
gtggccttag ccgctggaga atcacctgcc agaagaggct atccggtttc ggttttgat     840 agcttaccca gacttcttga aaggccagga aagttaaagg caggtggctc tattactgca     900
ttttacactg ttcttttgga ggatgatgat tttgctgatc cattagctga agaggtaaga     960
tccattttag atggacatat atatttgagc agaaatctag cccaaaaagg acaatttcct    1020
gcaattgatt ccttaaaaag tataagcagg gtatttacac aggttgttga tgaaaaacat    1080
cgtattatgg ccgctgcatt tcgggagcta ctttctgaaa tagaagagct aaggacaatt    1140
attgactttg gtaatacaa accgggggag aatgcctctc aggataaaat ctacaacaaa    1200
atatctgttt tgagagtttt tctgaagcaa gattatcgac tcggttttac ttatgagcag    1260
acaatggagc ttattggtga aacaattaga taa                                1293
```

<210> SEQ ID NO 66
<211> LENGTH: 430
<212> TYPE: PRT
<213> ORGANISM: Shigella flexneri

<400> SEQUENCE: 66

```
Met Ser Tyr Thr Lys Leu Leu Thr Gln Leu Ser Phe Pro Asn Arg Ile
1               5                   10                  15

Ser Gly Pro Ile Leu Glu Thr Ser Leu Ser Asp Val Ser Ile Gly Glu
                20                  25                  30

Ile Cys Asn Ile Gln Ala Gly Ile Glu Ser Asn Glu Ile Val Ala Arg
                35                  40                  45

Ala Gln Val Val Gly Phe His Asp Glu Lys Thr Ile Leu Ser Leu Ile
        50                  55                  60

Gly Asn Ser Arg Gly Leu Ser Arg Gln Thr Leu Ile Lys Pro Thr Ala
65                  70                  75                  80

Gln Phe Leu His Thr Gln Val Gly Arg Gly Leu Leu Gly Ala Val Val
                85                  90                  95

Asn Pro Leu Gly Glu Val Thr Asp Lys Phe Ala Val Thr Asp Asn Ser
                100                 105                 110

Glu Ile Leu Tyr Arg Pro Val Asp Asn Ala Pro Pro Leu Tyr Ser Glu
                115                 120                 125

Arg Ala Ala Ile Glu Lys Pro Phe Leu Thr Gly Ile Lys Val Ile Asp
        130                 135                 140

Ser Leu Leu Thr Cys Gly Glu Gly Gln Arg Met Gly Ile Phe Ala Ser
145                 150                 155                 160

Ala Gly Cys Gly Lys Thr Phe Leu Met Asn Met Leu Ile Glu His Ser
                165                 170                 175

Gly Ala Asp Ile Tyr Val Ile Gly Leu Ile Gly Glu Arg Gly Arg Glu
                180                 185                 190

Val Thr Glu Thr Val Asp Tyr Leu Lys Asn Ser Glu Lys Lys Ser Arg
                195                 200                 205

Cys Val Leu Val Tyr Ala Thr Ser Asp Tyr Ser Ser Val Asp Arg Cys
        210                 215                 220

Asn Ala Ala Tyr Ile Ala Thr Ala Ile Ala Glu Phe Phe Arg Thr Glu
225                 230                 235                 240

Gly His Lys Val Ala Leu Phe Ile Asp Ser Leu Thr Arg Tyr Ala Arg
                245                 250                 255

Ala Leu Arg Asp Val Ala Leu Ala Ala Gly Glu Ser Pro Ala Arg Arg
        260                 265                 270

Gly Tyr Pro Val Ser Val Phe Asp Ser Leu Pro Arg Leu Leu Glu Arg
                275                 280                 285

Pro Gly Lys Leu Lys Ala Gly Gly Ser Ile Thr Ala Phe Tyr Thr Val
                290                 295                 300

Leu Leu Glu Asp Asp Phe Ala Asp Pro Leu Ala Glu Glu Val Arg
305                 310                 315                 320

Ser Ile Leu Asp Gly His Ile Tyr Leu Ser Arg Asn Leu Ala Gln Lys
                325                 330                 335

Gly Gln Phe Pro Ala Ile Asp Ser Leu Lys Ser Ile Ser Arg Val Phe
                340                 345                 350

Thr Gln Val Val Asp Glu Lys His Arg Ile Met Ala Ala Ala Phe Arg
                355                 360                 365

Glu Leu Leu Ser Glu Ile Glu Glu Leu Arg Thr Ile Ile Asp Phe Gly
```

Glu Tyr Lys Pro Gly Glu Asn Ala Ser Gln Asp Lys Ile Tyr Asn Lys
385                 390                 395                 400

Ile Ser Val Val Glu Ser Phe Leu Lys Gln Asp Tyr Arg Leu Gly Phe
            405                 410                 415

Thr Tyr Glu Gln Thr Met Glu Leu Ile Gly Glu Thr Ile Arg
        420                 425                 430

<210> SEQ ID NO 67
<211> LENGTH: 1296
<212> TYPE: DNA
<213> ORGANISM: Salmonella enterica

<400> SEQUENCE: 67

```
atgaaaacac ctcgtttact gcaatatctg gcctacccac aaaaaataac cggcccaatt      60
attgaggcgg aattgcgcga tgtggccatt ggcgaactgt gtgaaatacg ccgtggctgg     120
caccaaaaac aggttgttgc acgtgcgcag gtggttggct acagcggga acgcaccgtg      180
ctgagcctta tcggcaatgc ccaggggctg agccgcgatg tcgtgcttta tcccactgga     240
cgtgcgttat cggcgtgggt gggatactcg gtattaggcg cggtgttgga tccgacaggg     300
aaaatcgttg agcgttttac ccctgaagtg gcgccgatta gcgaagaacg cgttattgat     360
gtcgcaccgc cgtcttacgc ttcacgcgtt ggcgtccgtg aaccgctgat taccggtgtg     420
cgcgcgattg acgggttatt gacctgtggc gtaggccagc gaatgggcat ttttgcctcc     480
gcaggatgcg gtaagaccat gctgatgcat atgctgatcg agcaaacgga ggcggatgtc     540
tttgttatcg gtcttatcgg tgaacgaggc cgtgaggtca ctgaattcgt ggatatgttg     600
cgcgcttcgc ataagaaaga aaatgcgtg ctggttttg ccacttccga tttcccctcg       660
gtcgatcgct gcaatgcggc gcaactggcg acaaccgtag cggaatattt tcgcgaccag     720
ggaaaacggg tcgtgctttt tatcgattcc atgacccgtt atgcgcgtgc tttgcgagac     780
gtggcactgg cgtcgggaga gcgtccggct cgtcgaggtt atcccgcctc cgtattcgat     840
aatttgcccc gcttgctgga acgcccaggg gcgaccagcg agggaagcat tactgccttt     900
tatacggtac tgctggaaag cgaggaagag gcggacccga tggcgatga aattcgctct      960
atccttgacg tcacctgta tctgagcaga aagctggccg gcagggaca ttacccggca     1020
atcgatgtac tgaaaagcgt aagccgcgtt tttggacaag tcacgacgcc gacacatgct    1080
gaacaggcat ctgccgtgcg taaattaatg acgcgtttgg aagagctcca gcttttcatt    1140
gacttgggag aatatcgtcc tggcgaaaat atcgataacg atcgggcgat gcagatgcgg    1200
gatagcctga agcctggtt atgccagccg gtagcgcagt attcatcctt tgatgacacg     1260
ttgagcggta tgaatgcatt cgctgaccag aattaa                              1296
```

<210> SEQ ID NO 68
<211> LENGTH: 431
<212> TYPE: PRT
<213> ORGANISM: Salmonella enterica

<400> SEQUENCE: 68

Met Lys Thr Pro Arg Leu Leu Gln Tyr Leu Ala Tyr Pro Gln Lys Ile
1               5                   10                  15

Thr Gly Pro Ile Ile Glu Ala Glu Leu Arg Asp Val Ala Ile Gly Glu
            20                  25                  30

Leu Cys Glu Ile Arg Arg Gly Trp His Gln Lys Gln Val Val Ala Arg
        35                  40                  45

Ala Gln Val Val Gly Leu Gln Arg Glu Arg Thr Val Leu Ser Leu Ile
            50                  55                  60

Gly Asn Ala Gln Gly Leu Ser Arg Asp Val Val Leu Tyr Pro Thr Gly
 65                  70                  75                  80

Arg Ala Leu Ser Ala Trp Val Gly Tyr Ser Val Leu Gly Ala Val Leu
                85                  90                  95

Asp Pro Thr Gly Lys Ile Val Glu Arg Phe Thr Pro Glu Val Ala Pro
            100                 105                 110

Ile Ser Glu Glu Arg Val Ile Asp Val Ala Pro Pro Ser Tyr Ala Ser
            115                 120                 125

Arg Val Gly Val Arg Glu Pro Leu Ile Thr Gly Val Arg Ala Ile Asp
            130                 135                 140

Gly Leu Leu Thr Cys Gly Val Gly Gln Arg Met Gly Ile Phe Ala Ser
145                 150                 155                 160

Ala Gly Cys Gly Lys Thr Met Leu Met His Met Leu Ile Glu Gln Thr
                165                 170                 175

Glu Ala Asp Val Phe Val Ile Gly Leu Ile Gly Glu Arg Gly Arg Glu
            180                 185                 190

Val Thr Glu Phe Val Asp Met Leu Arg Ala Ser His Lys Lys Glu Lys
            195                 200                 205

Cys Val Leu Val Phe Ala Thr Ser Asp Phe Pro Ser Val Asp Arg Cys
210                 215                 220

Asn Ala Ala Gln Leu Ala Thr Thr Val Ala Glu Tyr Phe Arg Asp Gln
225                 230                 235                 240

Gly Lys Arg Val Val Leu Phe Ile Asp Ser Met Thr Arg Tyr Ala Arg
                245                 250                 255

Ala Leu Arg Asp Val Ala Leu Ala Ser Gly Glu Arg Pro Ala Arg Arg
            260                 265                 270

Gly Tyr Pro Ala Ser Val Phe Asp Asn Leu Pro Arg Leu Leu Glu Arg
            275                 280                 285

Pro Gly Ala Thr Ser Glu Gly Ser Ile Thr Ala Phe Tyr Thr Val Leu
            290                 295                 300

Leu Glu Ser Glu Glu Ala Asp Pro Met Ala Asp Glu Ile Arg Ser
305                 310                 315                 320

Ile Leu Asp Gly His Leu Tyr Leu Ser Arg Lys Leu Ala Gly Gln Gly
                325                 330                 335

His Tyr Pro Ala Ile Asp Val Leu Lys Ser Val Ser Arg Val Phe Gly
            340                 345                 350

Gln Val Thr Thr Pro Thr His Ala Glu Gln Ala Ser Ala Val Arg Lys
            355                 360                 365

Leu Met Thr Arg Leu Glu Glu Leu Gln Leu Phe Ile Asp Leu Gly Glu
            370                 375                 380

Tyr Arg Pro Gly Glu Asn Ile Asp Asn Asp Arg Ala Met Gln Met Arg
385                 390                 395                 400

Asp Ser Leu Lys Ala Trp Leu Cys Gln Pro Val Ala Gln Tyr Ser Ser
                405                 410                 415

Phe Asp Asp Thr Leu Ser Gly Met Asn Ala Phe Ala Asp Gln Asn
            420                 425                 430

<210> SEQ ID NO 69
<211> LENGTH: 1233
<212> TYPE: DNA
<213> ORGANISM: Yersinia pestis

```
<400> SEQUENCE: 69
gtgacaggaa cgttattaaa agcggtagtg ccaggtgtgc gcatcggtga gttatgttac      60
ttacgtaacc ctgacaacag cctgtcttta caggctgaag tcataggttt tgcccaacat     120
caagcattac ttattccact tggtgaaatg tacgggatat cttctaatac tgaagttagc     180
ccgacaggga caatgcatca ggttggggtg ggtgaacatc tgctgggaca ggtgttggat     240
ggtttagggc agccttcga tgggggcat ctccctgaac cggcggcttg gtacccagtt      300
tatcaggatg ccccagcgcc gatgagccga aaacttatta ccacaccact ttctttgggg     360 atccggtta ttgacggttt gcttacctgt ggcgagggc aaagaatggg catcttcgcg      420
gccgccgggg gggggaaaag tacactgctt gcttcgctta ttcgtagtgc tgaagtagac     480
gtaaccgtgc tggcgcttat tggtgagcgt ggacgcgaag tgcgtgagtt tattgagtct     540
gatttaggcg aagagggtt acgcaaagcg ttctcgtgg tggccacctc ggatcggccc      600
tcaatggaaa gagccaaagc tggattcgtg gcgacatcta ttgctgaata ttttcgcgat     660
caagggaaac gcgtattgtt acttatggac tctgtaacac ggtttgctcg tgctcagcgt     720
gaaataggct tagctgcggg agaaccaccg actcgccgcg ttatcctcc gtcagtattt      780 gccgctttac cccgtttgat ggaaagggct ggtcagtcca gcaaagggtc aattacggct     840
ctctataccg tactggtcga aggggacgat atgaccgaac ccgtggccga cgaaacacgt     900
tcgatacttg atggtcatat tattctgtca cggaaattag cggcagctaa tcattatcct     960
gccattgacg tattacgttc agcgagcagg gtgatgaatc aaattgtcag caaggagcac    1020
aaaacctggg cggggactt acgccgttta ttggccaaat atgaagaagt ggaattgctg    1080
ttgcaaatcg gggagtacca gaaagggcaa gacaaagagg ccgatcaagc gattgaacgc    1140 atggggcga ttcgaggatg gctctgccag gggacgcacg agttaagcca tttcaatgag    1200
acgctgaact tattggagac gctgacccaa tga                                 1233

<210> SEQ ID NO 70
<211> LENGTH: 410
<212> TYPE: PRT
<213> ORGANISM: Yersinia pestis

<400> SEQUENCE: 70

Met Thr Gly Thr Leu Leu Lys Ala Val Val Pro Gly Val Arg Ile Gly
1               5                   10                  15

Glu Leu Cys Tyr Leu Arg Asn Pro Asp Asn Ser Leu Ser Leu Gln Ala
            20                  25                  30

Glu Val Ile Gly Phe Ala Gln His Gln Ala Leu Leu Ile Pro Leu Gly
        35                  40                  45

Glu Met Tyr Gly Ile Ser Ser Asn Thr Glu Val Ser Pro Thr Gly Thr
    50                  55                  60

Met His Gln Val Gly Val Gly Glu His Leu Leu Gly Gln Val Leu Asp
65                  70                  75                  80

Gly Leu Gly Gln Pro Phe Asp Gly Gly His Leu Pro Glu Pro Ala Ala
                85                  90                  95

Trp Tyr Pro Val Tyr Gln Asp Ala Pro Ala Pro Met Ser Arg Lys Leu
            100                 105                 110

Ile Thr Thr Pro Leu Ser Leu Gly Ile Arg Val Ile Asp Gly Leu Leu
        115                 120                 125

Thr Cys Gly Glu Gly Gln Arg Met Gly Ile Phe Ala Ala Ala Gly Gly
    130                 135                 140
```

```
Gly Lys Ser Thr Leu Leu Ala Ser Leu Ile Arg Ser Ala Glu Val Asp
145                 150                 155                 160

Val Thr Val Leu Ala Leu Ile Gly Glu Arg Gly Arg Glu Val Arg Glu
                165                 170                 175

Phe Ile Glu Ser Asp Leu Gly Glu Gly Leu Arg Lys Ala Val Leu
            180                 185                 190

Val Val Ala Thr Ser Asp Arg Pro Ser Met Glu Arg Ala Lys Ala Gly
            195                 200                 205

Phe Val Ala Thr Ser Ile Ala Glu Tyr Phe Arg Asp Gln Gly Lys Arg
    210                 215                 220

Val Leu Leu Leu Met Asp Ser Val Thr Arg Phe Ala Arg Ala Gln Arg
225                 230                 235                 240

Glu Ile Gly Leu Ala Ala Gly Glu Pro Pro Thr Arg Arg Gly Tyr Pro
                245                 250                 255

Pro Ser Val Phe Ala Ala Leu Pro Arg Leu Met Glu Arg Ala Gly Gln
            260                 265                 270

Ser Ser Lys Gly Ser Ile Thr Ala Leu Tyr Thr Val Leu Val Glu Gly
        275                 280                 285

Asp Asp Met Thr Glu Pro Val Ala Asp Glu Thr Arg Ser Ile Leu Asp
290                 295                 300

Gly His Ile Ile Leu Ser Arg Lys Leu Ala Ala Ala Asn His Tyr Pro
305                 310                 315                 320

Ala Ile Asp Val Leu Arg Ser Ala Ser Arg Val Met Asn Gln Ile Val
                325                 330                 335

Ser Lys Glu His Lys Thr Trp Ala Gly Asp Leu Arg Arg Leu Leu Ala
            340                 345                 350

Lys Tyr Glu Glu Val Glu Leu Leu Leu Gln Ile Gly Glu Tyr Gln Lys
        355                 360                 365

Gly Gln Asp Lys Glu Ala Asp Gln Ala Ile Glu Arg Met Gly Ala Ile
    370                 375                 380

Arg Gly Trp Leu Cys Gln Gly Thr His Glu Leu Ser His Phe Asn Glu
385                 390                 395                 400

Thr Leu Asn Leu Leu Glu Thr Leu Thr Gln
                405                 410

<210> SEQ ID NO 71
<211> LENGTH: 1341
<212> TYPE: DNA
<213> ORGANISM: Escherichia coli

<400> SEQUENCE: 71
atgatttcag agcatgattc tgtattggaa aaatacccac gtattcagaa agtgctcaat      60
agcactgtgc cggcattatc attaaattcg tctaccagat atgaaggcaa gattatcaat     120
atcggcggga cgattattaa ggcgcgttta ccaaaagcgc gtattggcgc ctttataag      180 atagaaccca gtcaacgttt agccgaggtg atcgctattg atgaagatga ggttttcttg     240
ttgccttttg agcatgtttc cggcatgtac tgtggtcagt ggttaagtta tcagggagat     300
gagttcaaga ttcgtgttgg agacgcacta cttgggcggc ttgttgatgg cataggcaga     360
ccaatggaga gtaatattgc tgcccccctat cttccgtttg aacgcagctt gtatgctgaa     420
ccaccagatc ctttattaag gcaggttatt gatcagccat ttatacttgg cgtcagggca     480
attgatgggc tactaacttg cggtattggg cagcgtatcg gtattttgc tggttcaggc     540 gttggtaaaa gtacgctttt ggggatgatt tgtaatggcg catccgcaga tattattgtc     600
```

```
cttgctctta tcggcgaacg tggtcgcgaa gtaaatgaat tcctcgcgct cttacctcaa    660
tccacgcttt ctaaatgtgt actggtcgtc acaacgtcag accgccccgc gctggaaagg    720
atgaaagccg catttacggc gacgactatt gcagagtact tccgcgatca aggtaaaaat    780
gtattattaa tgatggattc tgtaactcgt tatgcccgag ccgcacgtga tgttgggctt    840
gcatcgggag aacctgatgt aagggggggga ttccctccga gtgttttttc ttcgttaccc    900
aaattattag agcgagcggg gcctgcgcca aaaggttcaa taaccgcgat ttatacggtg    960
ttgttagaaa gcgataatgt taatgatcct attggcgatg aagtccgctc tattcttgat   1020
gggcacatcg tacttacccg agaacttgca gaggaaaacc atttccctgc aattgatatt   1080
ggtttaagtg ccagtcgtgt tatgcataac gttgttacat cggagcattt gcgtgcggcg   1140
gcagaatgca aaaagcttat tgcaacttat aaaaatgttg agctgcttat tcgtattggt   1200
gagtacacga tggggcaaga tcctgaagca gataaggcaa taaaaaatag gaattaatt   1260
cagaactttta tacaacaaag caccaaagat atcagtagtt acgaaaaaac gattgaaagc   1320
ctattcaaag tggttgcctg a                                             1341
```

<210> SEQ ID NO 72
<211> LENGTH: 446
<212> TYPE: PRT
<213> ORGANISM: Escherichia coli

<400> SEQUENCE: 72

```
Met Ile Ser Glu His Asp Ser Val Leu Glu Lys Tyr Pro Arg Ile Gln
1               5                   10                  15

Lys Val Leu Asn Ser Thr Val Pro Ala Leu Ser Leu Asn Ser Ser Thr
            20                  25                  30

Arg Tyr Glu Gly Lys Ile Ile Asn Ile Gly Gly Thr Ile Ile Lys Ala
        35                  40                  45

Arg Leu Pro Lys Ala Arg Ile Gly Ala Phe Tyr Lys Ile Glu Pro Ser
    50                  55                  60

Gln Arg Leu Ala Glu Val Ile Ala Ile Asp Glu Asp Glu Val Phe Leu
65                  70                  75                  80

Leu Pro Phe Glu His Val Ser Gly Met Tyr Cys Gly Gln Trp Leu Ser
                85                  90                  95

Tyr Gln Gly Asp Glu Phe Lys Ile Arg Val Gly Asp Ala Leu Leu Gly
            100                 105                 110

Arg Leu Val Asp Gly Ile Gly Arg Pro Met Glu Ser Asn Ile Ala Ala
        115                 120                 125

Pro Tyr Leu Pro Phe Glu Arg Ser Leu Tyr Ala Glu Pro Pro Asp Pro
    130                 135                 140

Leu Leu Arg Gln Val Ile Asp Gln Pro Phe Ile Leu Gly Val Arg Ala
145                 150                 155                 160

Ile Asp Gly Leu Leu Thr Cys Gly Ile Gly Gln Arg Ile Gly Ile Phe
                165                 170                 175

Ala Gly Ser Gly Val Gly Lys Ser Thr Leu Leu Gly Met Ile Cys Asn
            180                 185                 190

Gly Ala Ser Ala Asp Ile Ile Val Leu Ala Leu Ile Gly Glu Arg Gly
        195                 200                 205

Arg Glu Val Asn Glu Phe Leu Ala Leu Leu Pro Gln Ser Thr Leu Ser
    210                 215                 220

Lys Cys Val Leu Val Val Thr Thr Ser Asp Arg Pro Ala Leu Glu Arg
225                 230                 235                 240
```

Met Lys Ala Ala Phe Thr Ala Thr Thr Ile Ala Glu Tyr Phe Arg Asp
                245                 250                 255

Gln Gly Lys Asn Val Leu Leu Met Met Asp Ser Val Thr Arg Tyr Ala
            260                 265                 270

Arg Ala Ala Arg Asp Val Gly Leu Ala Ser Gly Glu Pro Asp Val Arg
        275                 280                 285

Gly Gly Phe Pro Pro Ser Val Phe Ser Ser Leu Pro Lys Leu Leu Glu
    290                 295                 300

Arg Ala Gly Pro Ala Pro Lys Gly Ser Ile Thr Ala Ile Tyr Thr Val
305                 310                 315                 320

Leu Leu Glu Ser Asp Asn Val Asn Asp Pro Ile Gly Asp Glu Val Arg
                325                 330                 335

Ser Ile Leu Asp Gly His Ile Val Leu Thr Arg Glu Leu Ala Glu Glu
            340                 345                 350

Asn His Phe Pro Ala Ile Asp Ile Gly Leu Ser Ala Ser Arg Val Met
        355                 360                 365

His Asn Val Val Thr Ser Glu His Leu Arg Ala Ala Glu Cys Lys
    370                 375                 380

Lys Leu Ile Ala Thr Tyr Lys Asn Val Glu Leu Leu Ile Arg Ile Gly
385                 390                 395                 400

Glu Tyr Thr Met Gly Gln Asp Pro Glu Ala Asp Lys Ala Ile Lys Asn
                405                 410                 415

Arg Lys Leu Ile Gln Asn Phe Ile Gln Gln Ser Thr Lys Asp Ile Ser
            420                 425                 430

Ser Tyr Glu Lys Thr Ile Glu Ser Leu Phe Lys Val Val Ala
        435                 440                 445

<210> SEQ ID NO 73
<211> LENGTH: 468
<212> TYPE: DNA
<213> ORGANISM: Shigella flexneri

<400> SEQUENCE: 73
atgtctttaa atatcaccga aaatgaaagc atctctactg cagtaattga tgcaattaac      60
tctggcgcta cactgaaaga tattaatgca attcctgatg atatgatgga tgacatttat     120
tcatatgctt atgacttttta caacaaagga agaatagagg aagctgaagt tttcttcagg     180
tttttatgta tatacgactt ttacaatgta gactacatta tgggactcgc agctatttat     240
cagataaaag aacagttcca acaagcagca gacctttatg ctgtcgcttt tgcattagga     300
aaaaatgact atacaccagt attccatact ggacaatgcc agcttcggtt gaaagccccc     360
ttaaaagcta agagtgcttc cgaactcgta attcaacaca gcaatgatga aaaattaaaa     420
ataaaagcac aatcatactt ggacgcaatt caggatatca aggagtaa                  468

<210> SEQ ID NO 74
<211> LENGTH: 155
<212> TYPE: PRT
<213> ORGANISM: Shigella flexneri

<400> SEQUENCE: 74

Met Ser Leu Asn Ile Thr Glu Asn Glu Ser Ile Ser Thr Ala Val Ile
1               5                   10                  15

Asp Ala Ile Asn Ser Gly Ala Thr Leu Lys Asp Ile Asn Ala Ile Pro
            20                  25                  30

Asp Asp Met Met Asp Asp Ile Tyr Ser Tyr Ala Tyr Asp Phe Tyr Asn
        35                  40                  45

```
Lys Gly Arg Ile Glu Glu Ala Glu Val Phe Phe Arg Phe Leu Cys Ile
    50                  55                  60

Tyr Asp Phe Tyr Asn Val Asp Tyr Ile Met Gly Leu Ala Ala Ile Tyr
65                  70                  75                  80

Gln Ile Lys Glu Gln Phe Gln Gln Ala Ala Asp Leu Tyr Ala Val Ala
                85                  90                  95

Phe Ala Leu Gly Lys Asn Asp Tyr Thr Pro Val Phe His Thr Gly Gln
            100                 105                 110

Cys Gln Leu Arg Leu Lys Ala Pro Leu Lys Ala Lys Glu Cys Phe Glu
                115                 120                 125

Leu Val Ile Gln His Ser Asn Asp Glu Lys Leu Lys Ile Lys Ala Gln
            130                 135                 140

Ser Tyr Leu Asp Ala Ile Gln Asp Ile Lys Glu
145                 150                 155

<210> SEQ ID NO 75
<211> LENGTH: 510
<212> TYPE: DNA
<213> ORGANISM: Salmonella enterica

<400> SEQUENCE: 75
caggagtaag taatggatta tcaaaataat gtcagcgaag aacgtgttgc ggaaatgatt      60
tgggatgccg ttagtgaagg cgccacgcta aaagacgttc atgggatccc tcaagatatg     120
atggacggtt tatatgctca tgcttatgag tttataacc agggacgact ggatgaagct     180
gagacgttct ttcgtttctt atgcatttat gattttaca atcccgatta ccatgggga      240 ctggcggcag tatgccaact gaaaaaacaa tttcagaaag catgtgacct ttatgcagta     300
gcgtttacgt tacttaaaaa tgattatcgc cccgtttttt ttaccgggca gtgtcaatta     360
ttaatgcgta aggcagcaaa agccagacag tgttttgaac ttgtcaatga acgtactgaa     420
gatgagtctc tgcgggcaaa agcgttggtc tatctggagg cgctaaaaac ggcggagaca     480
gagcagcaca gtgaacaaga aaaggaataa                                      510

<210> SEQ ID NO 76
<211> LENGTH: 165
<212> TYPE: PRT
<213> ORGANISM: Salmonella enterica

<400> SEQUENCE: 76

Met Asp Tyr Gln Asn Asn Val Ser Glu Arg Val Ala Glu Met Ile
1               5                   10                  15

Trp Asp Ala Val Ser Glu Gly Ala Thr Leu Lys Asp Val His Gly Ile
                20                  25                  30

Pro Gln Asp Met Met Asp Gly Leu Tyr Ala His Ala Tyr Glu Phe Tyr
            35                  40                  45

Asn Gln Gly Arg Leu Asp Glu Ala Glu Thr Phe Phe Arg Phe Leu Cys
        50                  55                  60

Ile Tyr Asp Phe Tyr Asn Pro Asp Tyr Thr Met Gly Leu Ala Ala Val
65                  70                  75                  80

Cys Gln Leu Lys Lys Gln Phe Gln Lys Ala Cys Asp Leu Tyr Ala Val
                85                  90                  95

Ala Phe Thr Leu Leu Lys Asn Asp Tyr Arg Pro Val Phe Phe Thr Gly
            100                 105                 110

Gln Cys Gln Leu Leu Met Arg Lys Ala Ala Lys Ala Arg Gln Cys Phe
                115                 120                 125
```

```
Glu Leu Val Asn Glu Arg Thr Glu Asp Glu Ser Leu Arg Ala Lys Ala
    130                 135                 140
Leu Val Tyr Leu Glu Ala Leu Lys Thr Ala Glu Thr Glu Gln His Ser
145                 150                 155                 160
Glu Gln Glu Lys Glu
                165
```

<210> SEQ ID NO 77
<211> LENGTH: 507
<212> TYPE: DNA
<213> ORGANISM: Yersinia pestis

<400> SEQUENCE: 77

```
atgcaacaag agacgacaga cactcaagaa taccagctgg caatggaatc cttcctaaaa     60
ggagggggaa ctatcgccat gctcaacgaa atttcaagtg acactttaga gcaactctac    120
tctcttgcat ttaaccaata ccagtcagga aaatacgagg atgctcacaa ggtctttcaa    180
gctctctgtg tgctagacca ctatgattca cgtttctttt tagggctagg cgcttgtcgt    240
caagccatgg ggcaatacga cttagcgatt catagctaca gctatggcgc cataatggat    300
ataaaagaac ctcgttttcc gtttcatgcg gccgaatgtt tactgcaaaa gggagagctt    360
gctgaagcag aaagtggctt gttcttggct caagagctta tcgcagacaa aactgagttt    420
aaggagcttt ccacccgagt tagctcaatg ttagaagcaa ttaaattgaa aaaggagatg    480
gaacatgagt gcgttgataa cccatga                                        507
```

<210> SEQ ID NO 78
<211> LENGTH: 168
<212> TYPE: PRT
<213> ORGANISM: Yersinia pestis

<400> SEQUENCE: 78

```
Met Gln Gln Glu Thr Thr Asp Thr Gln Glu Tyr Gln Leu Ala Met Glu
1               5                   10                  15

Ser Phe Leu Lys Gly Gly Gly Thr Ile Ala Met Leu Asn Glu Ile Ser
            20                  25                  30

Ser Asp Thr Leu Glu Gln Leu Tyr Ser Leu Ala Phe Asn Gln Tyr Gln
        35                  40                  45

Ser Gly Lys Tyr Glu Asp Ala His Lys Val Phe Gln Ala Leu Cys Val
    50                  55                  60

Leu Asp His Tyr Asp Ser Arg Phe Phe Leu Gly Leu Gly Ala Cys Arg
65                  70                  75                  80

Gln Ala Met Gly Gln Tyr Asp Leu Ala Ile His Ser Tyr Ser Tyr Gly
                85                  90                  95

Ala Ile Met Asp Ile Lys Glu Pro Arg Phe Pro Phe His Ala Ala Glu
            100                 105                 110

Cys Leu Leu Gln Lys Gly Glu Leu Ala Glu Ala Glu Ser Gly Leu Phe
        115                 120                 125

Leu Ala Gln Glu Leu Ile Ala Asp Lys Thr Glu Phe Lys Glu Leu Ser
    130                 135                 140

Thr Arg Val Ser Ser Met Leu Glu Ala Ile Lys Leu Lys Lys Glu Met
145                 150                 155                 160

Glu His Glu Cys Val Asp Asn Pro
                165
```

<210> SEQ ID NO 79

-continued

```
<211> LENGTH: 456
<212> TYPE: DNA
<213> ORGANISM: Escherichia coli

<400> SEQUENCE: 79
atgagcagga aatttagctc tctagaggat atttatgatt tctaccagga tggtggcaca    60
ttagcgtcat taacaaatct gacacaacaa gatctcaatg accttcattc ttatgcctat   120
acagcatatc aatctggtga tgtaataacc gcaagaaatc tattccattt gctcacatat   180
ctggaacact ggaattatga ctacacctta tctctgggct tatgccatca gcgtttatca   240
aatcatgaag atgcacaact gtgtttcgca cgctgtgcaa ctttagttat gcaagatccc   300
agggcatctt attattctgg aattagctac ttactcgtcg gaataagaa aatggccaag    360 aaagccttta aggcttgttt aatgtggtgt aatgaaaaag aaaaatacac tacatataaa   420
gaaaatatta aaaaattgtt aggtaataca gagtaa                             456

<210> SEQ ID NO 80
<211> LENGTH: 151
<212> TYPE: PRT
<213> ORGANISM: Escherichia coli

<400> SEQUENCE: 80

Met Ser Arg Lys Phe Ser Ser Leu Glu Asp Ile Tyr Asp Phe Tyr Gln
1               5                   10                  15

Asp Gly Gly Thr Leu Ala Ser Leu Thr Asn Leu Thr Gln Gln Asp Leu
            20                  25                  30

Asn Asp Leu His Ser Tyr Ala Tyr Thr Ala Tyr Gln Ser Gly Asp Val
        35                  40                  45

Ile Thr Ala Arg Asn Leu Phe His Leu Leu Thr Tyr Leu Glu His Trp
    50                  55                  60

Asn Tyr Asp Tyr Thr Leu Ser Leu Gly Leu Cys His Gln Arg Leu Ser
65                  70                  75                  80

Asn His Glu Asp Ala Gln Leu Cys Phe Ala Arg Cys Ala Thr Leu Val
                85                  90                  95

Met Gln Asp Pro Arg Ala Ser Tyr Tyr Ser Gly Ile Ser Tyr Leu Leu
            100                 105                 110

Val Gly Asn Lys Lys Met Ala Lys Lys Ala Phe Lys Ala Cys Leu Met
        115                 120                 125

Trp Cys Asn Glu Lys Glu Lys Tyr Thr Thr Tyr Lys Glu Asn Ile Lys
    130                 135                 140

Lys Leu Leu Gly Asn Thr Glu
145                 150

<210> SEQ ID NO 81
<211> LENGTH: 1029
<212> TYPE: DNA
<213> ORGANISM: Shigella flexneri

<400> SEQUENCE: 81
atggcaaata aaacagaaaa gccgacacct aaaaaactaa aggatgccgc aaaaaaagga    60
cagtcattta aatttaagga tttaacgact gttgttatta ttctggtagg gacatttact   120
ataatatcat tcttttcctt aagtgatgta atgctcttat acagatatgt aataattaat   180
gacttcgaaa ttaatgaggg taaatacttt tttgcagtgg ttattgtctt ttttaagata   240
attggcttcc cacttttttt ctgtgttctt tcggctgtgt tgccaacatt ggttcaaaca   300
aagtttgttc ttgcgactaa agctatcaag attgattttt cagtattaaa ccctgttaaa   360
```

```
gggttaaaaa aaatatttag tataaagaca ataaaagaat ttttcaaaag cattctgctt      420
cttattattc tagcattaac aacctatttc ttttggatta atgaccgaaa ataattttt      480 tctcaggtgt tttctagtgt tgatggctta tatcttattt gggggaggct gtttaaggat      540
ataatattat ttttcttggc attttctatt cttgttatta ttcttgactt tgtgattgag      600
ttcattttat acatgaaaga tatgatgatg ataaacagg agataaaaag agaatatata      660
gagcaagagg gacactttga gacaaagtcg agaaggcgtg agttgcatat cgagattctt      720
tcagagcaga ctaaatctga tatacgtaat tcaaaattag tggtaatgaa cccgactcat      780
attgcaattg gtatttattt taatccagaa atagcgcctg cacctttat ttctctcatt      840 gaaactaacc agtgtgcctt ggctgtcaga aaatatgcaa atgaagttgg tataccgact      900
gtgcgtgatg tgaaattagc tagaaaacta tataaaacac atacaaaata tagttttgtt      960
gattttgaac acttggatga agtcctacgt cttattgttt ggcttgagca ggttgaaaac     1020
actcattaa                                                             1029
```

<210> SEQ ID NO 82
<211> LENGTH: 342
<212> TYPE: PRT
<213> ORGANISM: Shigella flexneri

<400> SEQUENCE: 82

```
Met Ala Asn Lys Thr Glu Lys Pro Thr Pro Lys Lys Leu Lys Asp Ala
1               5                   10                  15

Ala Lys Lys Gly Gln Ser Phe Lys Phe Lys Asp Leu Thr Thr Val Val
            20                  25                  30

Ile Ile Leu Val Gly Thr Phe Thr Ile Ile Ser Phe Phe Ser Leu Ser
        35                  40                  45

Asp Val Met Leu Leu Tyr Arg Tyr Val Ile Ile Asn Asp Phe Glu Ile
    50                  55                  60

Asn Glu Gly Lys Tyr Phe Phe Ala Val Val Ile Val Phe Phe Lys Ile
65                  70                  75                  80

Ile Gly Phe Pro Leu Phe Phe Cys Val Leu Ser Ala Val Leu Pro Thr
                85                  90                  95

Leu Val Gln Thr Lys Phe Val Leu Ala Thr Lys Ala Ile Lys Ile Asp
            100                 105                 110

Phe Ser Val Leu Asn Pro Val Lys Gly Leu Lys Lys Ile Phe Ser Ile
        115                 120                 125

Lys Thr Ile Lys Glu Phe Phe Lys Ser Ile Leu Leu Leu Ile Ile Leu
    130                 135                 140

Ala Leu Thr Thr Tyr Phe Phe Trp Ile Asn Asp Arg Lys Ile Ile Phe
145                 150                 155                 160

Ser Gln Val Phe Ser Ser Val Asp Gly Leu Tyr Leu Ile Trp Gly Arg
                165                 170                 175

Leu Phe Lys Asp Ile Ile Leu Phe Phe Leu Ala Phe Ser Ile Leu Val
            180                 185                 190

Ile Ile Leu Asp Phe Val Ile Glu Phe Ile Leu Tyr Met Lys Asp Met
        195                 200                 205

Met Met Asp Lys Gln Glu Ile Lys Arg Glu Tyr Ile Glu Gln Glu Gly
    210                 215                 220

His Phe Glu Thr Lys Ser Arg Arg Arg Glu Leu His Ile Glu Ile Leu
225                 230                 235                 240

Ser Glu Gln Thr Lys Ser Asp Ile Arg Asn Ser Lys Leu Val Val Met
```

```
                245             250             255
Asn Pro Thr His Ile Ala Ile Gly Ile Tyr Phe Asn Pro Glu Ile Ala
            260                 265                 270

Pro Ala Pro Phe Ile Ser Leu Ile Glu Thr Asn Gln Cys Ala Leu Ala
        275                 280                 285

Val Arg Lys Tyr Ala Asn Glu Val Gly Ile Pro Thr Val Arg Asp Val
    290                 295                 300

Lys Leu Ala Arg Lys Leu Tyr Lys Thr His Thr Lys Tyr Ser Phe Val
305                 310                 315                 320

Asp Phe Glu His Leu Asp Glu Val Leu Arg Leu Ile Val Trp Leu Glu
                325                 330                 335

Gln Val Glu Asn Thr His
            340

<210> SEQ ID NO 83
<211> LENGTH: 1078
<212> TYPE: DNA
<213> ORGANISM: Salmonella enterica

<400> SEQUENCE: 83
gcgacgcatg tcctcgaata aaacagaaaa accgactaaa aaacggctgg aagactccgc        60 taaaaaggc cagtcattta aaagtaaaga tctcattatc gcctgcctga cgctgggagg       120
aattgcctat ctggtgtcgt atggctcatt taatgagttt atgggataa ttaagatcat       180 tattgcggat aattttgatc agagcatggc tgactacagt ttggccgttt ttgggatagg       240
gttaaaatat ctgattccat ttatgctgct ctgcttagtg tgttccgcat taccggcgtt       300
attacaggcc ggttttgtgc tggcgacaga agcattaaag cctaatttat cggcgttaaa       360
cccggtagaa ggggcaaaaa aactttttag tatgcgcacg gttaaagata cggtcaaaac       420
cctactgtat ctctcatcct ttgtggtggc cgccatcatt tgctggaaga aatataaggt       480
tgaaatcttt tctcagctaa atggcaatat tgtaggtatt gccgtcattt ggcgtgaact       540
tctcctcgca ttggtattaa cttgccttgc ttgcgcattg attgtcttat tattggatgc       600
tattgcggaa tatttcctga ccatgaaaga tatgaaaatg gataaggaag aagtgaagcg       660
tgaaatgaag gagcaggaag ggaacccaga ggttaaatct aaaagacgtg aagttcatat       720
ggaaattctg tctgaacagg tgaaatctga tattgaaaac tcacgcctga ttgttgccaa       780
ccccacgcat attacgatcg ggatttattt taaacccgaa ttgatgccga ttccgatgat       840
ctcggtgtat gaaacgaatc agcgcgcact ggccgtccgc gcctatgcgg agaaggttgg       900
cgtacctgtg atcgtcgata tcaaactggc gcgcagtctt ttcaaaaccc atcgccgtta       960
tgatctggtg agtctggaag aaattgatga agtttacgt cttctggttt ggctggaaga      1020
ggtagaaaac gcgggcaaag acgttattca gccacaagaa aacgaggtac ggcattga      1078

<210> SEQ ID NO 84
<211> LENGTH: 356
<212> TYPE: PRT
<213> ORGANISM: Salmonella enterica

<400> SEQUENCE: 84

Met Ser Ser Asn Lys Thr Glu Lys Pro Thr Lys Lys Arg Leu Glu Asp
1               5                   10                  15

Ser Ala Lys Lys Gly Gln Ser Phe Lys Ser Lys Asp Leu Ile Ile Ala
            20                  25                  30

Cys Leu Thr Leu Gly Gly Ile Ala Tyr Leu Val Ser Tyr Gly Ser Phe
```

```
            35                  40                  45
Asn Glu Phe Met Gly Ile Ile Lys Ile Ile Ile Ala Asp Asn Phe Asp
     50                  55                  60

Gln Ser Met Ala Asp Tyr Ser Leu Ala Val Phe Gly Ile Gly Leu Lys
 65                  70                  75                  80

Tyr Leu Ile Pro Phe Met Leu Leu Cys Leu Val Cys Ser Ala Leu Pro
                 85                  90                  95

Ala Leu Leu Gln Ala Gly Phe Val Leu Ala Thr Glu Ala Leu Lys Pro
            100                 105                 110

Asn Leu Ser Ala Leu Asn Pro Val Glu Gly Ala Lys Lys Leu Phe Ser
            115                 120                 125

Met Arg Thr Val Lys Asp Thr Val Lys Thr Leu Leu Tyr Leu Ser Ser
       130                 135                 140

Phe Val Val Ala Ala Ile Ile Cys Trp Lys Lys Tyr Lys Val Glu Ile
145                 150                 155                 160

Phe Ser Gln Leu Asn Gly Asn Ile Val Gly Ile Ala Val Ile Trp Arg
                165                 170                 175

Glu Leu Leu Leu Ala Leu Val Leu Thr Cys Leu Ala Cys Ala Leu Ile
            180                 185                 190

Val Leu Leu Leu Asp Ala Ile Ala Glu Tyr Phe Leu Thr Met Lys Asp
            195                 200                 205

Met Lys Met Asp Lys Glu Glu Val Lys Arg Glu Met Lys Glu Gln Glu
210                 215                 220

Gly Asn Pro Glu Val Lys Ser Lys Arg Arg Glu Val His Met Glu Ile
225                 230                 235                 240

Leu Ser Glu Gln Val Lys Ser Asp Ile Glu Asn Ser Arg Leu Ile Val
                245                 250                 255

Ala Asn Pro Thr His Ile Thr Ile Gly Ile Tyr Phe Lys Pro Glu Leu
            260                 265                 270

Met Pro Ile Pro Met Ile Ser Val Tyr Glu Thr Asn Gln Arg Ala Leu
       275                 280                 285

Ala Val Arg Ala Tyr Ala Glu Lys Val Gly Val Pro Val Ile Val Asp
290                 295                 300

Ile Lys Leu Ala Arg Ser Leu Phe Lys Thr His Arg Arg Tyr Asp Leu
305                 310                 315                 320

Val Ser Leu Glu Glu Ile Asp Glu Val Leu Arg Leu Leu Val Trp Leu
                325                 330                 335

Glu Glu Val Glu Asn Ala Gly Lys Asp Val Ile Gln Pro Gln Glu Asn
            340                 345                 350

Glu Val Arg His
       355

<210> SEQ ID NO 85
<211> LENGTH: 1065
<212> TYPE: DNA
<213> ORGANISM: Yersinia pestis

<400> SEQUENCE: 85
atgagcggag aaaagacaga gcaacccacc ccgaagaaaa tccgtgatgc gcgcaaaaag    60
ggacaggtag cgaaaagtaa ggaagtggtc tctactgcgc ttatcgtcgc gctgagtgcg   120
atgttaatgg gctttctga ctactatttc gagcatttta gtaagctgat gctaatcccc   180
gcagagcaga gctatcttcc tttctcgcag gcgcttagct atgtggttga caatgtgttg   240
ctcgagtttt tttatctctg ttttcctttg ttaacagtgg cggcattaat ggcgatcgca   300
```

```
tctcatgttg tgcagtatgg ttttcttata agtggtgaag caattaaacc ggatattaaa     360
aaaatcaatc caatagaggg tgccaagcgt atcttttcca tcaaaagttt agtggagttt     420
ctcaaatcca ttctcaaggt tgttttgctc agtatactca tctggataat cattaaggga     480
aatctagtca cactcttgca gttgccaacc tgtggaattg aatgtattac cccttttattg    540 gggcaaatac tccggcagtt gatggttatc tgtactgttg ctttgtggt catctccata      600 gccgactatg cctttgaata ctatcaatat attaaggaac ttaaaatgag caaggatgag     660
atcaaacgcg agtacaaaga atggagggt agcccagaaa tcaaaagcaa gcgtcgtcag      720
tttcatcaag agatccaatc gaggaacatg cgggaaaatg ttaaacgctc atcagtggtg     780
gtagctaatc cgacccatat tgctattggt attctttaca agcgagggga aacaccacta     840
ccgttggtaa cattcaaata taccgatgcc caagttcaga ctgtgcgcaa aatagcagaa     900
gaagaagggg tgcctatttt acaacgtatc ccattagccc gtgctcttta ttgggatgcg     960
ctcgtcgatc actatattcc ggctgagcaa atagaggcca cagctgaagt gctacgatgg    1020
ctagaaaggc aaaatatcga gaacaacat tccgaaatgt tataa                     1065
```

<210> SEQ ID NO 86
<211> LENGTH: 354
<212> TYPE: PRT
<213> ORGANISM: Yersinia pestis

<400> SEQUENCE: 86

```
Met Ser Gly Glu Lys Thr Glu Gln Pro Thr Pro Lys Lys Ile Arg Asp
1               5                   10                  15

Ala Arg Lys Lys Gly Gln Val Ala Lys Ser Lys Glu Val Val Ser Thr
            20                  25                  30

Ala Leu Ile Val Ala Leu Ser Ala Met Leu Met Gly Leu Ser Asp Tyr
        35                  40                  45

Tyr Phe Glu His Phe Ser Lys Leu Met Leu Ile Pro Ala Glu Gln Ser
    50                  55                  60

Tyr Leu Pro Phe Ser Gln Ala Leu Ser Tyr Val Val Asp Asn Val Leu
65                  70                  75                  80

Leu Glu Phe Phe Tyr Leu Cys Phe Pro Leu Leu Thr Val Ala Ala Leu
                85                  90                  95

Met Ala Ile Ala Ser His Val Val Gln Tyr Gly Phe Leu Ile Ser Gly
            100                 105                 110

Glu Ala Ile Lys Pro Asp Ile Lys Lys Ile Asn Pro Ile Glu Gly Ala
        115                 120                 125

Lys Arg Ile Phe Ser Ile Lys Ser Leu Val Glu Phe Leu Lys Ser Ile
    130                 135                 140

Leu Lys Val Val Leu Leu Ser Ile Leu Ile Trp Ile Ile Lys Gly
145                 150                 155                 160

Asn Leu Val Thr Leu Leu Gln Leu Pro Thr Cys Gly Ile Glu Cys Ile
                165                 170                 175

Thr Pro Leu Leu Gly Gln Ile Leu Arg Gln Leu Met Val Ile Cys Thr
            180                 185                 190

Val Gly Phe Val Val Ile Ser Ile Ala Asp Tyr Ala Phe Glu Tyr Tyr
        195                 200                 205

Gln Tyr Ile Lys Glu Leu Lys Met Ser Lys Asp Glu Ile Lys Arg Glu
    210                 215                 220

Tyr Lys Glu Met Glu Gly Ser Pro Glu Ile Lys Ser Lys Arg Arg Gln
225                 230                 235                 240
```

```
Phe His Gln Glu Ile Gln Ser Arg Asn Met Arg Glu Asn Val Lys Arg
                245                 250                 255

Ser Ser Val Val Val Ala Asn Pro Thr His Ile Ala Ile Gly Ile Leu
            260                 265                 270

Tyr Lys Arg Gly Glu Thr Pro Leu Pro Leu Val Thr Phe Lys Tyr Thr
        275                 280                 285

Asp Ala Gln Val Gln Thr Val Arg Lys Ile Ala Glu Glu Gly Val
    290                 295                 300

Pro Ile Leu Gln Arg Ile Pro Leu Ala Arg Ala Leu Tyr Trp Asp Ala
305                 310                 315                 320

Leu Val Asp His Tyr Ile Pro Ala Glu Gln Ile Glu Ala Thr Ala Glu
                325                 330                 335

Val Leu Arg Trp Leu Glu Arg Gln Asn Ile Glu Lys Gln His Ser Glu
            340                 345                 350

Met Leu

<210> SEQ ID NO 87
<211> LENGTH: 1038
<212> TYPE: DNA
<213> ORGANISM: Escherichia coli

<400> SEQUENCE: 87
atgagtgaaa aacagaaaaa gcccacaccc aaaaaactga gggatctaaa aagaagggc      60 gatgtaacaa aaagtgaaga ggtaatggct gcagtgcagt cattaatctt attttcattt    120
ttttctttat atggcatgag ttttttttgtt gatatagttg ggttagttaa tacgacaata   180
gactcgctaa atagaccgtt tttgtatgcc attcgagaaa tattaggtgc ggtgttaaat    240
atatttttat tatatatttt gccaatttct ttgattgtct ttgttggaac tgttacgact    300
ggtgtatcac aaataggatt catctttgcg gttgaaaaaa taaaaccatc ggctcagaag    360
attagtgtaa aaataaccct gaaaatatt ttttctgtaa agagcatttt tgagctactt     420
aaatcagtat ttaagttagt gataattgtt ctcattttttt attttatggg gcattcatat   480
gcaaatgagt ttgctaattt cacaggactg aacgcatatc aagctcttgt cgttgttgcc   540
ttttttgttt ttcttttatg gaaaggcgtg ctattcggat atctactctt ttcagtatttt  600 gatttctggt ccagaagca tgagggactg aagaaaatga aatgagtaa agatgaggtg     660 aaacgagaag ccaaggatac tgatggtaac cctgaaatta aggggagcg ccgtcgcctt    720 cattccgaga tacaaagtgg aagtttggcg aataacatca aaaatcaac cgttattgtt    780 aaaaacccga ctcacattgc gatttgccta tactataaac ttggggagac tccattacct   840
ttagttattg aaacaggaaa agatgccaaa gctctacaga tcattaaact ggctgaactc    900
tatgatattc cagtgattga agatattcct ttagcaagaa gtctctataa gaatacat     960 aaaggacaat atataacaga agactttttt gaacctgtgg cacaattgat tcgtattgcg   1020
atagaccttg attattaa                                                  1038

<210> SEQ ID NO 88
<211> LENGTH: 345
<212> TYPE: PRT
<213> ORGANISM: Escherichia coli

<400> SEQUENCE: 88

Met Ser Glu Lys Thr Glu Lys Pro Thr Pro Lys Lys Leu Arg Asp Leu
1               5                   10                  15
```

-continued

```
Lys Lys Lys Gly Asp Val Thr Lys Ser Glu Val Met Ala Ala Val
                20                  25                  30

Gln Ser Leu Ile Leu Phe Ser Phe Ser Leu Tyr Gly Met Ser Phe
         35                  40                  45

Phe Val Asp Ile Val Gly Leu Val Asn Thr Thr Ile Asp Ser Leu Asn
 50                  55                  60

Arg Pro Phe Leu Tyr Ala Ile Arg Glu Ile Leu Gly Ala Val Leu Asn
 65                  70                  75                  80

Ile Phe Leu Leu Tyr Ile Leu Pro Ile Ser Leu Ile Val Phe Val Gly
                 85                  90                  95

Thr Val Thr Thr Gly Val Ser Gln Ile Gly Phe Ile Phe Ala Val Glu
             100                 105                 110

Lys Ile Lys Pro Ser Ala Gln Lys Ile Ser Val Lys Asn Asn Leu Lys
         115                 120                 125

Asn Ile Phe Ser Val Lys Ser Ile Phe Glu Leu Leu Lys Ser Val Phe
         130                 135                 140

Lys Leu Val Ile Ile Val Leu Ile Phe Tyr Phe Met Gly His Ser Tyr
145                 150                 155                 160

Ala Asn Glu Phe Ala Asn Phe Thr Gly Leu Asn Ala Tyr Gln Ala Leu
                 165                 170                 175

Val Val Val Ala Phe Phe Val Phe Leu Leu Trp Lys Gly Val Leu Phe
             180                 185                 190

Gly Tyr Leu Leu Phe Ser Val Phe Asp Phe Trp Phe Gln Lys His Glu
         195                 200                 205

Gly Leu Lys Lys Met Lys Met Ser Lys Asp Glu Val Lys Arg Glu Ala
         210                 215                 220

Lys Asp Thr Asp Gly Asn Pro Glu Ile Lys Gly Glu Arg Arg Leu
225                 230                 235                 240

His Ser Glu Ile Gln Ser Gly Ser Leu Ala Asn Asn Ile Lys Lys Ser
                 245                 250                 255

Thr Val Ile Val Lys Asn Pro Thr His Ile Ala Ile Cys Leu Tyr Tyr
             260                 265                 270

Lys Leu Gly Glu Thr Pro Leu Pro Leu Val Ile Glu Thr Gly Lys Asp
         275                 280                 285

Ala Lys Ala Leu Gln Ile Ile Lys Leu Ala Glu Leu Tyr Asp Ile Pro
         290                 295                 300

Val Ile Glu Asp Ile Pro Leu Ala Arg Ser Leu Tyr Lys Asn Ile His
305                 310                 315                 320

Lys Gly Gln Tyr Ile Thr Glu Asp Phe Phe Glu Pro Val Ala Gln Leu
                 325                 330                 335

Ile Arg Ile Ala Ile Asp Leu Asp Tyr
             340                 345
```

<210> SEQ ID NO 89
<211> LENGTH: 1068
<212> TYPE: DNA
<213> ORGANISM: Shigella flexneri

<400> SEQUENCE: 89

| | | | | |
|---|---|---|---|---|
| atgcttgatg ttaaaaatac aggagttttt agctctgcat tcattgatag gttgaatgca | | | | 60 |
| atgacaaatt cagatgatgg agatgagact gctgatgcag agcttgattc tggcttggct | | | | 120 |
| aatagcaagt atattgactc atctgatgag atggcttccg ctctttcgtc atttataaac | | | | 180 |
| agaagagacc ttgagaaact gaaggaaca aatagtgata gtcaggaacg tattttagat | | | | 240 |

```
ggggaagaag atgaaattaa tcacaagatt tttgatttaa agagaacgtt aaaagataac      300
cttcctctag atcgggattt tatagacaga ctaaagagat attttaaaga tccaagtgat      360
caagtcttag cattaaggga acttttgaat gaaaaagatc ttactgctga acaagtcgaa      420
ttattaacta aaattattaa tgagataata tcaggtagtg aaaaaagtgt taatgctgga      480
ataaattcag ctatacaggc taaattattt ggcaacaaaa tgaaacttga accacagctt      540
ttgcgtgcat gttatcgtgg ttttatcatg gggaacatat caacaacaga tcagtatata      600
gaatggcttg gtaattttgg ttttaatcac agacatacaa ttgtgaattt tgtagagcag      660
tcactgattg tagacatgga ttctgagaaa ccgagctgta atgcttatga gtttggtttt      720
gtgttatcta aattaattgc aattaagatg attagaactt cagacgtaat ttttatgaag      780
aaactggaat cctcaagctt gctaaaagat ggcagtttaa gtgcagagca gctattgcta      840
actttattat atattttca atatccaagt gaaagtgagc aaattcttac ttctgttata       900
gaagtatcac gagccagtca tgaggattct gtagtgtatc aaacatatct atcttctgtt      960
aatgaaagtc ctcatgatat atttaaaagt gaaagtgaaa gagaaattgc gatcaatatt     1020
ctacgagagc ttgtcacaag tgcatacaag aaagagcttt ctagataa                   1068
```

<210> SEQ ID NO 90
<211> LENGTH: 355
<212> TYPE: PRT
<213> ORGANISM: Shigella flexneri

<400> SEQUENCE: 90

```
Met Leu Asp Val Lys Asn Thr Gly Val Phe Ser Ser Ala Phe Ile Asp
1               5                   10                  15

Arg Leu Asn Ala Met Thr Asn Ser Asp Asp Gly Asp Glu Thr Ala Asp
            20                  25                  30

Ala Glu Leu Asp Ser Gly Leu Ala Asn Ser Lys Tyr Ile Asp Ser Ser
        35                  40                  45

Asp Glu Met Ala Ser Ala Leu Ser Ser Phe Ile Asn Arg Arg Asp Leu
    50                  55                  60

Glu Lys Leu Lys Gly Thr Asn Ser Asp Ser Gln Glu Arg Ile Leu Asp
65                  70                  75                  80

Gly Glu Glu Asp Glu Ile Asn His Lys Ile Phe Asp Leu Lys Arg Thr
                85                  90                  95

Leu Lys Asp Asn Leu Pro Leu Asp Arg Asp Phe Ile Asp Arg Leu Lys
            100                 105                 110

Arg Tyr Phe Lys Asp Pro Ser Asp Gln Val Leu Ala Leu Arg Glu Leu
        115                 120                 125

Leu Asn Glu Lys Asp Leu Thr Ala Glu Gln Val Glu Leu Leu Thr Lys
    130                 135                 140

Ile Ile Asn Glu Ile Ile Ser Gly Ser Glu Lys Ser Val Asn Ala Gly
145                 150                 155                 160

Ile Asn Ser Ala Ile Gln Ala Lys Leu Phe Gly Asn Lys Met Lys Leu
                165                 170                 175

Glu Pro Gln Leu Leu Arg Ala Cys Tyr Arg Gly Phe Ile Met Gly Asn
            180                 185                 190

Ile Ser Thr Thr Asp Gln Tyr Ile Glu Trp Leu Gly Asn Phe Gly Phe
        195                 200                 205

Asn His Arg His Thr Ile Val Asn Phe Val Glu Gln Ser Leu Ile Val
    210                 215                 220

Asp Met Asp Ser Glu Lys Pro Ser Cys Asn Ala Tyr Glu Phe Gly Phe
```

```
                225                 230                 235                 240
        Val Leu Ser Lys Leu Ile Ala Ile Lys Met Ile Arg Thr Ser Asp Val
                            245                 250                 255

Ile Phe Met Lys Lys Leu Glu Ser Ser Ser Leu Leu Lys Asp Gly Ser
                            260                 265                 270

Leu Ser Ala Glu Gln Leu Leu Leu Thr Leu Leu Tyr Ile Phe Gln Tyr
                        275                 280                 285

Pro Ser Glu Ser Glu Gln Ile Leu Thr Ser Val Ile Glu Val Ser Arg
                    290                 295                 300

Ala Ser His Glu Asp Ser Val Val Tyr Gln Thr Tyr Leu Ser Ser Val
        305                 310                 315                 320

Asn Glu Ser Pro His Asp Ile Phe Lys Ser Glu Ser Glu Arg Glu Ile
                            325                 330                 335

Ala Ile Asn Ile Leu Arg Glu Leu Val Thr Ser Ala Tyr Lys Lys Glu
                        340                 345                 350

Leu Ser Arg
                355

<210> SEQ ID NO 91
<211> LENGTH: 1127
<212> TYPE: DNA
<213> ORGANISM: Salmonella enterica

<400> SEQUENCE: 91
gcaattaaat gattcctggc tcaacctccg gtatttcatt ttccagaata ttgtcccggc      60
agacatctca tcaggatgcg acccagcata ctgatgcgca acaggcggaa atacaacagg    120
ccgcagagga ttcgtctcca ggggcggaag tacaaaaatt tgtccagtcg acggacgaaa    180
tgtcagcggc gctggcgcaa tttcgtaacc gtcgcgatta tgaaaaaaaa tccagtaatt    240
tatctaacag ttttgaacgc gtgctggagg atgaggcttt accgaaggcg aagcaaatct    300
taaagctaat tagcgtacat gcggcgcgt tagaagattt tttacgtcag gcgcgtagct    360
tatttcctga ccccagtgat ttagtccttg tgttacgcga attgcttcgt cgtaaagacc    420
tggaagagat cgtgcggaaa aagctggagt cgttacttaa gcacgttgaa gagcaaaccg    480
atccgaagac cctcaaggca gggattaatt gtgcgttgaa ggcccggctt tttgggaaaa    540
cattatcgtt aaaaccaggc ttattgcgcg ccagctatcg gcaatttatc cagagtgaat    600
cacatgaagt ggagatttac tctgactgga tagccagtta tggctatcaa cgtcgactgg    660
tggtactgga tttttattgag ggttcgctat taaccgatat tgacgcgaat gacgccagct    720
gttcgcgcct ggagtttggc cagcttttac gacgcctgac gcaacttaaa atgttgcgct    780
ccgctgacct actgtttgtg agtacattgt tgtcgtattc gtttaccaaa gcgtttaatg    840
cggaggagtc gtcgtggtta ctactgatgc tttcgctatt gcaacagcca catgaagtgg    900
attcgctgtt agccgatatt ataggtttga atgcgttatt gcttagtcat aaagaacatg    960
catccttttt gcagatattt tatcaagtat gtaaagccat accctcttca ctctttttatg   1020 aagaatattg gcaggaagaa ttgttaatgg cgttacgtag tatgaccgat attgcctaca   1080
agcatgaaat ggcagaacag cgtcgtacta ttgaaaagct gtcttaa                 1127

<210> SEQ ID NO 92
<211> LENGTH: 372
<212> TYPE: PRT
<213> ORGANISM: Salmonella enterica

<400> SEQUENCE: 92
```

```
Met Ile Pro Gly Ser Thr Ser Gly Ile Ser Phe Ser Arg Ile Leu Ser
1               5                   10                  15

Arg Gln Thr Ser His Gln Asp Ala Thr Gln His Thr Asp Ala Gln Gln
            20                  25                  30

Ala Glu Ile Gln Gln Ala Ala Glu Asp Ser Ser Pro Gly Ala Glu Val
        35                  40                  45

Gln Lys Phe Val Gln Ser Thr Asp Glu Met Ser Ala Ala Leu Ala Gln
50                  55                  60

Phe Arg Asn Arg Arg Asp Tyr Glu Lys Lys Ser Ser Asn Leu Ser Asn
65                  70                  75                  80

Ser Phe Glu Arg Val Leu Glu Asp Glu Ala Leu Pro Lys Ala Lys Gln
                85                  90                  95

Ile Leu Lys Leu Ile Ser Val His Gly Gly Ala Leu Glu Asp Phe Leu
            100                 105                 110

Arg Gln Ala Arg Ser Leu Phe Pro Asp Pro Ser Asp Leu Val Leu Val
        115                 120                 125

Leu Arg Glu Leu Leu Arg Arg Lys Asp Leu Glu Glu Ile Val Arg Lys
130                 135                 140

Lys Leu Glu Ser Leu Lys His Val Glu Glu Gln Thr Asp Pro Lys
145                 150                 155                 160

Thr Leu Lys Ala Gly Ile Asn Cys Ala Leu Lys Ala Arg Leu Phe Gly
                165                 170                 175

Lys Thr Leu Ser Leu Lys Pro Gly Leu Leu Arg Ala Ser Tyr Arg Gln
            180                 185                 190

Phe Ile Gln Ser Glu Ser His Glu Val Glu Ile Tyr Ser Asp Trp Ile
        195                 200                 205

Ala Ser Tyr Gly Tyr Gln Arg Arg Leu Val Val Leu Asp Phe Ile Glu
210                 215                 220

Gly Ser Leu Leu Thr Asp Ile Asp Ala Asn Asp Ala Ser Cys Ser Arg
225                 230                 235                 240

Leu Glu Phe Gly Gln Leu Leu Arg Arg Leu Thr Gln Leu Lys Met Leu
                245                 250                 255

Arg Ser Ala Asp Leu Leu Phe Val Ser Thr Leu Leu Ser Tyr Ser Phe
            260                 265                 270

Thr Lys Ala Phe Asn Ala Glu Glu Ser Ser Trp Leu Leu Leu Met Leu
        275                 280                 285

Ser Leu Leu Gln Gln Pro His Glu Val Asp Ser Leu Leu Ala Asp Ile
290                 295                 300

Ile Gly Leu Asn Ala Leu Leu Ser His Lys Glu His Ala Ser Phe
305                 310                 315                 320

Leu Gln Ile Phe Tyr Gln Val Cys Lys Ala Ile Pro Ser Ser Leu Phe
                325                 330                 335

Tyr Glu Glu Tyr Trp Gln Glu Leu Leu Met Ala Leu Arg Ser Met
            340                 345                 350

Thr Asp Ile Ala Tyr Lys His Glu Met Ala Glu Gln Arg Thr Ile
        355                 360                 365

Glu Lys Leu Ser
    370

<210> SEQ ID NO 93
<211> LENGTH: 882
<212> TYPE: DNA
<213> ORGANISM: Yersinia pestis
```

<400> SEQUENCE: 93

```
atgacgacgc ttcataacct atcttatggc aataccccgc tgcataatga gcgtccagag      60
attgccagta gtcagatcgt aaatcagact ctgggtcaat tcggggaga atctgtgcag      120
atagtcagcg gcactctgca gtctatagct gatatggcag aagaggtaac atttgtcttc     180
tccgagcgta aggagttctc cctcgacaaa cgcaaattaa gtgacagcca ggctcgagtt    240
agcgacgttg aggagcaggt taatcaatac cttagcaaag ttccagagtt ggaacaaaaa    300
cagaatgtga gtgagctgct cagtctgttg agtaacagcc ccaatataag cttgtcccag    360
ttaaaggctt atctggaggg gaaatcagaa gaaccgagtg agcaattcaa aatgctctgc    420
ggcttgcgtg atgccctgaa agggcgccct gaattagcac atctttcgca tttggttgaa    480
caagctctgg tcagcatggc tgaagagcaa ggagaaacca ttgtattggg tgccaggata    540
accccggaag cgtacagaga atcccagtcg ggtgttaatc cactgcagcc gctccgtgat    600
acctaccgcg atgcagtgat gggttatcaa ggaatttatg cgatctggag tgatttacaa    660
aaacgttttc ctaatgggga tatagactcg gtgatattat tcctgcaaaa ggcgcttagt    720
gcagatctac aaagtcaaca aagcgggtct ggacgggaaa aattaggaat agttattagt    780
gacttacaga agctaaagga gtttggtagc gtgagtgacc aagttaaagg attttggcaa    840
ttttttttcag agggtaaaac taatggcgta cgacctttct ga                      882
```

<210> SEQ ID NO 94
<211> LENGTH: 293
<212> TYPE: PRT
<213> ORGANISM: Yersinia pestis

<400> SEQUENCE: 94

```
Met Thr Thr Leu His Asn Leu Ser Tyr Gly Asn Thr Pro Leu His Asn
1               5                   10                  15

Glu Arg Pro Glu Ile Ala Ser Ser Gln Ile Val Asn Gln Thr Leu Gly
            20                  25                  30

Gln Phe Arg Gly Glu Ser Val Gln Ile Val Ser Gly Thr Leu Gln Ser
        35                  40                  45

Ile Ala Asp Met Ala Glu Glu Val Thr Phe Val Phe Ser Glu Arg Lys
    50                  55                  60

Glu Phe Ser Leu Asp Lys Arg Lys Leu Ser Asp Ser Gln Ala Arg Val
65                  70                  75                  80

Ser Asp Val Glu Glu Gln Val Asn Gln Tyr Leu Ser Lys Val Pro Glu
                85                  90                  95

Leu Glu Gln Lys Gln Asn Val Ser Glu Leu Leu Ser Leu Leu Ser Asn
            100                 105                 110

Ser Pro Asn Ile Ser Leu Ser Gln Leu Lys Ala Tyr Leu Glu Gly Lys
        115                 120                 125

Ser Glu Glu Pro Ser Glu Gln Phe Lys Met Leu Cys Gly Leu Arg Asp
    130                 135                 140

Ala Leu Lys Gly Arg Pro Glu Leu Ala His Leu Ser His Leu Val Glu
145                 150                 155                 160

Gln Ala Leu Val Ser Met Ala Glu Glu Gln Gly Glu Thr Ile Val Leu
                165                 170                 175

Gly Ala Arg Ile Thr Pro Glu Ala Tyr Arg Glu Ser Gln Ser Gly Val
            180                 185                 190

Asn Pro Leu Gln Pro Leu Arg Asp Thr Tyr Arg Asp Ala Val Met Gly
        195                 200                 205
```

```
Tyr Gln Gly Ile Tyr Ala Ile Trp Ser Asp Leu Gln Lys Arg Phe Pro
    210                 215                 220

Asn Gly Asp Ile Asp Ser Val Ile Leu Phe Leu Gln Lys Ala Leu Ser
225                 230                 235                 240

Ala Asp Leu Gln Ser Gln Gln Ser Gly Ser Arg Glu Lys Leu Gly
                245                 250                 255

Ile Val Ile Ser Asp Leu Gln Lys Leu Lys Glu Phe Gly Ser Val Ser
                260                 265                 270

Asp Gln Val Lys Gly Phe Trp Gln Phe Ser Glu Gly Lys Thr Asn
                275                 280                 285

Gly Val Arg Pro Phe
            290

<210> SEQ ID NO 95
<211> LENGTH: 1056
<212> TYPE: DNA
<213> ORGANISM: Escherichia coli

<400> SEQUENCE: 95
atggctaatg gtattgaatt taatcaaaac cccgcatctg ttttaattc taattcatta      60
gattttgaat tagaatctca gcaattaacg caaaaaaatt cttctaatat ttcttcgcca    120
ttaataaatt tgcaaaatga attagcaatg attactagtt catcgctttc tgaaacgatt    180
gaagggctaa gctgggata tcgcaaaggt agcgcaagga agaagagga aggctcgaca      240
atcgagaagc tgctcaatga tatgcaagag ctgcttactc ttaccgatag tgataaaata    300
aaagaactat cattaaaaaa cagcgggctg ctggaacaac acgatcctac tttggcgatg    360
tttggcaaca tgccaaaggg ggaaattgtt gcgctaatat cttctttatt gcaatctaag    420
tttgttaaga ttgaattaaa aaagaaatat gccaggttat tattagattt attaggcgaa    480
gatgattggg agctggctct gctttcctgg ttaggggtgg gtgagttaaa tcaggaaggt    540
atccagaaga tcaagaagct ttatgaaaag gctaaggatg aggattctga aaatggcgcc    600
tcttacttg actggtttat ggagattaag gatcttcccg agcgtgagaa gcacttaaaa    660
gtcattatta gggcgctgtc gttcgatctc tcttatatgt cttcttttga agacaaagta    720
aagacatctt caattattag tgatttatgc agggtaatca ttttttttatc acttgataac    780
tatgcagata ttatttcgat ctctattaag aaagataaag atatcatttt aaatgaagtg    840
ttatcgatta ttgaacatgt ctggctaaca gaagactggt tgctggagag tccttctcgg    900
gtatcgattg tcgaagataa acatatttat tattttcatt tattgaaaga ctttttttaca    960
tcattaccag atgcttgctt tattgatagt gagcagagag agaatgcatt attaatgatt    1020
ggtaaagtta tcgactataa ggaggaaatt atttga                              1056

<210> SEQ ID NO 96
<211> LENGTH: 351
<212> TYPE: PRT
<213> ORGANISM: Escherichia coli

<400> SEQUENCE: 96

Met Ala Asn Gly Ile Glu Phe Asn Gln Asn Pro Ala Ser Val Phe Asn
1               5                   10                  15

Ser Asn Ser Leu Asp Phe Glu Leu Glu Ser Gln Gln Leu Thr Gln Lys
            20                  25                  30

Asn Ser Ser Asn Ile Ser Ser Pro Leu Ile Asn Leu Gln Asn Glu Leu
        35                  40                  45
```

Ala Met Ile Thr Ser Ser Ser Leu Ser Glu Thr Ile Glu Gly Leu Ser
    50                  55                  60

Leu Gly Tyr Arg Lys Gly Ser Ala Arg Lys Glu Glu Glu Gly Ser Thr
65                  70                  75                  80

Ile Glu Lys Leu Leu Asn Asp Met Gln Glu Leu Leu Thr Leu Thr Asp
                85                  90                  95

Ser Asp Lys Ile Lys Glu Leu Ser Leu Lys Asn Ser Gly Leu Leu Glu
                100                 105                 110

Gln His Asp Pro Thr Leu Ala Met Phe Gly Asn Met Pro Lys Gly Glu
                115                 120                 125

Ile Val Ala Leu Ile Ser Ser Leu Leu Gln Ser Lys Phe Val Lys Ile
            130                 135                 140

Glu Leu Lys Lys Lys Tyr Ala Arg Leu Leu Asp Leu Leu Gly Glu
145                 150                 155                 160

Asp Asp Trp Glu Leu Ala Leu Leu Ser Trp Leu Gly Val Gly Glu Leu
                165                 170                 175

Asn Gln Glu Gly Ile Gln Lys Ile Lys Lys Leu Tyr Glu Lys Ala Lys
                180                 185                 190

Asp Glu Asp Ser Glu Asn Gly Ala Ser Leu Leu Asp Trp Phe Met Glu
            195                 200                 205

Ile Lys Asp Leu Pro Glu Arg Glu Lys His Leu Lys Val Ile Ile Arg
210                 215                 220

Ala Leu Ser Phe Asp Leu Ser Tyr Met Ser Ser Phe Glu Asp Lys Val
225                 230                 235                 240

Lys Thr Ser Ser Ile Ile Ser Asp Leu Cys Arg Val Ile Ile Phe Leu
                245                 250                 255

Ser Leu Asp Asn Tyr Ala Asp Ile Ile Ser Ile Ser Ile Lys Lys Asp
            260                 265                 270

Lys Asp Ile Ile Leu Asn Glu Val Leu Ser Ile Glu His Val Trp
275                 280                 285

Leu Thr Glu Asp Trp Leu Leu Glu Ser Pro Ser Arg Val Ser Ile Val
            290                 295                 300

Glu Asp Lys His Ile Tyr Tyr Phe His Leu Leu Lys Asp Phe Phe Thr
305                 310                 315                 320

Ser Leu Pro Asp Ala Cys Phe Ile Asp Ser Glu Gln Arg Glu Asn Ala
                325                 330                 335

Leu Leu Met Ile Gly Lys Val Ile Asp Tyr Lys Glu Ile Ile
                340                 345                 350

<210> SEQ ID NO 97
<211> LENGTH: 208
<212> TYPE: PRT
<213> ORGANISM: Shigella flexneri

<400> SEQUENCE: 97

Met Gln Ile Leu Asn Lys Ile Leu Pro Gln Val Glu Phe Ala Ile Pro
1               5                   10                  15

Arg Pro Ser Phe Asp Ser Leu Ser Arg Asn Lys Leu Val Lys Lys Ile
                20                  25                  30

Leu Ser Val Phe Asn Leu Lys Gln Arg Phe Pro Gln Lys Asn Phe Gly
            35                  40                  45

Cys Pro Val Asn Ile Asn Lys Ile Arg Asp Ser Val Ile Asp Lys Ile
        50                  55                  60

Lys Asp Ser Asn Ser Gly Asn Gln Leu Phe Cys Trp Met Ser Gln Glu
65                  70                  75                  80

```
Arg Thr Thr Tyr Val Ser Ser Met Ile Asn Arg Ser Ile Asp Glu Met
                85                  90                  95

Ala Ile His Asn Gly Val Val Leu Thr Ser Asp Asn Lys Arg Asn Ile
            100                 105                 110

Phe Ala Ala Ile Glu Lys Lys Phe Pro Asp Ile Lys Leu Asp Glu Lys
            115                 120                 125

Ser Ala Gln Thr Ser Ile Ser His Thr Ala Leu Asn Glu Ile Ala Ser
            130                 135                 140

Ser Gly Leu Arg Ala Lys Ile Leu Lys Arg Tyr Ser Ser Asp Met Asp
145                 150                 155                 160

Leu Phe Asn Thr Gln Met Lys Asp Leu Thr Asn Leu Val Ser Ser Ser
                165                 170                 175

Val Tyr Asp Lys Ile Phe Asn Glu Ser Thr Lys Val Leu Gln Ile Glu
            180                 185                 190

Ile Ser Ala Glu Val Leu Lys Ala Val Tyr Arg Gln Ser Asn Thr Asn
            195                 200                 205

<210> SEQ ID NO 98
<211> LENGTH: 538
<212> TYPE: PRT
<213> ORGANISM: Shigella flexneri

<400> SEQUENCE: 98

Met His Ile Thr Asn Leu Gly Leu His Gln Val Ser Phe Gln Ser Gly
1               5                   10                  15

Asp Ser Tyr Lys Gly Ala Glu Glu Thr Gly Lys His Lys Gly Val Ser
            20                  25                  30

Val Ile Ser Tyr Gln Arg Val Lys Asn Gly Glu Arg Asn Lys Gly Ile
        35                  40                  45

Glu Ala Leu Asn Arg Leu Tyr Leu Gln Asn Gln Thr Ser Leu Thr Gly
    50                  55                  60

Lys Ser Leu Leu Phe Ala Arg Asp Lys Ala Glu Val Phe Cys Glu Ala
65                  70                  75                  80

Ile Lys Leu Ala Gly Gly Asp Thr Ser Lys Ile Lys Ala Met Met Glu
                85                  90                  95

Arg Leu Asp Thr Tyr Lys Leu Gly Glu Val Asn Lys Arg His Ile Asn
            100                 105                 110

Glu Leu Asn Lys Val Ile Ser Glu Glu Ile Arg Ala Gln Leu Gly Ile
            115                 120                 125

Lys Asn Lys Lys Glu Leu Gln Thr Lys Ile Lys Gln Ile Phe Thr Asp
            130                 135                 140

Tyr Leu Asn Asn Lys Asn Trp Gly Pro Val Asn Lys Asn Ile Ser His
145                 150                 155                 160

His Gly Lys Asn Tyr Ser Phe Gln Leu Thr Pro Ala Ser His Met Lys
                165                 170                 175

Ile Gly Asn Lys Asn Ile Phe Val Lys Glu Tyr Asn Gly Lys Gly Ile
            180                 185                 190

Cys Cys Ala Ser Thr Arg Glu Arg Asp His Ile Ala Asn Met Trp Leu
            195                 200                 205

Ser Lys Val Val Asp Asp Glu Gly Lys Glu Ile Phe Ser Gly Ile Arg
            210                 215                 220

His Gly Val Ile Ser Ala Tyr Gly Leu Lys Lys Asn Ser Ser Glu Arg
225                 230                 235                 240

Ala Val Ala Ala Arg Asn Lys Ala Glu Glu Leu Val Ser Ala Ala Leu
```

```
            245                 250                 255
Tyr Ser Arg Pro Glu Leu Leu Ser Gln Ala Leu Ser Gly Lys Thr Val
            260                 265                 270

Asp Leu Lys Ile Val Ser Thr Ser Leu Leu Thr Pro Thr Ser Leu Thr
        275                 280                 285

Gly Gly Glu Glu Ser Met Leu Lys Asp Gln Val Ser Ala Leu Lys Gly
    290                 295                 300

Leu Asn Ser Lys Arg Gly Gly Pro Thr Lys Leu Leu Ile Arg Asn Ser
305                 310                 315                 320

Asp Gly Leu Leu Lys Glu Val Ser Val Asn Leu Lys Val Val Thr Phe
                325                 330                 335

Asn Phe Gly Val Asn Glu Leu Ala Leu Lys Met Gly Leu Gly Trp Arg
                340                 345                 350

Asn Val Asp Lys Leu Asn Asp Glu Ser Ile Cys Ser Leu Leu Gly Asp
                355                 360                 365

Asn Phe Leu Lys Asn Gly Val Ile Gly Gly Trp Ala Ala Glu Ala Ile
            370                 375                 380

Glu Lys Asn Pro Pro Cys Lys Asn Asp Val Ile Tyr Leu Ala Asn Gln
385                 390                 395                 400

Ile Lys Glu Ile Val Asn Asn Lys Leu Gln Lys Asn Asp Asn Gly Glu
                405                 410                 415

Pro Tyr Lys Leu Ser Gln Arg Val Thr Leu Leu Ala Tyr Thr Ile Gly
            420                 425                 430

Ala Val Pro Cys Trp Asn Cys Lys Ser Gly Lys Asp Arg Thr Gly Met
            435                 440                 445

Gln Asp Ala Glu Ile Lys Arg Glu Ile Ile Arg Lys His Glu Thr Gly
    450                 455                 460

Gln Phe Ser Gln Leu Asn Ser Lys Leu Ser Ser Glu Glu Lys Arg Leu
465                 470                 475                 480

Phe Ser Thr Ile Leu Met Asn Ser Gly Asn Met Glu Ile Gln Glu Met
                485                 490                 495

Asn Thr Gly Val Pro Gly Asn Lys Val Met Lys Lys Leu Pro Leu Ser
            500                 505                 510

Ser Leu Glu Leu Ser Tyr Ser Glu Arg Ile Gly Asp Pro Lys Ile Trp
        515                 520                 525

Asn Met Val Lys Gly Tyr Ser Ser Phe Val
        530                 535

<210> SEQ ID NO 99
<211> LENGTH: 129
<212> TYPE: PRT
<213> ORGANISM: Shigella flexneri

<400> SEQUENCE: 99

Met Cys Arg Lys Leu Tyr Asp Lys Leu Tyr Glu Ile Thr Gly Ala Lys
1               5                   10                  15

Leu Asp Phe Asn Asp Lys Asn Gln Ala Phe Ile Leu Glu Glu Gln
                20                  25                  30

Ile Pro Val Cys Ile Thr Asp Asn Asp Glu Tyr Ile Phe Leu Thr Gly
            35                  40                  45

Leu Leu Asn Glu His Glu Leu Phe Thr Glu Asn Ile Ile Asn Pro Glu
        50                  55                  60

His Ile Leu Ile Leu Asn Tyr Ser Leu Ser Arg Asp Tyr Gly Ser Ser
65                  70                  75                  80
```

```
Ile Cys Leu Leu Pro Asp Thr His Gln Cys Val Leu Thr Lys Lys His
                85                  90                  95

Tyr Lys Lys Tyr Leu Ser Pro Asp Glu Leu Ile Glu Ser Leu Tyr Glu
            100                 105                 110

Phe Leu Phe Cys Ile Lys Leu Thr Ile Ala Asn Ile Thr Ser Glu Val
        115                 120                 125

Asn

<210> SEQ ID NO 100
<211> LENGTH: 494
<212> TYPE: PRT
<213> ORGANISM: Shigella flexneri

<400> SEQUENCE: 100

Met Ser Leu Lys Ile Ser Asn Phe Ile Asp Ala Ser Asn Thr Lys Gly
1               5                   10                  15

Pro Ile Arg Val Glu Asp Thr Glu His Gly Pro Ile Leu Ile Ala Gln
            20                  25                  30

Lys Phe Asn Leu Lys Asp Leu Phe Arg Thr Leu Ser Thr Ile Asn
        35                  40                  45

Ala Lys Ile Asn Ser Gln Ile Leu Asn Glu Gln Leu Lys Asn Tyr Arg
    50                  55                  60

Leu Glu Asn Gln Lys Ser Leu Leu Phe Leu Asn Thr Leu Ala Ser
65                  70                  75                  80

Glu Lys Ser Ala Glu Ser Ala Phe Ala Ala Tyr Glu Ala Ala Lys Asn
                85                  90                  95

Ser Ile Gln His Ser Phe Thr Gly Arg Asp Ile Lys Leu Met Leu Asn
            100                 105                 110

Thr Ala Glu Arg Phe His Gly Ile Gly Thr Ala Lys Asn Leu Glu Arg
        115                 120                 125

His Leu Val Phe Arg Cys Trp Gly Asn Arg Gly Ile Thr His Leu Gly
    130                 135                 140

His Thr Ser Ile Ser Ile Lys Asn Asn Leu Leu Gln Glu Pro Thr His
145                 150                 155                 160

Thr Tyr Leu Ser Trp Tyr Pro Gly Gly Asn Val Thr Lys Asp Thr Glu
                165                 170                 175

Ile Asn Tyr Leu Phe Glu Lys Arg Ser Gly Tyr Ser Val Asp Thr Tyr
            180                 185                 190

Lys Gln Asp Lys Leu Asn Met Ile Ser Glu Gln Thr Ala Glu Arg Leu
        195                 200                 205

Asp Ala Gly Gln Glu Val Arg Asn Leu Leu Asn Ser Lys Gln Asp Gln
    210                 215                 220

Asn Asn Asn Lys Lys Ile Phe Phe Pro Arg Ala Asn Gln Lys Lys Asp
225                 230                 235                 240

Pro Tyr Gly Tyr Trp Gly Val Ser Ala Asp Lys Val Tyr Ile Pro Leu
                245                 250                 255

Ser Gly Asp Asn Lys Thr Lys Asp Gly Lys Ile Ser His Asn Leu Phe
            260                 265                 270

Gly Leu Asp Glu Thr Asn Met Ser Lys Phe Ile Cys Lys Lys Ala
        275                 280                 285

Asp Ala Phe Arg Gln Leu Ala Asn Tyr Lys Leu Ile Ser Lys Ser Glu
    290                 295                 300

Asn Cys Ala Gly Met Ala Leu Asn Val Leu Lys Ala Gly Asn Ser Glu
305                 310                 315                 320
```

-continued

```
Ile Tyr Phe Pro Leu Pro Asp Val Lys Leu Val Ala Thr Pro Asn Asp
                325                 330                 335

Val Tyr Ala Tyr Ala Asn Lys Val Arg Gln Arg Ile Glu Ser Leu Asn
            340                 345                 350

Gln Ser Tyr Asn Glu Ile Met Lys Tyr Ile Glu Ser Asp Phe Asp Leu
        355                 360                 365

Ser Arg Leu Thr Gln Leu Arg Arg Ser Tyr Leu Lys Ser Phe Asn Lys
    370                 375                 380

Ile Asn Leu Ile His Thr Pro Lys Thr Phe Lys Pro Leu Ser Ile Ser
385                 390                 395                 400

Leu Tyr Lys His Pro Thr Glu Asn Val Ser Ser Glu Asp Phe Asp Ala
            405                 410                 415

Val Ile Asn Ala Cys His Ser Tyr Leu Val Lys Ser Ala Pro Ser Asn
        420                 425                 430

Met Thr Arg Val Leu Asn Glu Leu Lys Thr Glu Ala Thr Asp Lys Lys
    435                 440                 445

Glu Glu Ile Ile Glu Lys Ser Lys Ile Ile Asp Tyr Tyr Asn Ser
450                 455                 460

Leu Lys Ser Pro Asp Leu Gly Thr Lys Leu Tyr Ile His Asp Leu Leu
465                 470                 475                 480

Gln Ile Asn Lys Leu Leu Leu Asn Asn Ser His Ser Asn Ile
            485                 490

<210> SEQ ID NO 101
<211> LENGTH: 561
<212> TYPE: PRT
<213> ORGANISM: Salmonella enterica

<400> SEQUENCE: 101

Met Gln Ile Gln Ser Phe Tyr His Ser Ala Ser Leu Lys Thr Gln Glu
1               5                   10                  15

Ala Phe Lys Ser Leu Gln Lys Thr Leu Tyr Asn Gly Met Gln Ile Leu
            20                  25                  30

Ser Gly Gln Gly Lys Ala Pro Ala Lys Ala Pro Asp Ala Arg Pro Glu
        35                  40                  45

Ile Ile Val Leu Arg Glu Pro Gly Ala Thr Trp Gly Asn Tyr Leu Gln
    50                  55                  60

His Gln Lys Ala Ser Asn His Ser Leu His Asn Leu Tyr Asn Leu Gln
65                  70                  75                  80

Arg Asp Leu Leu Thr Val Ala Ala Thr Val Leu Gly Lys Gln Asp Pro
            85                  90                  95

Val Leu Thr Ser Met Ala Asn Gln Met Glu Leu Ala Lys Val Lys Ala
        100                 105                 110

Asp Arg Pro Ala Thr Lys Gln Glu Glu Ala Ala Ala Lys Ala Leu Lys
    115                 120                 125

Lys Asn Leu Ile Glu Leu Ile Ala Ala Arg Thr Gln Gln Asp Gly
130                 135                 140

Leu Pro Ala Lys Glu Ala His Arg Phe Ala Ala Val Ala Phe Arg Asp
145                 150                 155                 160

Ala Gln Val Lys Gln Leu Asn Asn Gln Pro Trp Gln Thr Ile Lys Asn
            165                 170                 175

Thr Leu Thr His Asn Gly His His Tyr Thr Asn Thr Gln Leu Pro Ala
        180                 185                 190

Ala Glu Met Lys Ile Gly Ala Lys Asp Ile Phe Pro Ser Ala Tyr Glu
    195                 200                 205
```

Gly Lys Gly Val Cys Ser Trp Asp Thr Lys Asn Ile His His Ala Asn
            210                 215                 220

Asn Leu Trp Met Ser Thr Val Ser Val His Glu Asp Gly Lys Asp Lys
225                 230                 235                 240

Thr Leu Phe Cys Gly Ile Arg His Gly Val Leu Ser Pro Tyr His Glu
                245                 250                 255

Lys Asp Pro Leu Leu Arg His Val Gly Ala Glu Asn Lys Ala Lys Glu
            260                 265                 270

Val Leu Thr Ala Ala Leu Phe Ser Lys Pro Glu Leu Leu Asn Lys Ala
        275                 280                 285

Leu Ala Gly Glu Ala Val Ser Leu Lys Leu Val Ser Val Gly Leu Leu
    290                 295                 300

Thr Ala Ser Asn Ile Phe Gly Lys Glu Gly Thr Met Val Glu Asp Gln
305                 310                 315                 320

Met Arg Ala Trp Gln Ser Leu Thr Gln Pro Gly Lys Met Ile His Leu
                325                 330                 335

Lys Ile Arg Asn Lys Asp Gly Asp Leu Gln Thr Val Lys Ile Lys Pro
            340                 345                 350

Asp Val Ala Ala Phe Asn Val Gly Val Asn Glu Leu Ala Leu Lys Leu
        355                 360                 365

Gly Phe Gly Leu Lys Ala Ser Asp Ser Tyr Asn Ala Glu Ala Leu His
    370                 375                 380

Gln Leu Leu Gly Asn Asp Leu Arg Pro Glu Ala Arg Pro Gly Gly Trp
385                 390                 395                 400

Val Gly Glu Trp Leu Ala Gln Tyr Pro Asp Asn Tyr Glu Val Val Asn
                405                 410                 415

Thr Leu Ala Arg Gln Ile Lys Asp Ile Trp Lys Asn Asn Gln His His
            420                 425                 430

Lys Asp Gly Gly Glu Pro Tyr Lys Leu Ala Gln Arg Leu Ala Met Leu
        435                 440                 445

Ala His Glu Ile Asp Ala Val Pro Ala Trp Asn Cys Lys Ser Gly Lys
    450                 455                 460

Asp Arg Thr Gly Met Met Asp Ser Glu Ile Lys Arg Glu Ile Ile Ser
465                 470                 475                 480

Leu His Gln Thr His Met Leu Ser Ala Pro Gly Ser Leu Pro Asp Ser
                485                 490                 495

Gly Gly Gln Lys Ile Phe Gln Lys Val Leu Leu Asn Ser Gly Asn Leu
            500                 505                 510

Glu Ile Gln Lys Gln Asn Thr Gly Gly Ala Gly Asn Lys Val Met Lys
        515                 520                 525

Asn Leu Ser Pro Glu Val Leu Asn Leu Ser Tyr Gln Lys Arg Val Gly
    530                 535                 540

Asp Glu Asn Ile Trp Gln Ser Val Lys Gly Ile Ser Ser Leu Ile Thr
545                 550                 555                 560

Ser

<210> SEQ ID NO 102
<211> LENGTH: 685
<212> TYPE: PRT
<213> ORGANISM: Salmonella enterica

<400> SEQUENCE: 102

Met Val Thr Ser Val Arg Thr Gln Pro Pro Val Ile Met Pro Gly Met
1               5                   10                  15

```
Gln Thr Glu Ile Lys Thr Gln Ala Thr Asn Leu Ala Ala Asn Leu Ser
                20                  25                  30

Ala Val Arg Glu Ser Ala Thr Ala Thr Leu Ser Gly Glu Ile Lys Gly
            35                  40                  45

Pro Gln Leu Glu Asp Phe Pro Ala Leu Ile Lys Gln Ala Ser Leu Asp
    50                  55                  60

Ala Leu Phe Lys Cys Gly Lys Asp Ala Glu Ala Leu Lys Glu Val Phe
65                  70                  75                  80

Thr Asn Ser Asn Asn Val Ala Gly Lys Lys Ala Ile Met Glu Phe Ala
                85                  90                  95

Gly Leu Phe Arg Ser Ala Leu Asn Ala Thr Ser Asp Ser Pro Glu Ala
            100                 105                 110

Lys Thr Leu Leu Met Lys Val Gly Ala Glu Tyr Thr Ala Gln Ile Ile
        115                 120                 125

Lys Asp Gly Leu Lys Glu Lys Ser Ala Phe Gly Pro Trp Leu Pro Glu
130                 135                 140

Thr Lys Lys Ala Glu Ala Lys Leu Glu Asn Leu Glu Lys Gln Leu Leu
145                 150                 155                 160

Asp Ile Ile Lys Asn Asn Thr Gly Gly Glu Leu Ser Lys Leu Ser Thr
                165                 170                 175

Asn Leu Val Met Gln Glu Val Met Pro Tyr Ile Ala Ser Cys Ile Glu
            180                 185                 190

His Asn Phe Gly Cys Thr Leu Asp Pro Leu Thr Arg Ser Asn Leu Thr
        195                 200                 205

His Leu Val Asp Lys Ala Ala Ala Lys Ala Val Glu Ala Leu Asp Met
    210                 215                 220

Cys His Gln Lys Leu Thr Gln Glu Gln Gly Thr Ser Val Gly Arg Glu
225                 230                 235                 240

Ala Arg His Leu Glu Met Gln Thr Leu Ile Pro Leu Leu Leu Arg Asn
                245                 250                 255

Val Phe Ala Gln Ile Pro Ala Asp Lys Leu Pro Asp Pro Lys Ile Pro
            260                 265                 270

Glu Pro Ala Ala Gly Pro Val Pro Asp Gly Gly Lys Lys Ala Glu Pro
        275                 280                 285

Thr Gly Ile Asn Ile Asn Ile Asn Ile Asp Ser Ser Asn His Ser Val
290                 295                 300

Asp Asn Ser Lys His Ile Asn Asn Ser Arg Ser His Val Asp Asn Ser
305                 310                 315                 320

Gln Arg His Ile Asp Asn Ser Asn His Asp Asn Ser Arg Lys Thr Ile
                325                 330                 335

Asp Asn Ser Arg Thr Phe Ile Asp Asn Ser Gln Arg Asn Gly Glu Ser
            340                 345                 350

His His Ser Thr Asn Ser Ser Asn Val Ser His Ser His Ser Arg Val
        355                 360                 365

Asp Ser Thr Thr His Gln Thr Glu Thr Ala His Ser Ala Ser Thr Gly
    370                 375                 380

Ala Ile Asp His Gly Ile Ala Gly Lys Ile Asp Val Thr Ala His Ala
385                 390                 395                 400

Thr Ala Glu Ala Val Thr Asn Ala Ser Ser Glu Ser Lys Asp Gly Lys
                405                 410                 415

Val Val Thr Ser Glu Lys Gly Thr Thr Gly Glu Thr Thr Ser Phe Asp
            420                 425                 430
```

```
Glu Val Asp Gly Val Thr Ser Lys Ser Ile Ile Gly Lys Pro Val Gln
            435                 440                 445

Ala Thr Val His Gly Val Asp Asp Asn Lys Gln Gln Ser Gln Thr Ala
    450                 455                 460

Glu Ile Val Asn Val Lys Pro Leu Ala Ser Gln Leu Ala Gly Val Glu
465                 470                 475                 480

Asn Val Lys Thr Asp Thr Leu Gln Ser Asp Thr Thr Val Ile Thr Gly
                485                 490                 495

Asn Lys Ala Gly Thr Thr Asp Asn Asp Asn Ser Gln Thr Asp Lys Thr
            500                 505                 510

Gly Pro Phe Ser Gly Leu Lys Phe Lys Gln Asn Ser Phe Leu Ser Thr
            515                 520                 525

Val Pro Ser Val Thr Asn Met His Ser Met His Phe Asp Ala Arg Glu
        530                 535                 540

Thr Phe Leu Gly Val Ile Arg Lys Ala Leu Glu Pro Asp Thr Ser Thr
545                 550                 555                 560

Pro Phe Pro Val Arg Arg Ala Phe Asp Gly Leu Arg Ala Glu Ile Leu
                565                 570                 575

Pro Asn Asp Thr Ile Lys Ser Ala Ala Leu Lys Ala Gln Cys Ser Asp
            580                 585                 590

Ile Asp Lys His Pro Glu Leu Lys Ala Lys Met Glu Thr Leu Lys Glu
            595                 600                 605

Val Ile Thr His His Pro Gln Lys Glu Lys Leu Ala Glu Ile Ala Leu
        610                 615                 620

Gln Phe Ala Arg Glu Ala Gly Leu Thr Arg Leu Lys Gly Glu Thr Asp
625                 630                 635                 640

Tyr Val Leu Ser Asn Val Leu Asp Gly Leu Ile Gly Asp Gly Ser Trp
                645                 650                 655

Arg Ala Gly Pro Ala Tyr Glu Ser Tyr Leu Asn Lys Pro Gly Val Asp
            660                 665                 670

Arg Val Ile Thr Thr Val Asp Gly Leu His Met Gln Arg
            675                 680                 685
```

METHODS AND COMPOSITIONS RELATING TO ENGINEERED MICROBIAL CELLS

CROSS-REFERENCE TO RELATED APPLICATIONS

This application is a 35 U.S.C. § 371 National Phase Entry Application of International Application No. PCT/US2017/016997 filed Feb. 8, 2017, which designates the U.S. and claims benefit under 35 U.S.C. § 119(e) of U.S. Provisional Application No. 62/292,961 filed Feb. 9, 2016, the contents of which are incorporated herein by reference in their entireties.

GOVERNMENT SUPPORT

This invention was made with government support under Grant Nos. R01GM094941 and R21AI103882 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 8, 2017, is named 030258-086071_SL.txt and is 194,046 bytes in size.

TECHNICAL FIELD

The technology described herein relates generally to engineered microbial cells, e.g., non-pathogenic bacterial cells that secrete payload polypeptides into the extracellular space by means of a secretion system engineered from a type 3 secretion system (T3SS) or non-pathogenic bacterial cells that have been engineered to carry an engineered type 3 secretion system (T3SS) to translocate payloads into cells.

BACKGROUND

As part of the disease process, a number of pathogenic bacteria deliver toxins to their host cells. Some of bacteria have evolved a structure referred to as a Type 3 Secretion System (T3SS). The T3SS is essentially a needle that the bacterium uses to penetrate the host cell. The bacterium then injects the toxins through the T3SS needle into the host cell.

We have previously described engineered non-pathogenic cells that use this system for delivering some kinds of payloads into cells (see, e.g. WO/2014/138324).

SUMMARY

The T3SS's can be utilized in engineered bacteria such that instead of delivering toxins, the bacteria are delivering therapeutic molecules. However, such a direct adaptation of the T3SS machinery means that the therapeutic molecules will necessarily be delivered to the inside of the host cell (the intracellular space). Large amount of signaling activity occurs on the exterior surface of host cells (in the extracellular space) and thus, a number of therapeutic targets are not accessible with such engineered bacteria. The inventors have surprisingly found that by specifically modifying the secretion systems, i.e., by engineering the T3SS, delivery of therapeutic molecules to the extracellular space can be achieved.

The inventors have also surprisingly found that non-pathogenic bacteria, e.g., bacteria that do not naturally express or comprise T3SS (e.g., commensal bacteria) but have been engineered to express a modified T3SS can be used to translocate the variable domains of single-domain antibodies, such as VHH or nanobodies.

In one aspect of any of the embodiments, described herein is an engineered, non-pathogenic, gram negative microbial cell comprising: a first nucleic acid sequence comprising genes encoding a type 3 secretion system (T3SS)-derived extracellular secretion system (TDESS); wherein the TDESS comprises at least virB; mxiG; mxiH; mxiI; mxiJ; mxiK; mxiN; mxiL; mxiM; mxiD; mxiA; spa47; spa13; spa32; spa33; spa24; spa9; spa29; and spa40; and a second nucleic acid sequence encoding an T3SS-compatible payload polypeptide. In some embodiments, the cell does not comprise or express at least one of: IpaB; IpaD; and MxiC. In some embodiments, the cell does not comprise or express at least one of: IpaB and IpaD; and MxiC. In some embodiments, the cell does not comprise or express IpaB; IpaD; and MxiC. In some embodiments, the cell does not comprise or express IpaB; IpaD; IpaC; and MxiC. In some embodiments, the cell has a mutated MxiH. In some embodiments, the cell has a D73A mutation in MxiH.

In some embodiments, the second nucleic acid sequence comprises 1) an inducible promoter sequence that is operably linked to 2) a sequence encoding an T3SS-compatible payload polypeptide. In some embodiments, the inducible promoter sequence is regulated by a master T3SS regulator (i.e., master T3SS transcriptional regulator). In some embodiments, the inducible promoter sequence comprises a (T3SS)-associated promoter or promoter element. In some embodiments, the T3SS-associated promoter or promoter element is a MxiE recognition sequence. In some embodiments, the cell comprises a third nucleic acid sequence encoding a master T3SS regulator (i.e., master T3SS transcriptional regulator). In some embodiments, the master T3SS regulator (i.e., master T3SS transcriptional regulator) is selected from the group consisting of: VirB and VirF. In some embodiments, the third nucleic acid sequence comprises 1) an inducible promoter sequence that is operably linked to 2) a sequence encoding a master T3SS regulator (i.e., master T3SS transcriptional regulator). In some embodiments, the inducible promoter is selected from the group consisting of: an arabinose-inducible promoter; pBAD arabinose-inducible promoter; tumor-induced promoters; ansB promoter; pflE promoter; napF promoter; and an inflammation-induced promoter.

In some embodiments, the TDESS comprises at least: virB; acp; ipaA; ipgC; ipgB1; ipgA; icsB; ipgD; ipgE; ipgF; mxiG; mxiH; mxiI; mxiJ; mxiK; mxiN; mxiL; mxiM; mxiE; mxiD; mxiA; spa15; spa47; spa13; spa32; spa33; spa24; spa9; spa29; and spa40. In some embodiments, the TDESS comprises polypeptides endogenous to a bacterium selected from the group consisting of: Shigella spp; Salmonella spp; enteropathogenic E. coli; and Yersinia spp. In some embodiments, the first nucleic acid sequence is located on a plasmid. In some embodiments, the first nucleic acid sequence is located on a chromosome. In some embodiments, the second nucleic acid sequence is located on a plasmid. In some embodiments, the second nucleic acid sequence is located on a chromosome.

In some embodiments, the T3SS-compatible payload polypeptide comprises a T3SS secretion sequence. In some embodiments, the T3SS-compatible payload polypeptide comprises an N-terminal T3SS secretion sequence. In some embodiments, the T3SS-compatible payload polypeptide comprises a OspC3 T3SS secretion sequence.

In some embodiments, the T3SS-compatible payload polypeptide comprises an anti-inflammatory polypeptide. In some embodiments, the anti-inflammatory polypeptide is IL-10 or IL-27.

In some embodiments, the T3SS-compatible payload polypeptide comprises an antibody reagent. In some embodiments, the antibody reagent is selected from the group consisting of: a nanobody; a VNA (VHH-based neutralizing agent); a multimeric VHH reagent; and a VHH. In some embodiments, the cell comprises at least one further nucleic acid sequence encoding an additional T3SS-compatible payload polypeptide comprising an antibody reagent. In some embodiments, the one or more antibody reagents form a multimeric complex. In some embodiments, the multimeric complex is multispecific.

In some embodiments, the antibody reagent specifically binds to a cancer cell marker. In some embodiments, the antibody reagent specifically binds to a cancer checkpoint polypeptide. In some embodiments, the antibody reagent is an anti-PD-L1; anti-PD-1; or anti-CTLA-4 reagent. In some embodiments, the antibody reagent is an anti-PD-L1; anti-PD-1; or anti-CTLA-4 VNA or VHH.

In some embodiments, the antibody reagent specifically binds to an inflammatory cytokine receptor or an inflammatory cytokine. In some embodiments, the antibody reagent binds to a molecule selected from the group consisting of: TNFα, IL-8; IL-6, IL-18, IL-21, Il-33 and IL-13. In some embodiments, the antibody reagent specifically hinds to a bacterial toxin. In some embodiments, the bacterial toxin is an *E. coli* or *C. difficile* toxin. In some embodiments, the bacterial toxin is selected from the group consisting of: shiga toxin; *C. difficile* toxin A (TcdA); *C. difficile* toxin B (TcdB); cholera toxin; anthrax toxin; and botulinum toxin.

In some embodiments, the T3SS-compatible payload polypeptide comprises a toxin. In some embodiments, the T3SS-compatible payload polypeptide comprises an antigen.

In some embodiments, the microbial cell is engineered from a microbial cell selected from the group consisting of: *E. coli* NISSLE 1917 (EcN); *E. coli* K12; MP; HS; and derivative strains thereof. In some embodiments, the strain which is derivative of *E. coli* K12 is selected from the group consisting of: *E. coli* DH10β and *E. coli* DH5α. In some embodiments, the microbial cell is engineered from *E. coli* NISSLE 1917 (EcN). In some embodiments, the microbial cell is engineered from a commensal intestinal microbial cell. In some embodiments, the commensal intestinal microbial cell is *E. coli* NISSLE 1917 (EcN). In some embodiments, the non-pathogenic microbial cell is engineered from a pathogenic microbial cell organism by deletion or mutation of one or more T3SS components. In some embodiments, the one or more T3SS components is selected from the group consisting of: a toxin; a T3SS effector; a structural T3SS polypeptide; and a master regulator of T3SS components (i.e. master T3SS transcriptional regulator). In some embodiments, the pathogenic microbial cell is selected from the group consisting of: *Salmonella* spp.; *Shigella* Spp; and *Yersinia* spp. In some embodiments, the pathogenic microbial cell is selected from the group consisting of *Salmonella typhimurium* SPI1 and *Shigella flexneri* mxi-spa.

In some embodiments, the microbial cell has been: contacted with a mutagenic treatment; and selected for increased secretion. In some embodiments, the cell has been: contacted with a mutagenic treatment; and selected for increased secretion of the T3SS-compatible payload polypeptide.

In some embodiments, the cell further comprises a nucleic acid sequence encoding one or more polypeptides that increase adhesion to a target cell. In some embodiments, the polypeptides that increase adhesion to the target cell comprise Tir and intimin. In some embodiments, the polypeptide that increases adhesion to the target cell is selected from a group consisting of: a bacterial adhesion; Afa1; AIDA; invasion; an antibody reagent specific for an extracellular epitope of a target cell polypeptide; and a single chain antibody specific for an extracellular epitope of a target cell polypeptide.

In some aspects of any of the embodiments, described herein is a method of introducing a polypeptide into a target tissue or organism, the method comprising contacting the target tissue or organism with a microbial cell as described herein.

In some aspects of any of the embodiments, described herein is a method of reducing inflammation in a subject, the method comprising administering a microbial cell as described herein to a subject in need thereof. In some embodiments, the inflammation is inflammation of the gastrointestinal tract. In some embodiments, the subject is in need of treatment for a condition selected from the group consisting of asthma; inflammatory bowel disease; Crohn's disease; obesity; and ulcerative colitis. In some embodiments, the subject is a subject in need of treatment for inflammatory bowel disease. In some embodiments, the microbial cell is administered orally.

In some aspects of any of the embodiments, described herein is a method of treating cancer in a subject, the method comprising administering an microbial cell as described herein to a subject in need thereof. In some embodiments, the microbial cell s administered systemically. In some embodiments, the microbial cell is administered intratumorally. In some embodiments, the cancer is a cancer of the gastrointestinal tract and the microbial cell is administered orally. In some embodiments, the microbial cell is engineered from *E. coli* NISSLE 1917 (EcN).

In some aspects of any of the embodiments, described herein is a method of treating an intestinal infection in a subject, the method comprising administering a microbial cell as described herein to a subject in need thereof. In some embodiments, the intestinal infection is EHEC and/or the subject has hemolytic uremic syndeom and the toxin is shiga toxin. In some embodiments, the intestinal infection is a *C. difficile* infection and/or the subject has *C. difficile* colitis and the toxin is TcdA and/or TcdB. In some embodiments, the intestinal infection is cholera and the toxin is cholera toxin. In some embodiments, the intestinal infection is gastrointestinal anthrax and the toxin is anthrax toxin. In some embodiments, the intestinal infection is botulism and the toxin is botulinum toxin. In some embodiments, the microbial cell is administered orally.

In some embodiments, secretion of the T3SS-compatible payload polypeptide is induced by further administering the subject a compound to induce expression of the T3SS-compatible payload polypeptide and/or the T3SS master regulator. In some embodiments, the compound is arabinose.

In some aspects of any of the embodiments, described herein is a method for delivering a polypeptide into a) the extracellular milieu of a subject's gastrointestinal tract or b) the extracellular milieu of a subject's tumor, the method comprising contacting administering a microbial cell as described herein to the subject.

BRIEF DESCRIPTION OF THE DRAWINGS

FIG. 2A depicts a schematic of MyoD fused to a 50 amino acid secretion sequence and separated by a flexible glycine linker. FIG. 2B depicts delivery of MyoD into MEFs exposed to T3-*E. coli* expressing each of the designated MyoD alleles. After 1 hr, MEF cell lysates were collected and probed with anti-MyoD and anti-actin antibodies. SS, secretion sequence. S, supernatant. L, whole cell lysate. See FIG. 7 for a secretion assay of the secretion sequence library of 50 amino acid-MyoD fusion proteins in T3-*E. coli*.

FIG. 4A depicted a schematic demonstrating that wild type T3SS are held in an off position by the tip complex and MxiC. Loss of either the tip complex or MxiC causes constitutive secretion in to the outside of the bacterial cell. FIG. 4B demonstrates that secretion profiles of the different *Shigella* strains are displayed on a commassie gel. SepA, loading control.

FIG. 8 depicts a schematic of a tunable bacterial protein delivery system composed of 3 parts: (1) The delivery apparatus, a region of DNA that encodes all the genes required to assemble a functional type 3 secretion system (T3SS). (2) the activator, VirF the master *Shigella* transcription activator, controls expression of the T3SS and (3) The type 3 secreted substrates, target therapeutic payloads fused to a type 3 secretion sequence (SS) at their N-termini.

FIG. 9 demonstrates that T3EcN can recognize VHH as secreted substrates. Immunoblots of the type 3 secreted substrates of T3EcN grown under conditions that induce type 3 secretion are shown. (top panel) Fusion of 4 different type 3 secretion sequences to the N-terminus of a representative VHH (VHH1) identified the OspC3 sequence as sufficient for secretion in a standard secretion assay. (bottom panel) Fusion of the OspC3 secretion sequence to 4 different VHH results in all of their secretion from T3EcN.

FIG. 10 depicts the plate based secretion assay distinguishes between substrates secreted at low, intermediate, and high levels, as demonstrated by the secretion of 4 FLAG-tagged native effectors from *Shigella*. This assay can be easily automated and scaled up in genetic screens using robots.

DETAILED DESCRIPTION

Figure 1:
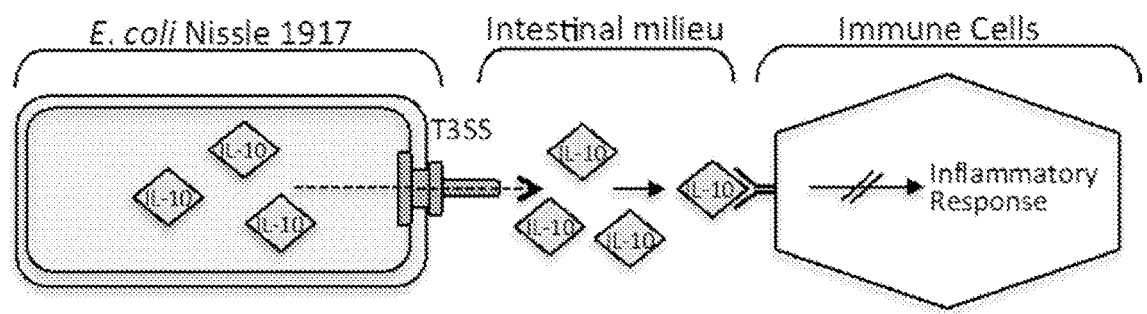
FIG. 1 depicts a schematic of the use of a commensal bacteria-based T3SS to deliver IL-10 into the intestines, leading to suppression of the inflammatory response in IBD patients.

In some aspects, described herein are engineered microbial cells that comprise an altered or modified type 3 secretion system (T3SS) that, instead of injecting proteins into a target cell, surprisingly secrete them into the extracellular space. This approach allows for the delivered proteins to interact with cell surface receptors and/or other molecules, e.g., toxins or signaling molecules, in the extracellular space, such as the gut lumen. Additionally, as the engineered microbial cells described herein can be commensal, non-pathogenic cells, the cells can persist in a subject and provide continued delivery of proteins directly to the target area, such as in the gut, providing improved efficacy and reduced side effects compared to traditional methods of administering therapeutic molecules themselves. It is also known that some non-pathogenic bacteria or commensal bacteria, which do not naturally express T3SS, migrate from the gut or blood stream to tumors, and the inventors also surprisingly found that engineering such bacteria to express the modified T3SS system wherein the functionality to deliver payloads into cells has been removed allows targeted delivery of peptides into the extracellular space in and/or surrounding tumors thus reducing the side effects of any anti-cancer peptides and increases the effectiveness of any such anti-cancer therapy. The inventors also found that single domain antibodies, or nanobodies, can be delivered either with bacteria, such as commercial non-pathogenic bacterial cells, with the functional T3SS capable of injecting a payload into a cell or with the altered T3SS without the capability to inject the payload into the cell, depending on whether the target is inside the cell or outside the cell either on cell surface or in the extracellular space.

Accordingly, in one aspect of any of the embodiments, described herein is an engineered, non-pathogenic or commensal gram negative microbial cell, wherein the cell in its natural state does not comprise T3SS, the cell comprising: a) a first nucleic acid sequence comprising genes encoding a type 3 secretion system (T3SS)-derived extracellular secretion system (TDESS) and h) a second nucleic acid sequence encoding a T3SS-compatible payload polypeptide. In one aspect of any of the embodiments, described herein is an engineered, non-pathogenic, gram negative microbial cell comprising: a) a first nucleic acid sequence comprising genes encoding a type 3 secretion system (T3SS)-derived extracellular secretion system (TDESS) b) a second nucleic acid sequence encoding a T3SS-compatible payload polypeptide; and c) a third nucleic acid sequence encoding a master T3SS regulator. As used herein, "T3SS-derived extracellular secretion system" or "MESS" refers to a system of proteins obtained and/or derived from a T3SS that can form a structure capable of delivering polypeptides from the microbial cell into the extracellular space instead of into the intracellular space of a target cell. In some embodiments of any of the aspects, a TDESS cannot deliver polypeptides from the microbial cell into the intracellular space of a target cell. In some embodiments, a microbial cell which does not naturally comprise a T3SS (e.g., a non-pathogenic and/or commensal bacteria) is engineered to comprise a TDESS.

In some embodiments of any of the aspects, the TDESS comprises at least virB; mxiG; mxiH; mxiI; mxiJ; mxiK; mxiN; mxiL; mxiM; mxiD; mxiA; spa47; spa13; spa32; spa33; spa24; spa9; spa29; and spa40 or homologs thereof. In some embodiments of any of the aspects, the TDESS comprises at least virB; virF; mxiG; mxiH; mxiI; mxiK; mxiN; mxiL; mxiM; mxiD; mxiA; spa47; spa13; spa32; spa33; spa24; spa9; spa29; and spa40 or homologs thereof. In some embodiments of any of the aspects, the TDESS comprises at least: virB; acp; ipaA; ipgC; ipgB1; ipgA; icsB; ipgD; ipgE; ipgF; mxiG; mxiH; mxiJ; mxiK; mxiN; mxiL; mxiM; mxiE; mxiD; mxiA; spa15; spa47; spa13; spa32; spa33; spa24; spa9; spa29; and spa40 or homologs thereof. In some embodiments of any of the aspects, the MESS comprises at least: virB; virF; acp; ipaA; ipgC; ipgB1; ipgA; icsB; ipgD; ipgE; ipgF; mxiG; mxiH; mxiI; mxiJ; mxiK; mxiN; mxiL; mxiM; mxiE; mxiD; mxiA; spa15; spa47; spa13; spa32; spa33; spa24; spa9; spa29; and spa40 or homologs thereof. Homologs of any of the foregoing from a given species are readily identified by one of skill in the art, e.g., by querying a database of sequence information (e.g., using NCBI BLAST) with the gene name and/or sequence of one of the given genes and selecting the closest matching sequence found in the genome of the given species. In some embodiments of any of the aspects, the homolog has at least 80%, at least 85%, at least 90%, at least 95%, at least 98% sequence identity with the nucleic acid or polypeptide sequences described herein. T3SSs are known in a number of species and individual polypeptides of an engineered TDESS can be obtained from any T3SS. In some embodiments of any of the aspects, the TDESS polypeptides can be, or be derived from, T3SS polypeptides endogenous to a *Shigella* spp; *Salmonella* spp; enteropathogenic *E. coli*; or *Yersinia* spp. bacterium. In some embodiments of any of the aspects described herein, a homolog can be a polypeptide with the same function, functional characteristics, and/or activity as the reference polypeptide. By way of non-limiting example, a homolog with the same function as one of the T3SS polypeptides described herein can be identified by engineering a bacteria to not express the given polypeptide and to instead express a putative functional homolog and then measuring the ability of the bacteria to secrete a payload polypeptide. If the bacteria retain at least 10% of the reference ability to secrete the payload polypeptide, the putative functional homolog is demonstrated to be a functional homolog. In some embodiments, a functional homolog has at least 10% of the activity of the reference polypeptide, e.g. 10% or more, 20% or more, 30% or more, 50% or more, 75% or more, 80% or more, 90% or more, 95% or more, or 100% or more of the activity of the reference polypeptide.

In some embodiments of any of the aspects, the TDESS comprises at least a needle monomer polypeptide (e.g. MxiH (e.g., NCBI Gene ID No: 1238256)); PrgI (e.g., NCBI Gene ID No: 1254396; YscF (e.g., NCBI Gene ID No: 1172700)); and/or EscF (e.g., NCBI Gene ID No: 8873370)), an inner rod polypeptide (e.g. MxiI (e.g., NCBI Gene ID No: 1238257)); PrgJ (e.g., NCBI Gene ID No: 1254395)); YscI (e.g., NCBI Gene ID No: 2767498)); and/or EscI (e.g., NCBI Gene ID No: 8219253)), ring polypeptides; a niter polypeptide (e.g. Spa32 (e.g., NCBI Gene ID No: 876502); InvJ (e.g., NCBI Gene ID No: 1254415); YscP (e.g., NCBI Gene ID No: 5798302); and/or Orf16 (e.g., NCBI Gene ID No: 8219247)); and an ATPase (e.g. Spa47 (e.g., NCBI Gene ID No: 876429); InvC (e.g., NCBI Gene ID No: 1254417); YscN (e.g., NCBI Gene ID No: 10216379); and/or SepB (also known as EscN) (e.g., NCBI Gene ID No: 8873386)); and one or more of a switch polypeptide (e.g. Spa40 (e.g., NCBI Gene ID No: 876433); SpaS (e.g., NCBI Gene ID No: 1254410); YscU (e.g., NCBI Gene ID No: 2767517); and/or EscU (e.g., NCBI Gene ID No: 7062687)). In some embodiments, a TDESS can further comprise one or more translocators (e.g., IpaC (e.g., NCBI Gene ID No: 876448); SipB (e.g., NCBI Gene ID No: 1254408); SipC (e.g., NCBI Gene ID No: 1254407); YopB (e.g., NCBI Gene ID No: 1449456); YopD (e.g., NCBI Gene ID No: 1449455); EspD (e.g., NCBI Gene ID No: 885777); and/or EspB (e.g., NCBI Gene ID No: 8474872)) and/or a chaperone for the one or more translocators (e.g. IpgC (e.g., NCBI Gene ID No: 1238043); SicA (e.g., NCBI Gene ID No: 1254409); SycD (e.g., NCBI Gene ID No: 2767486); and/or CesD (e.g., NCBI Gene ID No: 7063867)). In some embodiments, a TDESS does not comprise one or more translocators (e.g. IpaC (e.g., NCBI Gene ID No: 876448); SipB (e.g., NCBI Gene ID No: 1254408); SipC (e.g., NCBI Gene ID No: 1254407); YopB (e.g., NCBI Gene ID No: 1449456); YopD (e.g., NCBI Gene ID No: 1449455); EspD (e.g., NCBI Gene ID No: 885777); and/or EspB (e.g., NCBI Gene ID No: 8474872)) and/or a chaperone for the one or more translocators (e.g. IpgC (e.g., NCBI Gene ID No: 1238043); SicA (e.g., NCBI Gene ID No: 1254409); SycD (e.g., NCBI Gene ID No: 2767486); and/or CesD (e.g., NCBI Gene ID No: 7063867)).

A TDESS can be constructed from a T3SS by omitting and/or mutating key proteins that mediate protein delivery into a target cell. In some embodiments of any of the aspects, a microbial cell comprising a TDESS does not comprise or express at least one of IpaB (invasion Plasmid Antigen B); IpaD invasion Plasmid Antigen D); IpaC Invasion Plasmid Antigen C); and MxiC (Membrane eXpression of Invasion plasmid antigens C). In some embodiments of any of the aspects, a microbial cell comprising a TDESS does not comprise or express at least one of IpaB; IpaD; IpaC; and MxiC. In some embodiments of any of the aspects, a microbial cell comprising a TDESS does not comprise or express IpaB; IpaD; and MxiC. In some embodiments of any of the aspects, a microbial cell comprising a TDESS does not comprise or express IpaB; IpaD; IpaC; and MxiC. In some embodiments, a microbial cell comprising a TDESS does not comprise or express a gatekeeper polypeptide (e.g. MxiC (e.g., NCBI Gene ID No: 876426); InvE (e.g., NCBI Gene ID No: 1254420); YopN (e.g., NCBI Gene ID No: 2767534); and/or SepL (e.g., NCBI Gene ID No: 8873375)). In some embodiments, a microbial cell comprising a MESS does not comprise or express a needle-tip polypeptide (e.g. IpaD (e.g., NCBI Gene ID No: 876444); SipD (e.g., NCBI Gene ID No: 1254406); LcrV (e.g., NCBI Gene ID No: 1172676); and/or EspA (e.g., NCBI Gene ID No: 960865)).

In some embodiments of any of the aspects, a microbial cell comprising a TDESS comprises or expresses a mutated form of MxiH that constitutively secretes T3SS effectors.

Such mutations can be accomplished by mutating residues in the PSNP loop or residues P44 or Q51 and are described further in e.g., Kenjale et al. J. Biol. Chem. 2005 280:42929-42937; which is incorporated by reference herein in its entirely. In some embodiments of any of the aspects, the mutated form of MxiH is a D73A mutation in MxiH.

In some embodiments of any of the aspects, the first nucleic acid sequence is located on a plasmid. In some embodiments of any of the aspects, the one or more genes encoding a TDESS polypeptide can be located on a plasmid. In some embodiments of any of the aspects, the first nucleic acid sequence is located on a chromosome (e.g. a naturally-occurring chromosome, a modified endogenous chromosome, or a bacterial artificial chromosome (BAC)). In some embodiments of any of the aspects, the one or more genes encoding a TDESS polypeptide can be located on a chromosome. In some embodiments of any of the aspects, the first nucleic acid sequence can comprise one or more operons, e.g. one operon, two operons, three operons, or more operons. In some embodiments of any of the aspects, the first nucleic acid sequence can comprise one or more separate sequences and/or molecules (e.g. a portion of the genes are found on one plasmid and another portion of the genes are found on a second plasmid). In some embodiments, the first nucleic acid sequence can be integrated into the chromosome using, for example, landing pad technology, see, e.g. Kuhlman and Cox, 2010 Nucleic Acids Research 38:e92; which is incorporated by reference herein in its entirety.

A T3SS-compatible payload polypeptide refers to any polypeptide that can be transported out of the microbial cell by a T3SS and/or TDESS and which is exogenous to the microbial cell, i.e., not encoded by the microbial cell before introduction of said polypeptide-encoding nucleic acid into the microbial cell. In some embodiments of any of the aspects, the T3SS-compatible payload polypeptide can be exogenous to a target cell (i.e., not encoded by the target cell), target tissue or organ, and/or target organism or toxin. In some embodiments of any of the aspects, the T3SS-compatible payload polypeptide can be ectopic to a target cell, target tissue, and/or target organism. A payload polypeptide can be from any source, e.g. the polypeptide can have a prokaryotic origin, a eukaryotic origin, or a synthetic origin. A payload polypeptide can be a naturally occurring polypeptide or a mutant and/or variant thereof. In a variant payload polypeptide, one or more residues can be altered, deleted, and/or added as compared to a naturally-occurring and/or wild-type polypeptide so long as the function remains substantially the same.

The term "exogenous" refers to a substance present in a cell other than its native source. The term "exogenous" when used herein can refer to a nucleic acid (e.g. a nucleic acid encoding a payload polypeptide) or a polypeptide (e.g., a payload polypeptide) that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in low amounts and one wishes to increase the amount of the nucleic acid or polypeptide in the cell or organism. In contrast, the term "endogenous" refers to a substance that is native to the biological system or cell (e.g. the microbial cell and/or target cell). As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid, that is not naturally found or expressed in a given cell in its natural environment.

Naturally-occurring T3SS substrates comprise a secretion signal within the first 20 amino acids of the polypeptide. Certain naturally-occurring T3SS substrates comprise a chaperone-binding domain within the first 50 amino acids of the polypeptide. Accordingly, in some embodiments, the payload polypeptide can comprise an N-terminal type three secretion system (T3SS) signal, wherein the T3SS signal comprises a T3SS secretion signal. In some embodiments, the payload polypeptide can comprise an N-terminal type three secretion system (T3SS) signal, wherein the T3SS signal comprises the first 20 amino acids of a naturally occurring T3SS substrate. In some embodiments, the payload polypeptide can comprise an N-terminal type three secretion system (T3SS) signal, wherein the T3SS signal comprises a T3SS chaperone-binding domain. In some embodiments, the payload polypeptide can comprise T3SS chaperone-binding domain and an N-terminal type three secretion system (T3SS) signal, wherein the T3SS signal comprises from about the first 50 to about the first 70 amino acids of a naturally occurring T3SS substrate. In some embodiments, in the context of a T3SS signal polypeptide, the term "about" can refer to +3 amino acids. In some embodiments, in the context of a T3SS signal polypeptide, the term "about" can refer to ±2 amino acids. In some embodiments, in the context of a T3SS signal polypeptide, the term "about" can refer to ±1 amino acid.

Examples of T3SS secretion signals and chaperone-binding domains are known in the art, see, e.g. Costa et al. Mbio 2012 3:c00243-11 or Schmitz et al. Nat Methods 2009 6:500-2; which described the signals and domains of *Shigella* effectors and which is incorporated by reference herein in its entirety. Additional examples are known in the art, e.g. Sony et al. PNAS 1995 92:11998-20002; which is is incorporated by reference herein in its entirety.

In some embodiments of any of the aspects, the T3SS-compatible payload polypeptide comprises a T3SS secretion sequence. In some embodiments of any of the aspects, the T3SS-compatible payload polypeptide comprises an N-terminal T3SS secretion sequence. In some embodiments of any of the aspects, the T3SS-compatible payload polypeptide comprises a OspC3 T3SS secretion sequence. In some embodiments of any of the aspects, the T3SS-compatible payload polypeptide comprises a nanobody, VNA, or VHH and a OspC3 T3SS secretion sequence.

In some embodiments of any of the aspects, the T3SS-compatible payload polypeptide comprises an anti-inflammatory polypeptide, e.g., a human anti-inflammatory polypeptide and/or an anti-inflammatory polypeptide that is ectopic to the target cell, tissue, or organism. An anti-inflammatory polypeptide can be a polypeptide that suppresses inflammatory signaling in the target cell, tissue, or organism, including but not limited to, polypeptides which are part of the endogenous signaling pathways in the target cell, tissue, or organism. Non-limiting examples of anti-inflammatory polypeptides can include, IL-10 (e.g., human IL-10, NCBI Gene ID: 3586) or IL-27 (e.g., human IL-27, NCBI Gene ID: 246778).

In some embodiments of any of the aspects, the T3SS-compatible payload polypeptide comprises an antibody reagent. As used herein an "antibody" refers to IgG, IgM, IgA, IgD or IgE molecules or antigen-specific antibody fragments thereof (including, but not limited to, a Fab, F(ab')$_2$, Fv, disulphide linked Fv, say, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. Antibody reagents as used herein do not comprise a S—S bond or require a post-translational modification in order to specifically bind their target antigen. In some aspects, the antibody reagents have a molecular weight of 200 kDa or lower. In some aspects, the antibody reagents have a molecular weight of 150 kDa or lower. In some aspects, the antibody reagents have a molecular weight of 100 kDa or lower. In some aspects, the antibody reagents have a molecular weight of 90 kDa or lower. In some aspects, the antibody reagents have a molecular weight of between 50 and 100 kDa or between 50 and 150 kDa.

An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

In some embodiments, an antibody reagent can be a single domain antibody. A single-domain antibody (sdAb, called Nanobody by Ablynx, the developer of these molecular) is an antibody fragment consisting of a single monomeric variable antibody domain. Like a whole antibody, it is able to bind selectively to a specific antigen. With a molecular weight of only about 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Additionally, and as described herein, a recombinant humanized antibody, single domain antibody (VHH) can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a target.

In some embodiments of any of the aspects, the antibody reagent can be a single chain antibody reagent, e.g., one which, as a single polypeptide chain, can specifically bind the target antigen. In some embodiments of any of the aspects, the antibody reagent can be a VNA or a VHH. VHH's (camelid heavy-chain-only Ab $V_H$ domain) are antibodies produced by camelids and which comprise only a heavy chain. VHH's can be naturally-occurring, naturally-produced, engineered, and/or humanized. A VNA (VHH (heavy-chain-only Ab $V_H$)-based neutralizing agent) is a polypeptide comprising at least two linked individual. VHF's. VNAs can be heteromultimers, e.g., comprise at least two different individual VHHs. Nanobodies, VNA, and/or VHH are commercially available, see, e.g., Ablynx (Gent, Belgium).

In some embodiments of any of the aspects, the antibody reagent can be monomeric. In some embodiments of any of the aspects, the antibody reagent can be monospecific. In some embodiments of any of the aspects, the antibody reagent can be multimeric after secretion.

In some embodiments of any of the aspects, the cell comprises at least one further nucleic acid sequence encoding an additional T3SS-compatible payload polypeptide comprising an antibody reagent. In some embodiments of any of the aspects, the engineered cell can express multiple antibody reagents that are multimeric before or after secretion, e.g., they form a heteromeric complex. In some embodiments of any of the aspects, the engineered cell can express multiple antibody reagents that are multimeric after secretion, e.g., they form a heteromeric complex. In some embodiments of any of the aspects, the multimeric complex can be multispecific, e.g., each different antibody reagent can be specific for a different antigen. By way of non-limiting example, described below herein is VNA$^{TcdB/A}$, which comprises 4 VHH and specifically binds to both TcdB and TcdA. In some embodiments of any of the aspects, the microbial cell can comprise one or more payload polypeptides that collectively are specific for both TcdB and TcdA. In some embodiments of any of the aspects, the microbial cell can comprise one or more payload polypeptides that collectively are specific for both Six1 and Stx2.

In some embodiments of any of the aspects, the antibody reagent specifically hinds to an inflammatory cytokine receptor or an inflammatory cytokine. Non limiting examples of inflammatory cytokine receptor or an inflammatory cytokine can include TNFα (e.g., human TNFα, NCBI Gene ID: 7124), IL-8 (e.g., human IL-8, NCBI Gene ID: 3576); IL-6 (e.g., human IL-6, NCBI Gene ID: 3569), IL-18 (e.g., human IL-18, NCBI Gene ID: 3606), IL-21 (e.g., human IL-12, NCBI Gene ID: 59067), IL-33 (e.g., human IL-33, NCBI Gene ID: 90865) and IL-13 (e.g., human IL-13, NCBI Gene ID: 3596).

In some embodiments of any of the aspects, the antibody reagent specifically binds to an extracellular cancer cell marker. Cancer cell markers are molecules expressed on the surface of the cancer cell and which are preferentially expressed on cancer cells as compared to healthy cells. Non-limiting examples of suitable cancer cell markers can include PD-L1 (e.g., human PD-L1, NCBI Gene ID: 29126), PD-1 (e.g., human PD-1, NCBI Gene ID: 5133), and CTLA-4 (e.g., human CTLA-4, NCBI Gene ID: 1493). In some embodiments of any of the aspects, the antibody reagent is an anti-PD-L1; anti-PD-1; or anti-CTLA-4 reagent. In some embodiments of any of the aspects, the antibody reagent is an anti-PD-L1; anti-PD-1; or anti-CTLA-4 VNA or VHH. In some embodiments of any of the aspects, the antibody reagent specifically binds to a cancer checkpoint polypeptide, i.e. a polypeptide that serves as a checkpoint to inhibit activity of tumor immunite that blocks recognition and clearance by human immune response. Non-limiting examples of suitable cancer checkpoint polypeptides can include PD-L1 (e.g., human PD-L1, NCBI Gene ID: 29126), PD-1 (e.g., human PD-1, NCBI Gene ID: 5133), and CTLA-4 (e.g., human CTLA-4, NCBI Gene ID: 1493). In some embodiments of any of the aspects, the antibody reagent is an anti-PD-L1; anti-PD-1; or anti-CTLA-4 reagent.

In some embodiments of any of the aspects, the antibody reagent specifically binds to a bacterial toxin, e.g. a toxin released by a bacterium that is pathogenic to the target cell, tissue, and/or organism. In some embodiments of any of the aspects, the bacterial toxin is an E. coli or C. difficile toxin. Non-limiting examples of bacterial toxins can include shiga toxin (Stx, Stx1 and/or Stx2); C. difficile toxin A (TcdA); C. difficile toxin B (TcdB); cholera toxin; anthrax toxin; and botulinum toxin.

In some embodiments of any of the aspects, the T3SS-compatible payload polypeptide comprises a toxin. In some embodiments of any of the aspects, the T3SS-compatible payload polypeptide comprises an antigen. In some embodiments of any of the aspects, the T3SS-compatible payload polypeptide comprises a cytokine. In some embodiments of any of the aspects, the T3SS-compatible payload polypeptide comprises a pro-drug converting enzyme, e.g., cytosine deaminiase. In some embodiments of any of the aspects, the T3SS-compatible payload polypeptide comprises an anti-inflammatory cytokine. In some embodiments of any of the aspects, the T3SS-compatible payload polypeptide comprises a receptor agonist, e.g., to modulate immune responses. In some embodiments of any of the aspects, the T3SS-compatible payload polypeptide comprises an enzyme, e.g., a diagnostic factor or a lactose intolerance relevant enzyme.

In some embodiments of any of the aspects, the second nucleic acid sequence is located on a plasmid. In some embodiments of any of the aspects, the second nucleic acid sequence is located on a chromosome (e.g. a naturally-occurring bacterial chromosome, a modified endogenous chromosome, or a bacterial artificial chromosome (BAC)). In some embodiments of any of the aspects, the second nucleic acid sequence can comprise one or more operons, e.g. one operon, two operons, three operons, or more operons. In some embodiments, the second nucleic acid sequence can be integrated into the chromosome using, for example, landing pad technology, see, e.g. Kuhlman and Cox, 2010 Nucleic Acids Research 38:e92; which is incorporated by reference herein in its entirety.

In some embodiments of any of the aspects, expression of the TDESS-compatible payload polypeptide can controlled by an inducible promoter, e.g., to avoid constitutive expression of the polypeptide and/or control the timing and level of expression of the polypeptide. In some embodiments of any of the aspects, the second nucleic acid sequence comprises 1) an inducible promoter sequence that is operably linked to 2) a sequence encoding an T3SS-compatible payload polypeptide.

As expression of the TDESS-compatible payload polypeptide is advantageous when the TDESS itself expressed, it can be desirable to have the TDESS-compatible payload polypeptide expression regulated by a T3SS regulator such that expression of the polypeptide occurs when a TDESS is expressed and available for delivery of the polypeptide. In some embodiments of any of the aspects, the inducible promoter sequence is regulated by a master T3SS regulator (i.e. master T3SS transcriptional regulator). In some embodiments of any of the aspects, the inducible promoter sequence comprises a (T3SS)-associated promoter or promoter element. In some embodiments of any of the aspects, the T3SS-associated promoter or promoter element is an MxiE recognition sequence. In some embodiments, a T3SS-associated promoter and/or promoter element is a promoter and/or promoter element which endogenously controls the expression of a structural T3SS component, and/or a T3SS chaperone, and/or a T3SS substrate. Non-limiting examples of T3SS-associated promoters and/or promoter elements include MxiE or VirB or VirF recognition sequences, which are described, e.g. in Mavris et al. J Bact 2002 184:4409-19 and Beloin et al. JBC 2002 277:15333-15344; which are incorporated by reference herein in their entirety.

In order to control the expression of the TDESS and/or the TDESS-compatible payload polypeptide, a master T3SS regulator (i.e. master T3SS transcriptional regulator) can be provided. In some embodiments of any of the aspects, the cell comprises a third nucleic acid sequence encoding a master T3SS regulator. In some embodiments of any of the aspects, the master T3SS regulator is VirB, VirF, or a homolog thereof. As the master regulator will control the expression of the TDESS and the TDESS-compatible payload polypeptide, the expression of the master regulator itself can be manipulated to ensure that the TDESS and its payload polypeptide are expressed at the desired time, location, and/or level. Accordingly, in some embodiments of any of the aspects, the third nucleic acid sequence comprises 1) an inducible promoter sequence that is operably linked to 2) a sequence encoding a master T3SS regulator.

In order for a polypeptide described herein to be expressed, the nucleic acid encoding the polypeptide can be operatively linked to a promoter. In some embodiments, the polypeptide can be constitutively expressed. In some embodiments, nucleic acids encoding the polypeptide can be operatively linked to a constitutive promoter. In some embodiments, the polypeptide can be inducibly expressed. In some embodiments, nucleic acids encoding the polypeptide can be operatively linked to an inducible promoter.

As described herein, an "inducible promoter" is one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, and tetracycline, steroid-responsive promoters, rapamycin responsive promoters and the like. Inducible promoters for use in prokaryotic systems are well known in the art, see, e.g. the beta.-lactamase and lactose promoter systems (Chang et al., Nature, 275: 615 (1978, which is incorporated herein by reference); Goeddel et al., Nature, 281: 544 (1979), which is incorporated herein by reference), the arabinose promoter system, including the araBAD promoter (Guzman et al., J. Bacteriol., 174: 7716-7728 (1992), which is incorporated herein by reference; Guzman et al., J. Bacteriol., 177: 4121-4130 (1995), which is incorporated herein by reference; Siegele and Hu, Proc. Natl. Acad., Sci. USA, 94: 8168-8172 (1997), which is incorporated herein by reference), the rhamnose promoter (Haldimann et al., J. Bacteriol., 180: 1277-1286 (1998), which is incorporated herein by reference), the alkaline phosphatase promoter, a tryptophan (trp) promoter system (Goeddel, Nucleic Acids Res., 8: 4057 (1980), which is incorporated herein by reference), the $P_{LtetO-1}$ and $P_{lac/are-1}$ promoters (Lutz and Bujard, Nucleic Acids Res., 25: 1203-1210 (1997), which is incorporated herein by reference), and hybrid promoters such as the tac promoter. deBoer et al., Proc. Natl. Acad. Sci. USA, 80: 21-25 (1983), which is incorporated herein by reference.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including Cu2+ and Zn2+), galactose, tetracycline, IPTG (isopropyl-β-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur. In some embodiments of any of the aspects, the inducible promoter is selected from the group consisting of: an arabinose-inducible promoter; pBAD arabinose-inducible promoter (e.g., VirFara); tumor-induced promoters; ansB promoter; pflE promoter; and napF promoter; and an inflammation-induced promoter.

As described below herein, expression of certain Salmonella genes is known to be induced when the bacterium is present in a tumor. The promoters of these genes and/or E. coli homologs of these genes can be utilized to induce TDESS and payload polypeptide expression only once a cell has reached a tumor, reducing off-target side effects. Non-limiting examples of suitable promoters can include the promoters of ansB; pflE; and napF of Salmonella, which are described further in, e.g, Arrach et al. Cancer Res, 2008. 68(12): p. 4827-32; which is incorporated by reference herein in its entirety.

In some embodiments of any of the aspects, the engineered microbial cell described herein can be created by engineering and/or modifying a microbial cell selected from the group consisting of: *E. coli* NISSLE 1917 (EcN); *E. coli* K12; MP; HS; human commensal bacteria, marine commensal bacteria, and derivative strains thereof. In some embodiments of any of the aspects described herein, strain which is derivative of *E. coli* K12 is selected from the group consisting of *E. coli* DH10β and *E. coli* DH5α. In some embodiments of any of the aspects, the engineered microbial cell described herein can be created by engineering and/or modifying *E. coli* NISSLE 1917 (EcN). In some embodiments of any of the aspects, the engineered microbial cell described herein can be created by engineering and/or modifying a commensal intestinal microbial cell. In some embodiments of any of the aspects, the commensal intestinal microbial cell is *E. coli* NISSLE 1917 (EcN).

In some embodiments of any of the aspects, the engineered microbial cell described herein can be created by engineering and/or modifying a pathogenic microbial cell, wherein the modifications include deletion or mutation of one or more T3SS components. In some embodiments of any of the aspects, the one or more T3SS components is selected from the group consisting of: a toxin; a T3SS effector; a structural T3SS polypeptide; and a master regulator of T3SS components. Such deletions and/or mutations have been described in the art, e.g. non-limiting examples include virulence-curing of *S. typhimurium* by removing a virulence plasmid (see, e.g. Gulig and Curtiss. Infect Immun 1987 55:2891-2901; which is incorporated by reference herein in its entirety) and virulence-curing of *S. typhimurium* by mutation and/or of master regulators, e.g. master regulators of genes encoding endogenous T3SS substrates (see, e.g., Eichelberg and Galan. Infect immune 1999 67:4099-4105; which is incorporated by reference herein in its entirety). In some embodiments, the T3SS component is located on a plasmid. For example, *Yersinia* and *Shigella* encode type 3 secretion systems in plasmids. In some embodiments, a plasmid comprising the T3SS component is removed from the bacterial cell, such as *Shigella*. For example, one can introduce a T3SS encoding plasmid into virulence plasmid cured strains of *Shigella*. In some embodiments of any of the aspects, the pathogenic microbial cell is selected from the group consisting of: *Salmonella* spp.; *Shigella* Spp; and *Yersinia* spp. In some embodiments of any of the aspects, the pathogenic microbial cell is selected from the group consisting of: *Salmonella typhimurium* SPI1and *Shigella flexneri* mxi-spa.

In some embodiments of any of the aspects described herein, the engineered cell can be further engineered or modified to increase secretion of the payload polypeptide. Such modifications can include modifications to increase translation, transcription, T3SS system component production, and the like. In some embodiments of any of the aspects, the cell has been contacted with a mutagenic treatment; and selected for increased secretion. In some embodiments of any of the aspects, the cell has been contacted with a mutagenic treatment; and selected for increased secretion of the T3SS-compatible payload polypeptide.

In some embodiments of any of the aspects, delivery of the payload polypeptide to a desired location can be increased or improved by further engineering the microbial cell to permit binding and/or increased binding to a cell or molecule found at the desired location. Methods for modulating bacterial adherence to a given cell are known in the art. In some embodiments of any of the aspects, the cell further comprises a nucleic acid sequence encoding one or more polypeptides that increase adhesion to a target cell. In some embodiments of any of the aspects, the polypeptides that increase adhesion to the target cell comprise Tir and intimin, e.g. from enteropathogenic *E. coli*. Intimin is an outer membrane protein and Tir is a substrate of the T3SS which, upon delivery to a target cell, integrates into the plasma membrane and acts as a receptor for intimin. In some embodiments, an engineered microbial cell comprising a nucleic acid sequence encoding intimin and Tir can also comprise a nucleic acid sequence encoding the Tir chaperone CesT. In some embodiments of any of the aspects, the polypeptide that increases adhesion to the target cell is selected from a group consisting of: a bacterial adhesion; Afa1; AIDA; invasion; an antibody reagent specific for an extracellular epitope of a target cell polypeptide; and a single chain antibody specific for an extracellular epitope of a target cell polypeptide. Construction of adhesins that are specific for a given target, e.g., different regions of the gut, is known to one of skill in the art and described further in, e.g., Pinero-Lambea et al. ACS Synthetic Biology 2015 4:463-473; which is incorporated by reference herein in its entirety.

The engineered microbial cells described herein can permit delivery of one or more payload polypeptides to a desired extracellular location. In one aspect of any of the embodiments, described herein is a method of introducing a polypeptide into a target tissue or organism, the method comprising contacting the target tissue or organism with an engineered microbial cell as described herein.

In one aspect of any of the embodiments, described herein is a method of reducing inflammation in a subject, the method comprising administering an engineered microbial cell or a composition comprising an engineered microbial cell as described herein to a subject in need thereof. In some embodiments of any of the aspects, the microbial cell can comprise a payload polypeptide that is an anti-inflammatory polypeptide or an antibody reagent that specifically binds to an inflammatory cytokine in extracellular space or inflammatory cytokine receptor on a cell surface. In some embodiments of any of the aspects, the inflammation is inflammation of the gastrointestinal tract. In some embodiments of any of the aspects, the subject is in need of treatment for a condition selected from the group consisting of: asthma; inflammatory bowel disease; Crohn's disease; obesity; and ulcerative colitis. In some embodiments of any of the aspects, the subject is a subject in need of treatment for inflammatory bowel disease. In some embodiments of any of the aspects, the microbial cell or composition comprising the microbial cell an a pharmaceutically acceptable carrier is administered orally. In some embodiments of any of the aspects, the microbial cell is engineered from an intestinal commensal bacterium.

In one aspect of any of the embodiments, described herein is a method of treating a proliferative disease in a subject, the method comprising administering an engineered microbial cell as described herein to a subject in need thereof. In some embodiments of any of the aspects, the proliferative disease is a cancer. In some embodiments of any of the aspects, the payload polypeptide can be a toxin or an antibody reagent specific for a cancer cell marker and/or regulator and/or checkpoint polypeptide. In some embodiments of any of the aspects, the microbial cell can be engineered from *E. coli* NISSLE 1917 (EcN), which demonstrates a surprising ability to localize to tumors without inducing any immune responses. In some embodiments of any of the aspects, the microbial cell is administered systemically or orally. In some embodiments of any of the aspects, the microbial cell is administered intratumorally. In some embodiments of any of the aspects, the cancer is a cancer of the gastrointestinal tract and the microbial cell is administered orally. In some embodiments of any of the aspects of the invention, the microbial cell is administered orally for targeting either targets in the gastrointestinal (GI) track or in tumors into which the microbial cell in question is known to migrate from the gut.

In one aspect of any of the embodiments, described herein is a method of treating an intestinal infection in a subject, the method comprising administering an engineered microbial cell as described herein to a subject in need thereof. In some embodiments of any of the aspects, the microbial cell can comprise a payload polypeptide that is an antibody reagent that specifically binds a bacterial toxin. In some embodiments of any of the aspects, the intestinal infection is EHEC and/or the subject has hemolytic uremic syndeom and the toxin is Shiga toxin. In some embodiments of any of the aspects, the intestinal infection is a *C. difficile* infection and/or the subject has *C. difficile* colitis and the toxin is TcdA and/or TcdB. In some embodiments of any of the aspects, the intestinal infection is cholera and the toxin is cholera toxin. In some embodiments of any of the aspects, the intestinal infection is gastrointestinal anthrax and the toxin is anthrax toxin. In some embodiments of any of the aspects, the intestinal infection is botulism and the toxin is botulinum toxin. In some embodiments of any of the aspects, the microbial cell is administered orally.

In some embodiments of arty of the aspects, the method further comprises a step of inducing secretion of the T3SS-compatible payload polypeptide by further administering the subject a compound to induce expression of the T3SS-compatible payload polypeptide and/or the T3SS master regulator. In some embodiments of any of the aspects, expression of the T3SS-compatible payload polypeptide and/or the T3SS master regulator is controlled by an inducible promoter. In some embodiments of any of the aspects, the compound is arabinose and the inducible promoter is an arabinose-inducible promoter.

In one aspect of any of the embodiments, described herein is a method for delivering a polypeptide into a) the extracellular milieu of a subject's gastrointestinal tract or b) the extracellular milieu of a subject's tumor, the method comprising contacting administering a microbial cell as described herein to the subject. As used herein, "extracellular milieu" refers to the environment found in the extracellular space, e.g., the fluid environment in a subject which is not located within a cell. The extracellular milieu can include the interstitial fluid and/or the extracellular matrix.

In one aspect of any of the embodiments, described herein is a kit comprising an engineered microbial cell as described herein. A kit is any manufacture (e.g., a package or container) comprising at one engineered microbial cell in a container either in dry, or lyophilized form and usually with a pharmaceutically acceptable carrier as described herein, the manufacture being promoted, distributed, or sold as a unit for performing the methods described herein. When the kits, and methods described herein are used for diagnosis and/or treatment of a condition in patients, the reagents (e.g., detection probes) or systems can be selected such that a positive result is obtained in at least about 20% at least about 40%, at least about 60%, at least about 80%, at least about 90%, at least about 95%, at least about 99% or in 100% of subjects having or developing a sensitivity to the therapeutics described herein.

A kit can further comprising reagents and/or components for the preservation, culture, and/or Ihrther engineering of a cell as described herein, e.g., a cryopreservation solution, media, an inducer, a vector for introduction of a second nucleic acid sequence, etc. Such ingredients are known to the person skilled in the art and may vary depending on the method carried out. Additionally, the kit may comprise an instruction leaflet and/or may provide information about the cell or further medication of the cell.

In some embodiments, the methods described herein relate to treating a subject, such as a mammalian subject, including human, farm animals or pets, such as swine, bovine, dog, or cat. In some embodiments the subject is a fowl. The compositions and methods as described herein can be used in human or veterinary treatment. Subjects having a condition described here (e.g. inflammation or cancer) can be identified by a physician/veterinarian using current methods of diagnosing such conditions. Symptoms and/or complications which characterize these conditions and aid in diagnosis.

The compositions and methods described herein can be administered to a subject in need of treatment, e.g. in need of treatment for inflammation or cancer. In some embodiments, the methods described herein comprise administering an effective amount of compositions described herein, e.g. engineered microbial cells to a subject in order to alleviate a symptom. As used herein, "alleviating a symptom" is ameliorating any condition or symptom associated with a given condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, bin are not limited to oral, subcutaneous, transdermal, airway (aerosol), cutaneous, topical, injection, or intratumoral administration. Administration can be local or systemic.

The term "effective amount" as used herein refers to the amount of engineered microbial cells needed to alleviate at least one or more symptom of the disease or disorder, and relates to a sufficient amount of pharmacological composition to provide the desired effect. The term "therapeutically effective amount" therefore refers to an amount of engineered microbial cells that is sufficient to effect a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an engineered microbial cell which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inflammation, among others. The dosage can be determined by a physician and adjusted, as necessary, to suit observed effects of the treatment.

In some embodiments, the technology described herein relates to a pharmaceutical composition comprising an engineered microbial cell as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$, alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutical compositions comprising an engineered microbial cell can be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia, Pa. (2005).

The methods described herein can further comprise administering a second agent and/or treatment to the subject, e.g. as part of a combinatorial therapy.

The methods described herein can further comprise administering a second agent and/or treatment to the subject, e.g. as part of a combinatorial therapy. By way of non-limiting example, if a subject is to be treated for inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

Non-limiting examples of a second agent and/or treatment for a subject in need of treatment for cancer can include radiation therapy, surgery, gemcitabine, cisplastin, paclitaxel, carboplatin, bortezomib, AMG479, vorinostat, rituximb, temozolomide, rapamycin, ABT-737, PI-103; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullataeinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin pancratistatin; a sarcodictyin; spongistatin; nitrogen mustards such as chlorambucil, chlomaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 11 and calicheamicin omegaI1 (see, e.g., Agnew, Chem. Intl. Ed. Engl., 33: 18:3-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esonibicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, cannofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products. Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and auguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatraxate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In certain embodiments, an effective dose of a composition comprising engineered microbial cells as described herein can be administered to a patient once. In certain embodiments, an effective dose of a composition comprising engineered microbial cells can be administered to a patient repeatedly. In some embodiments, the dose can be a daily administration, for example oral administration, of, e.g., a capsule comprising bacterial cells as described herein. In some embodiments, the dose can be, e.g. an injection of bacterial cells into the desired area, e.g. a tumor. In some embodiments, the dose can be administered systemically, e.g. by intravenous injection. In some embodiments, a dose can comprise from $10^6$ to $10^{12}$ cells. In some embodiments, a dose can comprise from about $10^8$ to $10^{10}$ cells. A composition comprising engineered microbial cells can be administered over a period of time, such as over a 5 minute, 10 minute, 15 minute, 20 minute, or 25 minute period. The administration can be repeated, for example, on a regular basis, such as hourly for 3 hours, 6 hours, 12 hours, daily (i.e. one a day) or longer or such as once a week, or biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing, schedule can vary from once a week to daily depending on a number of clinical factors, such as the subject's sensitivity to engineered microbial cells. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of engineered microbial cells, according to the methods described herein depend upon, for example, the form of the cells, their potency, and the extent to which symptoms, markers, or indicators of a condition described herein are desired to be reduced, for example the percentage reduction desired. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of engineered microbial cells in, e.g. the treatment of a condition described herein, or to induce a response as described herein can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein. When using an experimental animal model, efficacy of treatment is evidenced when a statistically significant change in a marker is observed.

In some aspects of any of the embodiments, provided herein are methods and compositions relating to the delivery or translocation of antibody reagents, e.g., single chain antibodies or VHH, to the intracellular space of a target eukaryotic cell by engineering non-pathogenic bacterial cells which express a functional T3SS to create a biological delivery system. Also described herein are compositions and methods that relate to non-pathogenic microbial cells that have been engineered to express both I) a functional type three secretion system (T3SS) that is capable of injecting a payload into another cell and at least one antibody reagent that is compatible with the T3SS.

In one aspect of any of the embodiments, described herein is an engineered non-pathogenic microbial cell comprising (1) a first nucleic acid sequence comprising genes encoding a functional type three secretion system (T3SS); (2) a second nucleic acid sequence encoding an T3SS-compatible antibody reagent; wherein the engineered microbial cell is non-pathogenic with respect to the target cell or target organism. In one aspect of any of the embodiments, described herein is an engineered non-pathogenic microbial cell comprising (1) a first nucleic acid sequence comprising genes encoding a functional type three secretion system (T3SS); (2) a second nucleic acid sequence encoding an T3SS-compatible Wilt wherein the engineered microbial cell is non-pathogenic with respect to the target cell or target organism. For example, a plasmid comprising two operons encoding a functional *Shigella* T3SS (covering 31 kb) can be utilized.

As used herein, a "target cell" is a cell which can receive a polypeptide delivered by a bacterial T3SS. In some embodiments, a target cell is a eukaryotic cell. In some embodiments, a target cell is a cell comprised by, or originating from, a vertebrate. In some embodiments, a target cell is a cell comprised by, or originating from, a mammal. A "target organism" is an organism comprising at least one "target cell." A target cell can be located in vitro or in vivo. In some embodiments, a target cell is an isolated target cell. In some embodiments, a target cell is not an isolated target cell. In some embodiments, the target cell is part of the target organism.

A T3SS is a multi-protein structure found in gram negative bacteria. It moves poly peptides from the cytoplasm of the bacterial cell through the interior of the T3SS "needle" into the cytoplasm of a target cell. T3SS's are found in pathogenic strains and have been observed in pathogenic isolates of, e.g., *Shigella, Salmonella, E. coli, Burkholderia, Yersinia, Chlamydia, Pseudomonas, Erwinia, Ralstonia, Rizobium, Vibrio*, and *Xanthamonas*. Further discussion of T3SS's can be found, e.g. in Izore et al. Structure 2011 19:603-612; Korotkov et al. Nature Reviews Microbiology 2012 10:336-351; Wooldridge, K. (ed) Bacterial Secreted Proteins. Caster Academic Press 2009; Snyder and Champness (eds.) Molecular Genetics of Bacteria. $3^{rd}$ Ed. ASM Press: 2007; each of which is incorporated by reference herein in its entirety.

The suite of T3SS-related proteins in a given wild-type cell is typically divided into structural proteins (those proteins which form the needle itself), substrate proteins (those proteins which are transported through the needle to the host), and chaperones (these proteins that bind effectors in the cytoplasm to protect, process, and/or shuttle the effectors to the needle). As used herein, a "functional T3SS" refers, minimally, to the set of structural proteins which are required in order to transfer at least one polypeptide to a target cell. In some embodiments, a functional T3SS system can comprise one or more chaperone proteins. In some embodiments, a functional T3SS can comprise one or more, for example, two, three, or four, substrates which are not virulence factor (e.g. certain translocators). In some embodiments, a functional T3SS does not comprise a virulence factor which is delivered to the target cell.

As used herein, a "virulence factor" refers to those substrates which affect and/or manipulate a target cell in a manner which is beneficial to infection and deleterious to the target cell, i.e. they perturb the normal function of the target cell. Examples of actions of virulence factors include, but are not limited to, modulation of actin polymerization, induction of apoptosis, modulation of the cell cycle, modulation of gene transcription. Not all substrates are necessarily virulence factors. By way of non-limiting example, a T3SS (and a functional T3SS) can comprise proteins referred to as translocators. These substrates are secreted by the T3SS as it nears a complete form and create a pore in the target cell membrane, allowing further substrates to be delivered into the cytoplasm of the target cell, i.e. translocators are substrates in that they travel through the needle to the target cell and are also structural proteins in that they form part of the structure through which other substrates are delivered into the target cell. In some embodiments, a single polypeptide can be both a translocator and a virulence factor (e.g. IpaB of *Shigella*).

In some embodiments, a functional T3SS can comprise one or more translocators.

In some embodiments, a functional T3SS does not comprise a translocator that also has virulence factor activity.

The minimal set of proteins required for a functional T3SS can vary depending upon, e.g. the identity of the polypeptide which is to be transferred, the origin of the T3SS, the identity of the non-pathogenic bacterial cell, and/or the identity of the host cell.

In some embodiments, a functional T3SS can comprise one or more of a needle monomer polypeptide, an inner rod polypeptide, ring polypeptides, one or more translocators, a needle-tip polypeptide, a ruler polypeptide, and/or ATPase.

In some embodiments, a functional T3SS can comprise a needle monomer polypeptide (e.g. MxiH (e.g., NCBI Gene ID No: 1238256 (DNA sequence disclosed as SEQ ID NO: 19; PRT sequence disclosed as SEQ ID NO: 20)); PrgI (e.g., NCBI Gene ID No: 1254396 (DNA sequence disclosed as SEQ ID NO: 21; PRT sequence disclosed as SEQ ID NO: 22)); YscF (e.g., NCBI Gene ID No: 1172700 (DNA sequence disclosed as SEQ ID NO: 23; PRT sequence disclosed as SEQ ID NO: 24)); and/or EscF (e.g., NCBI Gene ID No: 8873370 (DNA sequence disclosed as SEQ ID NO: 25; PRT sequence disclosed as SEQ ID NO: 26) or NC_013941.1 (4477882. 4478103) (SEQ ID NO: 1) or WP_001053840 (SEQ ID NO: 2))), an inner rod polypeptide (e.g. MxiI (e.g., NCBI Gene ID No: 1238257 (DNA sequence disclosed as SEQ ID NO: 27; PRT sequence disclosed as SEQ ID NO: 28)); PrgJ (e.g., NCBI Gene ID No: 1254395 (DNA sequence disclosed as SEQ ID NO: 29; PRT sequence disclosed as SEQ ID NO: 30)); YscI NCBI Gene ID No: 2767498 (DNA sequence disclosed as SEQ ID NO: 31; PRT sequence disclosed as SEQ ID NO: 32) or NC_305813.1 (18395.18733) (SEQ ID NO: 3) or WP_032465675.1 (SEQ ID NO: 4)); and/or EscI (e.g., NCBI Gene ID No: 8219253 (DNA sequence disclosed as SEQ ID NO: 33; PRT sequence disclosed as SEQ ID NO: 34) or NC_013008.1 (4669108. 4669485) (SEQ ID NO: 5) or WP_001302733.1 (SEQ ID NO: 6))), ring polypeptides, one or more translocators (e.g. IpaC (e.g., NCBI Gene ID No: 876448 (DNA sequence disclosed as SEQ ID NO: 35; PRT sequence disclosed as SEQ H) NO: 36)); SipB (e.g., NCBI Gene ID No: 1254408 (DNA sequence disclosed as SEQ ID NO: 37; PRT sequence disclosed as SEQ ID NO: 38)); SipC (e.g., NCBI Gene ID No: 1254407 (DNA sequence disclosed as SEQ ID NO: 39; PRT sequence disclosed as SEQ ID NO: 40)); YopB (e.g., NCBI Gene ID No: 1449456 (DNA sequence disclosed as SEQ ID NO: 41; PRT sequence disclosed as SEQ ID NO: 42)); YopD (e.g., NCBI Gene ID No: 14.49455 (DNA sequence disclosed as SEQ ID NO: 43; PRT sequence disclosed as SEQ ID NO: 44)); EspD (e.g., NCBI Gene ID No: 885777 (DNA sequence disclosed as SEQ ID NO: 45; PRT sequence disclosed as SEQ ID NO: 46)); and/or EspB (e.g., NCBI Gene ID No: 8474872 (DNA sequence disclosed as SEQ ID NO: 47; PRT sequence disclosed as SEQ ID NO: 48))); a needle-tip polypeptide (e.g. IpaD (e.g., NCBI Gene ID No: 876444 (DNA sequence disclosed as SEQ ID NO: 49; PRT sequence disclosed as SEQ ID NO: 50)); SipD (e.g., NCBI Gene ID No: 1254406 (DNA sequence disclosed as SEQ ID NO: 51; PRT sequence disclosed as SEQ ID NO: 52)); LcrV (e.g., NCBI Gene ID No: 1172676 (DNA sequence disclosed as SEQ ID NO: 53; PRT sequence disclosed as SEQ ID NO: 54)); and/or EspA (e.g., NCBI Gene ID No: 960865 (DNA sequence disclosed as SEQ ID NO: 55; PRT sequence disclosed as SEQ ID NO: 56))); a paler polypeptide (e.g. Sp32 (e.g., NCBI Gene ID No: 876502 (DNA sequence disclosed as SEQ ID NO: 57; PRT sequence disclosed as SEQ ID NO: 58)); InvJ (e.g., NCBI Gene ID No: 1254415 (DNA sequence disclosed as SEQ ID NO: 59; PRT sequence disclosed as SEQ ID NO: 60)); YscP (e.g., NCBI Gene ID No: 5798302 (DNA sequence disclosed as SEQ ID NO: 61; PRT sequence disclosed, as SEQ ID NO: 62) or NC_010157.1 (27606. 28973) (SEQ ID NO: 7) or WP_02212950.1 (SEQ ID NO: 8)); and/or Orf16 (e.g., NCBI Gene ID No: 8219247 (DNA sequence disclosed as SEQ ID NO: 63; PRT sequence disclosed as SEQ ID NO: 64) or NC_013008.1 (4664050. 4664466) (SEQ ID NO: 9) or WP_001303723.1 (SEQ ID NO: 10))), and an ATPase (e.g. Spa47 (e.g., NCBI Gene ID No: 876429 (DNA sequence disclosed as SEQ ID NO: 65; PRT sequence disclosed as SEQ ID NO: 66)); InvC (e.g., NCBI Gene ID No: 1254417 (DNA sequence disclosed as SEQ ID NO: 67; PRT sequence disclosed as SEQ ID NO: 68)); YscN (e.g., NCBI Gene ID No: 10216379 (DNA sequence disclosed as SEQ ID NO: 69; PRT sequence disclosed as SEQ ID NO: 70)); and/or SepB (also known as EscN) (e.g., NCBI Gene ID No: 8873386 (DNA sequence disclosed as SEQ ID NO: 71; PRT sequence disclosed as SEQ I) NO: 72) or NC_013941.1 (4493198. 4494538) (SEQ ID NO: 11) or WP_300622545.1 (SEQ ID NO: 12))). In some embodiments, a functional T3SS can further comprise a chaperone for the one or more translocators (e.g. IpgC (e.g., NCBI. Gene ID No: 1238043 (DNA sequence disclosed as SEQ ID NO: 73; PRT sequence disclosed as SEQ ID NO: 74)); SicA (e.g., NCBI Gene ID No: 1254409 (DNA sequence disclosed as SEQ ID NO: 75; PRT sequence disclosed as SEQ ID NO: 76)); SycD (e.g., NCBI Gene ID No: 2767486 (DNA sequence disclosed as SEQ ID NO: 77; PRT sequence disclosed as SEQ ID NO: 78) or NC_005813.1 (38937. 39443) (SEQ ID NO: 13) or WP_302202758.1 (SEQ ID NO: 14)); and/or CesD (e.g., NCBI Gene ID No: 7063867 (DNA sequence disclosed as SEQ ID NO: 79; PRT sequence disclosed as SEQ ID NO: 80))). In some embodiments, a functional T3SS can further comprise one or more of a switch polypeptide (e.g. Spa40 (e.g., NCBI Gene ID No: 876433 (DNA sequence disclosed as SEQ ID NO: 81; PRT sequence disclosed as SEQ ID NO: 82)); SpaS (e.g., NCBI Gene ID No: 1254410 (DNA sequence disclosed as SEQ ID NO: 83; PRT sequence disclosed as SEQ H) NO: 84)), YscU (e.g., NCBI Gene ID No: 2767517 (DNA sequence disclosed as SEQ ID NO: 85; PRT sequence disclosed as SEQ ID NO: 86)); and/or EscU (e.g., NCBI Gene ID No: 7062687 (DNA sequence disclosed as SEQ ID NO: 87; PRT sequence disclosed as SEQ ID NO: 88))) and a gatekeeper polypeptide (e.g. MxiC (e.g., NCBI Gene ID No: 876426 (DNA sequence disclosed as SEQ H) NO: 89, PRT sequence disclosed as SEQ NO: 90)); InvE (e.g., NCBI Gene ID No: 125.4420 (DNA sequence disclosed as SEQ ID NO: 91; PRT sequence disclosed as SEQ ID NO: 92)); YopN (e.g., NCBI Gene ID No: 2767534 (DNA sequence disclosed as SEQ ID NO: 93; PRT sequence disclosed as SEQ ID NO: 94) or NC_005813.1 (32887. 033768) (SEQ ID NO: 15) or WP_011171994.1 (SEQ ID NO: 16)); and/or SepL (e.g., NCBI Gene ID No: 8873375 (DNA sequence disclosed as SEQ ID NO: 95; PRT sequence disclosed as SEQ ID NO: 96) or NC_013941.1 (4481286. 4482341) (SEQ ID NO: 17) or WP_001273445.1 (SEQ ID NO: 18))).

In some embodiments, the functional type three secretion system (T3SS) can comprise polypeptides endogenous to a bacterium selected from the group consisting of: *Shigella* spp; *Salmonella* spp; enteropathogenic *E. coli*; and *Yersinia* spp. In some embodiments, the genes encoding a functional type three secretion system (T3SS) comprise: virB; acp; ipaA; ipaB; ipaC; ipaD; ipgC; ipgB1; ipgA; icsB; ipgD; ipgE; ipgF; mxiG; mxiH; mxiN; mxiL; mxiM, mxiE, mxiD; mxiA, spa15; spa47; spa13, spa32, spa33, spa24, spa9; spa29; and spa40 and/or homologs thereof.

In some embodiments, the first nucleic acid sequence comprising genes encoding a functional type three secretion system (T3SS) can comprise one contiguous sequence. In some embodiments, the first nucleic acid sequence comprising genes encoding a functional type three secretion system (T3SS) is located on a plasmid. In some embodiments, the first nucleic acid sequence comprising genes encoding a functional type three secretion system (T3SS) is located on a chromosome (e.g. a naturally-occurring chromosome, a modified endogenous chromosome, or a bacterial artificial chromosome (BAC)). In some embodiments, the first nucleic acid sequence comprising genes encoding a functional type three secretion system (T3SS) can comprise one or more operons, e.g. one operon, two operons, three operons, or more operons. In some embodiments, the first nucleic acid sequence comprising genes encoding a functional type three secretion system (T3SS) can comprise one or more separate sequences and/or molecules (e.g. a portion of the genes are found on one plasmid and another portion of the genes are found on a second plasmid). In some embodiments, the first nucleic acid sequence can be integrating into the chromosome using, for example, landing pad technology, see, e.g. Kuhlman and Cox, 2010 Nucleic Acids Research 38:e92: which is incorporated by reference herein in its entirety.

In some embodiments, a functional T3SS system can be introduced into a non-pathogenic bacterial cell. In alternative embodiments, a pathogenic bacterial cell comprising a functional T3SS can be engineered to be non-pathogenic, e.g. by deleting or mutation one or more T3SS components. Non-limiting examples of T3SS components that can be deleted or mutated to engineer a non-pathogenic bacterial cell include: a toxin; a T3SS substrate; a structural T3SS polypeptide; a master regulator of T3SS components; and any combination thereof. Such deletions and/or mutations have been described in the art, e.g. non-limiting examples include virulence-curing of *S. typhimurium* by removing a virulence plasmid (see, e.g. Gulig and Curtiss. Infect Immun 1987 55:2891-2901; which is incorporated by reference herein in its entirety) and virulence-curing of *S. typhimurium* by mutation and/or of master regulators, e.g. master regulators of genes encoding endogenous T3SS substrates (see, e.g., Eichelberg and Galan. Infect immune 1999 67:4099-4105; which is incorporated by reference herein in its entirety). In some embodiments, the T3SS component is located on a plasmid. For example, *Yersinia* and *Shigella* encode type 3 secretion systems in plasmids. In some embodiments, a plasmid comprising the T3SS component is removed from the bacterial cell, such as *Shigella*. In some embodiments, the pathogenic microbial cell is selected from the group consisting of: *Salmonella* spp.; *Shigella* Spp; and *Yersinia* spp. In some embodiments, the pathogenic microbial cell is selected from the group consisting of: *Salmonella typhimurium* SPI1and *Shigella felxneri* mxi-spa. For example, one can introduce the T3SS encoding, plasmid into virulence plasmid cured steams of *Shigella*.

In some embodiments, the first nucleic acid sequence is no greater than 4 kb in size. In some embodiments, the first nucleic acid sequence is no greater than 3 kb in size, e.g., no greater than 2.5 kb, 2 kb, 115 kb, or 1 kb. In some embodiments, the Fast nucleic acid sequence and third nucleic acid sequence are, cumulatively, no greater than 4 kb in size. In some embodiments, the first nucleic acid sequence and third nucleic acid sequence are, cumulatively, no greater than 3 kb in size, e.g., no greater than 2.5 kb, 2 kb, ⅕ kb, or 1 kb.

In some embodiments, the first nucleic acid sequence and optionally, the third nucleic acid sequence, are found in or introduced to the cells by means of a plasmid or vector which is no greater than 6 kb in size, e.g., 6 kb or less, 5 kb or less, 4 kill or less, 3 kb or less, 2.5 kb or less, or 2 kb or less. In some embodiments, the first nucleic acid sequence and optionally, the third nucleic acid sequence, are found in or introduced to the cells by means of a plasmid or vector Which is no greater than 3 kb in size. The delivery of an antibody reagent, e.g., a VHH, via a T3SS requires close proximity of the microbial cell and the target cell. Accordingly, in some embodiments, delivery of an antibody reagent can be increased or enhanced by causing and/or increasing adhesion of the microbial cell to the target cell. In some embodiments, the engineered microbial cell further comprises a nucleic acid sequence encoding one or more polypeptides that increase adhesion to the target cell. A number of polypeptides can increase adhesion.

In some embodiments, the polypeptides that increase adhesion to the target cell comprise Tir and intimin, e.g., from enteropathogenic *E. coli*. Intimin is an outer membrane protein and Tir is a substrate of the T3SS which, upon delivery to a target cell, integrates into the plasma membrane and acts as a receptor for intimin. In some embodiments, an engineered microbial cell comprising a nucleic acid sequence encoding intimin and Tir can also comprise a nucleic acid sequence encoding the Tir chaperone CesT.

In some embodiments, the polypeptide that increases adhesion to the target cell can be selected from the group consisting of a bacterial adhesin; AfaI; AIDA; invasin; or a single chain antibody specific for an extracellular epitope of a target cell polypeptide. In some embodiments, the extracellular epitope of the target cell can be specific for a certain type of target cell, e.g. a cancer-cell specific epitope and/or a tissue-specific epitope in order to target delivery of polypeptides to a particular cell type.

As described herein, four endogenous *Shigella* polypeptides, when secreted by a functional type 3 secretion system, are sufficient to enable a bacterial cell to mediate its uptake into a target cell. Accordingly, engineered bacterial cells as described herein that comprise these four polypeptides (or homologs thereof) can be internalized by a target cell and can deliver their T3SS-compatible antibody reagent(s) before, during, and/or after internalization into the target cell. Their uptake by the target cell can also trigger, e.g. innate immune responses leading to cell death. In some embodiments, uptake can trigger innate immune responses potentially leading to cell death. Such engineered bacterial cells can be suitable, for example, for use in methods where it is desired to kill the target cell, e.g. in treating a solid tumor. In some embodiments, a commensal cell is engineered to comprise the four *Shigella* polypeptides and/or homologs thereof. In some embodiments, a pathogenic cell engineered to be avirulent is engineered such that it retains the four *Shigella* polypeptides and/or homologs thereof. In some embodiments, any one of the four *Shigella* polypeptides is sufficient to induce the uptake of the bacterial cell. In some embodiments, an engineered cell is engineered such that the engineered cell introduces less than four *Shigella* polypeptides and/or homologs thereof, e.g. only one of the polypeptides, only two of the polypeptides, or only three of the polypeptides.

Conversely, cells lacking all four of these endogenous *Shigella* polypeptides cannot mediate uptake by the target cell and remain in the extracellular environment. Such engineered bacterial cells can be suitable for use in methods where is undesirable to activate innate immune responses, e.g. when delivering anti-inflammatory antibody reagents to the target cell, in some embodiments, a commensal cell is engineered such that it does not any of the four *Shigella* polypeptides and/or homologs thereof, e.g. it retains none of the polypeptides. In some embodiments, a pathogenic cell engineered to be avirulent is engineered such that it does not any of the four *Shigella* polypeptides and/or homologs thereof, e.g. it retains none of the polypeptides.

The four endogenous *Shigella* polypeptides referred to above are IpgB1 (e.g., NCBI Ref Seq: NP_858263 (SEQ ID NO: 97)); IpgD (e.g., NCBI Ref Seq: NP_0852.96 (SEQ ID NO: 98)); ipaA (e.g., NCBI Ref Seq: NP_858264 (SEQ ID NO: 99)) and IcsB (e.g., NCBI Ref Seq: NP_085294 (SEQ ID NO: 100)). Homologs of the foregoing *Shigella* polypeptides are also contemplated for use in the compositions and methods described herein. By way of non-limiting example, SopB (e.g., NCBI Ref Seq: NP_460064 (SEQ ID NO: 101)) is a homolog of IpgD and SipA (e.g., NCBI Ref Seq: NP_461803 (SEQ ID NO: 102)) is a homolog of IpaA. Numerous species have a Rho GTP exchange factor that is a homolog of IpgB1.

Homologs of any given polypeptide or nucleic acid sequence can be found using, e.g., BLAST programs (freely available on the world wide web at http://blast.ncbi.nlm.nih.gov/), e.g. by searching freely available databases of sequence for homologous sequences, or by querying those databases for annotations indicating a homolog (e.g. search strings that comprise a gene mine or describe the activity of a gene). The homologous amino acid or DNA sequence can be at least 90%, at least 95%, at least 96%, at least 97%, at least 98%, at least 99%, or more, identical to a reference sequence. The degree of homology (percent identity) between a reference and a second sequence can be determined, for example, by comparing the two sequences using freely available computer programs commonly employed for this purpose on the world wide web.

In some embodiments of any of the aspect described herein, a homolog can be a poly peptide with the same function, functional characteristics, and/or activity as the reference polypeptide. By way of non-limiting example, a homolog with the same function as one of the four endogenous *Shigella* polypeptides mentioned above. (i.e. IpgB1; IpgD; IpaA; and IcsB) can be identified by engineering a bacteria to not express one of IpgB1; IpgD; IpaA; and IcsB and to instead express a putative functional homolog and then measuring the ability of the bacteria to invade a target cell. If the bacteria retains at least 10% of the reference ability to invade a target cell, the putative functional homolog is demonstrated to be a functional homolog. In some embodiments, a functional homolog has at least 10% Of the activity of the reference polypeptide, e.g. 10% or more, 20% or more, 30% or more, 50% or more, 75% or more, 80% or more, 90% or more, 95% or more, or 100% or more of the activity of the reference polypeptide.

In addition to a first nucleic acid sequence comprising genes encoding a functional type three secretion system (T3SS), the engineered non-pathogenic microbial cells described herein further comprise a second nucleic acid sequence encoding a T3SS-compatible antibody reagent. As used herein the term "T3SS-compatible antibody reagent" refers to any antibody reagent expressed in the microbial cell that, in the presence of a functional T3SS, can be delivered to the cytoplasm of a target cell. A T3SS-compatible antibody reagent can be from any source, e.g. the reagent can have a eukaryotic origin, or a synthetic origin. A T3SS-compatible antibody reagent can be a naturally-occuring antibody reagent or a mutant and/or variant thereof. In a variant T3SS-compatible antibody reagent, one or more residues can be altered, deleted, and/or added as compared to a naturally-occurring and/or wild-type antibody reagent so long as the function remains substantially the same. Antibody reagents, including VHH, are discussed in further detail elsewhere herein.

In some embodiments, the T3SS-compatible antibody reagent is exogenous to the microbial cell. In some embodiments, the T3SS-compatible antibody reagent is ectopic with respect to the target cell. In some embodiments, the T3SS-compatible antibody reagent is exogenous with respect to the target cell. In some embodiments, the T3SS-compatible polypeptide is antibody reagent with respect to the target cell.

In some embodiments, the T3SS-compatible antibody reagent can comprise an N-terminal type three secretion system (T3SS) signal. Naturally-occurring T3SS substrates comprise a secretion signal within the first 20 amino acids of the polypeptide. Certain naturally-occurring T3SS substrates comprise a chaperone-binding domain within the first 50 amino acids of the polypeptide.

In order for the T3SS-compatible antibody reagent to be expressed, the nucleic acid encoding the T3SS-compatible antibody reagent can be operatively linked to a promoter. In some embodiments, the T3SS-compatible antibody reagent can be constitutively expressed. In some embodiments, nucleic acids encoding the T3SS-compatible antibody reagent can be operatively linked to a constitutive promoter. In some embodiments, the T3SS-compatible antibody reagent can be inducibly expressed. In some embodiments, nucleic acids encoding the T3SS-compatible antibody reagent can be operatively linked to an inducible promoter. In some embodiments, the T3SS-compatible antibody reagent to can be operatively linked to a type three secretion system (T3SS)-associated promoter or promoter element.

In some embodiments, a nucleic acid encoding a T3SS-compatible antibody reagent is present within the prokaryotic genome, e.g. the nucleic acids can be incorporated into the genome. Typically, in bacteria, one uses homologous recombination to target genes to specific sites on bacterial chromosomes. In some embodiments, a nucleic acid encoding a T3SS-compatible antibody reagent is present within a vector. In some embodiments, a nucleic acid encoding a T3SS-compatible antibody reagent is present within a portion of a plasmid. In some embodiments, a nucleic acid encoding a T3SS-compatible single domain antibody reagent is present within a vector. In some embodiments, a nucleic acid encoding a T3SS-compatible single-domain antibody reagent is present within a portion of a plasmid.

In addition to a first nucleic acid sequence comprising genes encoding a functional type three secretion system (T3SS) and a second nucleic acid sequence encoding a T3SS-compatible antibody reagent, in some embodiments, the engineered non-pathogenic microbial cells described herein, further comprise a third nucleic acid sequence encoding a master T3SS regulator.

In some embodiments, an engineered microbial cell can comprise nucleic acid sequence(s) encoding multiple T3SS-compatible antibody reagents. The multiple T3SS-compatible antibody reagents can be encoded as part of the same operon and/or as part of separate operons.

In one aspect, described herein is a kit comprising an engineered microbial cell comprising a first nucleic acid sequence comprising genes encoding a functional type three secretion system (T3SS); and a second nucleic acid sequence encoding an T3SS-compatible antibody reagent; wherein the engineered microbial cell is non-pathogenic with respect to a target cell.

The antibody reagent comprised by an engineered microbial cell comprising a first nucleic acid sequence comprising genes encoding a functional type three secretion system (T3SS), can bind specifically to, e.g., pro-inflammatory factors (e.g., pro-inflammatory cytokines or signaling molecules) or cancer cell markers and/or factors that promote the growth, metastasis, and/or survival of cancer cells.

In one aspect, the technology described herein relates to a method of introducing a poly peptide into a target cell, the method comprising contacting the target cell with an engineered microbial cell comprising a T3SS and a T3SS-compatible antibody reagent as described herein. In some embodiments, the methods described herein relate to treating a subject. Subjects having a condition described here (e.g. inflammation or cancer) can be identified by a physician using current methods of diagnosing such conditions. For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

A T3SS is a multi-protein structure found in gram negative bacteria. It moves polypeptides from the cytoplasm of the bacterial cell through the interior of the T3SS "needle" into the cytoplasm of a target cell. T3SS's are found in pathogenic strains and have been observed in pathogenic isolates of, e.g., *Shingella, Salmonella, E. coli, Burkholderia, Yersinia, Chlamydia, Pseudomonas, Erwinia, Ralstonia, Rhizobium, Vibrio*, and *Xanthamonas*. Further discussion of T3SS's can be found, e.g. in Izore et al. Structure 2011 19:603-612; Korotkov et al. Nature Reviews Microbiology 2012 10:336-351; Wooldridge, K. (ed) Bacterial Secreted Proteins. Caster Academic Press 2009; Snyder and Champness (eds.) Molecular Genetics of Bacteria. 3$^{rd}$ Ed. ASM Press: 2007; each of which is incorporated by reference herein in its entirety. The suite of T3SS-related proteins in a given wild-type cell is typically divided into structural proteins (those proteins which form the needle itself), substrate proteins (those proteins which are transported through the needle to the host), and chaperones (those proteins that bind effectors in the cytoplasm to protect, process, and/or shuttle the effectors to the needle).

In some embodiments, a nucleic acid encoding a polypeptide is present within the prokaryotic genome, e.g. the nucleic acids can be incorporated into the genome. Typically, in bacteria, one uses homologous recombination to target genes to specific sites on bacterial chromosomes. In some embodiments, a nucleic acid encoding a polypeptide is present within a vector. The term "vector", as used herein, refers to a nucleic acid construct designed for delivery to cell or transfer between different cells. Many vectors useful for transferring exogenous genes into target cells are available, e.g. the vectors may be episomal, e.g., plasmids, virus derived vectors or may be integrated into the target cell genome, through homologous recombination or random integration. In some embodiments, a vector can be an expression vector. As used herein, the term "expression vector" refers to a vector that has the ability to incorporate and express heterologous nucleic acid fragments in a cell. An expression vector may comprise additional elements. The nucleic acid incorporated into the vector can be operatively linked to an expression control sequence when the expression control sequence controls and regulates the transcription and translation of that polynucleotide sequence.

In some embodiments, a nucleic acid encoding a polypeptide is present within a portion of a plasmid. Plasmid vectors can include, but are not limited to, pBR322, pBR325, pACYC177, pACYC184, pUC8, pUC9, pUC18, pUC1.9, pLG339, pR290, pKC37, pKC101, SV 40, pBluescript II SK+/− or KS+/− (see "Stratagem Cloning Systems" Catalog (1993) from Stratagem, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference in its entirety). In some embodiments, the plasmid is a low-copy number plasmid, pBR, pACYC, and/or SC101.

As used herein, a "subject" means a human or non-human animal. Usually the non-human animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, nit, dog, cat, horse, or cow, but is not limited to these examples. Mammals other than humans can be advantageously used as subjects that represent animal models of a given condition. A subject can be male or female and an adult or a child, including infants.

A subject can be one who has been previously diagnosed with or identified as suffering from or having a condition in need of treatment or one or more complications related to such a condition, and optionally, have already undergone treatment. Alternatively, a subject can also be one who has not been previously diagnosed as having a condition or one or more complications related to the condition as described herein.

A "subject in need" of treatment for a particular condition can be a subject having that condition, diagnosed as having that condition as described herein, such as inflammation or cancer.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the specific polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Gln; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into lie; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are also known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133. 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, "engineered" refers to the aspect of having been manipulated by the hand of man. For example, a cell is considered to be "engineered" when at least one aspect of the cell has been manipulated by the hand of man to differ from the aspect as it exists in nature. As is common practice and is understood by those in the art, progeny an engineered cell are typically still referred to as "engineered" even though the actual manipulation was performed on a prior entity.

As used herein, "microbe" or "microorganism" refers to an organism which is microscopic. A microbe can be a single-celled organism. In some embodiments of any of the aspects, a microbe can be a bacterium.

The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operatively linked to appropriate regulatory sequences. A gene may or may not include regions preceding and following the coding region, e.g. 5' untranslated (5'UTR) or "leader" sequences and 3' UTR or "trailer" sequences.

The term "operatively linked" includes having an appropriate start signal (e.g., ATG) in from of the polynucleotide sequence to be expressed, and maintaining the correct reading frame to permit expression of the polynucleotide sequence under the control of the expression control sequence, and, optionally, production of the desired polypeptide encoded by the polynucleotide sequence. In some examples, transcription of a nucleic acid is under the control of a promoter sequence (or other transcriptional regulatory sequence) which controls the expression of the nucleic acid in a cell-type in which expression is intended. It will also be understood that the nucleic acid can be under the control of transcriptional regulatory sequences which are the same or which are different from those sequences which control transcription of the naturally-occurring form of a protein.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

As used herein, a "target cell" is a cell close to which an engineered microbial cell as described herein delivers a payload polypeptide, e.g., the payload polypeptide is delivered to the extracellular space surrounding the target cell. In some embodiments, a target cell is a eukaryotic cell. In some embodiments, a target cell is a cell comprised by, or originating from, a vertebrate. In some embodiments, a target cell is a cell comprised by, or originating from, a mammal. A "target organism" is an organism comprising at least one "target cell." A target cell can be located in vitro or in vivo. In some embodiments, a target cell is an isolated target cell. In some embodiments, a target cell is not an isolated target cell. In some embodiments, the target cell is part of the target organism.

As used herein, the term "non-pathogenic" refers to a microbial cell which does not have a deleterious effect upon a target cell, i.e. in the presence of the non-pathogenic microbial cell, a target cell will not have a statistically significantly increased rate of cell death, nor a statistically significantly decreased metabolic rate or altered rate of growth and/or division. It is recognized that, therefore, whether a cell is non-pathogenic with respect to a target cell may vary depending upon, e.g. the environment in which the target cell is located and the concentration of the microbial cells. In some embodiments, a non-pathogenic microbial cell is non-pathogenic if it does not have a deleterious effect upon a target cell in vitro when the microbial cell is present at a concentration of less than 50× relative to the target cell. In some embodiments, a non-pathogenic microbial cell can be one that does not express a toxin having a deleterious effect upon the target cell. In some embodiments, a non-pathogenic microbial cell can be one that does not replicate within the target cell. In some embodiments, a non-pathogenic microbial cell can be one that is not found in the cytoplasm of the target cell. In some embodiments a non-pathogenic microbial cell can be one that is not found in the cytoplasm of the target cell but is found in the phagosome of the target cell. In some embodiments, a non-pathogenic microbial cell can be a commensal microbial cell. In some embodiments, a non-pathogenic microbial cell can be a non-immunogenic microbial cell, i.e. a cell that does not cause a target cell to secrete increased levels of, e.g. IL-8 when the microbial cell is present.

Non-limiting examples of non-pathogenic microbial cells with respect to human target cells can include, but are not limited to: E. coli K12; E. coli DH5α, E. coli HB101, E. coli BL21, E. coli DH10beta, E. coli JM110, E. coli MinT3, and virulence-cured Shigella strains (e.g. those missing the virulence plasmid encoding the T3SS and >20T3SS-compatible effectors). Non-limiting examples of commensal microbial cells with respect to human subjects include, but are not limited to: E. coli NISSLE 1917 (EcN); E. coli 83972; E. coli M17, In some embodiments of any of the aspects, E. coli NISSLE 1917 are used in some applications. In some embodiments of any of the aspects, E. coli K12 and/or DH5α are used in some applications.

As used herein, "commensal" refers to one of two organisms living in permanent close association, the referred to organism being one which gains a benefit from the association without causing serious disadvantage to the second organism under normal conditions. Commensal bacteria can include, e.g., non-pathogenic bacteria which form part of the normal flora of a healthy human alimentary tract.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994). As used herein, the term "cancer" refers to an uncontrolled growth of cells that interferes with the normal functioning of the bodily organs and systems. A subject who has a cancer or a tumor is a subject having objectively measurable cancer cells present in the subject's body. Included in this definition are benign and malignant cancers, as well as dormant tumors or micrometastases. Cancers that migrate from their original location and seed vital organs can eventually lead to the death of the subject through the functional deterioration of the affected organs.

A "tumor" as used herein refers to an uncontrolled growth of cells tumor interferes with the normal functioning of the bodily organs and systems. The terms "cancer" and "malignancy" refer to a tumor that is metastatic, i.e. that is it has become invasive, seeding tumor growth in tissues remote from the original tumor site. A subject that has a cancer or a tumor is a subject having objectively measurable cancer cells present in the subject's body. Included in this definition are benign tumors and malignant cancers, as well as potentially dormant tumors or micrometastases. Cancers that migrate from their original location and seed other vital organs can eventually lead to the death of the subject through the functional deterioration of the affected organs. Hematopoietic cancers, such as leukemia, are able to outcompete the normal hematopoietic compartments in a subject, thereby leading to hematopoietic failure (in the form of anemia, thrombocytopenia and neutropenia) ultimately causing death.

Examples of cancer include but are not limited to, carcinoma, blastoma, sarcoma, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantifies of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word or is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An engineered, non-pathogenic, gram negative microbial cell comprising:
  a) a first nucleic acid sequence comprising genes encoding a type 3 secretion system (T3SS)-derived extracellular secretion system (MESS); wherein the TDESS comprises at least virB; mxiG; mxiH; mxiI; mxiJ; mxiK; mxiN; mxiL; mxiM; mxiD; mxiA; spa47; spa13; spa32; spa33; spa24; spa9; spa29; and spa40; and
  b) a second nucleic acid sequence encoding an T3SS-compatible payload polypeptide.
2. The microbial cell of paragraph 1, wherein the cell does not comprise or express at least one of:
  a. IpaB;
  b. IpaD; and
  c. MxiC.
3. The microbial cell of paragraph 2, wherein the cell does not comprise or express at least one of:
  a. IpaB and IpaD; and
  b. MxiC.
4. The microbial cell of paragraph 3, wherein the cell does not comprise or express IpaB; IpaD; and MxiC.
5. The microbial cell of paragraph 3, wherein the cell does not comprise or express IpaB; IpaD; IpaC; and MxiC.
6. The microbial cell of any of paragraphs 1-5, wherein the cell has a mutated MxiH.
7. The microbial cell of paragraph 6, wherein the cell has a D7 3A mutation in MxiH.
8. The microbial cell of any of paragraphs 1-7, wherein the second nucleic acid sequence comprises 1) an inducible promoter sequence that is operably linked to 2) a sequence encoding an T3SS-compatible payload polypeptide.
9. The microbial cell of paragraph 8, wherein the inducible promoter sequence is regulated by a master T3SS regulator.
10. The microbial cell of any of paragraphs 8-9, wherein the inducible promoter sequence comprises a (T3SS)-associated promoter or promoter element.
11. The microbial cell of paragraph 10, wherein the T3SS-associated promoter or promoter element is a MxiE recognition sequence.

12. The microbial cell of any of paragraphs 1-11, wherein the cell comprises a third nucleic acid sequence encoding a master T3SS regulator.
13. The microbial cell of paragraph 12, wherein the master T3SS regulator is selected from the group consisting of: VirB and VirF.
14. The microbial cell of any of paragraphs 12-13, wherein the third nucleic acid sequence comprises 1) an inducible promoter sequence that is operably linked to 2) a sequence encoding a master T3SS regulator.
15. The microbial cell of paragraph 14, wherein the inducible promoter is selected from the group consisting of:
an arabinose-inducible promoter; pBAD arabinose-inducible promoter; tumor-induced promoters; ansB promoter; pflE promoter; napF promoter; and an inflammation-induced promoter.
16. The microbial cell of any of paragraphs 1-15, wherein the TDESS comprises at least: virB; acp; ipaA; ipgC; ipgB1; ipgA; icsB; ipgD; ipgE; ipgF; mxiG; mxiH; mxiK; mxiN; mxiL; mxiM; mxiE; mxiD; mxiA; spa15; spa47; spa13; spa32; spa33; spa24; spa9; spa29; and spa40.
17. The microbial cell of any of paragraphs 1-16, wherein the TDESS comprises polypeptides endogenous to a bacterium selected from the group consisting of: *Shigella* spp; *Salmonella* spp; enteropathogenic *E. coli*; and *Yersinia* spp.
18. The microbial cell of any of paragraphs 1-17, wherein the first nucleic acid sequence is located on a plasmid.
19. The engineered microbial cell of any of paragraphs 1-17, wherein the first nucleic acid sequence is located on a chromosome.
20. The microbial cell of any of paragraphs 1-19, wherein the second nucleic acid sequence is located on a plasmid.
21. The engineered microbial cell of any of paragraphs 1-19, wherein the second nucleic acid sequence is located on a chromosome.
22. The microbial cell of any of paragraphs 1-21, wherein the T3SS-compatible payload polypeptide comprises a T3SS secretion sequence.
23. The microbial cell of any of paragraphs 1-22, wherein the T3SS-compatible payload polypeptide comprises an N-terminal T3SS secretion sequence.
24. The microbial cell of any of paragraphs 1-23, wherein the T3SS-compatible payload polypeptide comprises a OspC3 T3SS secretion sequence.
25. The microbial cell of any of paragraphs 1-24, wherein the T3SS-compatible payload polypeptide comprises an anti-inflammatory polypeptide.
26. The microbial cell of paragraph 25, wherein the anti-inflammatory polypeptide is IL-10 or IL-27.
27. The microbial cell of any of paragraphs 1-24, wherein the T3SS-compatible payload polypeptide comprises an antibody reagent.
28. The microbial cell of paragraph 27, wherein the antibody reagent is selected from group consisting of:
a nanobody; a VNA; and a VHH.
29. The microbial cell of any of paragraphs 27-28, wherein the cell comprises at least one further nucleic acid sequence encoding an additional T3SS-compatible payload polypeptide comprising an antibody reagent.
30. The microbial cell of any of paragraphs 27-28, wherein the one or more antibody reagents form a multimeric complex.
31. The microbial cell of paragraph 30, wherein the multimeric complex is multispecific.
32. The microbial cell of any of paragraphs 27-31, wherein the antibody reagent specifically binds to a cancer cell marker.
33. The microbial cell of any of paragraphs 27-31, wherein the antibody reagent specifically binds to a cancer checkpoint polypeptide.
34. The microbial cell of any of paragraphs 27-33, wherein the antibody reagent is an anti-PD-L1; anti-PD-1; or anti-CTLA-4 reagent.
35. The microbial cell of any of paragraphs 27-34, wherein the antibody reagent is an anti-PD-L1; anti-PD-1; or anti-CTLA-4 VNA or VHH.
36. The microbial cell of any of paragraphs 27-31, wherein the antibody reagent specifically binds to an inflammatory cytokine receptor or an inflammatory cytokine.
37. The microbial cell of paragraph 36, wherein the antibody reagent binds to a molecule selected from the group consisting of:
TNFα, IL-8; IL-6, IL-18, IL-21, IL-33 and IL-13.
38. The microbial cell of any of paragraphs 27-31, wherein the antibody reagent specifically binds to a bacterial toxin.
39. The microbial cell of paragraph 38, wherein the bacterial toxin is an *E. coli* or *C. difficile* toxin.
40. The microbial cell of any of paragraphs 38-39, wherein the bacterial toxin is selected from the group consisting of:
Shiga toxin; *C. difficile* toxin A (TcdA); *C. difficile* toxin B (TcdB); cholera toxin; anthrax toxin; and botulinum toxin.
41. The microbial cell of any of paragraphs 1-24, wherein the T3SS-compatible payload polypeptide comprises a toxin.
42. The microbial cell of any of paragraphs 1-24, wherein the T3SS-compatible payload polypeptide comprises an antigen.
43. The microbial cell of any of paragraphs 1-42, wherein the microbial cell is engineered from a microbial cell selected from the group consisting of:
*E. coli* NISSLE 1917 (EcN); *E. coli* K12; MP; HS; and derivative strains thereof.
44. The microbial cell of paragraph 43, wherein the strain which is derivative of *E. coli* K12 is selected from the group consisting of:
*E. coli* DH1013 and *E. coli* DH5α.
45. The microbial cell of any of paragraphs 1-43, wherein the microbial cell is engineered from *E. coli* NISSLE 1917 (EcN).
46. The microbial cell of any of paragraphs 1-45, wherein the microbial cell is engineered from a commensal intestinal microbial cell.
47. The microbial cell of paragraph 46, wherein the commensal intestinal microbial cell is *E. coli* NISSLE 1917 (EcN).
48. The microbial cell of any of paragraphs 1-42, wherein the non-pathogenic microbial cell is engineered from a pathogenic microbial cell organism by deletion or mutation of one or more T3SS components.
49. The microbial cell of paragraph 48, wherein the one or more T3SS components is selected from the group consisting of:
a toxin; a T3SS effector; a structural T3SS polypeptide; and a master regulator of T3SS components.
50. The microbial cell of any of paragraphs 48-49, wherein the pathogenic microbial cell is selected from the group consisting of:
*Salmonella* spp.; *Shigella* Spp; and *Yersinia* spp.

51. The microbial cell of paragraph 48-50, wherein the pathogenic microbial cell is selected from the group consisting of:
*Salmonella typhimurium* SPI1 and *Shigella felxneri* mxi-spa.
52. The microbial cell of any of paragraphs 1-51, wherein cell has been:
a. contacted with a mutagenic treatment; and
b. selected for increased secretion.
53. The microbial cell of any of paragraphs 1-52, wherein cell has been:
a. contacted with a mutagenic treatment; and
b. selected for increased secretion of the T3SS-compatible payload polypeptide.
54. The microbial cell of any of paragraphs 1-53, wherein the cell further comprises a nucleic acid sequence encoding one or more polypeptides that increase adhesion to a target cell.
55. The microbial cell of paragraph 54, wherein the polypeptides that increase adhesion to the target cell comprise Tir and intimin.
56. The microbial cell of paragraph 55, wherein the polypeptide that increases adhesion to the target cell is selected from a group consisting of:
a bacterial adhesion; Afa1; AIDA; invasion; an antibody reagent specific for an extracellular epitope of a target cell polypeptide; and a single chain antibody specific for an extracellular epitope of a target cell polypeptide.
57. A method of introducing a polypeptide into a target tissue or organism, the method comprising contacting the target tissue or organism with a microbial cell of any of paragraphs 1-56.
58. A method of reducing inflammation in a subject, the method comprising administering an microbial cell of any of paragraphs 25-26 or 36-37 to a subject in need thereof.
59. The method of paragraph 58, wherein the inflammation is inflammation of the gastrointestinal tract.
60. The method of any of paragraphs 58-59, wherein the subject is in need of treatment for a condition selected from the group consisting of:
asthma; inflammatory bowel disease; Crohn's disease; obesity; and ulcerative colitis.
1. The method of paragraph 60, wherein the subject is a subject in need of treatment for inflammatory bowel disease.
62. The method of any of paragraphs 58-61, wherein the microbial cell is administered orally.
63. A method of treating cancer in a subject, the method comprising administering an microbial cell of any of paragraphs 26-35 to a subject in need thereof.
64. The method of paragraph 63, wherein the microbial cell is administered systemically.
65. The method of paragraph 63, wherein the microbial cell is administered intratumorally.
66. The method of paragraph 63, wherein the cancer is a cancer of the gastrointestinal tract and the microbial cell is administered orally.
67. The method of any of paragraphs 63-66, wherein the microbial cell is engineered from *E. coli* NISSLE 1917 (EcN).
68. A method of treating an intestinal infection in a subject, the method comprising administering a microbial cell of any of paragraphs 38-39 to a subject in need thereof.
69. The method of paragraph 68, wherein the intestinal infection is EHEC and/or the subject has hemolytic uremic syndeom and the toxin is Shiga toxin.
70. The method of paragraph 68, wherein the intestinal infection is a *C. difficile* infection and/or the subject has *C. difficile* colitis and the toxin is TcdA and/or TcdB.
71. The method of paragraph 68, wherein the intestinal infection is cholera and the toxin is cholera toxin.
72. The method of paragraph 68, wherein the intestinal infection is gastrointestinal anthrax and the toxin is anthrax toxin.
73. The method of paragraph 68, wherein the intestinal infection is botulism and the toxin is botulinum toxin.
74. The method of any of paragraphs 68-73, wherein the microbial cell is administered orally.
75. The method of any of paragraphs 57-74, wherein secretion of the T3SS-compatible payload polypeptide is induced by further administering the subject a compound to induce expression of the T3SS-compatible payload polypeptide and/or the T3SS master regulator.
76. The method of paragraph 75, wherein the compound is arabinose.
77. A method for delivering a polypeptide into a) the extracellular milieu of a subject's gastrointestinal tract orb) the extracellular milieu of a subject's tumor the method comprising contacting administering a microbial cell of any of paragraphs 1-56 to the subject.
78. A kit comprising the microbial cell of any of paragraphs 1-56.
79. The use of a microbial cell of any of paragraphs 25-26 or 36-37 to reduce inflammation in a subject in need thereof.
80. The use of paragraph 79, wherein the inflammation is inflammation of the gastrointestinal tract.
81. The use of any of paragraphs 79-80, wherein the subject is in need of treatment for a condition selected from the group consisting of:
asthma; inflammatory bowel disease; Crohn's disease; obesity; and ulcerative colitis.
82. The use of paragraph 81, wherein the subject is a subject in need of treatment for inflammatory bowel disease.
83. The use of any of paragraphs 79-82, wherein the microbial cell is administered orally.
84. The use of an microbial cell of any of paragraphs 26-35 treat cancer in a subject in need thereof.
85. The use of paragraph 84, wherein the microbial cell is administered systemically.
86. The use of paragraph 84, wherein the microbial cell is administered intratumorally.
87. The use of paragraph 84, wherein the cancer is a cancer of the gastrointestinal tract and the microbial cell is administered orally.
88. The use of any of paragraphs 84-87, wherein the microbial cell is engineered from *E. coli* NISSLE 1917 (EcN).
89. The use of a microbial cell of any of paragraphs 38-39 to treat an intestinal infection in a subject in need thereof.
90. The use of paragraph 89, wherein the intestinal infection is EHEC and/or the subject has hemolytic uremic syndeom and the toxin is shiga toxin.
91. The use of paragraph 89, wherein the intestinal infection is a *C. difficile* infection and/or the subject has *C. difficile* colitis and the toxin is TcdA and/or TcdB.
92. The use of paragraph 89, wherein the intestinal infection is cholera and the toxin is cholera toxin.
93. The use of paragraph 89, wherein the intestinal infection is gastrointestinal anthrax and the toxin is anthrax toxin.
94. The use of paragraph 89, wherein the intestinal infection is botulism and the toxin is botulinum toxin.

95. The use of any of paragraphs 89-94, wherein the microbial cell is administered orally.
96. The use of any of paragraphs 79-95, wherein secretion of the T3SS-compatible payload polypeptide is induced by further administering the subject a compound to induce expression of the T3SS-compatible payload polypeptide and/or the T3SS master regulator.
97. The use of paragraph 96, wherein the compound is arabinose.

Some embodiments of the technology described herein can be defined according to any of the following numbered paragraphs:

1. An engineered, non-pathogenic, gram negative microbial cell comprising:
    a) a first nucleic acid sequence comprising genes encoding a type 3 secretion system (T3SS)-derived extracellular secretion system (TDESS); wherein the TDESS comprises at least virB; mxiG; mxiK; mxiN; mxiM; mxiD; mxiA; spa47; spa13; spa32; spa33; spa24; spa9; spa29; and spa40; and
    b) a second nucleic acid sequence encoding an T3SS-compatible payload polypeptide.
2. The microbial cell of paragraph 1, wherein the cell does not comprise or express at least one of:
    a. IpaB;
    b. IpaD; and
    c. MxiC.
3. The microbial cell of paragraph 2, wherein the cell does not comprise or express at least one of:
    a. IpaB and IpaD; and
    b. MxiC.
4. The microbial cell of paragraph 3, wherein the cell does not comprise or express IpaB; IpaD; and MxiC.
5. The microbial cell of paragraph 3, wherein the cell does not comprise or express IpaB; IpaD; IpaC; and MxiC.
6. The microbial cell of any of paragraphs 1-5, wherein the cell has a mutated MxiH.
7. The microbial cell of paragraph 6, wherein the cell has a D73A mutation in MxiH.
8. The microbial cell of any of paragraphs 1-7, wherein the second nucleic acid sequence comprises 1) an inducible promoter sequence that is operably linked to 2) a sequence encoding an T3SS-compatible payload polypeptide.
9. The microbial cell of paragraph 8, wherein the inducible promoter sequence is regulated by a master T3SS transcriptional regulator.
10. The microbial cell of any of paragraphs 8-9, wherein the inducible promoter sequence comprises a (T3SS)-associated promoter or promoter element.
11. The microbial cell of paragraph 10, wherein the T3SS-associated promoter or promoter element is a MxiE recognition sequence.
12. The microbial cell of any of paragraphs 1-11, wherein the cell comprises a third nucleic acid sequence encoding a master T3SS transcriptional regulator.
13. The microbial cell of paragraph 12, wherein the master T3SS transcriptional regulator is selected from the group consisting of:
    VirB and VirF.
14. The microbial cell of any of paragraphs 12-13, wherein the third nucleic acid sequence comprises 1) inducible promoter sequence that is operably linked to 2) a sequence encoding a master T3SS transcriptional regulator.
15. The microbial cell of paragraph 14, wherein the inducible promoter is selected from the group consisting of:
    an arabinose-inducible promoter; pBAD arabinose-inducible promoter; an IPTG-inducible promoter; tumor-induced promoters; ansB promoter; pflE promoter; napF promoter; and an inflammation-induced promoter.
16. The microbial cell of any of paragraphs 1-15, wherein the TDESS comprises at least: virB; acp; ipaA; ipgC; ipgB1; ipgA; icsB; ipgD; ipgE; ipgF; mxiG mxiH; mxiI; mxiJ; mxiK; mxiN; mxiL; mxiM; mxiE; mxiD; mxiA; spa15; spa47; spa13; spa32; spa33; spa24; spa9; spa29; and spa40.
17. The microbial cell of any of paragraphs 1-16, wherein the TDESS comprises polypeptides endogenous to a bacterium selected from the group consisting of:
    *Shigella* spp; *Salmonella* spp; enteropathogenic *E. coli*; and *Yersinia* spp.
18. The microbial cell of any of paragraphs 1-17, wherein the first nucleic acid sequence is located on a plasmid.
19. The engineered microbial cell of any of paragraphs 1-17, wherein the first nucleic acid sequence is located on a chromosome.
20. The microbial cell of any of paragraphs 1-19, wherein the second nucleic acid sequence is located on a plasmid.
21. The engineered microbial cell of any of paragraphs 1-19, wherein the second nucleic acid sequence is located on a chromosome.
22. The engineered microbial cell of any of paragraphs 1-21, wherein the first nucleic acid sequence comprising genes encoding a type 3 secretion system (T3SS)-derived extracellular secretion system (TDESS) and/or the genes encoding a type 3 secretion system (T3SS)-derived extracellular secretion system (MESS) are exogenous to the microbial cell.
23. The engineered microbial cell of any of paragraphs 1-22, wherein the first nucleic acid sequence is no greater than 3 kb in size.
24. The engineered microbial cell of any of paragraphs 1-22, wherein the first nucleic acid sequence and third nucleic acid sequence are cumulatively no greater than 3 kb in size.
25. The engineered microbial cell of any of paragraphs 1-24, wherein the cell did not comprise a T3SS prior to being engineered to comprise the first and second nucleic acid sequences.
26. The microbial cell of any of paragraphs 1-25, wherein the T3SS-compatible payload polypeptide comprises a T3SS secretion sequence.
27. The microbial cell of any of paragraphs 1-26, wherein the T3SS-compatible payload polypeptide comprises an N-terminal T3SS secretion sequence.
28. The microbial cell of any of paragraphs 1-27, wherein the T3SS-compatible payload polypeptide comprises a OspC3 T3SS secretion sequence.
29. The microbial cell of any of paragraphs 1-28, wherein the T3SS-compatible payload polypeptide comprises an anti-inflammatory polypeptide.
30. The microbial cell of paragraph 29, wherein the anti-inflammatory polypeptide is IL-10 or IL-27.
31. The microbial cell of any of paragraphs 1-30, wherein the T3SS-compatible payload polypeptide comprises an antibody reagent.

32. The microbial cell of paragraph 31, wherein the antibody reagent is selected from group consisting of: a nanobody; a VNA; and a VHH.
33. The microbial cell of any of paragraphs 31-32, wherein the cell comprises at least one further nucleic acid sequence encoding an additional T3SS-compatible payload polypeptide comprising an antibody reagent, VHH, or VNA.
34. The microbial cell of any of paragraphs 31-32, wherein the one or more antibody reagents form a multimeric complex.
35. The microbial cell of paragraph 34, wherein the multimeric complex is multispecific.
36. The microbial cell of any of paragraphs 31-35, wherein the antibody reagent specifically binds to a cancer cell marker.
37. The microbial cell of any of paragraphs 31-35, wherein the antibody reagent specifically binds to a cancer checkpoint polypeptide.
38. The microbial cell of any of paragraphs 31-37, wherein the antibody reagent is an anti-PD-L1; anti-PD-1; or anti-CTLA-4 reagent.
39. The microbial cell of any of paragraphs 31-38, wherein the antibody reagent is an anti-PD-L1; anti-PD-1; or anti-CTLA-4 VNA or VHH.
40. The microbial cell of any of paragraphs 31-39, wherein the antibody reagent specifically binds to an inflammatory cytokine receptor or an inflammatory cytokine.
41. The microbial cell of paragraph 40, wherein the antibody reagent binds to a molecule selected from the group consisting of:
TNFα, IL-8; IL-6, IL-18, IL-21, IL-33 and IL-13.
42. The microbial cell of any of paragraphs 31-35, wherein the antibody reagent specifically binds to a bacterial toxin.
43. The microbial cell of paragraph 42, wherein the bacterial toxin is an *E. coli* or *C. difficile* toxin.
44. The microbial cell of any of paragraphs 42-43, wherein the bacterial toxin is selected from the group consisting of:
shiga toxin; *C. difficile* toxin A (TcdA); *C. difficile* toxin B (TcdB); cholera toxin; anthrax toxin; and botulinum toxin.
45. The microbial cell of any of paragraphs 1-28, wherein the T3SS-compatible payload polypeptide comprises a toxin.
46. The microbial cell of any of paragraphs 1-28, wherein the T3SS-compatible payload polypeptide comprises an antigen.
47. The microbial cell of any of paragraphs 1-46, wherein the microbial cell is engineered from a microbial cell selected from the group consisting of:
*E. coli* NISSLE 1917 (EcN); *E. coli* K12; MP; HS; and derivative strains thereof.
48. The microbial cell of paragraph 47, wherein the strain which is derivative of *E. coli* K12 is selected from the group consisting of: *E. coli* DH10β and *E. coli* DH5α.
49. The microbial cell of any of paragraphs 1-47, wherein the microbial cell is engineered from *E. coli* NISSLE 1917 (EcN).
50. The microbial cell of any of paragraphs 1-49, wherein the microbial cell is engineered from a commensal intestinal microbial cell.
51. The microbial cell of paragraph 50, wherein the commensal intestinal microbial cell is *E. coli* NISSLE 1917 (EcN).
52. The microbial cell of any of paragraphs 1-51, wherein the non-pathogenic microbial cell is engineered from a pathogenic microbial cell organism by deletion or mutation of one or more T3SS components.
53. The microbial cell of paragraph 52, wherein the one or more T3SS components is selected from the group consisting of:
a toxin; a T3SS effector; a structural T3SS polypeptide; and a master transcriptional regulator of T3SS components.
54. The microbial cell of any of paragraphs 52-53, wherein the pathogenic microbial cell is selected from the group consisting of:
*Salmonella* spp.; *Shigella* Spp; and *Yersinia* spp.
55. The microbial cell of paragraph 52-54, wherein the pathogenic microbial cell is selected from the group consisting of:
*Salmonella typhimurium* SPI1 and *Shigella flexneri* mxi-spa.
56. The microbial cell of any of paragraphs 1-55, wherein cell has been:
 a. contacted with a mutagenic treatment; and
 b. selected for increased secretion.
57. The microbial cell of any of paragraphs 1-56, wherein cell has been:
 a. contacted with a mutagenic treatment; and
 b. selected for increased secretion of the T3SS-compatible payload polypeptide.
58. The microbial cell of any of paragraphs 1-57, wherein the cell further comprises a nucleic acid sequence encoding one or more polypeptides that increase adhesion to a target cell.
59. The microbial cell of paragraph 58, wherein the polypeptides that increase adhesion to the target cell comprise Tir and intimin.
60. The microbial cell of paragraph 59, wherein the polypeptide that increases adhesion to the target cell is selected from a group consisting of:
 a bacterial adhesion; Afa1; AIDA; invasion; an antibody reagent specific for an extracellular epitope of a target cell polypeptide; and a single chain antibody specific for an extracellular epitope of a target cell polypeptide.
61. A method of introducing a polypeptide into a target tissue or organism, the method comprising contacting the target tissue or organism with a microbial cell of any of paragraphs 1-60.
62. A method of reducing inflammation in a subject, the method comprising administering an microbial cell of any of paragraphs 29-30 or 40-41 to a subject in need thereof.
63. The method of paragraph 62, wherein the inflammation is inflammation of the gastrointestinal tract.
64. The method of any of paragraphs 62-63, wherein the subject is in need of treatment for a condition selected from the group consisting of:
 asthma; inflammatory bowel disease; Crohn's disease; obesity; and ulcerative colitis.
65. The method of paragraph 64, wherein the subject is a subject in need of treatment for inflammatory bowel disease.
66. The method of any of paragraphs 62-65, wherein the microbial cell is administered orally.
67. A method of treating cancer in a subject, the method comprising administering an microbial cell of any of paragraphs 30-39 to a subject in need thereof.

68. The method of paragraph 67, wherein the microbial cell is administered systemically.
69. The method of paragraph 67, wherein the microbial cell is administered intratumorally.
70. The method of paragraph 67, wherein the cancer is a cancer of the gastrointestinal tract and the microbial cell is administered orally.
71. The method of any of paragraphs 67-70, wherein the microbial cell is engineered from *E. coli* NISSLE 1917 (EcN).
72. A method of treating an intestinal infection in a subject, the method comprising administering a microbial cell of any of paragraphs 42-43 to a subject in need thereof.
73. The method of paragraph 72, wherein the intestinal infection is EHEC and/or the subject has hemolytic uremic syndeom and the toxin is shiga toxin.
74. The method of paragraph 72, wherein the intestinal infection is a *C. difficile* infection and/or the subject has *C. difficile* colitis and the toxin is TcdA and/or TcdB.
75. The method of paragraph 72, wherein the intestinal infection is cholera and the toxin is cholera toxin.
76. The method of paragraph 72, wherein the intestinal infection is gastrointestinal anthrax and the toxin is anthrax toxin.
77. The method of paragraph 72, wherein the intestinal infection is botulism and the toxin is botulinum toxin.
78. The method of any of paragraphs 72-77, wherein the microbial cell is administered orally.
79. The method of any of paragraphs 61-78, wherein secretion of the T3SS-compatible payload polypeptide is induced by further administering the subject a compound to induce expression of the T3SS-compatible payload polypeptide and/or the T3SS master transcriptional regulator.
80. The method of paragraph 79, wherein the compound is arabinose.
81, A method for delivering a polypeptide into a) the extracellular milieu of a subject's gastrointestinal tract, b) the lumen of a tumor, or c) the extracellular milieu of a subject's tumor, the method comprising contacting administering a microbial cell of any of paragraphs 1-60 to the subject.
82. A kit comprising the microbial cell of any of paragraphs 1-60.
83. The use of a microbial cell of any of paragraphs 29-30 or 40-41 to reduce inflammation in a subject in need thereof.
84. The use of paragraph 83, wherein the inflammation is inflammation of the gastrointestinal tract.
85. The use of any of paragraphs 83-84, wherein the subject is in need of treatment for a condition selected from the group consisting of:
asthma; inflammatory bowel disease; Crohn's disease; obesity; and ulcerative colitis.
86. The use of paragraph 85, wherein the subject is a subject in need of treatment for inflammatory bowel disease.
87. The use of any of paragraphs 83-86, wherein the microbial cell is administered orally.
88. The use of an microbial cell of any of paragraphs 30-39 treat cancer in a subject in need thereof.
89. The use of paragraph 88, wherein the microbial cell is administered systemically.
90. The use of paragraph 88, wherein the microbial cell is administered intratumorally.
91. The use of paragraph 88, wherein the cancer is a cancer of the gastrointestinal tract and the microbial cell is administered orally.
92. The use of any of paragraphs 88-91, wherein the microbial cell is engineered from *E. coli* NISSLE 1917 (EcN).
93. The use of a microbial cell of any of paragraphs 42-4339 to treat an intestinal infection in a subject in need thereof.
94. The use of paragraph 93, wherein the intestinal infection is EHEC and/or the subject has hemolytic uremic syndeom and the toxin is Shiga toxin.
95. The use of paragraph 93, wherein the intestinal infection is a *C. difficile* infection and/or the subject has *C. difficile* colitis and the toxin is TcdA and/or TcdB.
96. The use of paragraph 93, wherein the intestinal infection is cholera and the toxin is cholera toxin.
97. The use of paragraph 93, wherein the intestinal infection is gastrointestinal anthrax and the toxin is anthrax toxin.
98. The use of paragraph 93, wherein the intestinal infection is botulism and the toxin is botulinum toxin.
99. The use of any of paragraphs 93-97, wherein the microbial cell is administered orally.
100. The use of any of paragraphs 83-99, wherein secretion of the T3SS-compatible payload polypeptide is induced by further administering the subject a compound to induce expression of the T3SS-compatible payload polypeptide and/or the T3SS master transcriptional regulator.
101. The use of paragraph 100, wherein the compound is arabinose.

EXAMPLES

Example 1

Engineering Novel Probiotics for the Treatment of Inflammatory Bowel Disease

Inflammatory bowel disease (IBD) which includes ulcerative colitis and Crohn's disease is a chronic intestinal disorder that affects over 3 million individuals in the Westernized world [1]. The inflammation associated with these disorders often results from a dysregulated immune response to the commensal microbiota that causes abdominal pain, diarrhea, and rectal bleeding, which in severe cases can require surgical interventions [1, 2]. The mainstay of current treatments is the use of anti-inflammatory drugs, including systemic immunosuppressants like parenteral antibodies that block TNFα activity. However, these treatment options, which are not always sufficient to relieve symptoms, are associated with serious side effects. For example, agents that cause systemic immunosuppression greatly increase the susceptibility of patients for developing serious infections including reactivation of latent tuberculosis, the development of brain abscesses, and disseminated fungal infections [1]. Described herein is a novel treatment for IBD that circumvents these issues by reengineering specialized bacterial secretion systems to target the delivery of the anti-inflammatory cytokine IL-10 to the intestines, thus limiting systemic side effects by directly targeting immunosuppression to the site of disease.

Role of IL-10 in Inflammatory Bowel Disease (IBD). IL-10 is one of the most important anti-inflammatory cytokines of the intestinal immune system. Its immunosuppressive activities include downregulating synthesis of proinflammatory cytokines by regulatory T cells and macrophages, increasing production of anti-inflammatory mediators, and inhibiting antigen presentation in macrophages and dendritic cells [3]. There is extensive data that IL-10 plays a role in suppressing the development of IBD. For example, genome-wide association studies (GWAS) demonstrate that a subset of patients with IBD have IL-10 promoter polymorphisms associated with reduced IL-10 serum levels [4-6] and IL-10 deficient mice develop colitis similar to that observed in IBD patients [7]. These observations indicate that the administration of recombinant IL-10 could be a good therapeutic candidate, at least for those patients with IBD that exhibit lower circulating levels of IL-10 [7]. However, limited clinical trials investigating parenteral IL-10 therapy in Crohn's disease patients observed no differences between the treatment and placebo groups, likely due to the short half-life and resultant low levels of recombinant IL-10 that reach the intestines [8-11].

Localized delivery of IL-10 by probiotics as IBD treatment. Treatment options that locally deliver recombinant IL-10 have been investigated as a therapeutic strategy. For example, the oral administration of IL-10 to the intestines of IBD patients by genetically-modified probiotic bacteria was pursued. For these studies, *Lactococcus lactis*, a Gram-positive lactic acid producing bacteria found in fermented diary products including cheese and yogurt, was genetically modified to express and secrete recombinant IL-10 [12, 13]. Ingestion of this strain results in a 50% reduction in gut inflammation in dextran sulfate sodium (DSS) and IL-10–/– mouse models of IBD [13]. However, when administered in human clinical trails, only minimal improvement in symptoms was observed when comparing treatment and placebo groups [13, 14]. It is contemplated here in that this outcome may be due to the inability of *L. lactis* to colonize the gut, such that recombinant IL-10 is only transiently delivered to the patient during passage of the bacteria through the intestines [15]. Described herein are genetically engineered bacteria that continuously deliver IL-10 to the intestines to provide more effective IBD treatment.

Described herein are methods and compositions which permit functional IL-10 to be secreted through the *Shigella flexneri* type 3 secretion system. Many Gram-negative enteric pathogens, including *Shigella, Salmonella* and *Yersinia* species, directly deliver proteins into host intestinal cells through specialized type 3 secretion systems (T3SSs) [16]. These protein delivery systems are complex nanomachines that form a syringe-like structure that spans the inner and outer membranes of Gram-negative bacteria to form a conduit for the direct delivery of bacterial proteins into the cytoplasm of target cells [17]. Proteins are recognized as secreted substrates by the type 3 machinery through the presence of an N-terminal secretion sequence. Notably, the addition of a type 3 secretion sequence to heterologous proteins is sufficient to target their secretion through the T3SS [18, 19].

Interestingly, IL-10 is functional when fused to a type 3 secretion sequence. Mice infected with wild type *Shigella flexneri* strains that express and secrete IL-10 exhibit a 2-fold reduction of inflammation in response to infection with *Shigella* [18]. Notably, IL-10 exerts its activity by binding to receptors on the outer cell surfaces [3]. However, the *Shigella* T3SS primarily delivers proteins into the cytosol of targeted cells. Therefore, the presumably small amounts of extracellular IL-10 released by the secretion system are sufficient to partially block *Shigella* induced inflammation. It is contemplated herein that increased localized secretion of into the intestinal lumen by the T3SS can more effectively limit inflammation, including in the context of IBD.

Engineering type 3 secretion systems as therapeutic vectors. Repurposing the T3SSs of pathogens to deliver therapeutic proteins as opposed to virulence factors is currently being pursued as a therapeutic strategy. This strategy has shown some promise delivering antigenic molecules for vaccine development and transcription factors to alter gene expression in mammalian cells [20-24]. However, to date, a major limitation of this approach has been the use of virulence-attenuated pathogenic bacteria for protein delivery. These attenuated strains still encode known, and likely unknown, virulence determinants, limiting their use in patients, particularly those that are immunocompromised. Described herein is the development of a system that takes advantage of the protein delivery capabilities of T3SSs that circumvents the issues associated with attenuated pathogens. Using recombineering, non-pathogenic laboratory strains of *E. coli* have been engineered to express the T3SS from *Shigella flexneri* [Reeves et al.]. These laboratory strains secrete and deliver a variety of heterologous proteins into mammalian cells at levels similar to pathogenic *Shigella* strains. Based on the success of this approach, the *Shigella* T3SS was introduced into the probiotic bacteria, *E. coli* Nissle 1917 (EcN) to develop therapeutic commensal bacterial strains. Wild-type EcN is already given as a treatment to patients with IBD in Europe and Canada where it has been observed to be as efficacious at preventing IBD flares as the oral agent, mesalazine [20-22]. Additionally, EcN is capable of colonizing of the gut of mice and humans, a trait that can provide a means for prolonged delivery of therapeutic proteins to patients [15]. Contemplated herein is the directed targeting of recombinant IL-10 to the intestines via a type 3 secretion competent strain of EcN could prove to be an effective innovative treatment for IBD (schematic in FIG. 1).

Described herein is the engineering of type 3 secretion competent strains of the probiotic *E. coli* Nissle 1917 (EcN) to secrete high levels of functional IL-10 into the intestinal lumen. This approach enhances the ability of this probiotic to target anti-inflammatory effects to the site of disease, thereby limiting the systemic immunosuppression observed with current therapeutic modalities like TNFα blockers. The ability of EcN to colonize the intestines means this strategy can provide a long-term cost-effective treatment for IBD patients. Importantly, although this proposal focuses specifically on delivery of IL-10, the paradigm described within can be applied to secreted alleles of additional cytokines/proteins of therapeutic value thus providing a highly adaptable and efficient platform for developing new treatment strategies that act to promote the localized delivery of therapeutic agents.

Engineer type 3 secretion competent strains of commensal *E. coli* Nissle 1917 (EcN) that secrete functional IL-10. These strains can be permit identification of conditions that maximize the expression of functional IL-10 alleles that are recognized and secreted into the extracellular millieu via genetically engineered EcN strains.

Development of non-pathogenic type 3 secretion competent *E. coli*. Described herein are non-pathogenic laboratory strains of *E. coli* that encode a functional T3SS, which enables them to secrete as well as deliver defined proteins directly into mammalian cells. This was accomplished by using yeast and bacterial homologous recombeering approaches to capture a 31 kB region that encodes all of the 25 proteins needed to form a functional *Shigella flexneri* T3SS onto an autonomously replicating plasmid. This plasmid was designed such that the large region of *Shigella*-derived DNA it contains can be maintained on the plasmid or integrated into a non-essential locus of the chromosome of DH10β *E. coli*, a strain referred to here as T3-*E. coli*. Similar to wild type *Shigella*, these bacteria can utilize their T3SS to deliver proteins into >80% of mammalian cells they come encounter (data not shown). After developing this cloning strategy in DH10β, it was used to introduce the type 3 secretion operons into the chromosome of *E. coli* Nissle 1917 (T3-EcN), which also expresses the T3SS (data not shown). Both strains are particularly well suited for use as in vivo therapeutic protein delivery systems for several reasons: (1) isolating the type 3 secretion components with this recombinational cloning strategy allows for the generation of delivery strains devoid of virulence factors, as opposed to attenuated pathogens which likely retain virulence determinants and (2) the introduction of the type 3 secretion operons into the chromosome alleviates the need for antibiotic selection and prevents horizontal transfer of these genes into other bacterial species.

Development of a screening platform to identify optimal type 3 secretion sequence-target protein combinations. All type 3 secreted proteins (effectors) are defined by an N-terminal secretion sequence within their first 20-100 amino acid residues [17, 23]. Previous studies have found that the addition of these sequences to heterologous proteins generates alleles that are recognized as secreted proteins [18, 24]. To rapidly identify the regions of *Shigella* effectors that are sufficient to generate a secreted allele when fused to heterologous proteins, a secretion sequence screening platform was developed. A collection of 14 plasmids, each of which carries the first 30 or 50 residues of a *Shigella* effector plus an upstream consensus Shine-Dalgarno sequence in a Gateway recombination-based entry plasmid was constructed. Using this plasmid collection, along with a Gateway-compatible destination vector for a target heterologous protein, it is possible to rapidly generate and test the secretion of a variety of N-terminal secretion sequence-target fusion proteins.

Figure 2A:
FIGS. 2A-2B demonstrate that modified alleles of MyoD are recognized as type 3 secreted substrates and directly delivered into mammalian cells.
Figure 2B:
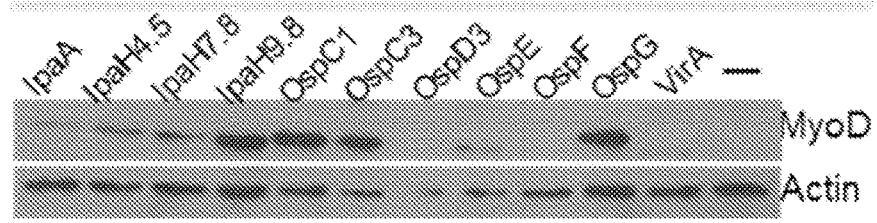
Figure 3:
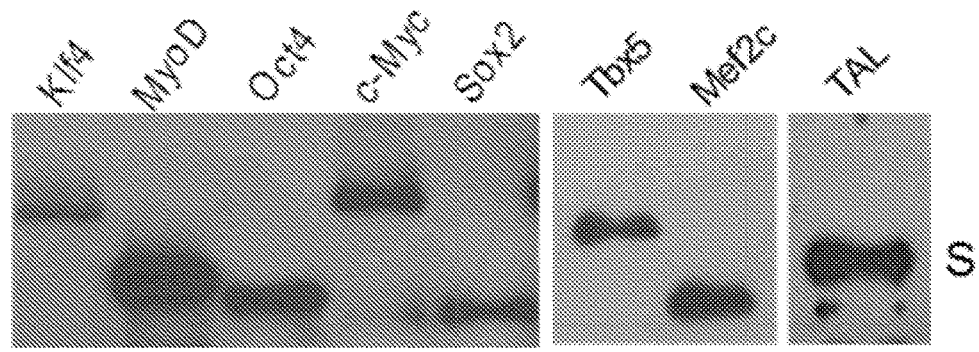
FIG. 3 demonstrates that T3-*E. coli* express and secrete a variety of target proteins modified by a *Shigella* type 3 secretion sequence and FLAG tag. S, supernatant.

The secretion sequence screening platform was used to identify sequences that promote the recognition of mammalian MyoD protein as a type 3 secreted substrate. Fusion of MyoD to 50 but not 30 residues of all effectors tested, resulted in alleles recognized as secreted substrates by T3-*E. coli* (50 amino acid fusions shown, FIGS. 2A and 2B). However, only a subset of the secreted alleles were detected within extracts of mammalian cells indicating that the individual secretion sequences differ in how efficiently they deliver heterologous proteins into mammalian cells (FIG. 2C). The MyoD fusion proteins were also tested for how the secretion sequence affects protein stability and localization (data not shown). Taken together, these data were used to successfully identify several secretion sequences that effectively transformed MyoD to be recognized as a type 3 secretion substrate without preturbing the normal properties of the wild type protein. Applying this strategy to each of four induced pluripotent stem (iPS) cell reprogramming factors, Oct4, Sox2, Klf4 and c-Myc [25], as well as two cardiac reprogramming factors (Mef2c and Tbx5) [26], and a TALE (transcription activator-like effector) protein [27], also resulted in alleles that are recognized as secreted substrates by T3-*E. coli* (FIG. 3). Secretion of IL-10 can be optimized using a similar strategy.

Engineer type 3 secretion competent strains of *E. coli* Nissle 1917 that secrete functional IL-10.

Rationale: A previous study demonstrated that *Shigella* expressing IL-10 limits inflammation in a mouse model of infection [18]. However, in addition to IL-10, *Shigella* delivers >20 virulence factors into cells, including several that promote inflammation in direct competition with the anti-inflammatory functions of IL-10. It is contemplated herein that IL-10 delivery from a non-pathogenic bacteria is even more efficacious.

The T3SS from *Shigella* has been introduced into the probiotic EcN using the genetic methodology described above. Though T3SSs normally deliver proteins into the cytosol of targeted cells; however, in order to confer anti-inflammatory activity, IL-10 can be secreted directly into the intestinal lumen and bind to extracelullar IL-10 receptors. Thus, described herein are modifications to the T3SS in T3-EcN strains such that IL-10 is exclusively secreted, rather than delivered into mammalian cells. Secretion and function of IL-10 can be optimized by screening a library of secretion sequences fused to IL-10.

Generate functional IL-10 alleles that are recognized as type 3 secreted substrates.

Figure 7:
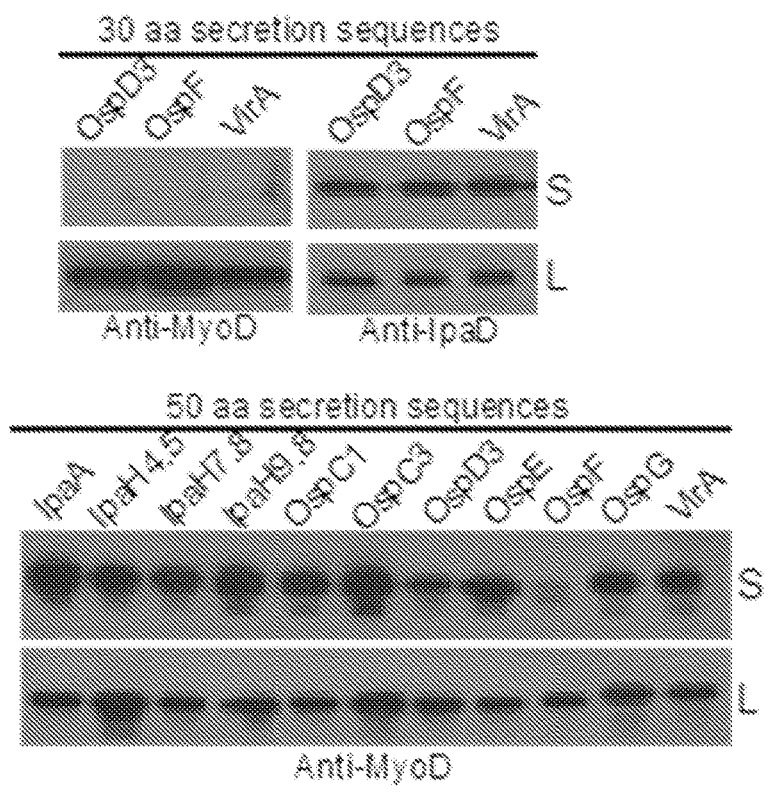
FIG. 7 demonstrates a screening platform to identify sequences sufficient to define heterologous proteins as secreted substrates. Immunoblots of T3Ec_VirFend expressing MyoD fused each of the designated secretion signals grown under conditions that induce type 3 secretion. Plots probed with designated antibodies. Supernatant (S) and whole cell lysates (L) shown.

The screening platform described above (FIG. 7) can permit identification of type 3 secretion sequences that when fused to IL-10 promote its recognition as a type 3 secreted substrate, but do not perturb its activity. Each allele can be cloned into a vector that places expression of the IL-10 fusion protein under control of the strong constitutive promoter, BBa_J23100, from the Registry of Standard Biological Parts. This promoter is optimized for binding to σ70, the main RNA polymerase sigma factor expressed in *E. coli* [28]. Placing IL-10 expression under 670 control will yield constitutive expression of IL-10, thereby preventing the need for the addition of an inducer for expression. Lambda red recombination can be used to introduce the IL-10 expression construct into the non-essential lacZ locus of the T3-EcN chromosome. Secretion of the IL-10 fusion proteins can be evaluated in T3-EcN using standard secretion assay conditions [29]. The amount of IL-10 secreted can be monitored by quantitative western blot analyses of cell lysates and super ants as well as via a standard IL-10 ELISA kit. Commercially available IL-10 cam be used as controls. Each supernatant sample can be probed for the presence of the cytoplasmic protein, DnaK, to check for bacterial cell lysis. The activity of the secretion sequence-IL-10 fusion proteins can be assayed by measuring proliferation of MC/9 mast cells following 3 days of incubation with T3-EcN supernatant containing the IL-10 fusion proteins and compared to purified commercial human IL-10 as reference [30]. IL-10 alleles that are efficiently secreted and maintain wild type immunomodulatory activity can be further pursued.

If the IL-10 fusion proteins do not express well from the BBa_J23100 promoter, additional variants available in the Standard Registry of Biological Parts can be screened. If the activity of IL-10 fusion proteins is disrupted, a flexible linker between IL-10 and the type 3 secretion sequence can be incorporated.

Engineer T3-EcN strains able to secrete IL-10 into the extracellular mileu.

Normally, in the absence of a signal from a host cell the type 3 secretion apparatus is inactive and plugged by the tip complex proteins, IpaB and IpaD (FIG. 4A) [31, 32]. Traffic through the secretion apparatus is also regulated by MxiC, which is present within in the machine physically blocking the path of type 3 substrates until secretion is activated [32]. IT is contemplated herein that deletion of either of the tip complex proteins or MxiC from *Shigella* can result in unregulated, constitutive secretion of type 3 effectors [31, 32] (FIG. 4B), further contemplated herein that cumulative loss of all three proteins might lead to even greater levels of secreted effectors proteins. Thus, to generate a strain of T3-EcN that constitutively secretes maximal levels of IL-10, a T3SS that lacks IpaB, IpaD and/or MxiC can be generated using a lambda red recombination based approach. After generating knockout strains in T3-EcN, ecretion of the IL-10 fusion protein can be tested in the individual as well as the triple knockout strains. A time course can be performed in which supernatant of the strains will be collected every 2 hours for 12 hours to determine the kinetics of secretion in each genetic background. These experiments can identify whether any of these strains can consistently secrete IL-10 over an extended time, a useful trait for a anti-inflammatory probiotic. Genetic backgrounds that secrete the most IL-10 for the most prolonged amount of time will be further tested.

If robust IL-10 secretion from T3-EcN strains is not demonstrated, the approach described herein can be applied to the T3-$E.$ $coli$ (DH10β) strain instead. Strains that lack IpaB, IpaD and/or MxiC can be generated and secretion of the IL-10 fusion proteins in each genetic background assessed. As an additional consideration, particularly before such strains are considered for administration to patients, auxotrophic derivatives of these therapeutic strains can be generated to prevent the growth of any bacteria that are inadvertently shed into the environment [33].

Evaluate anti-inflammatory properties of type 3 secretion competent $E.$ $coli$ Nissle 1917 IL-10 strains in mouse models of IBD.

The efficacy of the IL-10-secreting commensal bacteria can be tested, for example, in three complementary mouse models of IBD: (i) the administration of dextran sulfate sodium (DSS) which models acute colitis in wild type hosts, (ii) IL-10-/- mice to model chronic enterocolitis in the setting of intact adaptive and innate immune responses, and (iii) a translational humanized mouse model of colitis using newly developed immunodeficient NSAGAb0DR1 mice treated with 2,4,6-trinitrobenzene sulfonic acid (TNBS) to more closely mimic the effect of T3-EcN IL-10 on a human immune system. By using mouse models with different underlying pathophysiologies, the divergent host and microbial heterogeneity observed with IBD patients can be modeled.

Over a 14-day period, individual mice (n=5 per strain) will be evaluated by both daily fecal sampling to assess the presence/shedding of T3-EcN and by tissue examination upon sacrifice (1 mouse/strain genotype on d3, d6, d9, d12, d14) to assess inflammation. For these preliminary studies, the mice will receive a daily oral inoculation 1-2×10$^7$ CFU of T3-EcN IL-10 by providing bacteria in the drinking water in order to facilitate the bacteria taking up residence in the gut microbiota. For each condition, all mice can be administered the inocula when mild inflammation or injury has been observed in the specific pathogen free (SPF) mouse facility in each designated model: DSS treated wild type mice (day 3 of DSS exposure of 6 week old nice), IL-10-/- mice (6 weeks of age), and NSGAb0DR1 humanized mice (14 weeks of age). For each model, control groups can be included that receive either no bacteria, wild type EcN, or T3-EcN without IL-10. The latter control can be included to ensure that any differences in inflammation are due to IL-10 and not the presence of the type 3 secretion system.

To determine the overall effects on inflammation, the intestinal tissues can be fixed and paraffin embedded for histology-based assessment of intestinal inflammation. Sections can be scored in a blinded fashion with respect to intervention. For humanized and IL-10-/- mice, four parameters [mononuclear cell infiltration, polymorphonuclear cell infiltration, epithelial cell hyperplasia, and epithelial cell injury] can be used and scored as absent (0), mild (1), moderate (2), or severe (3) and summed for a final histologic severity score [34]. For DSS colitis, parameters can be scored on a scale of 0-4: percentage of colon involved by inflammation, percentage of crypt loss, presence of lymphoid follicles, edema, erosions, and density of inflammatory cells and the individual parameters are summed to give a total severity score. Statistical analysis can be performed to determine whether differences between groups are significant using a Student's T-test or analysis of variance (ANOVA) using STATA software.

To monitor for specific changes in the cytokine present in the inflammatory milieu of the treated mice, organ explant cultures [35] can be used. The distal colon (0.5 g dry weight) of humanized mice and DSS-treated mice and transverse colon (0.5 g dry weight) of IL-10-/- mice can be isolated [36] and explant supernatants will be analyzed using multiplex cytokine analysis for IL-1a, IL-2, IL-4, IL-6, KC, TNF-a, IFNγ, IL-10 (not applicable for IL-10-/-), IL-12p40, IL-12p70, IL-13, IL-17A, IL-21, and IL-23 using the Luminex platform. In addition, for the IL-10-/- mice, their peripheral blood can be sampled on a weekly basis for granulocytes, as peripheral blood granulocyte number increases and correlates with enterocolitis lesion development [37].

It is contemplated herein that the combination of EcN's natural anti-inflammatory properties combined with localized delivery of IL-10 to mouse intestines reduce inflammation more than administration of EcN alone. It is possible that expression of the T3SS could induce inflammation as purified needle components have been shown to induce TLR2 signaling [38], though given that type 3 secretion systems do not secrete needle subunits once the apparatus is assembled, this is not expected to be an issue. If no improvement in inflammatory symptoms is observed with T3-EcN IL-10, the amount of IL-10 delivered to the mouse intestines can be increased by generating T3-EcN strains that can colonize their host more efficiently. The introduction of an EnvZ P41L point mutation into the T3-EcN chromosome alters the outer membrane profile of EcN leading to enhanced colonization of mouse intestines and can lead to enhanced or prolonged delivery of IL-10 [39]. Alternatively, if minimal inhibition of inflammation is observed over the 14 day period, increasing the duration of T3-EcN IL-10 treatment to 4 or 6 weeks can be performed.

REFERENCES

1. Kaser, A. S. Zeissig, and R. S. Blumberg, Inflammatory bowel disease. Annu Rev Immunol, 2010. 28: p. 573-621.
2. Xavier, R. J. and D. K. Podolsky, Unraveling the pathogenesis of inflammatory bowel disease. Nature, 2007, 448(7152): p. 427-34.
3. Kole, A. and K. J. Maloy, Control of intestinal inflammation by interleukin-10. Curr Top Microbiol Immunol, 2014. 380: p. 19-38.
4. Franke, A., et al., Sequence variants in IL10, ARPC2 and multiple other loci contribute to ulcerative colitis susceptibility. Nat Genet, 2008. 40(11): p. 1319-23.
5. Aithal, G. P., et al., Role of polymorphisms in the interleukin-10 gene in determining disease susceptibility and phenotype in inflammatory bowel disease. Dig Dis Sci, 2001. 46(7): p. 1520-5.
6. Wang, Z. W., et al., Risk factors and gene polymorphisms of inflammatory bowel disease in population of Zhejiang, China. World J Gastroenterol, 2011. 17(1): p. 118-22.

7. Kuhn, R., et al., Interleukin-10-deficient mice develop chronic enterocolitis. Cell, 1993. 75(2): p. 263-74.
8. Colombel, J. F., Decade in review-IBD: IBD-genes, bacteria and new therapeutic strategies. Nat Rev Gastroenterol Hepatol, 2014. 11(11): p. 652-4.
9. Schreiber, S., et al., Safety and efficacy of recombinant human interleukin 10 in chronic active Crohn's disease. Crohn's Disease IL-10 Cooperative Study Group. Gastroenterology, 2000. 119(6): p. 1461-72.
10. Fedorak, R. N., et al., Recombinant human interleukin 10 in the treatment of patients with mild to moderately active Crohn's disease. The Interleukin 10 inflammatory Bowel Disease Cooperative Study Group. Gastroenterology, 2000. 119(6): p. 1473-82.
11. Colombel, J. F., et al., Interleukin 10 (Tenovil) in the prevention of postoperative recurrence of Crohn's disease. Gut, 2001. 49(1): p. 42-6.
12. Helwig, U., et al., Lactobacilli, bifidobacteria and *E. coli* nissle induce pro- and anti-inflammatory cytokines in peripheral blood mononuclear cells. World J Gastroenterol, 2006. 12(37): p. 5978-86.
13. Steidler, L., et al., Treatment of murine colitis by *Lactococcus lactis* secreting interleukin-10. Science, 2000. 289(5483): p. 1352-5.
14. Braat, H., et al., A phase I trial with transgenic bacteria expressing interleukin-10 in Crohn's disease. Clin Gastroenterol Hepatol, 2006. 4(6): p. 754-9.
15. Nouaille, S., et al., Heterologous protein production and delivery systems for *Lactococcus lactis*. Genet Mol Res, 2003. 2(1): p. 102-11.
16. Galan, J. E. and H. Wolf-Watz, Protein delivery into eukaryotic cells by type III secretion machines. Nature, 2006. 444(7119): p. 567-73.
17. Galan, J. E., et al., Bacterial type III secretion systems: specialized nanomachines for protein delivery into target cells. Annu Rev Microbiol, 2014. 68: p. 415-38.
18. Chamekh, M., et al., Delivery of biologically active anti-inflammatory cytokines IL-10 and IL-1ra in vivo by the *Shigella* type III secretion apparatus. J Immunol, 2008. 180(6): p. 4292-8.
19. Troisfontaines, P. and G. R. Cornelis, Type III secretion: more systems than you think. Physiology (Bethesda), 2005. 20: p. 326-39.
20. Kruis, W., et al., Maintaining remission of ulcerative colitis with the probiotic *Escherichia coli* Nissle 1917 is as effective as with standard mesalazine. Gut, 2004. 53(11): p. 1617-23.
21. Westendorf, A. M., et al., Intestinal immunity of *Escherichia coli* NISSLE 1917: a safe carrier for therapeutic molecules, FEMS Immunol Med Microbiol, 2005. 43(3): p. 373-84.
22. Sturm, A., et al., *Escherichia coli* Nissle 1917 distinctively modulates T-cell cycling and expansion via toll-like receptor 2 signaling. Infect Immun, 2005. 73(3): p. 1452-65.
23. Le Gall, T., et al., Analysis of virulence plasmid gene expression defines three classes of effectors in the type III secretion system of *Shigella flexneri*. Microbiology, 2005. 151(Pt 3): p. 951-62.
24. Bichsel, C., et al., Direct reprogramming of fibroblasts to myocytes via bacterial injection of MyoD protein. Cell Reprogram, 2013. 15(2): p. 117-25.
25. Takahashi, K. and S. Yamanaka, Induction of pluripotent stem cells from mouse embryonic and adult fibroblast cultures by defined factors. Cell, 2006. 126(4): p. 663-76.
26. Ieda, M., et al., Direct reprogramming of fibroblasts into functional cardiomyocytes by defined factors. Cell, 2010. 142(3): p. 375-86.
27. Maeder, M. L., et al., Robust, synergistic regulation of human gene expression using TALE activators. Nat Methods, 2013. 10(3): p. 243-5.
28. Kelly, J. R., et al., Measuring the activity of BioBrick promoters using an in vivo reference standard J Biol Eng, 2009. 3: p. 4.
29. Costa, C. P., et al., A new means to identify type 3 secreted effectors: functionally interchangeable class 1B chaperones recognize a conserved sequence. mBIO, 2012. 3: p. in press.
30. Thompson-Snipes, L., et al., Interleukin 10: a novel stimulatory factor for mast cells and their progenitors. J Exp Med, 1991. 173(2): p. 507-10.
31. Menard, R., P. J. Sansonetti, and C. Parsot, Nonpolar mutagenesis of the ipa genes defines IpaB, IpaC, and IpaD as effectors of *Shigella flexneri* entry into epithelial cells. J Bacteriol, 1993. 175(18): p. 5899-906.
32. Botteaux, A., et al., MxiC is secreted by and controls the substrate specificity of the *Shigella flexneri* type III secretion apparatus. Mol Microbiol, 2009. 71(2): p. 449-60.
33. Steidler, et al., Biological containment of genetically modified *Lactococcus lactis* for intestinal delivery of human interleukin 10. Nat Biotechnol, 2003. 21(7): p. 785-9.
34. Neurath, M. F., et al., The transcription factor T-bet regulates mucosal T cell activation in experimental colitis and Crohn's disease. J Exp Med, 2002. 195(9): p. 1129-43.
35. Garrett, W. S., et al., Communicable ulcerative colitis induced by T-bet deficiency in the innate immune system. Cell, 2007. 131(1): p, 33-45.
36. Hegazi, R. A., et al., Carbon monoxide ameliorates chronic murine colitis through a heme oxygenase 1-dependent pathway. J Exp Med, 2005. 202(12): p. 1703-13.
37. Podolsky, D. K., Inflammatory bowel disease. N Engl J Med, 2002. 347(6): p. 417-29.
38. Jessen, D. L., et al., Type III secretion needle proteins induce cell signaling and cytokine secretion via Toll-like receptors. Infect Immun, 2014. 82(6): p. 2300-9.
39. Adediran, J., et al., An *Escherichia coli* Nissle 1917 missense mutant colonizes the streptomycin-treated mouse intestine better than the wild type but is not a better probiotic. Infect Immun, 2014. 82(2): p. 670-82.

Example 2

Standard cancer therapy includes surgical resection, chemotherapy and radiation; approaches that often are not sufficient to lead to cure or stable disease and generally associated with numerous side effects. While targeted therapies have made significant inroads in survival, the war on cancer wages on. Current and evolving knowledge of immunotherapy and synthetic engineering of bacteria hold the potential to revolutionize cancer care and treatment. The genesis of these fields leads back to the first immune-based bacteriotherapy therapy called Coley's toxin and this application aims to effectively leverage this history along with decades of subsequent science and technology to develop a new cancer therapeutics platform (for review see [1, 2]).

A variety of bacterial species are inherently well suited to function as potential anti-cancer agents, as some exhibit a profound propensity to home to and colonize the hypoxic and often nutrient rich environments of tumors and neoplastic deposits. Upon reaching tumor tissue, flagellated bacteria can effectively penetrate areas remote from vasculature. In this way, bacteria offer a means to introduce 'anti-neoplastic payloads' in a highly targeted fashion by specifically accessing tumor tissue. Select bacterial pathogens, including *Salmonella* and Clostridial species [3, 4], can promote tumor clearance by direct immune-stimulatory effects in tumor environments which can be thought of as immune privileged, exhausted, or suppressed. Synthetic biology based approaches have recently capitalized on this characteristic by modifying bacteria to deliver therapeutic payloads, i.e., pro-inflammatory cytokines, siRNAs and cytotoxins directly to tumors to promote tumor killing and rouse anti-tumor immunity [5]. Such modifications have generally been developed using attenuated bacterial pathogens, given concerns of administrating live pathogens to patients, particularly late stage cancer patients who are systemically immunosuppressed from chemotherapy and radiation treatments. While these strains work well in mouse tumor models, to date they have demonstrated limited success in human clinical trials, presumably because the attenuated strains are cleared from the systemic circulation too rapidly to reach and establish residence in tumors [6, 7].

Nissle 1917 *Escherichia coli* (EcN), a probiotic commonly used in Europe and Canada for the treatment of inflammatory bowel disease [8], also shows a strong propensity for homing to tumors where it replicates to titers as high as $10^{10}$ colony forming units/gm [9-12]. However, unlike *Salmonella* which only reach titers of ~$10^5$ [11], the presence of EcN within tumors does not induce any immune responses or inhibit tumor growth. It is contemplated herein that modifications to EcN can engineer the strain to promote tumor cell death. For example, tumor colonization with EcN engineered to secrete azurin, a *Pseudomonas* redox protein that promotes tumor cell apoptosis, inhibits tumor growth but does not promote eradication [12]. While this result is encouraging, it does indicate that additional modifications to EcN are required to actualize EcN as a cancer therapeutic. To address these issues, described herein are synthetic biology based approaches to develop EcN strains capable of secreting proteins either directly into cancerous cells or into the tumor milieu. As a first step regarding the potential clinical utility of such strains, they are engineered to deliver single domain antibodies (nanobodies) that inhibit the activity of tumor cell immune checkpoints (PD-1 and CTLA-4) as the targeted deposition of such nanobodies into the tumor milieu promotes the recognition and clearance of neoplastic lesions resistant to anti-tumor immunity.

Both non-pathogenic and commensal Gram-negative bacteria, including EcN, rarely, if at all, secrete proteins directly into the extracellular environment. Rather they utilize type I and type II secretion systems to deliver proteins to the periplasmic space of the cell envelope. In contrast, many Gram-negative bacterial pathogens utilize complex protein delivery machines to efficiently transfer proteins directly from bacteria into the cytosol of mammalian cells. Type 3 secretion systems (T3SSs) are one, if not the best characterized, of these protein delivery nanomachines [13]. These complex machines have been reengineered to secrete therapeutic payloads, as opposed to virulence proteins, directly into or within the vicinity of mammalian cells. While most efforts have focused on engineering the T3SS systems of attenuated pathogens to deliver therapeutic payloads [14, 15], described herein is, e.g., the introduction and expression of a regulatable and functional type 3 secretion systems in non-pathogenic *E. coli*. In some embodiments, described herein are regulatable and functional T3SS-derived extracellular secretion systems in non-pathogenic bacteria. Furthermore, described herein is a platform to rapidly identify sequences that efficiently promote the recognition of a variety of heterologous proteins as type 3 secreted substrates. These approaches can be applied to the development of type 3 secretion competent strains of EcN that deliver nanobodies that activate anti-tumor immunity within the tumor microenvironment.

VHH are small (~12-15 kDa) single domain antibodies composed of a single variable immunoglobulin domain and are commonly found in camelids and cartilaginous fish [16]. These proteins are more stable than their traditional antibody counterparts and less dependent on disulfide bond formation for proper folding. These molecules have tremendous therapeutic potential, particularly those that mimic the activity of monoclonal immunomodulatory antibodies. Nanobodies that bind to and inhibit the activity of PD-L1 (programmed death ligand 1), PD-1 (programmed cell death inhibitor) and CTLA-4 (cytotoxic T-lymphocyte-associated antigen 4) have been described. Furthermore, the administration of the PD-L1 nanobody is effective as that of a commercially available PD-L1 antibody in promoting the regression of tumors in the B16 mouse model of melanoma. Nanobodies are readily produced by bacteria and are functional when engineered to be recognized as enteropathogenic *E. coli* type 3 secreted proteins [17].

Immune system checkpoints essentially serve as "brakes" that act to prevent over-activation of the immune system in response to pathogens as well as to maintain tolerance of self-antigens, thus protecting healthy tissues from damage. However, many malignant tumors block recognition by the host immune responses through the dysregulation of proteins that promote checkpoint activation. Three of the best-studied checkpoints in this scenario are PD-1, PD-L1 and CTLA-4, proteins that dampen T cell responses and are critical effectors in blocking anti-tumor T cell immunity [18-20]. Monoclonal antibodies that bind to and block PD-1, PD-L1 and CTLA-4 have shown extraordinary promise in clinical trials, particularly in the treatment of melanoma, renal cell cancer, and lung cancer. Therapies that combine the two agents show the most success, although they are often associated with marked side effects, including numerous 'autoimmune' sequelae and adverse immune related events including: life threatening colitis, hepatitis, pancreatitis, hypophysitis, and thyroiditis, due to the systemic effects of disinhibiting immune checkpoints [21]. It is contemplated herein that therapies that target the delivery of these checkpoint inhibitors to tumors and neoplastic deposits improve their efficacy while decreasing their off-target complications.

Figure 5:
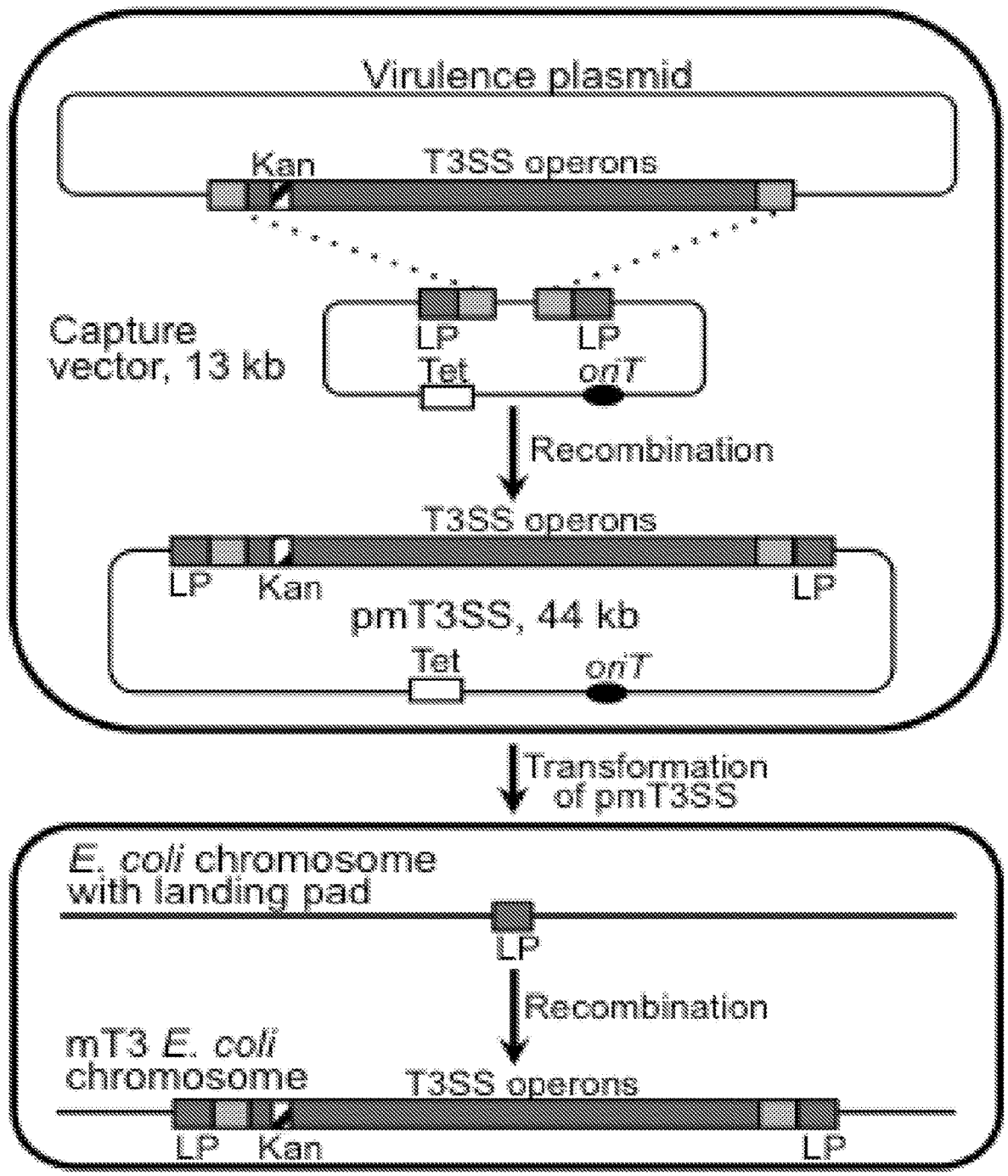
FIG. 5 depicts a schematic of strategy to capture and transfer T3SS operons from the *Shigella* virulence plasmid onto an autonomously replicating plasmid that can be introduced carried in *E. coli* as a plasmid or integrated into its chromosome.
Figure 6:
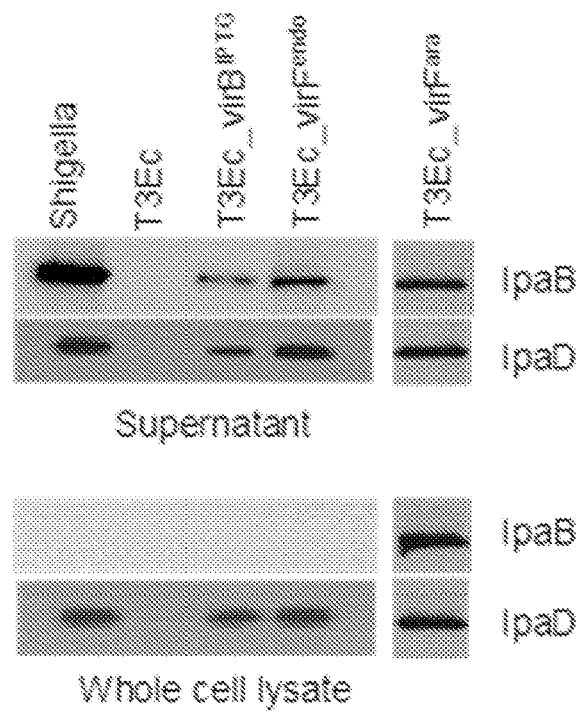
FIG. 6 demonstrates regulatable expression of T3SS in *E. coli* (T3Ec). Immunoblots of designated strains grown under conditions that induce type 3 secretion. IPTG or arabinose added for strains that carry regulatable type 3 transcriptional regulators (VirF or VirB). Plots probed with antibodies that recognize two secreted components of the type 3 secretion apparatus, IpaB and IpaD.

Stable integration of the *Shigella* operons needed to form a type 3 secretion system onto the *E. coli* chromosome. Described herein is a means to efficiently transfer the secretion apparatus from the highly related human pathogen, *Shigella flexneri*, into non-pathogenic strains of *E. coli* (FIG. 5). Using a combination of yeast and bacterial homologous recombination-based technologies, a 31 kB region that contains the operons that encode all of the ~25 proteins needed to form a functional T3SS [22] were transferred from the *Shigella* virulence plasmid onto an autonomously replicating plasmid. The backbone of this plasmid contains an oriT sequence which enables its transfer from strain to strain via conjugation. In addition, the T3SS operons are flanked on each sides by a synthetic unique landing pad (LP) sequences which enables the efficient insertion of this DNA fragment at defined sites on the *E. coli* chromosome engineered to have the corresponding "landing pad" sequence (FIG. 5) [23].

Introduction of a functional, regulatable type 3 secretion system into E. coli. The introduction of the Shigella T3SS operons into E. coli is not sufficient to generate a functional protein delivery strain as this region of DNA does not include the master *Shigella* T3SS transcriptional regulator, VirF. However, as shown in FIG. 6, secretion can be activated in a regulated manner, with introduction of a second plasmid that expresses under control of its endogenous or a regulatable promoter. This data demonstrates that by controlling VirF expression, via exogenously added agents like arabinose or EcN promoters active specifically within tumors, it is possible to restrict the expression of the T3SS.

Development of a platform for rapid identification of signal sequences that promote secretion of heterologous proteins. To complement the development of type 3 secretion competent non-pathogenic *E. coli*, a recombination based platform to rapidly identify secretion sequences that promote the recognition of heterologous proteins as type 3 secreted substrates was constructed. While all type 3 secreted proteins are defined by a N-terminal secretion sequence of ~20 residues, a region essentially only defined by its unstructured nature [24], many also encode and require a downstream chaperone-binding domain. As shown in FIG. 7, it is observed that the fusion of the first 50, but not 30, amino acids of native *Shigella* type 3 secreted proteins is sufficient to generate alleles of heterologous proteins that are recognized as a secreted substrate. As shown for MyoD, the levels of secreted proteins can vary. Similarly, fusion to some signals does effect MyoD function, particularly once the proteins are delivered into host cells, indicating that the secretion sequence-heterologous combination for each protein can be optimized (data not shown and [25]).

Develop type 3 secretion competent strains of EcN that secrete immunomodulatory nanobodies. Described herein is the development of type 3 secretion-competent strains of Nissle 1917 *E. coli* (T3EcN) that recognize and secrete functional nanobodies. In some embodiments, the secretion can be into the extracellular environment. In some embodiments, the secretion can be into the intracellular space of a target cell. Versions of T3EcN capable of either directly injecting nanobodies into the cytosol of cancerous cells or into the extracellular milieu of tumors can be developed. Described herein are strains of EcN that secrete proteins into the media rather than host cells, the identification of modifications to single domain antibodies that promote their efficient recognition as type secreted proteins but do not perturb their activity, and versions of EcN that induce the expression of the T3SS in tumors by administration of a small molecule inducer, such as arabinose, or via endogenous EcN promoters specifically activated within tumors.

Introduce the operons needed to form a functional type 3 secretion system into EcN. The *Shigella* T3SS operons can be introduced onto the chromosome of EcN. The operons can be integrated onto the chromosome to ensure that this large ~31 kB fragment of DNA is stably maintained when the bacteria are introduced into mice. A "landing pad" site in the EcN chromosome can be utilized. After the T3SS operons are introduced into EcN, the functionality of the strain, T3EcN, can be confirmed using conventional assays to monitor the ability of the strain to secrete as well as deliver type 3 effectors into host cells, (FIGS. 5, 6 [26, 27]). The expression of the T3SS can be controlled by the introduction of a plasmid that conditionally expresses VirF and study epitope-tagged effectors expressed from an IPTG-inducible promoter on a second plasmid. Using this approach, a functional type 3 secretion has been introduced into multiple strains of *E. coli* including DH10b, DH5a, HB101 and BL21.

Develop strains of EcN strains that efficiently secrete proteins into the extracellular milieu. Once T3EcN is confirmed as functional, a screen can be performed for modifications to the T3SS components that act to promote the efficient secretion proteins into the surrounding media as opposed to the direct injection of proteins into mammalian cells. Strains that lack combinations of each of the following 3 proteins can be generated: (1) IpaD, the outer most protein of the secretion apparatus which forms a "cap" that holds the secretion apparatus in an "off" position prior to contact with host cells [28], (2) IpaB, one of two proteins at that tip of the needle (the conduit through which the secreted substrates travel) that, upon contact with host cells, serves to form the pore in the plasma membrane through which proteins are translocated [28] and (3) MxiC, the "gatekeeper" protein, which prevents the internal loading of proteins into the needle prior to secretion apparatus [29]. A T3EcN strain that lacks the ipaBCD operon can be constructed first and then deletion of mxiC can be tested for increases the levels of constitutively secreted proteins. It can also be confirmed that these strains can no longer deliver proteins into host cells using the conventional TEM-1 β-lactamase translocation assay [26, 30].

Generate functional nanobodies of PD-1, PD-L1 and CTLA-4 that are recognized as type 3 secreted substrates. Alpaca-derived anti-mouse nanobodies that block the activity of three checkpoint proteins, PD-1, PD-L1 and CTLA-4 are available. Each VHH can be modified to be recognized as type 3 secreted substrates using the platform described herein (FIG. 6). Basically, Gibson cloning can be employed to generate "Gateway" destination vectors whereby alleles of the PD-1, PD-L1 and CTLA-4 nanobodies fused to 11 different secretion signal sequences that are expressed under the control of the virF promoter can be quickly generated. The vectors can also be designed to introduce a flexible linker between the type secretion signal sequence and the nanobody and an epitope-tag at the carboxy termini of the nanobody. The levels of secreted nanobodies fused to each secretion signal sequence can be confirmed and whether the modified type 3 secreted nanobodies retain function confirmed by quantifying their ability to recognize their cognate binding proteins. Notably, for the later, the binding activities of the type 3 secreted nanobodies can be compared to their unmodified purified cognate nanobodies. The genes encoding each of the three modified nanobody proteins under the control of the virF promoter can be introduced onto the chromosome of T3EcN strain using CRIM, Landing Pad, and/or lambda InCh methodologies [23, 32, 33].

Introduction of regulatable versions of the transcriptional regulator VirF. As demonstrated in FIG. 5, expression of the *Shigella* T3SS operons in *E. coli*, requires the addition of a plasmid that carries the transcriptional regulator, VirF. Notably, by placing VirF under the control of a regulatable promoter it should prove possible to control the expression of the T3SS in T3EcN in space and time, i.e., only once the bacteria colonize the tumors. Described herein are two complementary strategies to control VirF expression. First, virF can be placed under the control of the pBAD arabinose-inducible promoter (VirFara). This promoter, in EcN that carry a luciferase gene driven by the pBAD promoter, caused cells that have colonized tumors to exhibit GFP fluorescence when the mice are administered an L-arabinose solution orally or via a tail vein injection [11, 34]. A light signal is detected from tumors as early as 15-30 minutes post-arabinose administration, reaches a maximal intensity at 1-3 hours and is undetectable after 8 hours. Repeat administration of L-arabinose on consecutive days results in the "re-induction" of light emission [11]. Second, virF can be placed under the control of endogenous EcN promoters predicted to be markedly up-regulated once the bacteria colonize tumors. For example, multiple *Salmonella* promoters that are specifically induced when the bacteria invade solid tumors as compared to organs like the spleen and organs have been identified[35]. Based on these studies, we will generate alleles of virF under the control of the homologous EcN ansB (VirFansB) and pflE (VirFpflE) promoters that are induced in hypoxic conditions and napF (VirFnapF), a promoter that regulates a gene involved in flagella biosynthesis [35]. Using λ-InCh technology [32] fragments of DNA that carries the virF gene under the control of each of the 4 promoters (pBAD, ansB, pflE and napF) can be stably integrated at a specific site on the EcN chromosome. The ability of each to drive expression of a virF driven allele of phiLOV, a fluorescent protein that in contrast to GFP folds even under hypoxic conditions [36, 37], when EcN are grown in the presence of arabinose or under hypoxic conditions can be tested.

Investigating the Efficacy of T3EcN Nanobody Secreting Strains in Melanomas

Described herein is bacteria-mediated direct delivery into the tumor microenvironment of immunostimulatory nanobodies that block PD-1 and CTLA-4 activity to promote tumor regression. Further described herein is the establishment of conditions under which the genetically modified T3EcN strains selectively express VirF, the master T3SS transcriptional regulator, within tumors identification of inoculation conditions that ensure that the modified T3EcN_VirF strains home to and replicate within tumors. The ability of the nanobody-secreting T3EcN strains to promote mouse tumor clearance can be tested. It is contemplated herein that the directed delivery of immunostimulatory nanobodies that inhibit the activity of tumor checkpoints can treat a variety of tumor types.

Identify conditions under which VirF, the master type 3 secretion transcriptional regulator, is functional within tumors. Conditions under which VirF, the master T3SS transcription regulator, is activated only after the T3EcN strains colonize tumors can be identified. Two strategies are described herein: one strain, T3EcN_VirFara, where VirF activity is controlled by the administration of a small molecule, like arabinose and a second strain, T3EcN_Virfend, where VirF expression is activated by one of the 3 endogenous promoters discussed above herein (VirFansB, VirFPlfE or VirFnapF) that is activated by cues unique to the tumor microenvironment. To initially characterize the transcriptional activity of VirF under the control of each of the different promoters, T3EcN strains that carry an eGFP VirF-driven transcriptional reporter can be examined. BALB/c mice that have implanted syngeneic 0.2 $cm^3$ B16 tumors via the earlier injection of $1 \times 10^5$ B16 cells on the mid-right side of their flank [8] can be treated with the strain. Each mouse can receive a single tail vein inoculation of $2 \times 10^7$ CFU for each of 4 experimental strains plus strains that express no GFP, constitutive GFP or arabinose-inducible GFP, as controls. A non-bacteria/media alone injection can be performed as well. When administered at this dose. EcN has been observed to transiently colonize the spleen and liver at day 1 after which point it is rapidly cleared from the circulation. The pBAD-virE strain recipients can receive 200 ul of 25% arabinose daily via a gentle oral instillation, a condition previously demonstrated to promote activation of the pBAD promoter present within strains of EcN within solid tumors [44]. One (n=4 per group) and 3 (n=4 per group) days post-inoculation, the patterns of bacterial colonization within tumors and solid organs as well as their eGFP expression levels will be examined upon sacrifice. The organs and tumors of each can be formalin-fixed and paraffin embedded, sectioned and stained with commercially available antibodies that recognize both *E. coli* as well as eGFP. By visualizing GFB expression via indirect immunofluorescence, GFP expression can be detected within microaerophilic regions of the tumor, a condition that can inhibit the correct folding of GFP.

Expression of the arabinose-driven genes carried by T3EcN can be induced within tumors and the endogenous promoters with the best performance for particularly conditions can be identified. In addition, by examining the distribution of GFP+ bacteria within the tumors and solid organs (liver and spleen), an understanding regarding the relative activity of the different VirF alleles within different regions of the tumor can be developed, as well as confirming that EcN is cleared from the spleens and livers of mice within three days [12].

Identify conditions that promote the colonization of syngeneic B16 derived tumors by T3EcN. Delivery conditions that ensure homing to and residence of T3EcN_VirFara and T3EcN_VirFend strains within tumors can be identified. Several published studies have characterized the ability of unmodified EcN to colonize tumors [9-12]. However, given that the strains described herein have been modified to express a functional T3SS, the behavior of these strains in mice can be characterized, as it is theoretically possible that the expression of the T3SS alone could perturb EcN growth and/or induce host responses that promote the clearance of these bacteria. The published literature suggests that post-inoculation of $2 \times 10^6$ CFU or $2 \times 10^7$ CFU via tail vein injection into BALB/c mice, EcN will reach titers of $10^8$-$10^9$ CFU vs. $10^{10}$ CFU within tumors, respectively, by 24 hours. The bacteria will then persist at high titers for at least 14 days. While the group that inoculated the mice with $2 \times 10^7$ CFU observed low-levels of bacteria within the liver (~$10^4$) and spleen (~$10^5$), the group that utilized a 10× lower inoculum observed none. Based on these results, the levels of EcN, T3EcN_VirFara and T3EcN_VirFend that localize to the tumor, spleen and liver when administered at inoculums of $2 \times 10^6$ CFU or $2 \times 10^7$ CFU via tail vein injection can be compared. For the T3EcN_VirFara strain, starting one day post-inoculation, a time whereby the majority of EcN have presumably been cleared from the liver and spleen, the mice wcanll receive a daily oral instillation of 200 ul of 25% arabinose solution. A cohort of mice infected with unmodified EcN will also receive arabinose to control for any effects of the sugar inoculum on colonization. On days 1, 2, 3, 7 and 14, 4 mice receiving each inoculum can be sacrificed and each of these time courses can be repeated two additional times. Tumors, spleens, and livers can be dissected out, weighed and homogenized and plated to determine colony counts.

Given that the T3EcN we are studying should not invade mammalian cells, it is not expected that any host cell innate immune signaling responses will be triggered. Nevertheless, if it is observed that the T3EcN are altered in their ability to colonize tumors, the inoculum frequency and/or dose can be altered to modulate tumor colonization. Lastly, if the strains do not reach tumors after introduced via tail vein injections, the bacteria can be directly introduced into the neoplastic lesions via intratumoral injections, as once the bacteria reach the tumor they will be an immune-privileged environment protected from host innate immune response and thus able to establish residence and act to inject the immunostimulatory nanobodies into the tumors.

T3EcN immunostimulatory nanobody secreting strains can promote the regression of melanoma. T3EcN strains that secrete the anti-PD-1, anti-PD-L1 and anti-CTLA-4 immunostimulatory nanobodies promote B16 tumor regression. In clinical trials, combinations therapies that combine two of these three antibodies have shown great promise but patients experience a high rate of severe related adverse effects [21]. It is contemplated herein that the targeted delivery of nanobodies to tumors via T3EcN_VirF prevents or markedly alleviates the development of systemic off-target effects. T3EcN_VirF strains that secrete all three immunostimulatory nanobodies can be utilized. Using the inocula established above to promote T3EcN_VirF tumor residence, B16+ mice that have ~0.2 cm$^3$ flank tumors can be inoculated with each of the following 5 strains: EcN, T3EcN_VirFara, T3EcN_VirFend. T3EcN_VirFara(PD-1/PD-L1/CTLA-4) and T3EcN_VirFend(PD-1/PD-L1/CTLA-4) plus a media-only control. The mice can be injected weekly with each strain. Mice that receive the arabinose-driven system can receive daily oral doses of 200 ul of 25% arabinose. The size of the tumors, located on their flanks, can be assessed every two days using calipers. The mice can be monitored daily for up to 4 weeks, a time frame which permit assessment of the health status of the mice more fully, as based on the published literature, untreated mice (those receiving unmodified EcN) are expected to become moribound at ~14 days, at which point they will be sacrificed for humane endpoint considerations. The experiment can be repeated three times.

If the mice do not tolerate the targeted delivery of all 3 immunostimulatory nanobodies, strains that only deliver combinations of 2 nanobodies, i.e., PD-1/CTLA-4 vs. PD-L1/CTLA-4 can be utilized. In addition, minimal tumor regression is observed under a given condition, tumors can be isolated and flow cytometry utilized to interrogate whether the T3EcN immunostimulatory nanobody secreting strains act to alter intratumoral T-cell populations, specifically the balance of effector T cells (both activated and exhausted) and regulatory T cells, as well as investigate the distribution of secreted nanobodies present in the tumors.

REFERENCES

1. Bernardes, N., A. M. Chakrabarty, and A. M. Fialho, Engineering of bacterial strains and their products for cancer therapy. Appl Microbiol Biotechnol, 2013. 97(12): p. 5189-99.
2. Forbes, N. S., Engineering the perfect (bacterial) cancer therapy. Nat Rev Cancer, 2010. 10(11): p. 785-94.
3. Minton, N. P., Clostridia in cancer therapy. Nat Rev Microbiol, 2003. 1(3): p. 237-42.
4. Saccheri, F., et al, Bacteria-induced gap junctions in tumors favor antigen cross-presentation and antitumor immunity. Sci Transl Med, 2010. 2(44): p. 44ra57.
5. Wall, D. M., C. V. Srikanth, and B. A. McCormick, Targeting tumors with Salmonella typhimurium-potential for therapy. Oncotarget, 2010. 1(8): p. 721-8.
6. Cunningham, C. and J. Nemunaitis, A phase I trial of genetically modified Salmonella typhimurium expressing cytosine deaminase (TAPET-CD, VNP20029) administered by intratumoral injection in combination with 5-fluorocytosine for patients with advanced or metastatic cancer. Protocol no: C1-017. Version: Apr. 9, 2001, Hum Gene Ther, 2001. 12(12): p. 1594-6.
7. Toso, J. F., et al., Phase I study of the intravenous administration of attenuated Salmonella typhimurium to patients with metastatic melanoma. J Clin Oncol, 2002. 20(1): p. 142-52.
8. Overwijk, W. W. and N. P. Restifo. B16 as a mouse model for human melanoma. Curr Protoc Immunol, 2001. Chapter 20: p. Unit 20 1.
9. Hill, P. J., et al., Magnetic resonance imaging of tumors colonized with bacterial ferritin-expressing Escherichia coli. PLoS One, 2011. 6(10): p. e25409.
10. Stritzker, J., et al., Myristoylation negative msbB-mutants of probiotic E. coli Nissle 1917 retain tumor specific colonization properties but show less side effects in immunocompetent mice. Bioeng Bugs, 2010. 1(2): p. 139-45.
11. Stritzker, J., et al., Tumor-specific colonization, tissue distribution, and gene induction by probiotic Escherichia coli Nissle 1917 in live mice. Int J Med Microbiol, 2007. 297(3): p. 151-62.
12. Zhang, Y., et al., Escherichia coli Nissle 1917 targets and restrains mouse B16 melanoma and 4T1 breast tumors through expression of azurin protein. Appl Environ Microbiol, 2012. 78(21): p. 7603-10.
13. Galan, J. E., et al., Bacterial type III secretion systems: specialized nanomachines for protein delivery into target cells. Annu Rev Microbiol, 2014. 68: p. 415-38.
14. Bichsel. C., et al., Bacterial delivery of nuclear proteins into pluripotent and differentiated cells. PLoS One, 2011. 6(1): p. e16465.
15. Russmann, H., et al., Delivery of epitopes by the Salmonella type III secretion system for vaccine development. Science, 1998. 281(5376): p. 565-8.
16. Muyldermans, S., Nanobodies: natural single-domain antibodies. Annu Rev Biochem, 2013. 82: p. 775-97.
17. Blanco-Toribio, A., et al., Direct injection of functional single-domain antibodies from E. coli into human cells, PLoS One, 2010. 5(12): p. e15227.
18. Naidoo, J., D. B. Page, and J. D. Wolchok, Immune modulation for cancer therapy. Br J Cancer, 2014. 111 (12): p. 2214-9.
19. Page, D. B., et al., Immune modulation in cancer with antibodies. Annu Rev Med, 2014. 65: p. 185-202.
20. Shin, D. S. and A. Ribas, The evolution of checkpoint blockade as a cancer therapy: what's here, what's next? Curr Opin Immunol, 2015, 33C: p. 23-35.
21. Postow, M. A., M. K. Callahan, and J. D. Wolchok, Immune Checkpoint Blockade in Cancer Therapy. J Clin Oncol, 2015.
22. Buchrieser, C., et al., The virulence plasmid pWR100 and the repertoire of proteins secreted by the type III secretion apparatus of Shigella flexneri. Mol Microbiol, 2000. 38(4): p. 760-71.
23. Kuhlman, T. E. and E. C. Cox. Site-specific chromosomal integration of large synthetic constructs. Nucleic Acids Res, 2010. 38(6): p. e92.
24. Buchko, G. W., et al., A multi-pronged search for a common structural motif in the secretion signal of Salmonella enterica serovar Typhimurium type III effector proteins. Mol Biosyst, 2010. 6(12): p. 2448-58.
25. Widmaier, D. M., et al., Engineering the Salmonella type 111 secretion system to export spider silk monomers. Mol Syst Biol, 2009. 5: p. 309.
26. Costa, S. C., et al., A New Means To Identify Type 3 Secreted Effectors: Functionally Interchangeable Class IB Chaperones Recognize a Conserved Sequence. MBio, 2012. 3(1).

27. Schmitz, A. M., et al., Protein interaction platforms: visualization of interacting proteins in yeast. Nat Methods, 2009. 6(7): p. 500-2.
28. Menard, R., P. Sansonetti, and C. Parsot, The secretion of the *Shigella flexneri* Ipa invasins is activated by epithelial cells and controlled by IpaB and IpaD. EMBO J, 1994. 13(22): p. 5293-302.
29. Cherradi, Y., et al., Interplay between predicted inner-rod and gatekeeper in controlling substrate specificity of the type III secretion system. Mol Microbiol, 2013. 87(6): p. 1183-99.
30. Charpentier, X. and E. Oswald, Identification of the secretion and translocation domain of the enteropathogenic and enterohemorrhagic *Escherichia coli* effector Cif, using TEM-1 beta-lactamase as a new fluorescence-based reporter. J Bacteriol, 2004. 186(16): p. 5486-95.
31. Datsenko, K. A. and B. L. Wanner, One-step inactivation of chromosomal genes in *Escherichia coli* K-12 using PCR products. Proc Natl Acad Sci USA, 2000. 97(12): p. 6640-5.
32. Boyd, D., et al., Towards single-copy gene expression systems making gene cloning physiologically relevant: lambda InCh, a simple *Escherichia coli* plasmid-chromosome shuttle system. J Bacteriol, 2000, 182(3): p. 842-7.
33. Haldimann, A. and B. L. Wanner, Conditional-replication, integration, excision, and retrieval plasmid-host systems for gene structure-function studies of bacteria. J Bacteriol, 2001. 183(21): p. 6384-93.
34. Loessner, H., et al., Drug-inducible remote control of gene expression by probiotic *Escherichia coli* Nissle 1917 in intestine, tumor and gall bladder of mice. Microbes Infect, 2009. 11(14-15): p. 1097-105.
35. Arrach, N., et al., *Salmonella* promoters preferentially activated inside tumors. Cancer Res, 2008. 68(12): p. 4827-32.
36. Christie, J. M., et al., Structural tuning of the fluorescent protein iLOV for improved photostability. J Biol Chem, 2012. 287(26): p. 22295-304.
37. Nishikawa, H., et al., In vivo antigen delivery by a *Salmonella typhimurium* type III secretion system for therapeutic cancer vaccines. J Clin Invest, 2006. 116(7): p. 1946-54.
38. Prehna, G., et al., A protein export pathway involving *Escherichia coli* porins. Structure, 2012. 20(7): p. 1154-66.
39. Zhang, G., S. Brokx, and J. H. Weiner, Extracellular accumulation of recombinant proteins fused to the carrier protein YebF in *Escherichia coli*. Nat Biotechnol, 2006. 24(1): p. 100-4.
40. Curran, M. A., et al., PD-1 and CTLA-4 combination blockade expands infiltrating T cells and reduces regulatory T and myeloid cells within B16 melanoma tumors. Proc Natl Acad Sci USA, 2010. 107(9): p. 4275-80.
41. Dai, M., et al., Curing mice with large tumors by locally delivering combinations of immunomodulatory antibodies. Clin Cancer Res, 2015. 21(5): p. 1127-38.
42. Kim, T., et al., Combining targeted therapy and immune checkpoint inhibitors in the treatment of metastatic melanoma, Cancer Biol Med, 2014. 11(4): p. 237-46.
43. Ott, P. A., F. S. Hodi, and C. Robert, CTLA-4 and PD-1/PD-L1 blockade: new immunotherapeutic modalities with durable clinical benefit in melanoma patients. Clin Cancer Res, 2013. 19(19): p. 5300-9.
44. Anderson, J. C., et al., Environmentally controlled invasion of cancer cells by engineered bacteria. J Mol Biol, 2006. 355(4): p. 619-27.

Example 3

Designer Probiotics for the Prevention/Treatment of Intestinal Infection and Inflammation New drug delivery platforms are vitally needed for the targeted delivery of high-specificity therapeutics to sites of disease to maximize efficacy and limit off-target side effects. To address this challenge, described herein is a synthetic biology approach to equip a safely administered probiotic, *Escherichia coli* Nissle 1917, with a programmable type 3 secretion system, a nanomachine used by bacteria to inject proteins into host cells. These nanomachines can be genetically reengineered to directly secrete therapeutic payloads into the gut milieu, providing a novel in situ platform for delivery to the intestinal mucosa. This targeted delivery of cargo can be capitalized by engineering these designer probiotics to recognize and secrete single domain antibodies (VHHs), a new class of therapeutic biomolecules with exquisite neutralizing specificity. VHH-based neutralizing agents (VNA) that target essential bacterial toxins and pro-inflammatory cytokines can be used with the compositions and methods described herein, e.g., for treatment of intestinal infections and inflammation disorders, including *Clostridium difficile* colitis, hemolytic uremic syndrome (HUS) and inflammatory bowel disease (IBD).

The majority of efforts currently underway for the development of targeted drug delivery systems are focused on the development of synthetic nanoparticles, materials which are costly to produce, store, and distribute. Described herein is are cost-effective, self-replicating and flexible, programmable designer probiotics for the targeted delivery of therapeutics directly to sites of disease. Such an approach can overcome many issues associated with the wide-spread usages of antibiotics and systemic immunosuppressive agents. In some embodiments of any of the aspects, the methods and compositions described herein can further comprise means for biocontainment of "escaped" strains including kill switches that can engineered into the strains proposed herein before moving forward into human clinical trials.

Described herein are designer strains of the probiotic *E. coli* Nissle 1917 for the prevention and treatment of intestinal infection and inflammation. VNA can serve as novel therapeutics for the treatment of *Clostridium difficile* infections, HUS, botulism and anthrax. Described herein are *E. coli* Nissle 1917 that can recognize modified VHH as secreted substrates and secrete VNAs.

Designer probiotics are described herein for the treatment of *Clostridium difficile* infections, Shiga-toxin driven HUS, and IBD, and these designer probiotics can be modified to deliver a variety of protein-based therapeutic payloads, including cytokines, such as IL-10, that suppress intestinal inflammation or VNAs designed to target essential exposed virulence proteins of enteric bacterial pathogens, e.g., adhesins or essential components of virulence factor delivery systems. Furthermore, given the predilection of *E. coli* Nissle 1917 to colonize solid tumors when administered via a parenteral route, these stains can potentially be engineered for the targeted delivery of cancer therapeutics including VHH that act as immune checkpoint inhibitors.

Urgent need for new therapies for diarrheal illnesses and inflammatory bowel disease. Gastrointestinal diseases of inflammatory or infectious origin are major sources of morbidity and mortality worldwide. Diarrheal diseases are responsible for the deaths of an estimated 2.2 million people globally each year (WHO), mostly children in the developing world. Indeed, one in nine child deaths are due to diarrheal illness. Inflammatory bowel disease (IBD) is more prevalent in developed countries, with 1.6 million cases annually in the U.S., and an annual direct cost estimated as high as $28 billion (Crohn's and Colitis Foundation of America). The high burden of these diseases reflects the unfortunate limitations of treatments to combat them. Both conventional antibiotics and anti-inflammatories are eventually distributed throughout the body, and with (often) limited specificity, promote detrimental off-target effects. For example, anti-inflammatory treatments are associated with systemic immunosuppression, and antibiotics alter the normal microbial flora, leading to overgrowth of pathogens such as *C. difficile* or enhanced virulence factor production such as Shiga toxin from enterohemorrhagic *E. coli*. Finally, the general efficacy of antibiotics is being diminished due to the inexorable emergence of drug resistance indeed, widespread antibiotic use undoubtedly promotes the spread of resistance, already a growing medical crisis.

In response to the limitations of conventional antibiotics and immunomodulatory treatments, two therapeutic strategies have recently received considerable attention. First, probiotics have shown considerable therapeutic promise and have been used for the treatment of diarrheal illnesses and IBD. Unfortunately, most current probiotic strategies are not based on a mechanistic understanding of pathogenesis of these illnesses, resulting in empiric treatment and limited application. Second, monoclonal antibody-based "magic bullet" therapeutics with high target molecule specificity have revolutionized treatments of some cancers and chronic inflammatory diseases. However, these antibody-based therapies still suffer from frequent off-target effects due to their systemic administration and from high cost due to the specialized methodologies needed to manufacture and purify these complex proteins.

It is clear that new drug delivery platforms are vitally needed to enable the directed delivery of novel high-specificity therapeutics to sites of disease in order to both maximize efficacy and limit off-target side effects. As described below, described herein is the utilization of synthetic biology to generate genetically engineered probiotics that locally deliver to the site of disease a new class of well-documented therapeutic biomolecules of exquisite neutralizing specificity and at a fraction of the cost of conventional biological drugs.

VHH (nanobodies), small versatile antibody-based high affinity therapeutic agents. A new exciting avenue of antibody-mediated therapies is currently emerging that circumvents many of the obstacles of conventional monoclonal antibody-based therapies. In the 1990s, studies of the immunoglobulin repertoire of Camelidae (such as camels, llamas and alpacas) revealed that some of their heavy chain immunoglobulins are naturally devoid of light chains [1]. These "heavy chain only antibodies" (HcAbs) bind antigens via a single variable-domain heavy-chain region, a VHH. VHH, small ~15 kDa protein domains, bind substrates with $K_d$'s in the nM to pM range and exhibit a predilection for binding protein active sites [2]. Furthermore they can be used as modular building blocks to generate multimeric constructs that exhibit enhanced binding potential, both in terms of binding affinity and breath of epitope recognition. Their remarkable solubility, stability and small size overcome many of the barriers that currently limit the production of monoclonal antibodies, resulting in significant decreases in production costs. Several VHH- (or nanobody-) based therapies are now in clinical trials. For example, caplaczumab, an anti-vWF (van Willebrand factor) VHH produced by Abynx, is now in phase 3 trials for the treatment of acquired thrombotic thrombocytopenia purpura (TTP).

Although the small size of VHH and their concomitant utility in the construction of multimeric proteins of exceedingly high target specificity and affinity provides new therapeutic opportunities, potential off-target effects associated with their systemic administration remain a major concern. Described herein is the direct delivery of therapeutic payloads such as VHH into the intestinal lumen for the prevention and treatment of infection and inflammation. Specifically, as outlined in detail below, the well established and widely administered human probiotic, *E. coli* 1917, is engineered with a flexible programmable protein delivery machine that can be tuned to deliver therapeutic protein payloads, including VHH, into the intestinal lumen.

*E. coli* Nissle 1917, a human commensal exhibits probiotic activity in intestinal infection and inflammation. *E. coli* Nissle 1917, referred to hereafter as EcN, was originally isolated from the feces of a WWI soldier who was unique in not developing enterocolitis during a shigellosis outbreak. Analyses of its genome sequence suggest that although the strain does not produce known virulence factors, it encodes multiple adhesins [3]. Thus, unlike some other probiotic strains, such as *Lactococcus lactis*, which are being evaluated for the delivery of therapeutics, EcN can colonize both human and murine intestines, where it resides predominantly in the cecum and colon [4, 5]. Moreover, EcN is flagellated and able to penetrate the mucus to reside in close proximity to intestinal cells. Although it is not yet known why the strain was protective against *Shigella*, it was recently shown that, due its strong affinity for binding iron [6], EcN outcompeted intestinal *Salmonella typhimurium*, reducing *S. typhimurium* colonization, in murine acute colitis and chronic persistent infection models. Today, due to its earlier observed general anti-inflammatory properties, EcN is widely administered as a probiotic in Canada and Europe, where it has been observed to be as effective as an oral agent, mesalazine, in preventing flares in patients with ulcerative colitis [7]. The genetic tractability, impressive safety record and intestinal colonization properties, make EcN a highly attractive substrate for the development of designer probiotics.

Bacterial type 3 secretion systems, nanomachines for protein translocation into mammalian cells. Bacteria use a variety of secretion systems to deliver proteins into their periplasmic space, a major structural component of their outer cell envelopes, but generally few, if any, secrete proteins into their extracellular environment. Notably, however, many Gram-negative pathogens utilize complex nanomachines to directly deliver or translocate tens or even hundreds of virulence proteins and/or toxins into the cytosol of targeted mammalian host cells. Type 3 secretion systems (T3SSs) are currently the best characterized of these protein delivery machines [8]. They are composed of 20-25 proteins that form a conduit to deliver proteins directly from the bacterial cytosol, through its inner and outer membranes as well as the host cell plasma membrane, into the cytosol of the target cell (FIG. 8).

Engineering non-pathogenic laboratory strains of *E. coli* into a protein delivery system. Most of the work focused on reengineering bacterial T3SSs for therapeutic purposes has focused on the generation of virulence-attenuated versions of pathogenic bacteria that still encode a functional machine. However, the introduction of such strains into patients, particularly immunocompromised patients, will likely be limited. Instead, described herein is a synthetic biology based approach to transfer the T3SS from a pathogen, Shigella flexneri, into its close phylogenetic relative, E. coli [12]. As outlined in FIG. 8, described herein is a tunable protein delivery system composed of three discrete components: (1) the delivery apparatus which encodes the genes required to form a fully assembled and functionally T3SS. (2) an activator of the Shigella T3SS operons whose production can be controlled via constitutive or regulated promoters and (3) a system to produce alleles of heterologous proteins of therapeutic valve that are recognized as type 3 secreted substrates. Notably, as described in detail below, by introducing additional well defined modifications, this system can be converted from one that delivers proteins into mammalian cells to one that secretes defined proteins into the extracellular environment, i.e., the intestinal lumen.

Recognition of heterologous proteins as type 3 secreted substrates. While all type 3 secreted proteins encode an N-terminal secretion sequence, a stretch of 15-20 residues characterized only by its unstructured nature [13], many also encode and require a downstream chaperone-binding domain. Little is known regarding what determines the relative levels of effectors that are delivered into cells, particularly in the context of an infection. It appears that all type 3 secretion sequences are not equivalent and, curiously, that the type 3 secretion sequence optimal for the secretion of one protein may not promote the optimal secretion of another [14]. To extend the development of the of type 3 secretion competent non-pathogenic E. coli as a general platform for the recognition and secretion of heterologous proteins, including those of therapeutic value, a recombination-based platform is described herein, to rapidly identify secretion sequences that promote the recognition of heterologous proteins as type 3 secreted substrates [12]. This platform permitted the modification of multiple proteins, including many mammalian reprogramming factors, to be recognized as type 3-secreted factors [12]. An N-terminal type 3 secretion sequence does not perturb the function of the transcription factor MyoD within mammalian cells [12]. Thus, fusion of type 3 secretion sequences to VHH and VNA, described below, is very unlikely to interfere with their function. This is particularly true in light of the fact that VHH exhibit full function when assembled into heteromers as well as when flanked by epitope-tags at both their amino and carboxy termini [15, 16].

Conversion of a human probiotic into an intestine-specific protein delivery machine capable of recognizing VHH as secreted substrates. Given the well established safety record of EcN (E. coli Nissle 1917) as a human probiotic, its genetic tractability and its close phylogenetic relationship to laboratory K12 strains of E. coli, it was investigated whether the Shigella T3SS could also function when present in EcN. Given the observations that, in the absence of antibiotic selection, laboratory strains of E. coli do not maintain the large (>40 kB) plasmid that carries the operons encoding the components needed to form the T3SS, landing pad" technology [17] was used to stably introduce this region of DNA into the EcN chromosome, to generate T3EcN. The introduction of a plasmid encoding the Shigella master transcriptional regulator VirF provides a means to regulate expression of these operons. Indeed, these T3EcN strains that express this regulator, can express and secrete type 3 secreted proteins at levels similar to that of Shigella flexneri. Thus, described herein is the first probiotic strain engineered to express a transkingdom protein delivery system, a system capable of directly transferring proteins from bacteria into the cytosol of mammalian cells. As a first test of the possibility of developing a T3EcN VHH delivery system, the fate of two distinct VHH when fused to four different N-terminal type 3 secretion sequences was examined. Interestingly, only one of the four secretion sequences promoted T3SS recognition of both VHH sequences (FIG. 10). Notably, this secretion signal also promoted the recognition of 3 additional VHH tested as type 3 secreted substrates, each of which was efficiently secreted (FIG. 10).

VNAs, VHH-based neutralizing agents with vastly improved activity. Described herein is the use of VHH-based neutralizing agents or VNAs. VNAs exploit the modularity of VHH subunits. When fused together, multiple VHH act synergistically (rather than simply additively) in binding and inactivating bacterial toxins. This is especially true with combinations of VHH that bind non-overlapping epitopes. Using this strategy VNAs that neutralize numerous bacterial toxins, including those from Clostridium difficile (TcdA and TcdB) [19], Clostridium botulinim (BoNT/A) [15], enterohemorrhagic E. coli 0157 (Stx1 and Stx2) [20] and Bacillus anthracis (PA) [21], have been generated. A similar phenomenon occurs with dimeric VHH that recognize TNFα [22].

VNAs are can be recognized as type 3 secreted substrates and maintain activity when secreted into the intestinal lumen. Described herein are EcN strains that recognize and secrete these more complex proteins as their therapeutic payloads. The increased size of VNAs as compared to VIM, is highly unlikely to pose a problem, as the addition of an N-terminal T3SS secretion sequence is sufficient to generate variants of heterologous proteins as large as 98.6 kDA that are recognized as secreted substrates [12]. Furthermore, do not require disulfide bonds for proper folding and are markedly stable, e.g. bivalent functional VHH have been found within the intestinal lumen after secretion in an unfolded state by the Sec system of Lactococcus and Lactobacillus species [23, 24]. Hence, T3EcN can be successfully engineered to secrete functional, highly stable VNAs into the intestinal milieu.

Described herein are T3EcN that secrete VNAs into the intestinal lumen, permitting their use as therapeutics for intestinal infection and inflammation. For example, described herein are variants of T3EcN for the treatment of disease cause by EHEC and C. difficile, two toxin-driven enteric infections, and inflammatory bowel disease, a disease well established to be responsive to agents that neutralize the activity of TNF. T3EcN can also be engineered for the treatment of a variety of diseases by engineering them to deliver a variety of protein-based therapeutic payloads, including cytokines, like IL-10, that suppress intestinal inflammation, or VNAs that neutralize essential exposed virulence proteins of enteric bacterial pathogens, i.e., adhesins or outer-bacterial components of virulence factor delivery systems. In addition, given the predilection of E. coli Nissle 1917 to colonize solid tumors when administered via a parenteral route [25-28], these stains can be engineered for the targeted delivery of cancer therapeutics including VHH that act as immune checkpoint inhibitors.

Develop T3EcN$^{VNA}$ that Maximally Secrete Functional VNA into the Intestinal Lumen Development of T3EcN that secrete high levels of functional VNAs into the intestinal lumen. Described herein is the development of strains of EcN that secrete proteins into the media rather than into host cells, identification of promoters that promote expression of high levels of the EcN T3SS, and screening for modifications to VNA that promote maximal secretion without perturbing function. The ability of the T3EcN$^{VNA}$ strains to colonize and deliver VNA into the intestinal lumen can be evaluated as described below herein.

Develop strains of EcN that efficiently secrete proteins into the media rather than host cells. Under physiologic conditions, prior to contact with host cells, T3SSs including that present in T3EcN, are fully assembled and held in an "off" but primed condition such that upon contact with host cells type 3 secreted substrates are rapidly injected into host cells. This "off" conformation is maintained by the presence of proteins at the exposed and inner surfaces of the type 3 secretion conduit. In the case of the *Shigella* T3SS, the system produced by T3EcN, the outer proteins are IpaB and IpaD, and the inner "gatekeeper" protein is MxiC (see schematic, FIG. 4A). Strains that lack any of these three proteins no longer deliver proteins into host cells in a regulated manner, but rather constitutively secrete proteins into the media when grown at 37° C., a condition sufficient to activate expression of the T3SS, when present in either *Shigella* or *E. coli* [29, 30]. A similar phenotype is observed in a few strains that carry mutations in MxiH, the subunit protein that forms the channel that extends from the bacteria to host cells. Such mutations, i.e., MxiH D73A, are hypothesized to result in conformational changes that mimic those relayed from the needle to the secretion apparatus upon contact with host cells [31, 32].

The T3SS present in T3EcN can be converted into one that secretes proteins into the extracellular milieu rather than host cells by removing the operon that encodes IpaB, IpaC, IpaD and their cognate chaperone as well as MxiC. The wild type MxiH gene can be replaced with one that encodes for MxiH D73A variant, the mutant previously observed to result in the highest observed levels of constitutive secretion. The resulting secretor strain will be used for the initial (phase 1) T3EcN$^{VNA}$ studies in our animal model experiments.

Genetic screens can identify either mutations in MxiH or T3EcN that result in increased VNA secretion. Described herein is a quantitative plate-based type 3 secretion assay to facilitate these studies (FIG. 10). In this screen, bacteria, like T3EcN, are grown on solid media under conditions that induce type 3 secretion and then overlaid with nitrocellulose filters. The secreted proteins are transferred to the filters, which are then probed with an antibody that recognizes the secreted protein. In this assay, only under conditions that induce activity of the nanomachines are secreted proteins seen, i.e., bacterial lysis is not an issue. Selected mutations can be tested to determine if they alter the ability of the EcN strains to colonize the murine intestinal tract.

Development of T3EcN that exhibit maximal type 3 secretion activity. As illustrated in FIG. 8, the expression of the operons that carry the genes needed to form a functional T3SS are controlled in trans via a plasmid encoded transcription factor. Interestingly, the levels of expression and activity of the T3SS in *E. coli* depends on the level of expression of the master regulator. The modularity of the system permits control of the levels and the timing of delivery of VNA into the intestinal lumen, i.e., in response to the development of intestinal inflammation or a bacterial pathogen. Described herein is the development of strains of EcN that express high levels of the *Shigella* T3SS, as this will correlate with increased levels of secreted VNAs. Thus, alleles of the master *Shigella* T3SS transcriptional factor, VirF, that are under control of strong constitutive promoters, i.e., BBa_J23100, a synthetic sequence optimized for binding by σ70, the main RNA polymerase sigma factor expressed in *E. coli* [33] are generated. A promoter identified as permitting high levels of secreted VNAs can be further examined to confirm that high level constitutive activity of the T3SS does not perturb T3EcN growth, and the the transcription factor expression DNA cassettes can be introduced onto the chromosome of T3EcN using λ inch [35] or "landing pad" technology [17], ensuring that this DNA is stably maintained in the absence of antibiotic selection.

Generate type 3 secreted VNA variants that maximally neutralize TcdA/TcdB, Stx2 and TNFα. The following strategy will be used develop type 3 secreted active variants of VNAs that neutralize TcdA/TcdB, Stx2, the causative agents of CDI and HUS, respectively, and TNFα, a proinflammatory cytokine linked to IBD. The maximal number of fused VHH, up to six, that are recognized as secreted substrates when linked to an OspC3 type 3 secretion sequence can be determined. Whether fusion to any of the as of yet untested ~15 secretion signal sequences in this context, results in increased levels of secreted VNAs can be determined. Combinations of VHH that, when combined to form VNAs and secreted via T3EcN exhibit maximal toxin neutralization, call be tested using, cell culture intoxication assays [19, 20, 36]. For each target VHH demonstrated to exhibit strong TcdA, TcdB and Stx2 neutralization and binding activities can be combined [19, 20]. A library generated from lymphocytes isolated from two alpacas immunized with purified murine TNFα using approaches that were previously used to identify and characterize VHH that recognize ovine TNFα [18] can be generated. Genes for VNAs for each of the targets that exhibit the desired activity can be placed under the control of the same promoter that is chosen to drive the expression of the type 3 secretion system master regulator, VirF, such that expression of the T3SS and the secreted VNA are coordinately regulated. A DNA fragment that carries this expression cassette can be introduced onto the EcN chromosome at a defined loci using λ inch [35] or "landing pad" technology [17].

Characterization of colonization and secretion patterns of T3EcN$^{VNA}$ within the intestines of mice. The biogeography, persistence and colonization dynamics of T3EcN$^{VNA}$ when administered orally to mice can be investigated to optimize these parameters to ensure ideal efficacy. Although EcN is not a 'normal' constituent of the mouse intestinal microbiota, it can stably colonize the intestines of mice at high titers after a single inoculum [5, 37]. The biogeography, persistence and colonization dynamics of EcN, T3EcN and T3EcN$^{VNA}$ after administration of $10^9$-$10^{10}$ bacteria [5, 37] to mice by gavage can be characterized. T3EcN colonization can be monitored initially by quantifying (using conventional culture and confirmatory qPCR) bacterial load in shed feces as well as in homogenates of various intestinal segments. To facilitate visualization of the EcN strains, versions of T3EcN$^{VNA}$ that stably express eGFP can be used, a modification previously established to have no effect on EcN marine colonization [38]. To characterize VNA localization, particularly to the mucosa, the distribution of epitope-tagged type 3 secreted VNA can be examined by immunohistochemical staining [39, 40]. To compare the relative activities of VNAs secreted by T3EcN$^{VNA}$ strains, toxin neutralization assays and/or ELISAs with colonic homogenates can be penn formed. The behavior of EcN. T3EcN and T3EcN$^{VNA}$ when administered to conventionally reared mice that harbor a diverse gut microbiota can be characterized, as these mice can be used in the STEC/HUS model. Similar subsequent studies can be conducted with the antibiotic-perturbed CDI mouse models, as well as the IBD models, as gut microbiota and host genetics may influence the colonization of EcN-derived strains. These studies are designed to not only confirm that T3EcN can deliver functional VNA into the intestinal lumen, provide guidance in determining the dosing frequency and titers with which the T3EcN$^{VNA}$ strains can be administered when assessed for efficacy in the murine diseases models.

Modifications to promote adhesin of T3EcN to intestinal epithelial cells Wild type EcN is well established to colonize the colons of mice [4, 5], the primary site of pathology observed with CDI, Shiga-toxigenic *E. coli* and IBD. It is possible that the introduction of a functional T3SS into EcN might interfere with its ability to colonize. If this is observed to be an issue when analyzing the behavior of strains in mice using the assays described below, the strains can be engineered to express adhesins that promote attachment to intestinal epithelial cells, including *Salmonella* SiiE [41]. Interestingly, it was recently demonstrated that it is possible to generate synthetic bacterial adhesins that are basically fusion proteins of bacterial adhesins and VHH, such that the VHH is positioned to mediate interactions with defined mammalian cell proteins [42]. This technology can permit targeting of VNA T3EcN secreting bacteria to specific intestinal cell types and/or regions of the gastrointestinal tract.

VHH can be engineered to be recognized as secreted substrates, permitting the T3EcN$^{VNA}$ platform to be used for the secretion of functional neutralizing VNA into the intestinal lumen. Alternatively VNA can be secreted via the EcN native flagella type 3 secretion system flagella. Furthermore, EcN strains that express synthetic adhesins designed to display the VNA on the outer bacterial surface can be used. In addition, VNA secreting T3EcN strains can be modified to make them autotrophic for amino acids present in the gut, to prevent their survival outside of the intestines. Additionally, "kill switches" can be introduced into the strains such that we can control their spread between humans as well as eradicate the bacteria from the intestinal lumen, if needed [43, 44].

Investigate the Utility of T3EcN$^{VNA}$ in Murine Models of Infection and Inflammation Shiga toxin-producing *E. coli* (STEC), a life-threatening infection with no established anti-microbial treatment. STEC, as exemplified by enterohemorrhagic *E. coli* (EHEC) O157:H7, cause both sporadic and major outbreaks of diarrheal disease worldwide. EHEC asymptomatically colonizes cattle, resulting in contaminated beef as well as fecally contaminated foodstuff such as spinach, sprouts, and apple cider [45-49] that are the major sources of human EHEC infection. Shiga toxin (Stx) is the primary EHEC virulence determinant, and is the causative agent of hemolytic uremic syndrome (HUS), a clinical syndrome defined by the triad of hemolytic anemia, thrombotic thrombocytopenia, and uremia. HUS is the leading cause of renal failure in children. Stx, of which there are two major serotypes, Stx1 and Stx2, is encoded by a lysogenic phage and is produced only upon phage induction. Stx produced in the gut enters systemic circulation and targets the endothelium of the glomeruli and the central nervous system, causing HUS. Many antibiotics trigger phage induction, so there are currently no specific therapies for treating life-threatening Stx-associated HUS.

Towards developing a VHH toxin neutralization therapy for HUS a VHH phage display library derived from the HcAbs of alpacas immunized with catalytically inactive Stx1 and Stx2 [20] has been generated and screened. These experiments led to the identification of VHH that inactivate Stx1 or Stx2 at nM concentrations which they then combined to develop a VNA (VNA$^{Stx1,2}$), comprised of three VHH, capable of neutralizing either toxin at pM concentrations. Mice were significantly protected from intravenous Stx2 when co-administered VNA$^{Stx1,2}$, and gnotobiotic piglets were protected from the lethal effects of EHEC 0157:H7 intestinal infection by intramuscular injection of a nonreplicating adenovirus vector that expresses VNA$^{Stx1,2}$ [16]. While the murine and piglet studies demonstrate the efficacy of toxin neutralizing VNA when administered systemically, there is also data to suggest that that intra-intestinal absorption of Stx can prevent the development of HUS, as Patton and colleagues have demonstrated that *E. coli* engineered to express a receptor that sequesters Stx1 and Stx2, prevents the development of lethal renal damage in an antibiotic treated murine STEC model [50]. T3EcN$^{VNA}$ that secrete VNA$^{Stx1,2}$ can not only act as a preventive measure pre-exposure during an outbreak, but also benefit individuals who present soon after exposure or early in the course of STEC infection, scenarios likely to become more common with ongoing improvements in the tracking of major outbreaks and the development of rapid and sensitive diagnostics.

Murine model for STEC infection: A major obstacle in understanding the pathogenesis of Stx-mediated disease has been the lack of murine model that reflects human disease. EHEC, the STEC of greatest clinical significance, does not efficiently colonize conventional mice, necessitating the use of germ-free or antibiotic-treated mice, which lack a normal microbiota [51, 52]. *Citrobacter rodentium* (CR), a natural murine pathogen and a close relative of EHEC, provides an excellent model to study conserved virulence factors [51, 53-57]. However, CR does not encode Stx, limiting its use as a model for the serious systemic manifestations of EHEC infection such as HUS. CR that express Stx2 have been developed by lysogenizing CR with an Six-producing phage, termed 4Stx2dact, derived from a naturally occurring STEC strain to generate a strain herein referred to as CR_Stx2 pat Upon phage induction, CR_Stx2 produces and secretes Stx2 at levels equivalent to human EHEC isolates. Upon infection of conventional mice, CR_Stx2 not only colonizes the intestine, but also triggers systemic manifestations including weight loss, increased fecal moisture, intestinal inflammation, renal pathology and proteinuria, that reflect human disease [36].

T3EcN-mediated prophylaxis from STEC infection: The murine CR_Stx2 model can be used to investigate the ability of T3EcN$^{VNA\text{-}Stx2}$ to prevent or treat STEC infections. The utility of the engineered probiotic strain to act as a prophylactic intervention can be evaluated. Mice can be gavaged with T3EcN$^{VNA\text{-}Stx2}$ (or, as controls, T3EcN or EcN) for up to 3 days prior to inoculation with CR_Stx2. The mice can then be followed daily for up to 14 days for signs of clinical disease as assessed by weight loss, proteinuria and changes in appearance or behavior, e.g. ruffled fur, hunched posture and lethargy. Colonization of EcN and CR_Stx2 over the course of the experiment can be assessed by fecal shedding. If EcN-derived strain colonization does not reach desired levels, they are be administered both pre- and post-infection with CR_Stx2. Upon necropsy, as dictated by poor clinical condition or at completion of experiment, the intestines and kidneys of mice can be examined for histopathologic evidence of inflammation bacterial colonization, and tissue damage.

T3EcN-mediated treatment of STEC infection: To assess the potential of using T3EcN$^{VNA}$ administration as a therapeutic measure to resolve CR_Stx2 infections, once a T3EcN$^{VNA}$ strain variant identified as an effective prophylactic, can be used to prevent the development of systemic disease in mice that are one, three or five days post-inoculation with CR_Stx2. In addition, the therapeutic value of T3EcN$^{VNA}$ when administered concurrently with antibiotics that target CR, given that high titers of an Stx2-neutralizing probiotic may eliminate the risk of phage-activating (and thus Stx-inducing) antibiotic treatment exacerbating the disease can be evaluated. Indeed, if antibiotic treatment concurrent with T3EcN$^{VNA}$ administration promotes survival and diminishes intestinal and systemic damage treatment, this could lead to changes in treatment strategies, when applied to human infection, that fundamentally alter current guidelines that eschew antibiotic treatment in the setting of an EHEC infection.

*Clostridium difficile* infection (CDI), a burgeoning epidemic. CDI, which is associated with antibiotic administration, is the most common hospital-acquired infection in the U.S., and is also increasingly being recognized as a cause of diarrhea within the community. The yearly incidence of CDI is currently a half million and skyrocketing, with current annual costs approaching 4.8 billion USD. *C. difficile* can cause pseudomembranous colitis, a severe infection, particularly in the elderly, with mortality rates as high as 16.7% [58]. Furthermore, CDI is difficult to treat with relapse rates are as high as 25%. Current therapeutic options for *C. difficile* are limited to three antibiotics that reach high concentrations within the intestinal lumen and there is concern for the emergence of antibiotic resistance strains. While fecal bacteriotherapy has shown promise in preliminary trials, its long-term effects on human health remain unknown. New therapies, particularly those that prevent the occurrence of CDI in patients receiving antibiotics for unrelated life-threatening infections, are greatly needed.

Two co-regulated and homologous *C. difficile* toxins, TcdA and TcdB, disrupt epithelial tight junctions and concomitant barrier function, as well as induce epithelial cell death, leading to acute inflammation. Notably, the past decade has witnessed the emergence of a more lethal *C. difficile* strain (*C. difficile* BI/NAP1/027), which secretes higher toxin levels [59]. Strains deleted for TcdB demonstrate diminished loss of pathogenicity in mouse models and a small molecule TcdB inhibitor completely blocked CDI development in mice [60]. Merck recently announced that in two phase 3 human trials, bezlotoxumab, a monoclonal antibody directed against TcdB significantly reduced CDI recurrence rates, suggesting a major and perhaps unique role for TcdB in the pathogenesis of CDI.

By screening a VHH phage display library derived from alpacas immunized with TcdA or TcdB, four anti-TcdA and three anti-TcdB VHH each of which recognizes a unique toxin epitopes and neutralizes the toxins at nM concentrations, have been identified. VNA$^{TcdB/A}$, a VNA composed of four VHH, two directed against each toxin, completely inhibits toxin-mediated cytopathogenic effects on cultured cells at pM concentrations [19]. Upon intraperitoneal injection, VNA$^{TcdB/A}$ not only blocked a lethal murine TcdA and TcdB challenge upon co-administration, but also fully rescued previously intoxicated mice suffering from severe CDI, including diarrhea and weight loss, with a projected mortality rate of 60% [19]. T3EcN-mediated delivery of VNA, such as VNA$^{TcdB/A}$, that target TcdB and TcdA in the intestinal lumen of infected mice can provide prophylactic as well as therapeutic value in patients with preexisting CDI or at risk for new or recurrent CDI.

Murine model for CDI infection: The indigenous gut microbiota of conventionally raised mice, like that of humans, provides colonization resistance against *C. difficile*, and mice, like humans, do not develop CDI unless first exposed to antibiotics. Mice that are exposed to a broad-spectrum cephalosporin, cefoperazone, in their drinking water for 5 days are highly susceptible to infection with vegetative colonies or spores of *C. difficile* [61, 62]. Mice are typically infected two days after the discontinuation of antibiotics, but the mice remain fully susceptibility for the following seven days. The disease course of mice varies with the infectious dose as well as the strain. Whereas mice infected with strains that secrete lower toxin levels develop only a subclinical infection, those infected with spores from strains such as VPI 10463 that produce high levels of toxin develop severe colitis [62]. After high doses of VPI 10463, mice develop lethargy, diarrhea and a hunched posture within 1 to 2 days post infection and ≥20% weight loss by day 2 post-infection, necessitating euthanasia. With lower inoculums of VPI 10463, the onset of symptoms is delayed for ~2 days. Notably, when treated with oral vancomycin for 5 days, mice appear to control the infection. Although, upon the discontinuation of antibiotics, mice almost uniformly develop recurrent disease, as is often observed in patients after the completion of antibiotics, thus demonstrating the utility of the murine model for studying relapsing CDI [63].

T3EcN-mediated prophylaxis from CDI infection: The ability of T3EcN$^{VNA}$ as a preventive intervention for the development of CDI can be tested. After treating mice with oral cefoperazone for 5 days, we they can be inoculated with T3EcN$^{VNA}$ (or, as controls, EcN or T3EcN) for 5 days before administering VPI 10463 spores via oral gavage. Mice can be observed for seven days post-infection for CDI as characterized by lethargy, diarrhea, changes in posture and weight loss. Fecal shedding of T3EcN$^{VNA}$ and *C. difficile* can be assessed daily by viable counts. At day seven post-infection, the intestinal inflammation and the integrity of its epithelium can be assessed by histopathology.

T3EcN-mediated treatment of CDI injection: Once conditions under which the daily administration of T3EcN$^{VNA}$ is protective are established, it can be tested whether 12 or 24 hours post-inoculation with the *C. difficile* spores the addition of T3EcN$^{VNA}$ is sufficient to mitigate CDI, using the above disease readouts.

T3EcN-mediated prevention of CDI relapse: Notably, the resolution of CDI of both mice and humans is thought to involve the reconstitution of the indigenous microbiota as well as the clearance of *C. difficile*. For this reason, patients who develop CDI while on extended courses of antibiotics for unrelated infections are maintained on anti-*C. difficile* (typically vancomycin) therapy until 10-14 days after completion of their broad-spectrum antibiotics. In addition, empiric anti-*C. difficile* antibiotics are given to patients with a recent history CDI who are receiving prolonged antibiotic regimens, even if they show no evidence of active CDI. To test whether T3EcN$^{VNA}$ administration can substitute for anti-C antibiotic treatment in preventing CDI relapse, cefoperazone-treated mice will first be inoculated with *C. difficile* to develop a primary CDI, then treated for 5 days with oral vancomycin to suppress disease. This protocol permits the recovery, but upon subsequent cessation of vancomycin treatment, nearly all mice experience relapse of CDI [63]. We can orally inoculate T3EcN$^{TcdB/TcdA}$ one day prior to completion of vancomycin treatment and follow mice using the parameters described above for 10 days to determine if T3EcN$^{VNA}$ can prevent relapse.

In some embodiments of any of the aspects, T3EcN that secrete a heteromeric VNA that carries VHH that recognize both TcdA and TcdB can be utilized. In some embodiments of any of the aspects, given the growing evidence that TcdB is the prime virulence determinant [60, 64], VNA composed solely of TcdB-neutralizing VHH (VNA$^{TcdB}$) can be utilized. It is contemplated that when inoculating T3EcN$^{VNA}$ during cefoperazone treatment, stable colonization of the intestine by T3EcN$^{VNA}$ may be hindered by antibiotic treatment, in which case higher titers or more frequent doses of T3EcN$^{VNA}$ can be administered.

IBD, a chronic inflammatory disease mitigated by TNFα neutralization. Inflammatory bowel diseases (IBD) which includes ulcerative colitis (UC) and Crohn's disease (CD) are chronic relapsing intestinal disorders that affect over 3 million individuals in the Westernized world [65]. Patients often present with abdominal pain, diarrhea, and rectal bleeding, which in severe cases can require surgical interventions [65, 66]. Indeed the current standard of care of severe cases includes surgical resection. Although the etiologies of these diseases are multi-factorial and not fully understood, the inflammation associated with these disorders is often due to a dysregulated immune response to the gut microbiota, and broadly characterized by activation of proinflammatory cytokines including TNFα. Over the past decade, anti-TNFα monoclonal antibodies have transformed the management of both CD and UC and are currently the standard therapy in preventing induction and maintaining remission in patients with moderate to severe disease. Unfortunately, this type of treatment is not always sufficient to relieve symptoms, and is associated with increased risk of developing infection (and even cancers, i.e., lymphomas) due to systemic immunosuppression, reflecting the fact that these systemically administered antibodies are not restricted to the gut [65].

It is contemplated herein that, similar to anti-TNFα monoclonal antibodies, anti-TNFα, VNA have the potential to provide efficacious treatment of chronic inflammatory diseases. A bivalent llama-derived VNA that recognizes murine TNFα, when applied directly at pM concentrations, has been reported to prevent TNFα toxicity to a TNFα-sensitive mouse fibroblast cell line [22]. In addition, in a murine collagen-induced arthritis model, the administration of VNA$^{TNF}$ reduced joint inflammation similarly to a murine anti-TNFα monoclonal antibody [22].

Similarly, the daily administration of high doses of Lactococcus lactis engineered to secrete a VNA$^{TNF}$ composed of a single duplicated VHH via their Sec secretion system moderately suppressed intestinal inflammation (30-40%) in DSS (dextran sulfate sodium) induced intestinal injury and Il10$^{-/-}$ mouse models of IBD [24]. These observations support that the direct delivery of VNA into the intestinal lumen is worth pursuing as a novel therapeutic. Notably, unlike EcN, L. lactis do not colonize the intestines, thus presumably VNA are released as the bacteria travel through the murine gastrointestinal tract. Furthermore, not only does EcN colonize the intestines, but the bacteria also penetrate and adhere to the intestinal mucosa [62]. Thus, it is contemplated herein that the T3EcN$^{VNA}$ can improve upon the L. lactis based therapy by secreting high levels of VNA$^{TNF}$ in close proximity to the intestinal epithelium, the site of disease.

Murine models for IBD: The utility of T3EcN$^{VNA}$ for suppressing inflammation can be assessed using three complementary murine models including TRUC (T-bet$^{-/-}$ x Rag2$^{-/-}$ ulcerative colitis) and Il10$^{-/-}$ mice that spontaneously develop IBD and DSS-treated mice, which display acute intestinal injury and inflammation TRUC nice lack an adaptive immune response and develop a spontaneous, highly penetrant, and communicable distal colitis that resembles human ulcerative colitis. TRUC-associated colitis is characterized by diminished colonic barrier function and elevated TNFα, levels, resulting in detectable histological inflammatory intestinal damage by 3.5 weeks of age [63]. In contrast, Il10$^{-/-}$ mice have intact adaptive and innate immune cell populations but the lack of IL-10 compromises T-regulatory and myeloid cell subsets, resulting in chronic enterocolitis in the presence of a conventional microbiota [64]. The DSS model utilizes mice with intact innate and adaptive immune systems but the injury-induced inflammation leads to bloody stool and histological symptoms within 5 days. All three models exhibit high levels of mucosal pro-inflammatory cytokines such as TNF-α and IL-8 that are suppressed when the mice are treated systemically with anti-TNF-α antibody [68, 70, 71].

T3EcN-mediated treatment of IBD: After optimizing inoculation conditions, TRUC, DSS-treated and Il10$^{-/-}$ mice can be orally gavaged with T3EcN$^{VNA}$ (or as controls, EcN or T3EcN). For the TRUC and intestinal inflammation can be determined after two and four weeks using multiple complementary assays, while the DSS treated mice can be examined after 7 days. First, the nature and extent of colonic inflammation can be assessed by histopathologically [75]. Second, organ explant cultures can be employed to monitor for changes in the cytokines present in the inflammatory milieu of the treated mice [68]. The distal colon of TRUC mice and transverse and distal colon of Il10$^{-/-}$ mice and the entire colon distal to the cecum of DSS-treated wild type mice can be isolated [76] and explant supernatants will be analyzed using multiplex cytokine analysis for IL-1α, IL-1β, IL-2, IL-4, IL-6, KC, TNF-α, IFNγ, IL-10 (not applicable for Il10$^{-/-}$), IL-12p40, IL-12p70, IL-13, IL-17A, IL-21, and IL-23 using the Luminex platform. Third, fecal lipocalin can be used to non-invasively monitor intestinal inflammation in the TRUC and Il10$^{-/-}$ mice. Finally, the cell populations (cell surface markers and intracellular cytokines) present in the intestines of mice can be examined by flow cytometry.

Described herein are probiotic strains that secrete single domain antibodies that sequester proteins, including toxins and pro-inflammatory cytokines. Specifically the toxins associated with hemolytic uremic syndrome caused by enterohemorrhagic E. coli and the Clostridium difficile toxins that cause C. difficile colitis can be targeted as described herein. Bacteria to secrete single domain antibodies that bind and sequester TNFalpha, thus developing a treatment for inflammatory bowel disease, are also described herein.

Example 4

Described herein are laboratory and commensal strains of E. coli that express modified type 3 secretion systems that act to secrete proteins into their surroundings as opposed to directly into host cells using the following modifications (alone or in combination):

1) Removal of genes that encode components of the translocon apparatus (IpaB+/−IpaC)—this is the outer most portion of the type 3 secretion apparatus (T3SA) which is inserted into host cells 2) Removal of the gene encode IpaD, the component of the T3SA that serves as the plug that normally holds the machine in a closed state prior to contact with host cells 3) Removal of the gene encoding MxiC, a component of the T3SA that serves as the gatekeeper that normally prevents the loading of secreted substrates into the machine until it is activated. In its absence the T3SA constitutively secretes proteins into the media/extracellular milieu 4) Introduce mutations in MxiH, the portion of the T3SA that forms the needle, the portion of the machine that extends from the body of the secretion apparatus towards the host cell. When the T3SA contacts host cells, the pressure results in changes in the needle that signal activation of protein secretion. Mutations of the needle protein, have been identified which, when present as the sole copy in the cell, result in a secretion system that secretes proteins into the media as opposed to host cells.

5) Conduct genetic screens to identify E. coli variants that exhibit increased levels of secreted proteins.

The E. coli strains MP (PMID 24563035, Lasaro et al J Bact. 2014) and HS can be used in any of the aspects or embodiments herein.

These modified bacteria can be engineered to recognize one or more of the following proteins as type 3 secreted substrates a. single domain antibodies or nanobodies
b. cytokines—e.g., IL-10
c. toxins
d. pro-drug converting enzymes, i.e., cytosine deaminase
e. Other anti-inflammatory cytokines
f. Peptides with anti-inflammatory function or other functions
g. receptor agonists (to modulate immune responses)
h. antigenic proteins—for vaccine development
i. Enzymes—e.g., diagnostic factors. Lactose intolerance relevant enzymes Cancer Therapeutics Contemplated herein is the targeted secretion of immunostimulatory single domain antibodies (VHH) and/or toxins directly into solid tumors. Nissle E. coli homes to tumors and thus can serve as a targeted delivery system. In some embodiments of any of the aspects, single domain antibodies (VHH) that recognize PD-1, PD-L1, CTLA-4 can be utilized for this purpose.

Inflammatory Bowel Disease

Secretion of cytokines that suppress inflammation, i.e., IL-10 and IL-27 directly into the lumen of the intestines is contemplated herein as a targeted therapy for inflammatory bowel disease Secretion of VHH (monomeric and/or multimeric) that bind to cytokines, and/or their receptors, that promote inflammation, including, TNFalpha, IL-6, IL-18, IL-21, IL-33 and IL-13 is contemplated herein as a targeted therapy for IBD.

Treatment of Intestinal Infections

Secretion of VHH or VNA (VHH neutralizing agents=multimeric VHH) that bind Shiga toxin (treatment for hemolytic uremic syndrome linked to EHEC infections, C. dif toxin A and B (treatment for C. dif colitis), cholera toxin (treatment for cholera), anthrax toxin (gastrointestinal anthrax), botulinum toxin (botulism).

Example 5

Development of "Secretor" Strains of mT3sec_E. Coli.

Figures 4A, 4B:
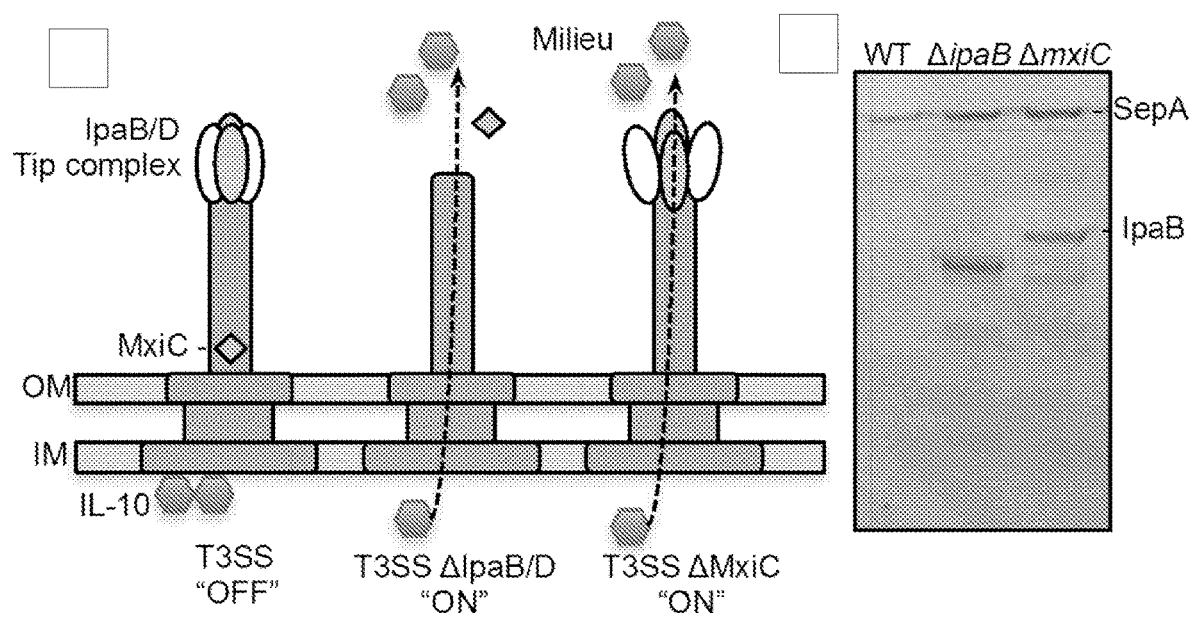
FIGS. 4A-4B depict a model of the different T3-EcN strains and how they work.
Figure 11:
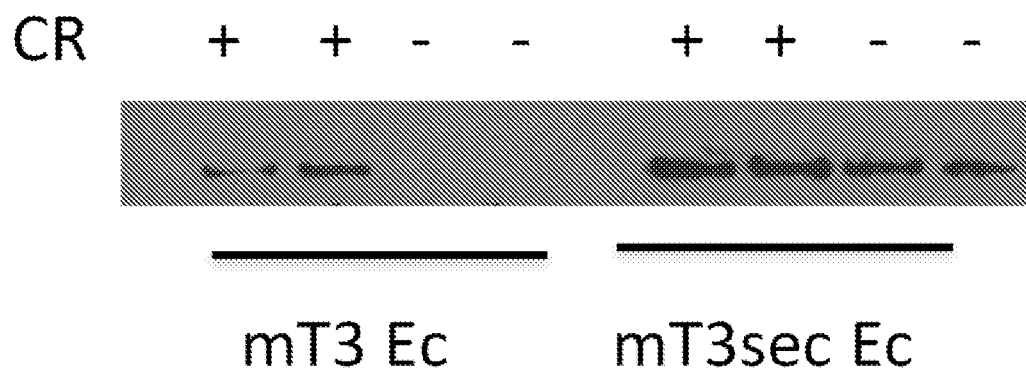
FIG. 11 demonstrates that mT3sec *E. coli* constitutively secrete type III secreted substrates. The designated bacterial strains were grown under conditions that induce expression of the type III secretion. The bacteria were then transferred to PBS+/−Congo red (CR), a dye that is normally require for the secretion of effectors.

Under physiologic conditions, prior to contact with host cells, T3SSs are fully assembled and held in an "off" but primed condition such that upon contact with host cells type 3 secreted substrates are rapidly injected into host cells. This "off" conformation is maintained by the presence of proteins at the exposed and inner surfaces of the type 3 secretion conduit. In the case of the Shigella T3SS, the system produced by minT3_E. coli, the outer proteins are IpaB and IpaD, and the inner "gatekeeper" protein is MxiC (FIG. 4A). Strains that lack any of these three proteins no longer deliver proteins into host cells in a regulated manner, but rather constitutively secrete proteins into the media when grown at 37° C., a condition sufficient to activate expression of the T3SS, when present in either Shigella or E. coli. Based on these observations, a recombination platform was used to develop strains of minT3_E. coli that no longer encode the translocon apparatus, the outer portion of the T3SA that is composed of IpaB, IpaC and IpaD. As predicted, it is observed that this strain is capable of constitutive secreting heterologous proteins into the extracellular milieu, as it is capable of secreting type III substrates in the absence of Congo red, a well established in vitro inducer of the secretion of effectors from Shigella (FIG. 11). Development of monomeric and multimeric single domain camelids that are recognized as type III secreted effectors.

Figure 12:
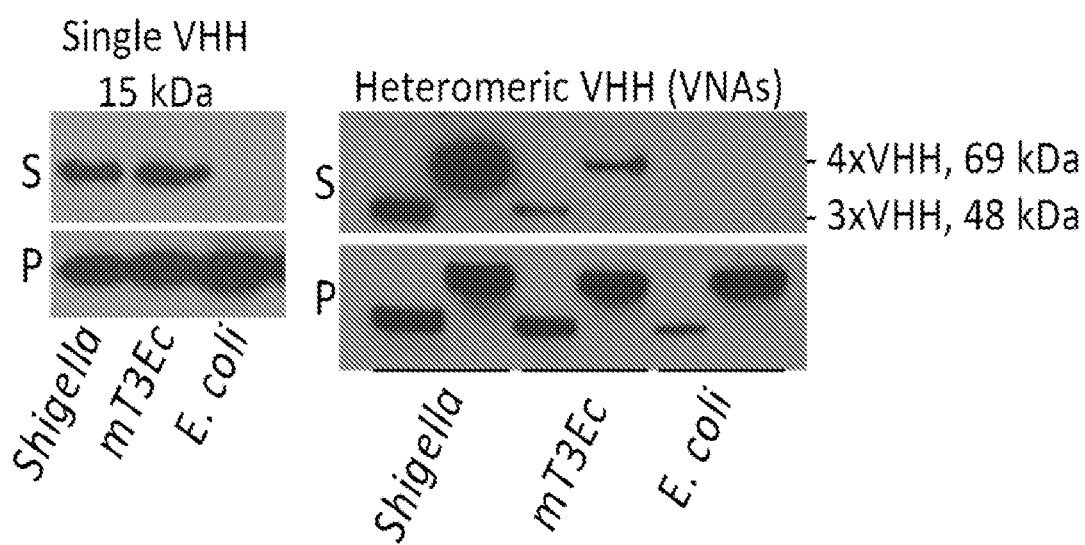
FIG. 12 demonstrates secretion of a single variable-domain heavy-chain region (VHH or nanobody) and heterometric VHH-neutralizing agents (VNA)s. Both wild type *Shigella flexneri* and mT3 *E. coli*, but not wild type *E. coli*, recognize VHH and VNAs as secreted substrates. Bacterial strains were grown under conditions that induce type III secretion. The heteromeric VHH (VNAs) are fused to the OspC3 secretion sequence at their N-terminus and FLAG-tagged at the C-terminus in this standard secretion assay. Immunoblots are probed with anti-FLAG antibody. S, supernatant. P, pellet of whole cell lysate.

Monoclonal antibody-based "magic bullet" therapeutics with high TNFα specificity are dramatically altering approaches towards the treatment of inflammatory bowel disease. Patients administered such drugs systemically have marked improvement of systems, but unfortunately can suffer from off-target effects including systemic immunosuppression. Monoclonal antibodies are highly complex, composed of multiple subunits linked together by disulfide bonds and thus are highly unlikely to be functional when engineered to be recognized as type III secreted substrates. A new exciting avenue of antibody-mediated therapies is currently emerging that circumvents many of the obstacles of conventional monoclonal antibody-based therapies based on Camelid heavy chain only immunoglobulins (HcAbs). HcAb bind antigens via a single variable-domain heavy-chain region, a VHH. VHH, small ~15 kDa protein domains, bind substrates with Kd's in the nM to pM range and exhibit a predilection for binding protein active sites. Furthermore they can be used as modular building blocks to generate multimeric constructs that exhibit enhanced binding potential, both in terms of binding affinity and breath of epitope recognition. Their remarkable solubility, stability and small size overcome many of the barriers that currently limits the production of monoclonal antibodies, resulting in significant decreases in production costs. Thus, it was next investigated whether functional variants of HcAbs that are recognized as secreted substrates by minT3_E. coli can be developed. As shown in FIG. 12, relatively high levels of secretion of monomeric VHH were observed when fused to an OspC3 or OspG type III secretion signal sequence as well as trimeric VHH when fused to an OspC3 type III secretion signal sequence. It has also been demonstrated that VHH fold correctly and maintain function when secreted by minT3 E. coli.

What is claimed herein is:

1. An engineered, non-pathogenic, gram negative microbial cell comprising:
    a) a first nucleic acid sequence comprising genes encoding a type 3 secretion system (T3SS)-derived extracellular secretion system (TDESS); wherein the TDESS comprises at least virulence regulon transcriptional activator (vir) B (virB); membrane expression of invasion plasmid antigens (mxi) G (mxiG); mxiH; mxiI; mxiJ; mxiK; mxiN; mxiL; mxiM; mxiD; mxiA; surface presentation antigens (spa) 47 (spa47); spa13; spa32; spa33; spa24; spa9; spa29; and spa40;
    b) a second nucleic acid sequence encoding an T3SS-compatible payload polypeptide; and not comprising or expressing at least one of
    invasion plasmid antigen (Ipa) B (IpaB);
    IpaD; or
    MxiC wherein the TDESS comprises polypeptides endogenous to a bacterium selected from the group consisting of: *Shigella* spp; *Salmonella* spp; enteropathogenic *E. coli*; and *Yersinia* spp.

2. The microbial cell of claim 1, wherein the cell has a mutated MxiH.

3. The microbial cell of claim 1, wherein the second nucleic acid sequence comprises 1) an inducible promoter sequence that is operably linked to 2) a sequence encoding an T3SS-compatible payload polypeptide.

4. The microbial cell of claim 1, wherein the cell comprises a third nucleic acid sequence encoding a master T3SS transcriptional regulator.

5. The microbial cell of claim 4, wherein the master T3SS transcriptional regulator is selected from the group consisting of:
    VirB and VirF.

6. The microbial cell of claim 1, wherein the TDESS comprises at least: virB; acyl carrier protein (acp); ipaA; invasion plasmid gene (ipg) C (ipgC); ipgB1; ipgA; intra-inter-cellular spread (ics) B (icsB); ipgD; ipgE; ipgF; mxiG; mxiH; mxiI; mxiJ; mxiK; mxiN; mxiL; mxiM; mxiE; mxiD; mxiA; spa15; spa47; spa13; spa32; spa33; spa24; spa9; spa29; and spa40.

7. The engineered microbial cell of claim 1, wherein the first nucleic acid sequence comprising genes encoding a type 3 secretion system (T3SS)-derived extracellular secretion system (TDESS) and/or the genes encoding a type 3 secretion system (T3SS)-derived extracellular secretion system (TDESS) are exogenous to the microbial cell.

8. The engineered microbial cell of claim 1, wherein the cell did not comprise a T3SS prior to being engineered to comprise the first and second nucleic acid sequences.

9. The microbial cell of claim 1, wherein the T3SS-compatible payload polypeptide comprises an anti-inflammatory polypeptide.

10. The microbial cell of claim 1, wherein the T3SS-compatible payload polypeptide comprises an antibody reagent; a nanobody; a VNA; or a VHH.

11. The microbial cell of claim 10, wherein the antibody reagent specifically binds to a cancer checkpoint polypeptide.

12. The microbial cell of claim 11, wherein the antibody reagent is an anti-PD-L1; anti-PD-1; or anti-CTLA-4 reagent.

13. The microbial cell of claim 10, wherein the antibody reagent specifically binds to an inflammatory cytokine receptor or an inflammatory cytokine.

14. The microbial cell of claim 10, wherein the antibody reagent specifically binds to a bacterial toxin.

15. The microbial cell of claim 1, wherein the microbial cell is engineered from a microbial cell selected from the group consisting of:
   *E. coli* NISSLE 1917 (EcN); *E. coli* K12; MP; HS; *E. coli* DH1013 and *E. coli* DH5a.

16. The microbial cell of claim 1, wherein the microbial cell is engineered from a commensal intestinal microbial cell.

17. A method of introducing a polypeptide into a target tissue or organism, the method comprising contacting the target tissue or organism with a microbial cell of claim 1.

18. A method for delivering a polypeptide into a) the extracellular milieu of a subject's gastrointestinal tract, b) the lumen of a tumor, or c) the extracellular milieu of a subject's tumor, the method comprising contacting administering a microbial cell of claim 1 to the subject.

* * * * *

UNITED STATES PATENT AND TRADEMARK OFFICE
CERTIFICATE OF CORRECTION

PATENT NO. : 10,702,559 B2
APPLICATION NO. : 16/075410
DATED : July 7, 2020
INVENTOR(S) : Cammie Lesser and Analise Reeves It is certified that error appears in the above-identified patent and that said Letters Patent is hereby corrected as shown below:

In the Claims

At Column 218, Claim 15, Lines 4-5:
"E. coli NISSLE 1917 (EcN); E. coli K12; MP; HS; E. coli DH1013 and E. coli DH5a."
Should be replaced with:
-- E. coli NISSLE 1917 (EcN); E. coli K12; MP; HS; E. coli DH10β and E. coli DH5α. --

Signed and Sealed this
Nineteenth Day of January, 2021

Andrei Iancu
*Director of the United States Patent and Trademark Office*